(12) United States Patent
Goldberg et al.

(10) Patent No.: US 12,215,111 B2
(45) Date of Patent: Feb. 4, 2025

(54) IMIDAZOPYRIDAZINE IL-17 INHIBITOR COMPOUNDS

(71) Applicant: Janssen Pharmaceutica NV, Beerse (BE)

(72) Inventors: Steven D. Goldberg, San Diego, CA (US); Douglas C. Behenna, San Juan Capistrano, CA (US); Deane Gordon, San Diego, CA (US); Luke E. Hanna, San Diego, CA (US); Steven A. Loskot, San Diego, CA (US); Stefan McCarver, San Diego, CA (US); Steven P. Meduna, San Diego, CA (US); Brock T. Shireman, Poway, CA (US); Alexander E. Valdes, San Diego, CA (US); Jennifer D. Venable, Solana Beach, CA (US); Dongpei Wu, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/935,329

(22) Filed: Sep. 26, 2022

(65) Prior Publication Data

US 2023/0147458 A1 May 11, 2023

Related U.S. Application Data

(60) Provisional application No. 63/371,910, filed on Aug. 19, 2022, provisional application No. 63/273,407, filed on Oct. 29, 2021, provisional application No. 63/248,563, filed on Sep. 27, 2021.

(51) Int. Cl.
C07D 487/04 (2006.01)
(52) U.S. Cl.
CPC .................... C07D 487/04 (2013.01)
(58) Field of Classification Search
CPC .................................................. C07D 487/04
See application file for complete search history.

(56) References Cited

U.S. PATENT DOCUMENTS

2022/0402922 A1  12/2022  Goldberg et al.

FOREIGN PATENT DOCUMENTS

| CN | 116143777 | | 5/2023 | |
|---|---|---|---|---|
| WO | WO-2020146194 A1 | * | 7/2020 | ......... A61K 31/5025 |
| WO | 2020261141 A1 | | 12/2020 | |
| WO | 2023025783 A1 | | 3/2023 | |
| WO | 2023049886 A1 | | 3/2023 | |
| WO | WO 2023/078319 A1 | | 5/2023 | |

OTHER PUBLICATIONS

Abu El-Asrar A. et al., "Cytokine profiles in aqueous humor of patients with different clinical entities of endogenous uveitis", Clin. Immunol., vol. 139, No. 2, pp. 177-184, 2011.
Adamopoulos, I.E. et al., "Alternative pathways of osteoclastogenesis in inflammatory arthritis", Nat. Rev. Rheumatol., vol. 11, pp. 189-194, 2015.
Amatya, N. et al., "IL-17 Signaling: The Yin and the Yang", Trends in Immunology, vol. 38 No. 5, pp. 310-322, 2017.
Appel, H. et al., "Analysis of IL-17+ cells in facet joints of patients with spondyloarthritis suggests that the innate immute pathway might be of greater relevance than the Th17-mediated adaptive immune response", Arthritis Research & Therapy, vol. 13 Issue 03, 9 pages, 2011.
Baeten, D. et al., "Risankizumab, an IL-23 inhibitor, for ankylosing spondylitis: results of a randomised, double-blind, placebo-controlled, proof-of-concept, dose-finding phase 2 study", Ann Rheum Dis, vol. 77 Issue 09, pp. 1295-1302, 2018.
Blauvelt et al., "The Immunologic Role of IL-17 in Psoriasis and Psoriatic Arthritis Pathogenesis", Clinical Reviews Allergy & Immunology. vol. 55 Issue 03, pp. 379-390, Aug. 14, 2018.
Camargo, LDN et al., "Effects of Anti-IL-17 Inflammation, Remodeling, and Oxidative Stress in an Experimental Model of Asthma Exacerbated by LPS", Frontiers in Immuno., vol. 8, Article 1835, 14 pages, Jan. 2018.
Chakievska, L. et al., "IL-17A is functionally relevant and a potential therapeutic target in bullous pemphigoid", Journal of Autoimmunity, vol. 96, pp. 104-112, 2019.
Chakir, J. et al., "Airway remodeling-associated mediators in moderate to severe asthma: Effect of steroids on TGF-β, IL-11, IL-17, and type I and type III collagen expression". J. Allergy Clin Immunol., vol. 111 No. 06, pp. 1293-1298, Jun. 2003.
Chen, X. et al., "Plasma IL-17A Is Increased in New-Onset SLE Patients and Associated with Disease Activity", J. Clin. Immunol., vol. 30 No. 2, pp. 221-225, 2010.
Chen, Y. et al., "The Effects of Th17 Cytokines on the inflammatory Mediator Production and Barrier Function of ARPE-19 Cells", PLoS One, vol. 6 Issue 3, Mar. 2011, 6 pages, e18139.
Christenson, S. et al., "An Airway Epithelial IL-17A Response Signature Identifies A Steroid-Unresponsive COPD Patient Subgroup", J Clin Invest., vol. 129 No. 1, pp. 169-181, Jan. 2019.

(Continued)

*Primary Examiner* — Noble E Jarrell
*Assistant Examiner* — Richard Grant Peckham
(74) *Attorney, Agent, or Firm* — Guodong Liu

(57) ABSTRACT

The present application discloses compounds having the following formula:

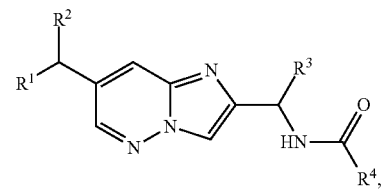

or pharmaceutically acceptable salts thereof, wherein $R^1$, $R^2$, $R^3$, and $R^4$ are defined in the specification, as well as methods of making and using the compounds disclosed herein for treating or ameliorating an IL-17 mediated syndrome, disorder and/or disease.

24 Claims, No Drawings

Specification includes a Sequence Listing.

(56) References Cited

OTHER PUBLICATIONS

ClinicalTrials.gov Identifier: NCT03099538, "Ixekizumab in the Treatment of Bullous Pemphigoid", Last Update Posted May 21, 2020, 10 pages.

ClinicalTrials.gov Identifier: NCT04586920, "A Study of LY3509754 in Healthy Non-Japanese and Japanese Participants", Last Update Posted Dec. 21, 2022, 7 pages.

ClinicalTrials.gov Identifier: NCT04883333, "A Single and Multiple Ascending-dose Trial of LEO 153339 in Healthy Adults", Last Update Posted Jan. 12, 2023, 8 pages.

Cross, et al., "Rules For The Nomenclature Of Organic Chemistry", Section E: Stereochemistry, Pure and Appl. Chem., vol. 45, pp. 11-30, 1976.

Deodhar, A. et al., "Three Multicentre, Randomized, Double-Blind, Placebo-Controlled Studies Evaluating the Efficacy and Safety of Ustekinumab in Axial Spondyloarthritis", Arthritis & Rheumatology, vol. 71 No. 02, pp. 258-270, Feb. 2, 2019.

Dick, A. et al., "Secukinumab in the Treatment of Noninfectious Uveitis: Results of Three Randomized, Controlled Clinical Trials", Ophthalmology, vol. 120 No. 4, pp. 777-787, 2013.

Dolff, S. et al., "Disturbed Th1, Th2, Th17 and Treg balance in patients with systemic lupus erythematosus", Clin. Immunol., vol. 141, Issue 2, pp. 197-204. Nov. 2011.

dos Santos TM. et al., "Effect of Anti-IL-17 Antibody Treatment Alone and in Combination With Rho-Kinase Inhibitor in a Murine Model of Asthma", Frontiers in Physiology, vol. 09, Article 1183, 19 pages, 2018.

Eby, J. et al., "Immune responses in a mouse model of vitiligo with spontaneous epidermal de- and repigmentation", Pigment Cell And Melanoma Res., vol. 27, Issue 6, pp. 1075-1085, 2014.

Gaffen, S., "Structure and signaling in the IL-17 receptor family", Nature Reviews, Immunology, vol. 09, pp. 556-567. Aug. 2009.

Havrdova, E. et al., "Activity of Secukinumab, an anti-IL-17A antibody, on brain lesions in RRMS: results from a randomised, proof-of-concept study", J Neurol., vol. 263, pp. 1287-1295, 2016.

Hawkes et al., "Psoriasis Pathogenesis and the Development of Novel Targeted Immune Therapies", J Allergy Clin Immunol., vol. 140 No. 3, pp. 645-653, 2017.

International Search Report and Written Opinion received for Application No. PCT/US2022/077000, 15 pages, dated Nov. 16, 2022.

Jansen, D. et al., "IL-17-producing CD4+ T cells are increased in early, active axial spondyloarthritis including patients without imaging abnormalities", Rheumatology, vol. 54 Issue 04, pp. 728-735, 2015.

Jawad, S. et al., "Elevated Serum Levels of Interleukin-17A in Uveitis Patients", Ocul. Immunol. Inflamm., vol. 21 No. 6, pp. 434-439, Dec. 2013.

Kelly, G. et al., "Dysregulated Cytokine Expression in Lesional and Nonlesional skin in hidradenitis suppurativa", British Journal of Dermatology, vol. 173 Issue 06, pp. 1431-1439, 2015.

Khattri, S. et al., "Efficacy and Safety of Ustekinumab treatment in adults with moderate-to-severe atopic dermatitis", Experimental Dermatology, vol. 26 Issue 01, pp. 28-35, 2017.

Koga, C. et al., "Possible Pathogenic Role of Th17 Cells for Atopic Dermatitis", Journal of Investigative Dermatology, vol. 128, pp. 2625-2630, 2008.

Koga, T. et al.,"The role of IL-17 in systemic lupus erythematosus and its potential as a therapeutic target", Expert Rev. of Clin. Immunol., vol. 15, No. 6, pp. 629-637, 2019.

Kuiper, J. et al., "Intraocular Interleukin-17 and Proinflammatory Cytokines in HLA-A29-Associated Birdshot Chorioretinopathy", American J. Ophthalmol., vol. 152, No. 2, pp. 177-182, 2011.

Le Jan, S. et al., "Innate Immune Cell Produced IL-17 Sustains Inflammation in Bullous Pemphigoid", Journal Of Investigative Dermatology, vol. 134, No. 12, pp. 2908-2917, 2014.

Lemancewicz, D. et al., "The Role of Interleukin-17A and Interleukin-17E in multiple myeloma patients", Med Sci Monit., vol. 18 Issue 01, pp. 54-59, 2012.

Letko, E. et al., "Efficacy and Safety of Intravenous Secukinumab in Noninfectious Uveitis Requiring Steroid-Sparing Immunosuppressive Therapy", Ophthalmology, vol. 122, No. 5, pp. 939-948, 2015.

Lock, C. et al., "Gene-Microarray Analysis of Multiple Sclerosis lesions yields new targets validated in Autoimmune encephalomyelitis", Nature Medicine, vol. 8, No. 5, pp. 500-508, May 2002.

Ma, J. et al., "The imbalance between regulatory and IL-17-secreting CD4+ T cells in lupus patients", Clin. Rheumatol., vol. 29 No. 11, pp. 1251-1258, 2010.

Matusevicius, D. et al., "Interleukin-17 mRNA expression in blood and CSF mononuclear cells is augmented in multiple sclerosis", Multiple Sclerosis, vol. 5, pp. 101-104, 1999.

Mease PJ, et al., "A head-to-head comparison of the efficacy and safety of ixekizumab and adalimumab in biological-naïve patients with active psoriatic arthritis: 24-week results of a randomised, open-label, blinded-assessor trial", Ann Rheum Dis., vol. 79, pp. 123-131, 2020.

Mease, P. et al., "Comparative effectiveness of Secukinumab and Etanercept in Biologic-Naïve Patients with Psoriatic Arthritis assessed by Matching-adjusted indirect Comparison", Eur J Rheumatol, vol. 6 No. 03, pp. 113-121, 2019.

Menon, B. et al., "Interleukin-17+ CD8+ T Cells are Enriched in the Joints of Patients With Psoriatic Arthritis and Correlate With Disease Activity and Joint Damage Progression", Arth Rheumatology, vol. 66, No. 5, pp. 1272-1281, May 2014.

Molet, S. et al., "IL-17 is Increased in Asthmatic Airways and Induces Human Bronchial Fibroblasts to Produce Cytokines", J Allergy Clin Immuno., vol. 108 Issue 03, pp. 430-438, Sep. 2001.

Moran, B. et al., "Hidradenitis Suppurativa Is Characterized by Dysregulation of the Th17:Treg Cell Axis, Which Is Corrected by Anti-TNF Therapy", J of Investigative Dermatology, vol. 137, Issue 11, pp. 2389-2395, 2017.

Mugheddu, C. et al., "Successful Ustekinumab Treatment of Non-infectious uveitis and Concomitant severe psoriatic Arthritis and Plaque Psoriasis", Dermatologic Therapy, vol. 30 Issue 05, pp. 1-4, 2017.

Nash, P. et al., "Secukinumab Versus Adalimumab for Psoriatic Arthritis: Comparative Effectiveness up to 48 Weeks Using a Matching-Adjusted Indirect Comparison", Rheumatol Ther., vol. 05 Issue 01, pp. 99-122, 2018.

Prabhala, R. et al., "Targeting IL-17A in Multiple Myeloma: a potential novel therapeutic approach in myeloma", Leukemia, vol. 30 Issue 02, pp. 379-389, 2016.

Prelog V. et al., "Basic Principles of the CIP-System and Proposals for a Revision", Angew. Chem. Int. Ed. Engl., vol. 21, pp. 567-583, 1982.

Prussick, L. et al., "Open-label, investigator-initiated, single-site exploratory trial evaluating secukinumab, an anti-interleukin-17A monoclonal antibody, for patients with moderate-to-severe hidradenitis suppurativa", Brit. J of Dermatology, vol. 181 Issue 03, pp. 609-611, 2019.

Robert M. et al., "IL 17 in Rheumatoid Arthritis and Precision Medicine: From Synovitis Expression to Circulating Bioactive Levels", Front. Med., vol. 05, Article 364, 10 pages, Jan. 2019.

Schlapbach, C. et al., "Expression of the IL-23/Th17 pathway in lesions of Hidradenitis Suppurativa", J. American Academy Dermatology, vol. 65, No. 04, pp. 790-798, Oct. 1, 2011.

Setiadi AF et al., "IL-17A is Associated with the breakdown of the blood-brain barrier in relapsing-remitting multiple sclerosis", J Neuroimmuno., vol. 332, pp. 147-154, 2019.

Shen, H. et al., "Frequency and Phenotype of Peripheral Blood Th17 Cells in Ankylosing Spondylitis and Rheumatoid Arthritis", Arthritis & Rheumatism, vol. 60, No. 06, pp. 1647-1656, Jun. 2009.

Singh, R. et al., "The role of IL-17 in vitiligo: A review", Autoimmun, Rev., vol. 15, pp. 397-404, 2016.

Stamp, L. et al., "Interleukin-17: the missing link between T-cell accumulation and effector cell actions in rheumatoid arthritis?", Immunol. Cell Biol., vol. 82 No. 1, pp. 1-9, 2004.

Strand, V. et al., "Matching-adjusted indirect Comparison: secukinumab versus infliximab in biologic-naive patients with psoriatic arthritis", J. of Comparative Effectiveness Research, vol. 8, No. 07, pp. 497-510, 2019.

(56) References Cited

OTHER PUBLICATIONS

Thomi, R. et al., "Association of Hidradenitis Suppurativa With T Helper 1/ T Helper 17 Phenotypes—A Semantic Map Analysis", JAMA Derma., vol. 154, No. 05, pp. 592-595, May 2018.

Tzartos, J. et al., "Interleukin-17 Production in Central Nervous System-Infiltrating T Cells and Glial Cells Is Associated with Active Disease in Multiple Sclerosis.", American J. Of Pathology, vol. 172 No. 1, pp. 146-155, Jan. 2008.

van Vollenhoven, R. et al.,"Efficacy and safety of ustekinumab, an IL-12 and IL-23 inhibitor, in patients with active systemic lupus erythematosus: results of a multicentre, double-blind, phase 2, randomised, controlled study", Lancet, vol. 392, pp. 1330-1339, 2018.

Vargas-Rojas M. et al., "Increase of Th17 in peripheral blood of patients with chronic obstructive pulmonary disease", Respir. Med.,vol. 105 No. 11, pp. 1648-1654, 2011.

Wen, Z. et al., "Interleukin-17 Expression Positively Correlates with Disease Severity of Lupus Nephritis by Increasing Anti-Double-Stranded DNA Antibody Production in a Lupus Model Induced by Activated Lymphocyte Derived DNA", PLoS One., vol. 8, Issue 3, e58161, 10 pages, Mar. 2013.

Wendling, D. et al., "Serum IL-17, BMP-7, and bone turnover markers in patients with ankylosing spondylitis", Joint Bone Spine, vol. 74, pp. 304-305, 2007.

Willing A. et al., "Production of IL-17 by MAIT Cells Is Increased in Multiple Sclerosis and is Associated with IL-7 Receptor Expression", J. Of Immunology, vol. 200, No. 03, pp. 974-982, 2018.

Wong, C. et al., "Elevation of Proinflammatory Cytokine (IL-18, IL-17, IL-12) and Th2 Cytokine (IL-4) Concentrations in patients with systemic lupus Erythematosus", Lupus, vol. 9, pp. 589-593, 2000.

Wong, C. et al., "Hyperproduction of IL-23 and IL-17 in patients with systemic lupus erythematosus: Implications for Th17-mediated inflammation in auto-immunity", Clinical Immunology, vol. 127, pp. 385-393, 2008.

Xing Q. et al., "Elevated Th17 cells are accompanied by FoxP3+ Treg cells decrease in patients with lupus nephritis", Rheumatol. Int., vol. 32, pp. 949-958, 2012.

Zhang L. et al., "Increased Frequencies of Th22 Cells as well as Th17 Cells in the Peripheral Blood of Patients with Ankylosing Spondylitis and Rheumatoid Arthritis", PLoS one, vol. 7, Issue 04, 9 pages, Apr. 2012.

Zhang, R. et al., "Suppression of Experimental Autoimmune Uveoretinitis by Anti-IL-17 Antibody", Curr. Eye Res., vol. 34, No. 4, pp. 297-303, 2009.

Zhao X-F. et al., "Increased serum interleukin 17 in patients with systemic lupus erythematosus", Mol. Biol, Rep., vol. 37, pp. 81-85, 2010.

\* cited by examiner

```
                        SEQUENCE LISTING

Sequence total quantity: 2
SEQ ID NO: 1            moltype = AA  length = 182
FEATURE                 Location/Qualifiers
REGION                  1..182
                        note = Synthetic polypeptide
source                  1..182
                        mol_type = protein
                        organism = synthetic construct
SEQUENCE: 1
MATGSRTSLL LAFGLLCLPW LQEGSAGSDY KDDDDKGSGS GSLEVLFQGP GITIPRNPGC     60
PNSEDKNFPR TVMVNLNIHN RNTNTNPKRS SDYYNRSTSP WNLHRNEDPE RYPSVIWEAQ    120
CRHLGCINAD GNVDYHMNSV PIQQEILVLR REPPHCPNSF RLEKILVSVG CTCVTPIVHH    180
VQ                                                                   182

SEQ ID NO: 2            moltype = AA  length = 323
FEATURE                 Location/Qualifiers
REGION                  1..323
                        note = Synthetic polypeptide
source                  1..323
                        mol_type = protein
                        organism = synthetic construct
SEQUENCE: 2
MKFLVNVALV FMVVYISYIY ALRLLDHRAL VCSQPGLNCT VKNSTCLDDS WIHPRNLTPS     60
SPKDLQIQLH FAHTQQGDLF PVAHIEWTLQ TDASILYLEG AELSVLQLNT NERLCVRFEF    120
LSKLRHHHRR WRFTFSHFVV DPDQEYEVTV HHLPKPIPDG DPNHQSKNFL VPDCEHARMK    180
VTTPCMSSGS LWDPNITVET LEAHQLRVSF TLWNESTHYQ ILLTSFPHME NHSCFEHMHH    240
IPAPRPEEFH QRSNVTLTLR NLKGCCRHQV QIQPFFSSCL NDCLRHSATV SCPEMPDTPE    300
PIPDYMPLWG SGGHHHHHHH HHH                                            323
```

IMIDAZOPYRIDAZINE IL-17 INHIBITOR COMPOUNDS

This application claims the benefit of U.S. Provisional Application 63/248,563, filed on Sep. 27, 2021, U.S. Provisional Application 63/273,407, filed on Oct. 29, 2021, and U.S. Provisional Application 63/371,910, filed on Aug. 19, 2022.

REFERENCE TO SEQUENCE LISTING SUBMITTED ELECTRONICALLY

This application contains a sequence listing, which is submitted electronically as an ST.26 XML formatted sequence listing with a file name "PRD4155WOPCT1_SL", creation date of Aug. 19, 2022, and having a size of 3.72 KB. The sequence listing submitted is part of the specification and is herein incorporated by reference in its entirety.

FIELD

Disclosed herein are imidazopyridazine compounds, and pharmaceutical compositions thereof, which modulate Interleukin-17A. Also disclosed herein is the therapeutic use of such compounds, for example, in treating and/or ameliorating an IL-17A mediated inflammatory syndrome, disorder, or disease.

BACKGROUND

Interleukin-17 ("IL-17"), also known as IL-17A and CTLA-8, is produced mainly by CD4+ Th17 cells, and also by other immune cells such as CD8+ T cells, γδ T cells, NK cells, NKT cells, and innate lymphoid cells (ILCs). IL-17A exists as a homodimer (A/A) or as a heterodimer (A/F) with IL-17F and signals through binding to dimeric receptor complex IL-17RA and IL-17RC. IL-17RA is ubiquitously expressed at particularly high levels by haematopoietic cell types, whereas IL-17RC is preferentially expressed by non-haematopoietic cells (Gaffen, S. Structure and signaling in the IL-17 receptor family. Nat. Rev. Immunol. 2009, 9, 556-567). IL-17A/IL-17R signaling induces de novo gene transcription by triggering NF-kB, C/EBP and MAPK pathways through ACT1-TRAF6-TRAF4. It can also stabilize target mRNA transcripts through the ACT1-TRAF2-TRAF5 complex (Amatya N. et al., Trends in Immunology, 2017, 38, 310-322). IL-17A stimulates the release of inflammatory mediators including IL-6, IL-8, G-CSF, TNF-α, and IL-1β that recruit and activate lymphocytes to the site of injury or inflammation and maintain a proinflammatory state.

As discussed below, preclinical and clinical data have demonstrated the significant pathological role of IL-17A in multiple autoimmune and inflammatory diseases.

For psoriasis: IL-17A mRNA and/or protein levels are elevated in the lesional skin and blood of patients with psoriasis and correlate with disease severity. IL-17A acts directly in synergy with other cytokines (such as TNFα, IFNγ or IL-22) on keratinocytes triggering a self-amplifying inflammatory response in the skin and leading to the formation of psoriatic plaques. The blockade of IL-17A by means of antibodies to IL-17A or IL-23 results in complete reversal of the molecular and clinical disease features in majority of psoriasis patients, manifesting the significant role of IL-17A and IL-17-producing T-cells in the immunopathogenesis of psoriasis. (Hawkes et al., Psoriasis Pathogenesis and the Development of Novel, Targeted Immune Therapies. J Allergy Clin Immunol. 2017, 140(3): 645-653).

The development and approval of IL-17 monoclonal antibodies such as secukinumab, ixekizumab, and brodalumab and their transformational efficacy for psoriasis have demonstrated IL-17A as a valid target for psoriasis treatments. (Blauvelt A. and Chiricozzi A. The Immunologic Role of IL-17 in Psoriasis and Psoriatic Arthritis Pathogenesis. Clin Rev Allergy Immunol. 2018, 55(3):379-390).

For psoriatic arthritis (PsA): IL-17A is mechanistically relevant to PsA through NFκB activation that triggers transcription of several PsA related genes including the receptor activator of nuclear factor κB ligand (RANKL). RANKL triggers the differentiation of osteoclast precursor cells into activated osteoclasts, resulting in bone resorption and subsequently joint deformity in PsA (Adamopoulos I. and Mellins E. Nature reviews Rheumatology 2015; 11:189-94). PsA joint is enriched for IL-17+CD8+ T cells, and the levels of this T cell subset are correlated with disease activity (Menon B. et al., Arthritis & Rheumatology 2014; 66: 1272-81). Synovial fibroblasts isolated from PsA patients also contain elevated IL-17R expression and secrete increased IL-6, CXCL8 and MMP3 ex vivo compared to osteoarthritis patients. Both secukinumab and ixekizumab are FDA approval drugs for PsA. In matching-adjusted indirect comparison analysis, secukinumab was associated with higher ACR 20/50/70 response rates in patients with active PsA than anti-TNFα antibodies (Mease P. et al., Eur. J. Rheumatol. 2019 Jul. 1; 6(3):113-121; Strand V. et al., J. Comp. Eff. Res. 2019, 8(7):497-510; Nash P. et al., Rheumatol. Ther. 2018, 5(1):99-122). In a recent head-to-head study, ixekizumab was superior to adalimumab in achieving simultaneous improvement of joint and skin disease (ACR50 and PASI100) in patients with PsA and inadequate response to conventional synthetic disease-modifying anti-rheumatic drug (Mease, P. et al. Ann Rheum Diss 2020; 79:123-131). By hitting the same target, IL-17A small molecule inhibitor compounds may exert similar or better efficacy than biologics considering that small molecules generally have better tissue penetration.

For rheumatoid arthritis (RA): IL-17A has been recognized as critical to the progression of rheumatoid arthritis. "The recognition of IL-17 as a pro-inflammatory T cell derived cytokine, and its abundance within rheumatoid joints, provides the strongest candidate mechanism to date through which T cells can capture and localize macrophage effector functions in rheumatoid arthritis" Stamp, L. et al., Immunol. Cell Biol. 2004, 82(1): 1-9. Moreover, in rheumatoid arthritis IL-17A acts locally on synoviocytes and osteoblasts contributing to synovitis and joint destruction. Robert and Miossec have proposed the use of synovial biopsies and/or biomarkers to precisely identify patients that would respond to IL-17A inhibition. Their work concludes that IL-17 inhibitors should now be considered in the development of precision medicine in RA. (Robert M. and Miossec P., Front. Med., 2019, 5:364).

For Ankylosing Spondylitis (AS): Various studies have reported elevated IL-17A and Th17 and other cells producing IL-17 in AS blood samples (Wendling D. et al., Joint Bone Spine. 2007; 74:304-305; Shen H. et al., Arthritis Rheum. 2009; 60(6):1647-56; Zhang L. et al., PLoS One. 2012; 7(4):e31000; Jansen D. et al., Rheumatology (Oxford). 2015 April; 54(4): 728-735). In situ analysis of AS spine has revealed increased IL-17A-producing cells in bone of facet (zygapophyseal) joints (Appel H. et al., Arthritis Res. Ther. 2011; 13(3):R95). Two advanced IL-17A neutralizing antibodies, secukinumab, approved by FDA for AS, and ixekizumab, have demonstrated efficacy over placebo even in anti-TNF inadequate responders. In contrast, anti- IL-23 p40 and p19 biologics failed to demonstrate beneficial effect (Deodhar A. et al., Arthritis Rheumatol. 2019, 71(2): 258-270; Baeten D. et al., Ann. Rheum. Dis. 2018, 77(9): 1295-1302), indicating the differential underling mechanism along IL-23/IL-17 pathway in AS and providing strong evidence to support continuing developing IL-17A inhibitors.

For hidradenitis suppurativa (HS): Increased IL-17 and IL-17-producing T helper cells in the skin lesions of HS patients were reported and molecular proteomics and gene expression data indicate that the IL-23/Th17 pathway is upregulated in HS lesions (Schlapbach C. et al., J. Am. Acad. Dermatol. 2011; 65(4):790; Kelly G. et al., British J. Dermatol. 2015 December; 173(6):1431-9; Moran B. et al., J. Invest. Dermatol. 2017; 137(11):2389; Thomi R. et al., JAMA Dermatol. 2018; 154(5):592). Seven of nine (78%) patients with moderate-to-severe HS achieved HiSCR in an open-label pilot-trial with Secukinumab (Prussick L. et al., British J. Dermatol. 2019 September; 181(3):609-611), and more clinical trials with anti-IL-17 mAbs in HS are on-going.

For bullous pemphigoid (BP): IL-17 is elevated in the blister fluid and perilesional skin of BP patients. (Le Jan S. et al., J. Invest. Dermatol. 2014; 134 (12):2908-2917; Chakievska L. J Autoimmun. 2019, 96:104-112). Exome sequencing of BP patients revealed mutations in twelve IL-17-related genes in one third of patients, providing the genetic link between IL-17 pathway and BP (Chakievska L. J Autoimmun. 2019, 96:104-112). In experimental murine BP, IL-17A−/− mice are protected, and anti-IL-17A treatment significantly reduced skin lesions in wild type (Chakievska L. J Autoimmun. 2019, 96:104-112). Ixekizumab Phase 2 of treatment naive and refractory BP patients is on-going (NCT03099538).

For atopic dermatitis (AD): IL-17 was found to be elevated in peripheral blood and lesions in AD patients and Th17 cells infiltrated more markedly in acute than chronic lesions, suggesting its role in acute phase of AD (Koga C. et al., J. Invest. Dermatol. 2008, 128, 2625-2630). Molecular profile analysis from ustekinumab Phase II suggest likely contribution of IL-23/Th17/IL-17 pathway in AD (Khattri S. et al., Exp. Dermatol. 2017 January; 26(1):28-35).

For vitiligo: Many studies in vitiligo patients have demonstrated an increased frequency of Th17 cells and higher levels of IL-17 in both circulation and lesions that positively correlates with disease duration, extent, and activity (Singh R. et al., Autoimmun. Rev 2016, April; 15(4):397-404). Mouse studies demonstrated that depigmentation correlates with greater IL-17 expression/secretion, which modulates vitiligo development (Eby J. et al., Pigment Cell & Melanoma Res. 2014, November; 27(6):1075-85).

For multiple sclerosis (MS): IL-17 expression is increased in PBMCs, cerebrospinal fluid (CSF) as well as in brain lesions and cells from MS patients (Lock, C. et al., Nat. Med. 2002, 8: 500-508; Matusevicius, D. et al., Mult. Scler. 1999, 5: 101-104; Tzartos, J. et al., Am. J. Pathol. 2008, 172: 146-155). IL-17-producing T cells are enriched in active MS lesions (Tzartos, J. et al., Am. J. Pathol. 2008, 172: 146-155; Willing A. et al., J. Immunol. 2018, 200(3):974-982). IL-17A levels were elevated in the CSF of relapsing-remitting MS (RRMS) patients and correlated with the CSF/serum albumin quotient, a measure of blood-brain barrier (BBB) dysfunction, together with in vitro data that IL-17A in combination with IL-6 reduced the expression of tight junction-associated genes and disrupted monolayer integrity in a BBB cell line, highlighting the potential importance of targeting IL-17A in preserving BBB integrity in RRMS (Setiadi A F et al., J Neuroimmunol. 2019, 332:147-154). Secukinumab yielded promising first results in a proof-of-concept study in MS patients (Havrdova, E. et al., J. Neurol. 2016, 263: 1287-1295).

For Asthma: IL-17 expression is increased in the lung, sputum, bronchoalveolar lavage fluid, and sera in patients with asthma, and the severity of airway hyperresponsiveness is positively correlated with IL-17 expression levels. (Chakir J. et al., J. Allergy Clin. Immunol. 2003,111(6):1293-8). IL-17 was reported to be increased in asthmatic airways and induce human bronchial fibroblasts to produce cytokines (Molet S. et al., J. Allergy Clin. Immunol. 2001, 108(3): 430-8). Anti-IL-17 antibody modulates airway responsiveness, inflammation, tissue remodeling, and oxidative stress in chronic mouse asthma models (Camargo LdN. et al., Front Immunol. 2018; 8:1835; dos Santos T. et al., Front. Physiol. 2018, 9:1183).

For Chronic Obstructive Pulmonary Disease (COPD): An increase in Th17 cells was observed in patients with COPD compared with current smokers without COPD and healthy subjects, and inverse correlations were found between Th17 cells with lung function (Vargas-Rojas M. et al., Respir. Med. 2011 November; 105(11):1648-54). In three recent human COPD studies, gene expression profile in bronchial epithelia showed that higher IL-17 signature expression is associated with a lack of response to inhaled corticosteroid, suggesting that there is a COPD subgroup that may benefit from IL-17 inhibitor therapy (Christenson S. et al., J. Clin. Invest. 2019; 129(1):169-181).

For Uveitis: IL-17 promotes the release of inflammatory mediators from retinal pigment epithelium cell line, disrupting the retinal pigment epithelium barrier function (Chen Y. et al., PLoS One. 2011; 6:e18139). IL-17 levels were elevated in the serum or aqueous humor of uveitis patients (El-Asrar A. et al., Clin. Immunol. 2011; 139(2):177-84; Jawad S. et al., Ocul. Immunol. Inflamm. 2013; 21(6):434-9; Kuiper J. et al., Am. J. Ophthalmol. 2011; 152(2):177-182.). Anti-IL-17 antibody delayed the onset of ocular inflammation and markedly inhibited the development of experimental autoimmune uveitis in rats (Zhang R. et al., Curr. Eye Res. 2009 April; 34(4):297-303). The analysis of secondary efficacy data from subcutaneous (sc) secukinumab phase 3 trials in uveitis suggested a beneficial effect of secukinumab in reducing the use of concomitant immunosuppressive medication (Dick A. et al., Ophthalmology 2013; 120(4): 777-87). Later study of intravenous secukinumab in uveitis demonstrated greater efficacy than sc dosing, suggesting requiring optimal exposure for efficacy and confirming the therapeutic potential of IL-17A inhibition (Letko E. et al., Ophthalmology 2015, 122(5), 939-948). Ustekinumab that blocks IL-23/IL-17 pathway was also reported to successfully treat a noninfectious uveitis patient who had severe concomitant psoriasis and PsA and failed to respond to conventional immune suppressants (Mugheddu C. et al., Dermatol. Ther. 2017 September; 30(5); e12527.).

For multiple myeloma (MM): IL-17A serum levels were significantly higher in MM patients and also in patients with advanced stage compared with healthy subjects (Lemancewicz D. et al., Med. Sci. Monit. 2012; 18(1): BR54-BR59). Administration of secukinumab in the SCIDhu model of human myeloma weekly for 4 weeks after the first detection of tumor in mice led to a significant inhibition of tumor growth and reduced bone damage compared to isotype control mice (Prabhala R. et al., Leukemia. 2016 February; 30(2): 379-389).

For systemic lupus erythematosus (SLE): Increased serum or plasma levels of IL-17, expansion of IL-17- producing T cells in the peripheral blood, and infiltration of Th17 cells in target organs like the kidneys was observed in SLE patients (Wong C. et al., Lupus. 2000; 9(8):589-593; Wong C. et al., Clinical Immunology. 2008; 127(3):385-393; Zhao X—F. et al., Mol. Biol. Rep. 2010 January; 37(1):81-5; Chen X. et al., J. Clin. Immunol. 2010 March; 30(2):221-5; Xing Q. et al., Rheumatol. Int. 2012 April; 32(4):949-58). Imbalance between Th17 cells and regulatory T (Treg) cells has been observed in SLE patients including quiescent stage (Ma J. et al., Clin. Rheumatol. 2010; 29(11):1251-1258; Dolff S. et al., Clin. Immunol. 2011, 141(2):197-204). Overexpression of IL-17A using adenovirus enhanced the severity of lupus nephritis, while blockade of IL-17A using neutralizing antibody resulted in decreased severity of lupus nephritis (Wen, Z. et al., PLoS One. 2013, 8: e58161). In a phase 2 study, ustekinumab, an anti-IL-12/23 p40 monoclonal antibody blocking IL-23/IL-17 pathway, has demonstrated efficacy in SLE patients (van Vollenhoven R. et al., Lancet 2018; 392: 1330-39). Human expression studies, animal models, and clinical trials indicate that IL-17 blockade may become a promising therapeutic strategy for SLE (Koga T. et al., Expert Rev. Clin. Immunol. 2019, 15 (6) 629-637).

In summary, animal and human studies have shown that IL-17A plays crucial role in pathogenesis of the multiple diseases and/or conditions discussed above. The significance of targeting IL-17A has been demonstrated by the transformational efficacy of injectable IL-17A neutralizing antibodies in patients Despite the advances achieved with injectable IL-17A antagonist antibodies, there is a long-felt need for the development of an oral small molecule IL-17A inhibitor as it may broaden treatment options for many patients without access to biologics. In addition, a safe and efficacious small molecule IL-17A inhibitor may offer significant benefits to patients over the injectable IL-17A neutralizing antibodies such as convenient dosing regimens and cost savings, which in turn may provide effective long-term disease management.

However, the development of an oral small molecule treatment has remained challenging. For example, no oral small molecule IL-17A inhibitor has progressed into late-stage clinical trials yet, and only two oral small molecule IL-17A inhibitors have progressed into phase I clinical trials (NCT04586920 and NCT04883333) as of Sep. 28, 2021. Additionally, as of December 2021, one of these clinical trials (NCT04586920) was suspended due to safety review. Accordingly, there is a need for new small molecule IL-17A modulators (e.g., inhibitors).

SUMMARY

The present application discloses a compound of Formula I:

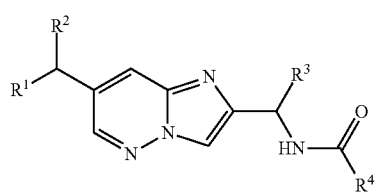

(I)

or a pharmaceutically acceptable salt thereof, wherein $R^1$, $R^2$, $R^3$, and $R^4$ are as defined herein.

The present application also discloses a pharmaceutical composition comprising a compound of Formula I, or a pharmaceutically acceptable salt thereof, and a pharmaceutically acceptable carrier.

The present application also discloses a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof. In some embodiments, the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus.

DETAILED DESCRIPTION

Definitions

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

In an attempt to help the reader of the application, the description has been separated in various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples.

The term "administering" with respect to the methods of the invention, means a method for therapeutically or prophylactically preventing, treating or ameliorating a syndrome, disorder or disease as described herein by using a compound of the disclosure, or pharmaceutically acceptable salt thereof, composition thereof, or medicament thereof. Such methods include administering a therapeutically effective amount of a compound of the disclosure, or pharmaceutically acceptable salt thereof, composition thereof, or medicament thereof, at different times during the course of a therapy or concurrently or sequentially as a combination therapy.

The term "subject" refers to a patient, which may be an animal, preferably a mammal, most preferably a human, whom will be or has been treated by a method according to an embodiment of the application. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

The term "therapeutically effective amount" or "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, "IL-17" or "IL-17A" refers to interleukin 17A. It is also named IL17, CTLA8, CTLA-8. Interleukin 17A is a pro-inflammatory cytokine. This cytokine is produced by a group of immune cells in response to their stimulation. An exemplary amino acid sequence of human IL-17 is represented in GenBank Accession No. NP_002181.1, which can be encoded by a nucleic acid sequence such as that of GenBank Accession No. NM_002190.3.

The term "Modulator" as used herein refers to any agents or molecules that can bind to IL-17, including small molecule compounds.

"Active moiety" refers to a molecule or ion responsible for a physiological or pharmacological action. A compound of formula (I), as exemplified in the Examples and also described herein, is an active moiety.

As used herein, the term "composition" is intended to encompass a product comprising the specified ingredients in the specified amounts, as well as any product which results, directly or indirectly, from combinations of the specified ingredients in the specified amounts.

As used herein, the term "treat," "treating," or "treatment" of any disease, condition, syndrome or disorder refers, in one embodiment, to ameliorating the disease, condition, syndrome or disorder (i.e., slowing or arresting or reducing the development of the disease or at least one of the clinical symptoms thereof). In another embodiment, "treat," "treating," or "treatment" refers to alleviating or ameliorating at least one physiological or biochemical parameter associated with or causative of the disease, condition, syndrome or disorder, including those which may not be discernible by the patient. In a further embodiment, "treat," "treating," or "treatment" refers to modulating the disease, condition, syndrome or disorder either physically (e.g. stabilization of a discernible symptom), physiologically, (e.g. stabilization of a physical parameter), or both. In yet another embodiment, "treat," "treating," or "treatment" refers to preventing or delaying the onset or development or progression of the disease, condition, syndrome or disorder.

As used herein, the term "QD" means once daily.

As used herein, the term "BID" means twice daily.

The term "alkyl" is a straight or branched saturated hydrocarbon. For example, an alkyl group can have 1 to 12 carbon atoms (i.e., $(C_1-C_{12})$alkyl) or 1 to 6 carbon atoms (i.e., $(C_1-C_6)$alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), isopropyl (i-Pr, i-propyl, —$CH(CH_3)_2$), 1-butyl (n-bu, n-butyl, —$CH_2CH_2CH_2CH_3$), 2-butyl (s-bu, s-butyl, —$CH(CH_3)CH_2CH_3$), tert-Butyl (t-bu, t-butyl, —$C(CH_3)_3$), 1-pentyl (n-pentyl, —$CH_2CH_2CH_2CH_2CH_3$), 2-pentyl (—$CH(CH_3)$ $CH_2CH_2CH_3$), neopentyl (—$CH_2C(CH_3)_3$), 1-hexyl (—$CH_2CH_2CH_2CH_2CH_2CH_3$), 2-hexyl (—$CH(CH_3)$ $CH_2CH_2CH_2CH_3$), heptyl (—$(CH_2)_6CH_3$), octyl (—$(CH_2)_7CH_3$), 2,2,4-trimethylpentyl (—$CH_2C$ $(CH_3)_2CH_2CH(CH_3)_2$), nonyl (—$(CH_2)_8CH_3$), decyl (—$(CH_2)_9CH_3$), undecyl (—$(CH_2)_{10}CH_3$), and dodecyl (—$(CH_2)_{11}CH_3$). Any alkyl group may be unsubstituted or substituted.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated all carbon ring system having 3 to 8 carbon atoms (i.e., $C_{(3-8)}$cycloalkyl), and preferably 3 to 6 carbon atoms (i.e., $C_{(3-6)}$cycloalkyl), wherein the cycloalkyl ring system has a single ring or multiple rings in a spirocyclic or bicyclic form. Exemplary cycloalkyls include, but are not limited to, cyclopropyl, cyclobutyl, cyclopentyl, cyclohexyl, cycloheptyl, and cyclooctyl. Unless otherwise stated specifically in the specification, a cycloalkyl group may be unsubstituted or substituted. Some cycloalkyl groups may exist as spirocycloalkyls, wherein two cycloalkyl rings are fused through a single carbon atom; for example and without limitation, an example of a spiropentyl group is

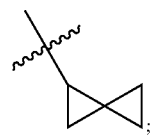 [SMILES: *C1CC12CC2 ; ";"]

for example and without limitation, examples of spirohexyl groups include

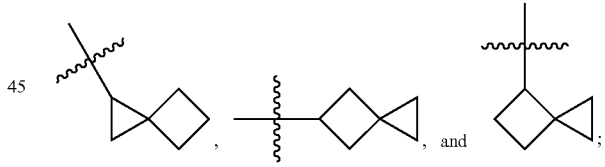

for example and without limitation examples of cycloheptyl groups include

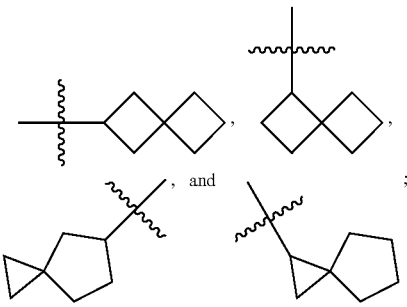

for example and without limitation examples of cyclooctyl groups include

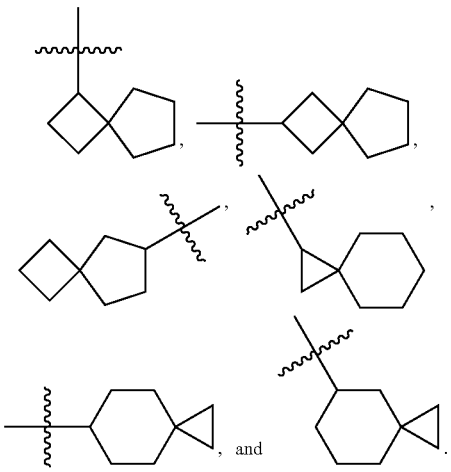

Unless otherwise stated specifically in the specification, a siprocycloalkyl group may be unsubstituted or substituted. Bicyclic cycloalkyl ring systems also include

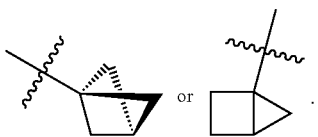

The term "heteroaryl" refers to a single aromatic ring that has at least one atom other than carbon in the ring, wherein the atom is selected from the group consisting of oxygen, nitrogen and sulfur. The term "heteroaryl" includes single aromatic rings of from 1 to 6 carbon atoms and 1 to 4 heteroatoms selected from the group consisting of oxygen, nitrogen and sulfur. Exemplary heteroaryl ring systems include but are not limited to pyridinyl, pyrimidinyl, pyrazinyl, pyridazinyl, pyrimidinyl, pyrazolyl, oxazolyl, oxadiazolyl, isoxazolyl, triazolyl, imidazolyl, tetrazolyl, thienyl, thiazolyl, isothiazolyl, thiadiazolyl, or furyl.

The term "halogen" or "halo" refers to bromo (—Br), chloro (—Cl), fluoro (—F) or iodo (—I).

Where the compounds disclosed herein have at least one stereocenter, they may accordingly exist as enantiomers or diastereomers. It is to be understood that all such isomers and mixtures thereof are encompassed within the scope of the present invention.

"Diastereoisomers" are stereoisomers that have at least two asymmetric atoms, but which are not mirror images of each other.

"Enantiomers" are a pair of stereoisomers that are non-superimposable mirror images of each other. A "racemic" mixture is a 1:1 mixture of a pair of enantiomers. A "scalemic" mixture of enantiomers is mixture of enantiomers at a ratio other than 1:1.

Where the processes for the preparation of the compounds according to the invention give rise to mixture of stereoisomers, these isomers may be separated by conventional techniques such as preparative chromatography. The compounds may be prepared in racemic form, a scalemic mixture, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral column vial HPLC or SFC. In some instances rotamers of compounds may exist which are observable by $^1$H NMR leading to complex multiplets and peak integration in the $^1$H NMR spectrum.

The absolute stereochemistry is specified according to the Cahn-Ingold-Prelog R—S system. Chiral centers, of which the absolute configurations are known, are labelled by prefixes R and S, assigned by the standard sequence-rule procedure, and preceded when necessary by the appropriate locants (*Pure & Appl. Chem.* 45, 1976, 11-30). Certain examples contain chemical structures that are depicted or labelled as an (R*) or (S*). When (R*) or (S*) is used in the name of a compound or in the chemical representation of the compound, it is intended to convey that the compound is a pure single isomer at that stereocenter; however, absolute configuration of that stereocenter has not been established. Thus, a compound designated as (R*) refers to a compound that is a pure single isomer at that stereocenter with an absolute configuration of either (R) or (S), and a compound designated as (S*) refers to a compound that is a pure single isomer at that stereocenter with an absolute configuration of either (R) or (S). For example, 4-cyclopropyl-N-((1S)-(7-(((3aR*)-5,5-difluoro-2-oxohexahydrocyclopenta[d]imidazol-1(2H)-yl)methyl)imidazo[1,2-b]pyridazin-2-yl)(4,4-difluorocyclohexyl)methyl)-1,2,5-oxadiazole-3-carboxamide:

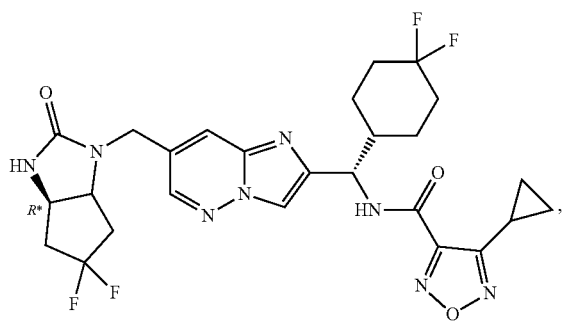

refers to a compound that is either:

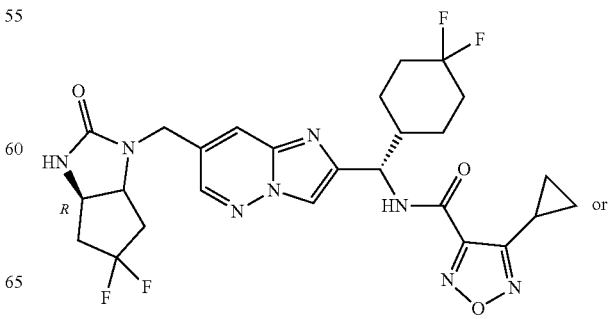

11
-continued

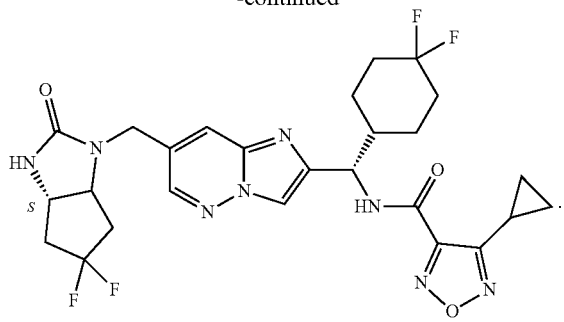

Pseudoasymmetric stereogenic centers are treated in the same way as chiral centers, but are given lower-case symbols, r or s (*Angew. Chem. Int. Ed. Engl.* 1982, 21, 567-583).

During any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Furthermore, it is intended that within the scope of the present invention, any element, in particular when mentioned in relation to a compound of the disclosure, or pharmaceutically acceptable salt thereof, shall comprise all isotopes and isotopic mixtures of said element, either naturally occurring or synthetically produced, either with natural abundance or in an isotopically enriched form. For example, a reference to hydrogen includes within its scope $^1$H, $^2$H (i.e., deuterium or D), and $^3$H (i.e., tritium or T). In some embodiments, the compounds described herein include a $^2$H (i.e., deuterium) isotope. By way of example, the group denoted —$C_{(1-6)}$alkyl includes not only —$CH_3$, but also —$CD_3$; not only —$CH_2CH_3$, but also —$CD_2CD_3$, etc. Similarly, references to carbon and oxygen include within their scope respectively $^{12}$C, $^{13}$C and $^{14}$C and $^{15}$O and $^{16}$O and $^{17}$O and $^{18}$O. The isotopes may be radioactive or non-radioactive. Radiolabelled compounds of the disclosure may include a radioactive isotope selected from the group comprising $^3$H, $^{11}$C, $^{18}$F, $^{35}$S, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Compounds of the Disclosure

The present application discloses a compound of Formula I:

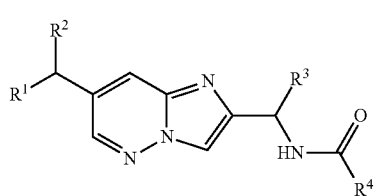

(I)

12 or a pharmaceutically acceptable salt thereof, wherein:
$R^1$ is:

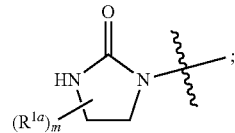

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms and wherein the —$C_{(3-5)}$cycloalkyl is unsubstituted or substituted with one —CN group, or two $R^{1a}$ groups together with the carbon atom or atoms to which they are attached form a spirocyclic or fused $C_{(3-7)}$cycloalkyl, wherein the $C_{(3-7)}$cycloalkyl is unsubstituted or substituted with one to five fluorine atoms;

m is 0, 1, 2, or 3;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(1-3)}$alkyl, —$C_{(3-5)}$cycloalkyl, —$C_{(1-3)}$alkyl-O—$C_{(1-3)}$alkyl, and —$C_{(1-3)}$alkyl-O—$C_{(3-5)}$cycloalkyl groups are unsubstituted or substituted with one to six $R^{2a}$ groups;

$R^{2a}$ independently for each occurrence is fluorine or —CN;

$R^3$ is —$C_{(1-6)}$alkyl, —$C_{(1-6)}$alkyl-O—$C_{(1-6)}$alkyl, —$C_{(1-6)}$alkyl-O—$C_{(3-5)}$cycloalkyl, or —$C_{(3-8)}$cycloalkyl, each of which is unsubstituted or substituted with one to six fluorine atoms;

$R^4$ is a 5-membered heteroaryl that is unsubstituted or substituted with one to two $R^{4a}$ groups or a —$C_{(3-5)}$cycloalkyl that is unsubstituted or substituted with one to two $R^{4b}$ groups;

$R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$; and $R^{4b}$ is —$C_{(1-6)}$alkyl that is unsubstituted or substituted with one to six fluorine atoms;

provided that:
when m is 1 and $R^{1a}$ is —$CF_3$, then $R^3$ is —$C_{(1-6)}$alkyl, —$C_{(1-6)}$alkyl-O—$C_{(1-6)}$alkyl, or —$C_{(1-6)}$alkyl-O—$C_{(3-5)}$cycloalkyl, each of which is unsubstituted or substituted with one to six fluorine atoms; or
when m is 1 and $R^{1a}$ is —$CF_3$, then $R^2$ is —$C_{(3-5)}$cycloalkyl, —$C_{(2-3)}$alkyl-O—$C_{(1-3)}$alkyl, or —$C_{(1-3)}$alkyl-O—$C_{(3-5)}$cycloalkyl, wherein the —$C_{(3-5)}$cycloalkyl, —$C_{(2-3)}$alkyl-O—$C_{(1-3)}$alkyl, and —$C_{(1-3)}$alkyl-O—$C_{(3-5)}$cycloalkyl groups are unsubstituted or substituted with one to six $R^{2a}$ groups.

In some embodiments, disclosed herein is a compound of Formula I, or a pharmaceutically acceptable salt thereof, wherein
$R^1$ is:

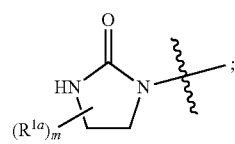

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms and wherein the —$C_{(3-5)}$cycloalkyl is unsubstituted or substituted with one —CN group, or two $R^{1a}$ groups together with the carbon atom or atoms to which they are attached form a spirocyclic or fused $C_{(3-7)}$cycloalkyl, wherein the $C_{(3-7)}$cycloalkyl is unsubstituted or substituted with one to five fluorine atoms;

m is 0, 1, 2, or 3;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(1-3)}$alkyl, —$C_{(3-5)}$cycloalkyl, —$C_{(1-3)}$alkyl-O—$C_{(1-3)}$alkyl, and —$C_{(1-3)}$alkyl-O—$C_{(3-5)}$cycloalkyl groups are unsubstituted or substituted with one to six $R^{2a}$ groups;

$R^{2a}$ independently for each occurrence is fluorine or —CN;

$R^3$ is —$C_{(1-6)}$alkyl, —$C_{(1-6)}$alkyl-O—$C_{(1-6)}$alkyl, or —$C_{(1-6)}$alkyl-O—$C_{(3-5)}$cycloalkyl, each of which is unsubstituted or substituted with one to six fluorine atoms;

$R^4$ is a 5-membered heteroaryl that is unsubstituted or substituted with one to two $R^{4a}$ groups or a —$C_{(3-5)}$cycloalkyl that is unsubstituted or substituted with one to two $R^{4b}$ groups;

$R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$; and $R^{4b}$ is —$C_{(1-6)}$alkyl that is unsubstituted or substituted with one to six fluorine atoms.

In some embodiments, disclosed herein is a compound of Formula I, or a pharmaceutically acceptable salt thereof, wherein:

$R^1$ is:

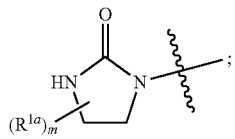

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms and wherein the —$C_{(3-5)}$cycloalkyl is unsubstituted or substituted with one —CN group, or two $R^{1a}$ groups together with the carbon atom or atoms to which they are attached form a spirocyclic or fused $C_{(3-7)}$cycloalkyl, wherein the $C_{(3-7)}$cycloalkyl is unsubstituted or substituted with one to five fluorine atoms;

m is 0, 1, 2, or 3;

$R^2$ is —$C_{(3-5)}$cycloalkyl, —$C_{(2-3)}$alkyl-O—$C_{(1-3)}$alkyl, or —$C_{(1-3)}$alkyl-O—$C_{(3-5)}$cycloalkyl, wherein the —$C_{(3-5)}$cycloalkyl, —$C_{(2-3)}$alkyl-O—$C_{(1-3)}$alkyl, and —$C_{(1-3)}$alkyl-O—$C_{(3-5)}$cycloalkyl groups are unsubstituted or substituted with one to six $R^{2a}$ groups;

$R^{2a}$ independently for each occurrence is fluorine or —CN;

$R^3$ is —$C_{(1-6)}$alkyl, —$C_{(1-6)}$alkyl-O—$C_{(1-6)}$alkyl, —$C_{(1-6)}$alkyl-O—$C_{(3-5)}$cycloalkyl, or —$C_{(3-8)}$cycloalkyl, each of which is unsubstituted or substituted with one to six fluorine atoms;

$R^4$ is a 5-membered heteroaryl that is unsubstituted or substituted with one to two $R^{4a}$ groups or a —$C_{(3-5)}$cycloalkyl that is unsubstituted or substituted with one to two $R^{4b}$ groups;

$R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$; and $R^{4b}$ is —$C_{(1-6)}$alkyl that is unsubstituted or substituted with one to six fluorine atoms;

provided that:

when m is 1 and $R^{1a}$ is —$CF_3$, then $R^2$ is —$C_{(3-5)}$cycloalkyl, —$C_{(2-3)}$alkyl-O—$C_{(1-3)}$alkyl, or —$C_{(1-3)}$alkyl-O—$C_{(3-5)}$cycloalkyl, wherein the —$C_{(3-5)}$cycloalkyl, —$C_{(2-3)}$alkyl-O—$C_{(1-3)}$alkyl, and —$C_{(1-3)}$alkyl-O—$C_{(3-5)}$cycloalkyl groups are unsubstituted or substituted with one to six $R^{1a}$ groups.

In some embodiments, disclosed herein is a compound of Formula I, or a pharmaceutically acceptable salt thereof, wherein:

$R^1$ is:

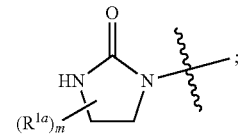

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atom or atoms to which they are attached form a spirocyclic or fused $C_{(3-7)}$cycloalkyl, wherein the $C_{(3-7)}$cycloalkyl is unsubstituted or substituted with one to five fluorine atoms;

m is 0, 1, 2, or 3;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(1-3)}$alkyl, —$C_{(3-5)}$cycloalkyl, —$C_{(1-3)}$alkyl-O—$C_{(1-3)}$alkyl and —$C_{(1-3)}$alkyl-O—$C_{(3-5)}$cycloalkyl groups are unsubstituted or substituted with one to six $R^{2a}$ groups;

$R^{2a}$ independently for each occurrence is fluorine;

$R^3$ is —$C_{(1-6)}$alkyl, —$C_{(1-6)}$alkyl-O—$C_{(1-6)}$alkyl, —$C_{(1-6)}$alkyl-O—$C_{(3-5)}$cycloalkyl, or —$C_{(3-8)}$cycloalkyl, each of which is unsubstituted or substituted with one to six fluorine atoms;

$R^4$ is a 5-membered heteroaryl that is unsubstituted or substituted with one to two $R^{4a}$ groups; and $R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$;

provided that when m is 1 and $R^{1a}$ is —$CF_3$, then $R^3$ is —$C_{(1-6)}$alkyl, —$C_{(1-6)}$alkyl-O—$C_{(1-6)}$alkyl, or —$C_{(1-6)}$alkyl-O—$C_{(3-5)}$cycloalkyl, each of which is unsubstituted or substituted with one to six fluorine atoms.

In some embodiments, disclosed herein is a compound of Formula I, or a pharmaceutically acceptable salt thereof, wherein:

$R^1$ is:

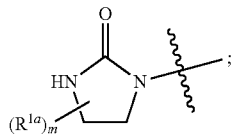

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atom or atoms to which they are attached form a spirocyclic or fused $C_{(3-7)}$cycloalkyl, wherein the $C_{(3-7)}$cycloalkyl is unsubstituted or substituted with one to five fluorine atoms;

m is 0, 1, 2, or 3;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(1-3)}$alkyl, —$C_{(3-5)}$cycloalkyl, —$C_{(1-3)}$alkyl-O—$C_{(1-3)}$alkyl, and —$C_{(1-3)}$alkyl-O—$C_{(3-5)}$cycloalkyl groups are unsubstituted or substituted with one to six $R^{2a}$ groups;

$R^{2a}$ independently for each occurrence is fluorine;

$R^3$ is —$C_{(1-6)}$alkyl, —$C_{(1-6)}$alkyl-O—$C_{(1-6)}$alkyl, or —$C_{(1-6)}$alkyl-O—$C_{(3-5)}$cycloalkyl, each of which is unsubstituted or substituted with one to six fluorine atoms;

$R^4$ is a 5-membered heteroaryl that is unsubstituted or substituted with one to two $R^{4a}$ groups; and $R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

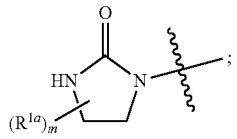

$R^{1a}$ independently for each occurrence is —$C_{(1-3)}$alkyl or two $R^{1a}$ groups together with the carbon atom or atoms to which they are attached form a spirocyclic or fused $C_{(3-7)}$cycloalkyl, wherein the $C_{(3-7)}$cycloalkyl is unsubstituted or substituted with one to five fluorine atoms;

m is 0, 1, 2, or 3;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(1-3)}$alkyl, —$C_{(3-5)}$cycloalkyl, —$C_{(1-3)}$alkyl-O—$C_{(1-3)}$alkyl, and —$C_{(1-3)}$alkyl-O—$C_{(3-5)}$cycloalkyl groups are unsubstituted or substituted with one to six $R^{2a}$ groups;

$R^{2a}$ independently for each occurrence is fluorine;

$R^3$ is —$C_{(1-6)}$alkyl, —$C_{(1-6)}$alkyl-O—$C_{(1-6)}$alkyl, —$C_{(1-6)}$alkyl-O—$C_{(3-5)}$cycloalkyl, or —$C_{(3-8)}$cycloalkyl, each of which is unsubstituted or substituted with one to six fluorine atoms;

$R^4$ is a 5-membered heteroaryl that is unsubstituted or substituted with one to two $R^{4a}$ groups; and $R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

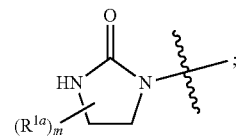

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms and wherein the —$C_{(3-5)}$cycloalkyl is unsubstituted or substituted with one —CN group, or two $R^{1a}$ groups together with the carbon atom or atoms to which they are attached form a spirocyclic or fused $C_{(3-7)}$cycloalkyl, wherein the $C_{(3-7)}$cycloalkyl is unsubstituted or substituted with one to five fluorine atoms;

m is 0, 1, 2, or 3;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(3-5)}$cycloalkyl is unsubstituted or substituted with one —CN group;

$R^3$ is —$C_{(1-6)}$alkyl, —$C_{(1-6)}$alkyl-O—$C_{(1-6)}$alkyl, —$C_{(1-6)}$alkyl-O—$C_{(3-5)}$cycloalkyl, or —$C_{(3-8)}$cycloalkyl, each of which is unsubstituted or substituted with one to six fluorine atoms;

$R^4$ is a 5-membered heteroaryl that is unsubstituted or substituted with one to two $R^{4a}$ groups or a —$C_{(3-5)}$cycloalkyl that is unsubstituted or substituted with one to two $R^{4b}$ groups;

$R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$; and $R^{4b}$ is —$C_{(1-6)}$alkyl that is unsubstituted or substituted with one to six fluorine atoms;

provided that:

when m is 1 and $R^{1a}$ is —$CF_3$, then $R^3$ is —$C_{(1-6)}$alkyl, —$C_{(1-6)}$alkyl-O—$C_{(1-6)}$alkyl, or —$C_{(1-6)}$alkyl-O —C$_{(3-5)}$cycloalkyl, each of which is unsubstituted or substituted with one to six fluorine atoms; or when m is 1 and R$^{1a}$ is —CF$_3$, then R$^2$ is —C$_{(3-5)}$cycloalkyl, —C$_{(2-3)}$alkyl-O—C$_{(1-3)}$alkyl, or —C$_{(1-3)}$alkyl-O—C$_{(3-5)}$cycloalkyl, wherein the —C$_{(3-5)}$cycloalkyl is unsubstituted or substituted with one —CN group.

In some embodiments, disclosed herein is a compound of Formula I, or a pharmaceutically acceptable salt thereof, wherein:

R$^1$ is:

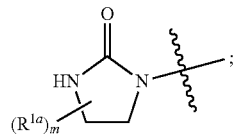

R$^{1a}$ independently for each occurrence is —C$_{(1-3)}$alkyl or —C$_{(3-5)}$cycloalkyl, wherein the —C$_{(1-3)}$alkyl is unsubstituted or substituted with one to five fluorine atoms and wherein the —C$_{(3-5)}$cycloalkyl is unsubstituted or substituted with one —CN group, or two R$^{1a}$ groups together with the carbon atom or atoms to which they are attached form a spirocyclic or fused C$_{(3-7)}$cycloalkyl, wherein the C$_{(3-7)}$cycloalkyl is unsubstituted or substituted with one to five fluorine atoms;

m is 0, 1, 2, or 3;

R$^2$ is H, —C$_{(1-3)}$alkyl, —C$_{(3-5)}$cycloalkyl, —C$_{(1-3)}$alkyl-O—C$_{(1-3)}$alkyl, or —C$_{(1-3)}$alkyl-O—C$_{(3-5)}$cycloalkyl, wherein the —C$_{(3-5)}$cycloalkyl is unsubstituted or substituted with one —CN group;

R$^3$ is —C$_{(1-6)}$alkyl, —C$_{(1-6)}$alkyl-O—C$_{(1-6)}$alkyl, or —C$_{(1-6)}$alkyl-O—C$_{(3-5)}$cycloalkyl, each of which is unsubstituted or substituted with one to six fluorine atoms;

R$^4$ is a 5-membered heteroaryl that is unsubstituted or substituted with one to two R$^{4a}$ groups or a —C$_{(3-5)}$cycloalkyl that is unsubstituted or substituted with one to two R$^{4b}$ groups;

R$^{4a}$ is halo, —C$_{(1-6)}$alkyl, —O—C$_{(1-6)}$alkyl, —C$_{(1-6)}$alkyl-O—C$_{(1-6)}$alkyl, or —C$_{(0-2)}$alkyl-C$_{(3-6)}$cycloalkyl, wherein the —C$_{(1-6)}$alkyl, —O—C$_{(1-6)}$alkyl, —C$_{(1-6)}$alkyl-O—C$_{(1-6)}$alkyl, and —C$_{(0-2)}$alkyl-C$_{(3-6)}$cycloalkyl are unsubstituted or substituted with one to six substituents independently selected from fluorine, —CH$_3$, —CD$_3$, —CD$_2$CD$_3$, —CH$_2$F, —CHF$_2$, and —CF$_3$; and R$^{4b}$ is —C$_{(1-6)}$alkyl that is unsubstituted or substituted with one to six fluorine atoms.

In some embodiments, disclosed herein is a compound of Formula I, or a pharmaceutically acceptable salt thereof, wherein:

R$^1$ is:

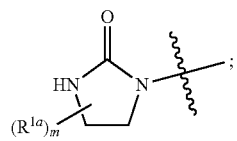

R$^{1a}$ independently for each occurrence is —C$_{(1-3)}$alkyl or —C$_{(3-5)}$cycloalkyl, wherein the —C$_{(1-3)}$alkyl is unsubstituted or substituted with one to five fluorine atoms and wherein the —C$_{(3-5)}$cycloalkyl is unsubstituted or substituted with one —CN group, or two R$^{1a}$ groups together with the carbon atom or atoms to which they are attached form a spirocyclic or fused C$_{(3-7)}$cycloalkyl, wherein the C$_{(3-7)}$cycloalkyl is unsubstituted or substituted with one to five fluorine atoms;

m is 0, 1, 2, or 3;

R$^2$ is —C$_{(3-5)}$cycloalkyl, —C$_{(2-3)}$alkyl-O—C$_{(1-3)}$alkyl, or —C$_{(1-3)}$alkyl-O—C$_{(3-5)}$cycloalkyl, wherein the —C$_{(3-5)}$cycloalkyl is unsubstituted or substituted with one —CN group;

R$^3$ is —C$_{(1-6)}$alkyl, —C$_{(1-6)}$alkyl-O—C$_{(1-6)}$alkyl, —C$_{(1-6)}$alkyl-O—C$_{(3-5)}$cycloalkyl, or —C$_{(3-8)}$cycloalkyl, each of which is unsubstituted or substituted with one to six fluorine atoms;

R$^4$ is a 5-membered heteroaryl that is unsubstituted or substituted with one to two R$^{4a}$ groups or a —C$_{(3-5)}$cycloalkyl that is unsubstituted or substituted with one to two R$^{4b}$ groups;

R$^{4a}$ is halo, —C$_{(1-6)}$alkyl, —O—C$_{(1-6)}$alkyl, —C$_{(1-6)}$alkyl-O—C$_{(1-6)}$alkyl, or —C$_{(0-2)}$alkyl-C$_{(3-6)}$cycloalkyl, wherein the —C$_{(1-6)}$alkyl, —O—C$_{(1-6)}$alkyl, —C$_{(1-6)}$alkyl-O—C$_{(1-6)}$alkyl, and —C$_{(0-2)}$alkyl-C$_{(3-6)}$-cycloalkyl are unsubstituted or substituted with one to six substituents independently selected from fluorine, —CH$_3$, —CD$_3$, —CD$_2$CD$_3$, —CH$_2$F, —CHF$_2$, and —CF$_3$; and R$^{4b}$ is —C$_{(1-6)}$alkyl that is unsubstituted or substituted with one to six fluorine atoms.

In some embodiments, disclosed herein is a compound of Formula I, or a pharmaceutically acceptable salt thereof, wherein:

R$^1$ is:

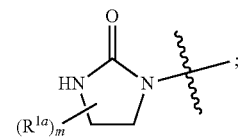

R$^{1a}$ independently for each occurrence is —C$_{(1-3)}$alkyl, wherein the —C$_{(1-3)}$alkyl is unsubstituted or substituted with one to five fluorine atoms, or two R$^{1a}$ groups together with the carbon atoms to which they are attached form a fused C$_{(3-7)}$cycloalkyl, wherein the C$_{(3-7)}$cycloalkyl is unsubstituted or substituted with one to five fluorine atoms;

m is 0, 1, 2, or 3;

R$^2$ is H, —C$_{(1-3)}$alkyl, —C$_{(3-5)}$cycloalkyl, —C$_{(1-3)}$alkyl-O—C$_{(1-3)}$alkyl, or —C$_{(1-3)}$alkyl-O—C$_{(3-5)}$cycloalkyl;

R$^3$ is —C$_{(1-6)}$alkyl, —C$_{(1-6)}$alkyl-O—C$_{(1-6)}$alkyl, —C$_{(1-6)}$alkyl-O—C$_{(3-5)}$cycloalkyl, or —C$_{(3-8)}$cycloalkyl, each of which is unsubstituted or substituted with one to six fluorine atoms;

R$^4$ is a 5-membered heteroaryl that is unsubstituted or substituted with one to two R$^{4a}$ groups; and R$^{4a}$ is halo, —C$_{(1-6)}$alkyl, —O—C$_{(1-6)}$alkyl, —C$_{(1-6)}$alkyl-O—C$_{(1-6)}$alkyl, or —C$_{(0-2)}$alkyl-C$_{(3-6)}$cycloalkyl, wherein the —C$_{(1-6)}$alkyl, —O—C$_{(1-6)}$alkyl, —C$_{(1-6)}$alkyl-O—C$_{(1-6)}$alkyl, and —C$_{(0-2)}$alkyl-C$_{(3-6)}$cycloalkyl are unsubstituted or substituted with one to six substituents independently selected from fluorine, —CH$_3$, —CD$_3$, —CD$_2$CD$_3$, —CH$_2$F, —CHF$_2$, and —CF$_3$;

provided that when m is 1 and $R^{1a}$ is —$CF_3$, then $R^3$ is —$C_{(1-6)}$alkyl, —$C_{(1-6)}$alkyl-O—$C_{(1-6)}$alkyl, or —$C_{(1-6)}$alkyl-O—$C_{(3-5)}$cycloalkyl, each of which is unsubstituted or substituted with one to six fluorine atoms.

In some embodiments, disclosed herein is a compound of Formula I, or a pharmaceutically acceptable salt thereof, wherein:

$R^1$ is:

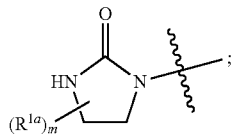

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atoms to which they are attached form a fused $C_{(3-7)}$cycloalkyl, wherein the $C_{(3-7)}$cycloalkyl is unsubstituted or substituted with one to five fluorine atoms;

m is 0, 1, 2, or 3;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is —$C_{(1-6)}$alkyl, —$C_{(1-6)}$alkyl-O—$C_{(1-6)}$alkyl, or —$C_{(1-6)}$alkyl-O—$C_{(3-5)}$cycloalkyl, each of which is unsubstituted or substituted with one to six fluorine atoms;

$R^4$ is a 5-membered heteroaryl that is unsubstituted or substituted with one to two $R^{4a}$ groups; and $R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

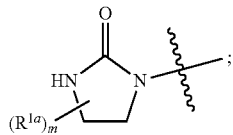

$R^{1a}$ independently for each occurrence is —$C_{(1-3)}$alkyl or two $R^{1a}$ groups together with the carbon atoms to which they are attached form a fused $C_{(3-7)}$cycloalkyl, wherein the $C_{(3-7)}$cycloalkyl is unsubstituted or substituted with one to five fluorine atoms;

m is 0, 1, 2, or 3;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is —$C_{(1-6)}$alkyl, —$C_{(1-6)}$alkyl-O—$C_{(1-6)}$alkyl, —$C_{(1-6)}$alkyl-O—$C_{(3-5)}$cycloalkyl, or —$C_{(3-8)}$cycloalkyl, each of which is unsubstituted or substituted with one to six fluorine atoms;

$R^4$ is a 5-membered heteroaryl that is unsubstituted or substituted with one to two $R^{4a}$ groups; and $R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

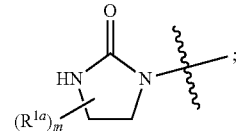

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms and wherein the —$C_{(3-5)}$cycloalkyl is unsubstituted or substituted with one —CN group, or two $R^{1a}$ groups together with the carbon atom or atoms to which they are attached form a spirocyclic or fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(3-5)}$cycloalkyl is unsubstituted or substituted with one —CN group;

$R^3$ is —$C_{(1-6)}$alkyl, —$C_{(1-4)}$alkyl-O—$C_{(1-4)}$alkyl, —$C_{(1-3)}$alkyl-O—$C_{(3-5)}$cycloalkyl, or cyclohexyl, each of which is substituted or unsubstituted with one to six fluorine atoms;

$R^4$ is a 5-membered heteroaryl that is unsubstituted or substituted with one to two $R^{4a}$ groups or a —$C_{(3-5)}$cycloalkyl that is unsubstituted or substituted with one to two $R^{4b}$ groups;

$R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$; and $R^{4b}$ is —$C_{(1-3)}$alkyl that is unsubstituted or substituted with one to three fluorine atoms;

provided that:

when m is 1 and $R^{1a}$ is —$CF_3$, then $R^3$ is —$C_{(1-6)}$alkyl, —$C_{(1-4)}$alkyl-O—$C_{(1-4)}$alkyl, or —$C_{(1-3)}$alkyl-O—$C_{(3-5)}$cycloalkyl, each of which is substituted or unsubstituted with one to six fluorine atoms; or when m is 1 and $R^{1a}$ is —$CF_3$, then $R^2$ is —$C_{(3-5)}$cycloalkyl, —$C_{(2-3)}$alkyl-O—$C_{(1-3)}$alkyl, or —$C_{(1-3)}$alkyl-O—$C_{(3-5)}$cycloalkyl, wherein the —$C_{(3-5)}$cycloalkyl is unsubstituted or substituted with one —CN group.

In some embodiments, disclosed herein is a compound of Formula I, or a pharmaceutically acceptable salt thereof, wherein:

$R^1$ is:

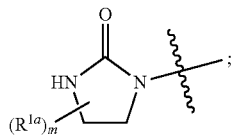

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms and wherein the —$C_{(3-5)}$cycloalkyl is unsubstituted or substituted with one —CN group, or two $R^{1a}$ groups together with the carbon atom or atoms to which they are attached form a spirocyclic or fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(3-5)}$cycloalkyl is unsubstituted or substituted with one —CN group;

$R^3$ is —$C_{(1-6)}$alkyl, —$C_{(1-4)}$alkyl-O—$C_{(1-4)}$alkyl, or —$C_{(1-3)}$alkyl-O—$C_{(3-5)}$cycloalkyl, each of which is substituted or unsubstituted with one to six fluorine atoms;

$R^4$ is a 5-membered heteroaryl that is unsubstituted or substituted with one to two $R^{4a}$ groups or a —$C_{(3-5)}$cycloalkyl that is unsubstituted or substituted with one to two $R^{4b}$ groups;

$R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$; and $R^{4b}$ is —$C_{(1-3)}$alkyl that is unsubstituted or substituted with one to three fluorine atoms.

In some embodiments, disclosed herein is a compound of Formula I, or a pharmaceutically acceptable salt thereof, wherein:

$R^1$ is:

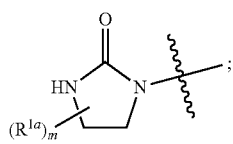

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms and wherein the —$C_{(3-5)}$cycloalkyl is unsubstituted or substituted with one —CN group, or two $R^{1a}$ groups together with the carbon atom or atoms to which they are attached form a spirocyclic or fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is —$C_{(3-5)}$cycloalkyl, —$C_{(2-3)}$alkyl-O—$C_{(1-3)}$alkyl, or —$C_{(1-3)}$alkyl-O—$C_{(3-5)}$cycloalkyl, wherein the —$C_{(3-5)}$cycloalkyl is unsubstituted or substituted with one —CN group;

$R^3$ is —$C_{(1-6)}$alkyl, —$C_{(1-4)}$alkyl-O—$C_{(1-4)}$alkyl, —$C_{(1-3)}$alkyl-O—$C_{(3-5)}$cycloalkyl, or cyclohexyl, each of which is substituted or unsubstituted with one to six fluorine atoms;

$R^4$ is a 5-membered heteroaryl that is unsubstituted or substituted with one to two $R^{4a}$ groups or a —$C_{(3-5)}$cycloalkyl that is unsubstituted or substituted with one to two $R^{4b}$ groups;

$R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$; and $R^{4b}$ is —$C_{(1-3)}$alkyl that is unsubstituted or substituted with one to three fluorine atoms.

In some embodiments, disclosed herein is a compound of Formula I, or a pharmaceutically acceptable salt thereof, wherein:

$R^1$ is:

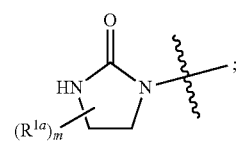

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is —$C_{(1-6)}$alkyl, —$C_{(1-4)}$alkyl-O—$C_{(1-4)}$alkyl, —$C_{(1-3)}$alkyl-O—$C_{(3-5)}$cycloalkyl, or cyclohexyl, each of which is substituted or unsubstituted with one to six fluorine atoms;

$R^4$ is a 5-membered heteroaryl that is unsubstituted or substituted with one to two $R^{4a}$ groups; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$;

provided that when m is 1 and $R^{1a}$ is —$CF_3$, then $R^3$ is —$C_{(1-6)}$alkyl, —$C_{(1-4)}$alkyl-O—$C_{(1-4)}$alkyl, or —$C_{(1-3)}$alkyl-O—$C_{(3-5)}$cycloalkyl, each of which is substituted or unsubstituted with one to six fluorine atoms.

In some embodiments, disclosed herein is a compound of Formula I, or a pharmaceutically acceptable salt thereof, wherein:

$R^1$ is:

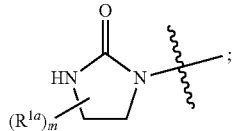

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is —$C_{(1-6)}$alkyl, —$C_{(1-4)}$alkyl-O—$C_{(1-4)}$alkyl, or —$C_{(1-3)}$alkyl-O—$C_{(3-5)}$cycloalkyl, each of which is substituted or unsubstituted with one to six fluorine atoms;

$R^4$ is a 5-membered heteroaryl that is unsubstituted or substituted with one to two $R^{4a}$ groups; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

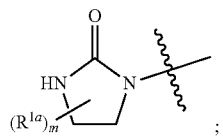

$R^{1a}$ independently for each occurrence is —$C_{(1-3)}$alkyl or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is —$C_{(1-6)}$alkyl, —$C_{(1-4)}$alkyl-O—$C_{(1-4)}$alkyl, —$C_{(1-3)}$alkyl-O—$C_{(3-5)}$cycloalkyl, or cyclohexyl, each of which is substituted or unsubstituted with one to six fluorine atoms;

$R^4$ is a 5-membered heteroaryl that is unsubstituted or substituted with one to two $R^{4a}$ groups; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

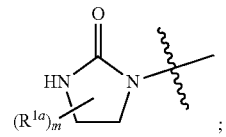

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms and wherein the —$C_{(3-5)}$cycloalkyl is unsubstituted or substituted with one —CN group, or two $R^{1a}$ groups together with the carbon atom or atoms to which they are attached form a spirocyclic or fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(3-5)}$cycloalkyl is unsubstituted or substituted with one —CN group;

$R^3$ is —$C_{(1-5)}$alkyl substituted with one —$CF_3$,

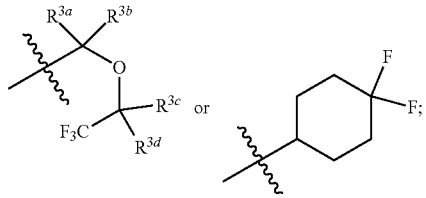

$R^{3a}$, $R^{3b}$, $R^{3c}$, and $R^{3d}$ are each independently H or —$CH_3$;

$R^4$ is a 5-membered heteroaryl that is unsubstituted or substituted with one to two $R^{4a}$ groups or a —$C_{(3-5)}$cycloalkyl that is unsubstituted or substituted with one —$CF_3$ group; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$;

provided that:

when m is 1 and $R^{1a}$ is —$CF_3$, then $R^3$ is —$C_{(1-5)}$alkyl substituted with one —$CF_3$ or

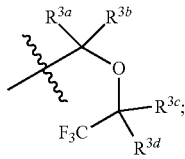

or
when m is 1 and $R^{1a}$ is —$CF_3$, then $R^2$ is —$C_{(3-5)}$cycloalkyl or —$C_{(1-3)}$alkyl-O—$C_{(3-5)}$cycloalkyl, wherein the —$C_{(3-5)}$cycloalkyl is unsubstituted or substituted with one —CN group.

In some embodiments, disclosed herein is a compound of Formula I, or a pharmaceutically acceptable salt thereof, wherein:

$R^1$ is:

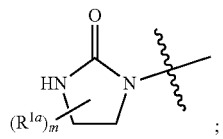

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms and wherein the —$C_{(3-5)}$cycloalkyl is unsubstituted or substituted with one —CN group, or two $R^{1a}$ groups together with the carbon atom or atoms to which they are attached form a spirocyclic or fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(3-5)}$cycloalkyl is unsubstituted or substituted with one —CN group;

$R^3$ is —$C_{(1-5)}$alkyl substituted with one —$CF_3$ or

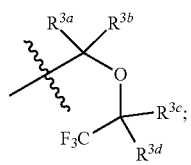

$R^{3a}$, $R^{3b}$, $R^{3c}$, and $R^{3d}$ are each independently H or —$CH_3$;

$R^4$ is a 5-membered heteroaryl that is unsubstituted or substituted with one to two $R^{4a}$ groups or a —$C_{(3-5)}$ cycloalkyl that is unsubstituted or substituted with one —$CF_3$ group; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

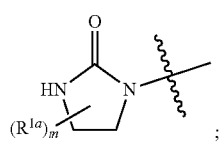

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms and wherein the —$C_{(3-5)}$cycloalkyl is unsubstituted or substituted with one —CN group, or two $R^{1a}$ groups together with the carbon atom or atoms to which they are attached form a spirocyclic or fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is —$C_{(3-5)}$cycloalkyl or —$C_{(1-3)}$alkyl-O—$C_{(3-5)}$cycloalkyl, wherein the —$C_{(3-5)}$cycloalkyl is unsubstituted or substituted with one —CN group;

$R^3$ is —$C_{(1-5)}$alkyl substituted with one —$CF_3$,

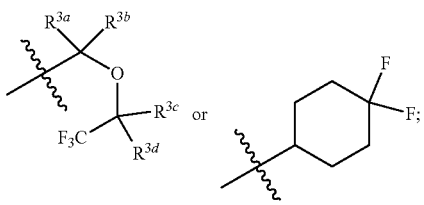

$R^{3a}$, $R^{3b}$, $R^{3c}$, and $R^{3d}$ are each independently H or —$CH_3$;

$R^4$ is a 5-membered heteroaryl that is unsubstituted or substituted with one to two $R^{4a}$ groups or a —$C_{(3-5)}$ cycloalkyl that is unsubstituted or substituted with one —$CF_3$ group; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

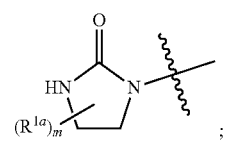

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is —$C_{(1-5)}$alkyl substituted with one —$CF_3$,

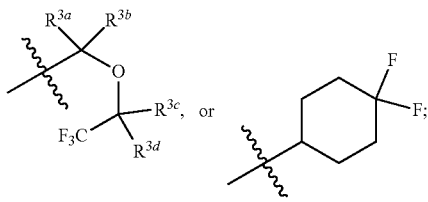

$R^{3a}$, $R^{3b}$, $R^{3c}$, and $R^{3d}$ are each independently H or —$CH_3$;
$R^4$ is a 5-membered heteroaryl that is unsubstituted or substituted with one to two $R^{4a}$ groups; and
$R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$;
provided that when m is 1 and $R^{1a}$ is —$CF_3$, then $R^3$ is —$C_{(1-5)}$alkyl substituted with one —$CF_3$ or

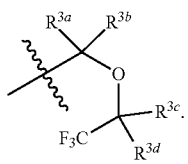

In some embodiments, disclosed herein is a compound of Formula I, or a pharmaceutically acceptable salt thereof, wherein:
$R^1$ is:

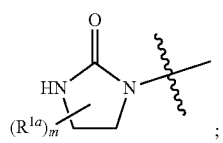

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;
m is 0, 1, 2, or 3;
$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;
$R^3$ is —$C_{(1-5)}$alkyl substituted with one —$CF_3$ or

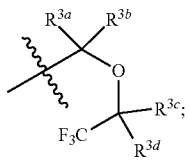

$R^{3a}$, $R^{3b}$, $R^{3c}$, and $R^{3d}$ are each independently H or —$CH_3$;
$R^4$ is a 5-membered heteroaryl that is unsubstituted or substituted with one to two $R^{4a}$ groups; and
$R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:
$R^1$ is:

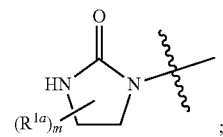

$R^{1a}$ independently for each occurrence is —$C_{(1-3)}$alkyl or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;
m is 0, 1, 2, or 3;
$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;
$R^3$ is —$C_{(1-5)}$alkyl substituted with one —$CF_3$,

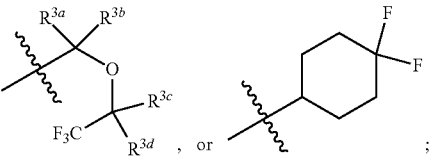

$R^{3a}$, $R^{3b}$, $R^{3c}$, and $R^{3d}$ are each independently H or —$CH_3$;
$R^4$ is a 5-membered heteroaryl that is unsubstituted or substituted with one to two $R^{4a}$ groups; and
$R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:
$R^1$ is:

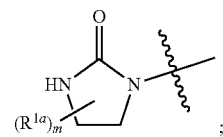

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is:

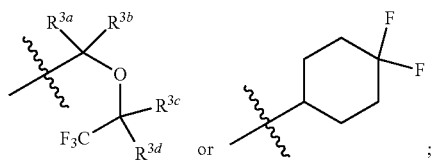

$R^{3a}$, $R^{3b}$, $R^{3c}$, and $R^{3d}$ are each independently H or —$CH_3$;

$R^4$ is a 5-membered heteroaryl that is unsubstituted or substituted with one to two $R^{4a}$ groups; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$;

provided that when m is 1 and $R^{1a}$ is —$CF_3$, then $R^3$ is:

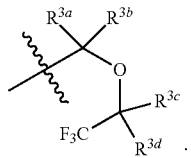

In some embodiments, disclosed herein is a compound of Formula I, or a pharmaceutically acceptable salt thereof, wherein:

$R^1$ is:

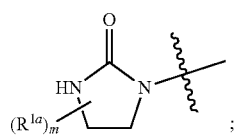

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is:

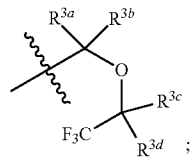

$R^{3a}$, $R^{3b}$, $R^{3c}$, and $R^{3d}$ are each independently H or —$CH_3$;

$R^4$ is a 5-membered heteroaryl that is unsubstituted or substituted with one to two $R^{4a}$ groups; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

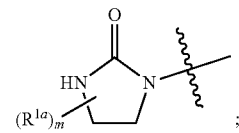

$R^{1a}$ independently for each occurrence is —$C_{(1-3)}$alkyl or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;

m is 0, 1, 2, or 3;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is:

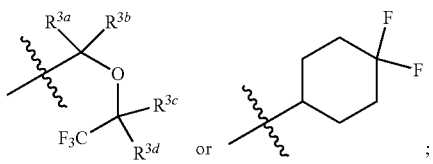

$R^{3a}$, $R^{3b}$, $R^{3c}$, and $R^{3d}$ are each independently H or —$CH_3$;

$R^4$ is a 5-membered heteroaryl that is unsubstituted or substituted with one to two $R^{4a}$ groups; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

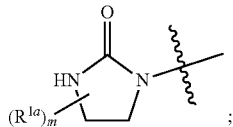

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;

m is 1 or 2;

$R^2$ is H, —$C_{(1-3)}$alkyl-O—$C_{(1-3)}$alkyl, or —$C_{(1-3)}$alkyl-O—$C_{(3-5)}$cycloalkyl;

$R^3$ is —$C_{(1-5)}$alkyl substituted with one —$CF_3$,

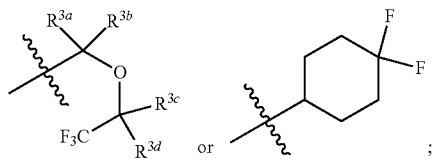

$R^{3a}$, $R^{3b}$, $R^{3c}$, and $R^{3d}$ are each independently H or —$CH_3$;

$R^4$ is a 5-membered heteroaryl that is unsubstituted or substituted with one to two $R^{4a}$ groups; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$;

provided that:

when m is 1 and $R^{1a}$ is —$CF_3$, then $R^3$ is —$C_{(1-5)}$alkyl substituted with one —$CF_3$ or

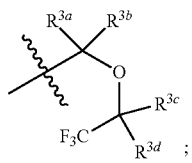

or when m is 1 and $R^{1a}$ is —$CF_3$, then $R^2$ is —$C_{(2-3)}$alkyl-O—$C_{(1-3)}$alkyl or —$C_{(1-3)}$alkyl-O—$C_{(3-5)}$cycloalkyl.

In some embodiments, disclosed herein is a compound of Formula I, or a pharmaceutically acceptable salt thereof, wherein:

$R^1$ is:

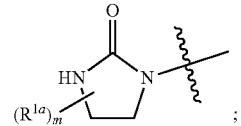

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;

m is 1 or 2;

$R^2$ is H, —$C_{(1-3)}$alkyl-O—$C_{(1-3)}$alkyl, or —$C_{(1-3)}$alkyl-O—$C_{(3-5)}$cycloalkyl;

$R^3$ is —$C_{(1-5)}$alkyl substituted with one —$CF_3$ or

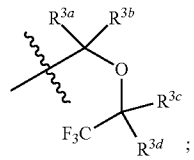

$R^{3a}$, $R^{3b}$, $R^{3c}$, and $R^{3d}$ are each independently H or —$CH_3$;

$R^4$ is a 5-membered heteroaryl that is unsubstituted or substituted with one to two $R^{4a}$ groups; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

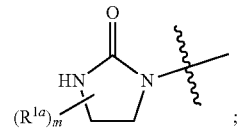

$R^{1a}$ independently for each occurrence is —$C_{(1-3)}$alkyl, wherein the —$C_{(1-3)}$alkyl is unsubstituted or substituted with one to five fluorine atoms, or two $R^{1a}$ groups together with the carbon atoms to which they are attached form a fused $C_{(3-5)}$cycloalkyl, wherein the $C_{(3-5)}$cycloalkyl is unsubstituted or substituted with one to five fluorine atoms;

m is 1 or 2;

$R^2$ is —$C_{(2-3)}$alkyl-O—$C_{(1-3)}$alkyl or —$C_{(1-3)}$alkyl-O—$C_{(3-5)}$cycloalkyl;

R$^3$ is —C$_{(1-5)}$alkyl substituted with one —CF$_3$,

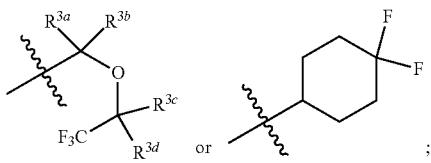

R$^{3a}$, R$^{3b}$, R$^{3c}$, and R$^{3d}$ are each independently H or —CH$_3$;

R$^4$ is a 5-membered heteroaryl that is unsubstituted or substituted with one to two R$^{4a}$ groups; and R$^{4a}$ is —C$_{(1-4)}$alkyl, —O—C$_{(1-4)}$alkyl, —C$_{(1-4)}$alkyl-O—C$_{(1-4)}$alkyl, or —C$_{(0-2)}$alkyl-C$_{(3-4)}$cycloalkyl, wherein the —C$_{(1-4)}$alkyl, —O—C$_{(1-4)}$alkyl, —C$_{(1-4)}$alkyl-O—C$_{(1-4)}$alkyl, and —C$_{(0-2)}$alkyl-C$_{(3-4)}$cycloalkyl are unsubstituted or substituted with one to six substituents independently selected from fluorine, —CH$_3$, —CD$_3$, —CD$_2$CD$_3$, —CH$_2$F, —CHF$_2$, and —CF$_3$.

In some embodiments, disclosed herein is a compound of Formula I, or a pharmaceutically acceptable salt thereof, wherein R$^{1a}$ independently for each occurrence is —C$_{(1-3)}$alkyl or —C$_{(3-5)}$cycloalkyl, wherein the —C$_{(3-5)}$cycloalkyl is unsubstituted or substituted with one —CN group, or two R$^{1a}$ groups together with the carbon atom or atoms to which they are attached form a spirocyclic or fused C$_{(3-5)}$cycloalkyl, wherein the C$_{(3-5)}$cycloalkyl is unsubstituted or substituted with one to five fluorine atoms.

In some embodiments, disclosed herein is a compound of Formula I, or a pharmaceutically acceptable salt thereof, wherein Iea independently for each occurrence is —C$_{(1-3)}$alkyl or two R$^{1a}$ groups together with the carbon atoms to which they are attached form a fused C$_{(3-7)}$cycloalkyl, wherein the C$_{(3-7)}$cycloalkyl is unsubstituted or substituted with one to five fluorine atoms.

In some embodiments, disclosed herein is a compound of Formula I, or a pharmaceutically acceptable salt thereof, wherein R$^{1a}$ independently for each occurrence is —C$_{(1-3)}$alkyl, wherein the —C$_{(1-3)}$alkyl is unsubstituted or substituted with one to five fluorine atoms, or two R$^{1a}$ groups together with the carbon atoms to which they are attached form a fused C$_{(3-5)}$cycloalkyl, wherein the C$_{(3-5)}$cycloalkyl is unsubstituted or substituted with one to five fluorine atoms.

In some embodiments, disclosed herein is a compound of Formula I, or a pharmaceutically acceptable salt thereof, wherein R$^{1a}$ independently for each occurrence is —C$_{(1-3)}$alkyl or two R$^{1a}$ groups together with the carbon atoms to which they are attached form a fused C$_{(3-5)}$cycloalkyl, wherein the C$_{(3-5)}$cycloalkyl is unsubstituted or substituted with one to five fluorine atoms.

In some embodiments, disclosed herein is a compound of Formula I, or a pharmaceutically acceptable salt thereof, wherein R$^{1a}$ independently for each occurrence is —CH$_3$, —CH$_2$F, —CHF$_2$, —CF$_3$, —CH(CH$_3$)$_2$, —CH$_2$CF$_3$, cyclopropyl, cyanocyclopropyl, or two R$^{1a}$ groups together with the carbon atom or atoms to which they are attached form a spirocyclic or fused C$_{(3-5)}$cycloalkyl, wherein the C$_{(3-5)}$cycloalkyl is unsubstituted or substituted with one to five fluorine atoms.

In some embodiments, disclosed herein is a compound of Formula I, or a pharmaceutically acceptable salt thereof, wherein R$^{1a}$ independently for each occurrence is —CH$_3$, —CH$_2$F, —CHF$_2$, —CF$_3$, or two R$^{1a}$ groups together with the carbon atoms to which they are attached form a fused C$_{(3-5)}$cycloalkyl, wherein the C$_{(3-5)}$cycloalkyl is unsubstituted or substituted with one to five fluorine atoms.

In some embodiments, disclosed herein is a compound of Formula I, or a pharmaceutically acceptable salt thereof, wherein R$^{1a}$ independently for each occurrence is —CH$_3$, —CH$_2$F, —CHF$_2$, —CF$_3$, or two R$^{1a}$ groups together with the carbon atoms to which they are attached form a fused C$_{(5)}$cycloalkyl, wherein the C$_{(5)}$cycloalkyl is unsubstituted or substituted with one to five fluorine atoms.

In some embodiments, disclosed herein is a compound of Formula I, or a pharmaceutically acceptable salt thereof, wherein R$^{1a}$ independently for each occurrence is —CH$_3$, —CH(CH$_3$)$_2$, cyclopropyl, cyanocyclopropyl, or two R$^{1a}$ groups together with the carbon atom or atoms to which they are attached form a spirocyclic or fused C$_{(3-5)}$cycloalkyl, wherein the C$_{(3-5)}$cycloalkyl is unsubstituted or substituted with one to five fluorine atoms.

In some embodiments, disclosed herein is a compound of Formula I, or a pharmaceutically acceptable salt thereof, wherein R$^{1a}$ independently for each occurrence is —CH$_3$ or two R$^{1a}$ groups together with the carbon atoms to which they are attached form a fused C$_{(5)}$cycloalkyl, wherein the C$_{(5)}$cycloalkyl is unsubstituted or substituted with one to five fluorine atoms.

In some embodiments, disclosed herein is a compound of Formula I, or a pharmaceutically acceptable salt thereof, wherein R$^{1a}$ independently for each occurrence is —C$_{(1-3)}$alkyl that is unsubstituted or substituted with one to five fluorine atoms. In some embodiments, disclosed herein is a compound of Formula I, or a pharmaceutically acceptable salt thereof, wherein R$^{1a}$ independently for each occurrence is —C$_{(1-3)}$alkyl. In some embodiments, disclosed herein is a compound of Formula I, or a pharmaceutically acceptable salt thereof, wherein Ria independently for each occurrence is —CH$_3$, —CH$_2$F, —CHF$_2$, —CF$_3$, —CH(CH$_3$)$_2$, or —CH$_2$CF$_3$.

In some embodiments, disclosed herein is a compound of Formula I, or a pharmaceutically acceptable salt thereof, wherein R$^{1a}$ is not —CF$_3$.

In some embodiments, disclosed herein is a compound of Formula I, or a pharmaceutically acceptable salt thereof, wherein R$^{1a}$ independently for each occurrence is —C$_{(3-5)}$cycloalkyl that is unsubstituted or substituted with one —CN group. In some embodiments, disclosed herein is a compound of Formula I, or a pharmaceutically acceptable salt thereof, wherein R$^{1a}$ independently for each occurrence is cyclopropyl or cyanocyclopropyl.

In some embodiments, disclosed herein is a compound of Formula I, or a pharmaceutically acceptable salt thereof, wherein two R$^{1a}$ groups together with the carbon atom to which they are attached form a spirocyclic C$_{(3-7)}$cycloalkyl that is unsubstituted or substituted with one to five fluorine atoms. In some embodiments, disclosed herein is a compound of Formula I, or a pharmaceutically acceptable salt thereof, wherein two R$^{1a}$ groups together with the carbon atom to which they are attached form a spirocyclic C$_{(3-5)}$cycloalkyl that is unsubstituted or substituted with one to five fluorine atoms. In some embodiments, disclosed herein is a compound of Formula I, or a pharmaceutically acceptable salt thereof, wherein two R$^{1a}$ groups together with the carbon atom to which they are attached form a spirocyclic C$_{(3-4)}$cycloalkyl that is unsubstituted or substituted with one to two fluorine atoms.

In some embodiments, disclosed herein is a compound of Formula I, or a pharmaceutically acceptable salt thereof, wherein two R$^{1a}$ groups together with the carbon atoms to which they are attached form a fused $C_{(3-7)}$cycloalkyl that is unsubstituted or substituted with one to five fluorine atoms. In some embodiments, disclosed herein is a compound of Formula I, or a pharmaceutically acceptable salt thereof, wherein two $R^{1a}$ groups together with the carbon atoms to which they are attached form a fused $C_{(3-5)}$cycloalkyl that is unsubstituted or substituted with one to five fluorine atoms. In some embodiments, disclosed herein is a compound of Formula I, or a pharmaceutically acceptable salt thereof, wherein two $R^{1a}$ groups together with the carbon atoms to which they are attached form a fused $C_{(5)}$cycloalkyl that is unsubstituted or substituted with one to two fluorine atoms.

In some embodiments, disclosed herein is a compound of Formula I, or a pharmaceutically acceptable salt thereof, wherein m is 0, 1, or 2. In some embodiments, disclosed herein is a compound of Formula I, or a pharmaceutically acceptable salt thereof, wherein m is 1 or 2. In some embodiments, disclosed herein is a compound of Formula I, or a pharmaceutically acceptable salt thereof, wherein m is 0. In some embodiments, disclosed herein is a compound of Formula I, or a pharmaceutically acceptable salt thereof, wherein m is 1. In some embodiments, disclosed herein is a compound of Formula I, or a pharmaceutically acceptable salt thereof, wherein m is 2.

In some embodiments, disclosed herein is a compound of Formula I, or a pharmaceutically acceptable salt thereof, wherein $R^1$ is:

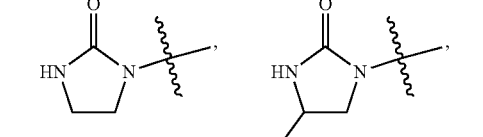
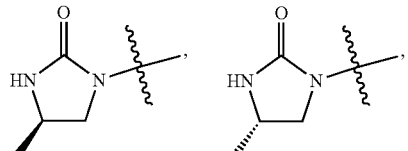
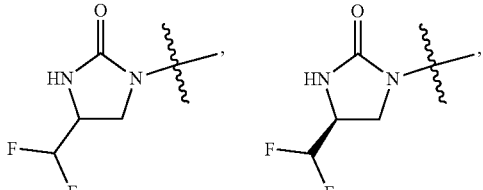
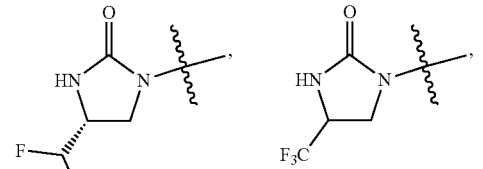
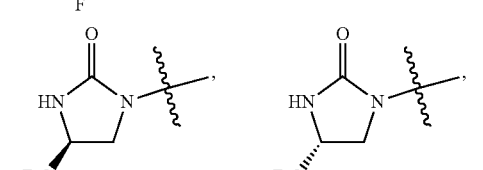

-continued

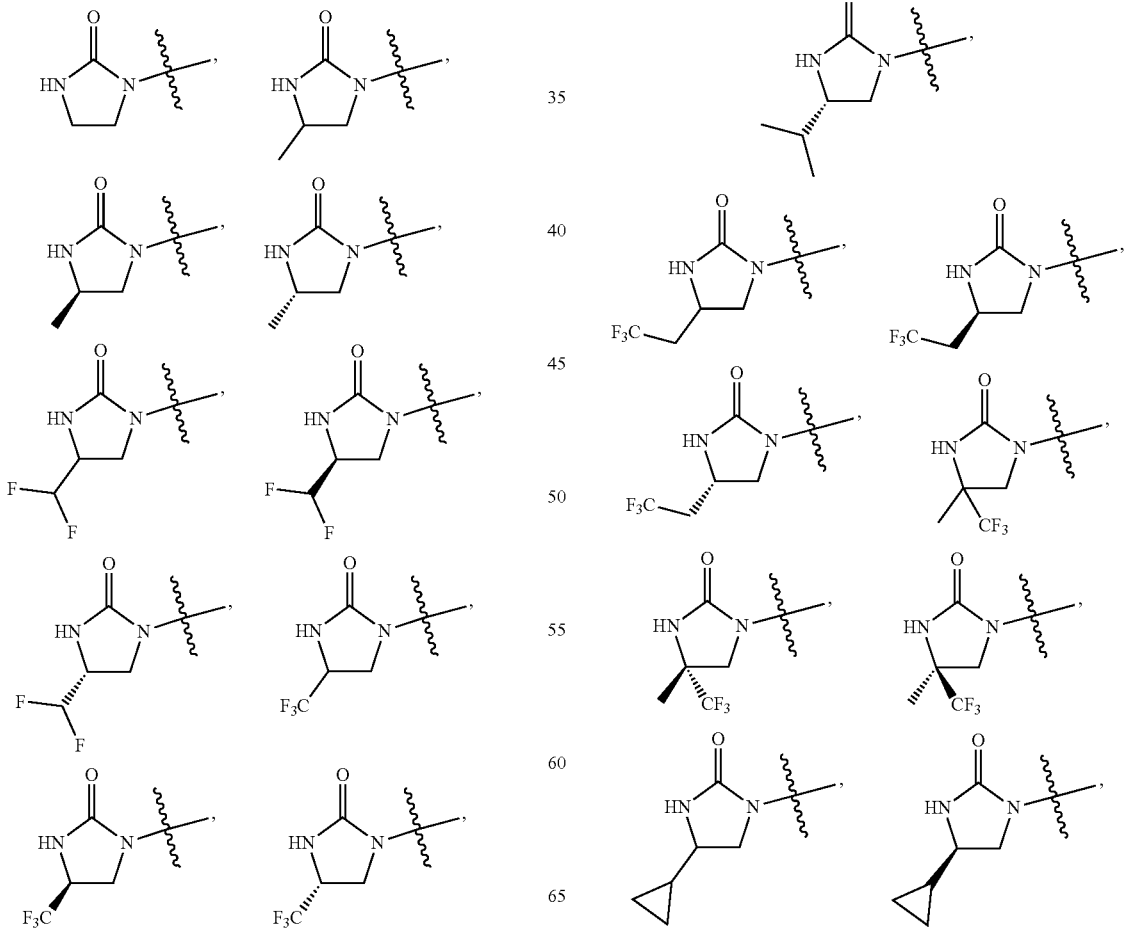

-continued

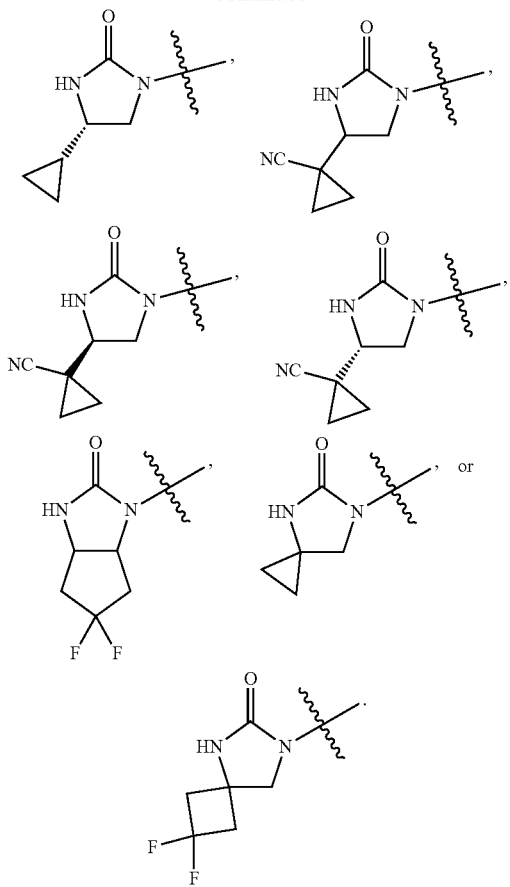

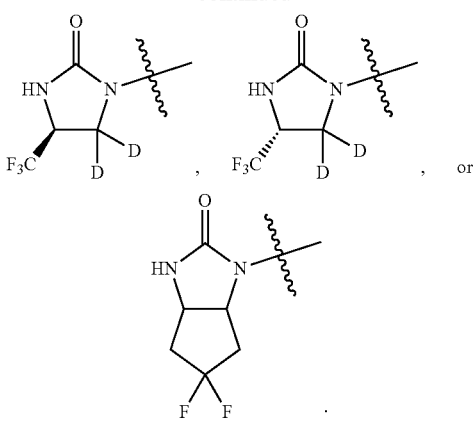

In some embodiments, disclosed herein is a compound of Formula I, or a pharmaceutically acceptable salt thereof, wherein R¹ is:

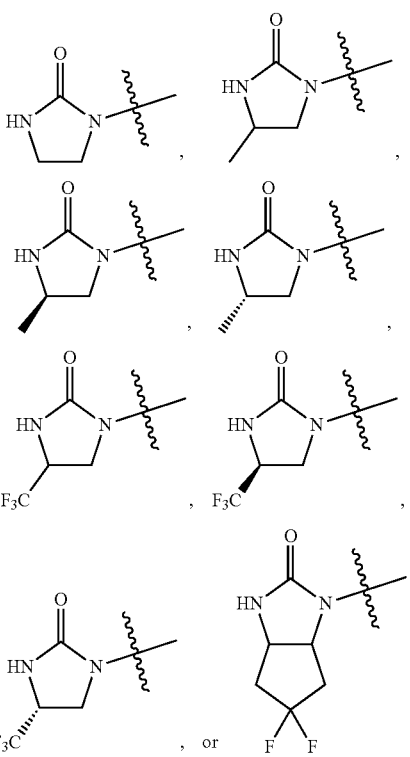

In some embodiments, disclosed herein is a compound of Formula I, or a pharmaceutically acceptable salt thereof, wherein R¹ is:

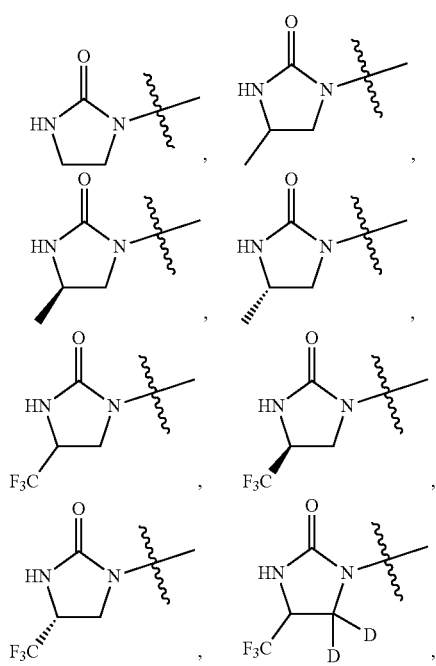

In some embodiments, disclosed herein is a compound of Formula I, or a pharmaceutically acceptable salt thereof, wherein R¹ is:

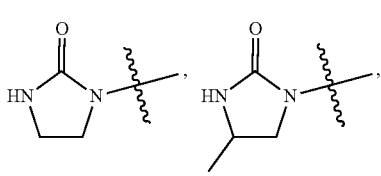

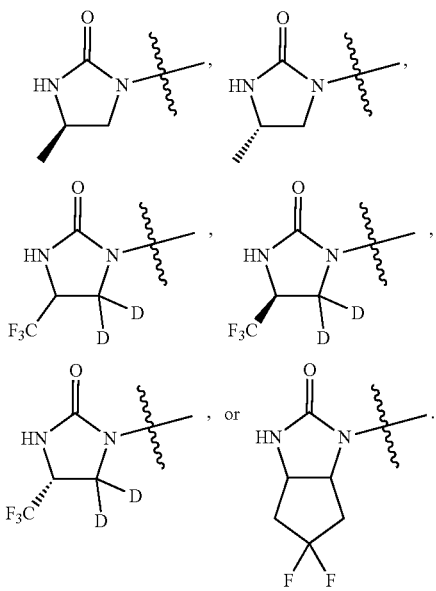

In some embodiments, disclosed herein is a compound of Formula I, or a pharmaceutically acceptable salt thereof, wherein R¹ is:

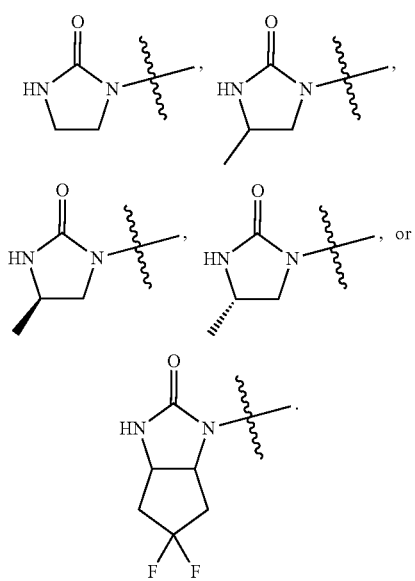

In some embodiments, disclosed herein is a compound of Formula I, or a pharmaceutically acceptable salt thereof, wherein R¹ is:

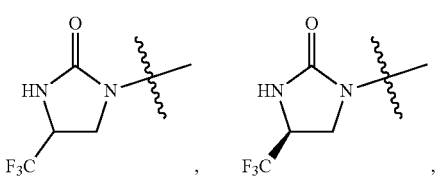

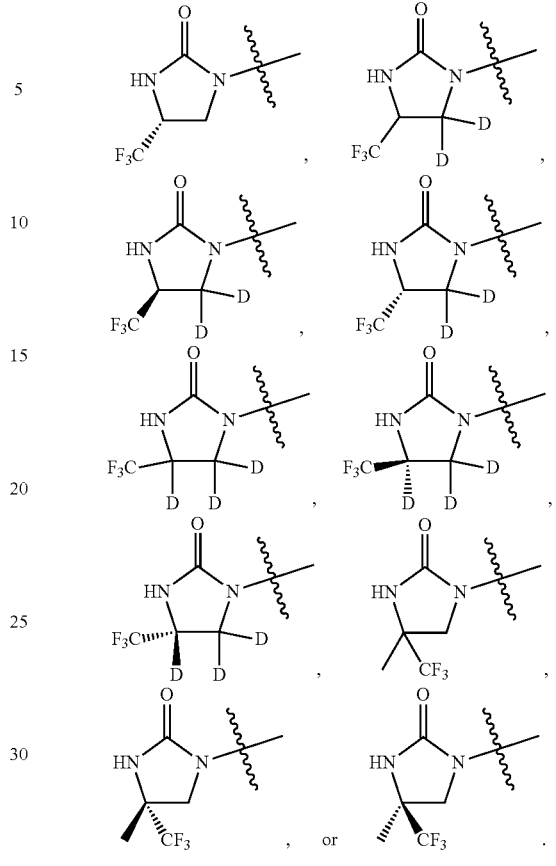

In some embodiments, disclosed herein is a compound of Formula I, or a pharmaceutically acceptable salt thereof, wherein R² is —C$_{(3-5)}$cycloalkyl, —C$_{(2-3)}$alkyl-O—C$_{(1-3)}$alkyl, or —C$_{(1-3)}$alkyl-O—C$_{(3-5)}$cycloalkyl, wherein the —C$_{(3-5)}$cycloalkyl, —C$_{(2-3)}$alkyl-O—C$_{(1-3)}$alkyl, and —C$_{(1-3)}$alkyl-O—C$_{(3-5)}$cycloalkyl groups are unsubstituted or substituted with one to six R$^{2a}$ groups. In some embodiments, disclosed herein is a compound of Formula I, or a pharmaceutically acceptable salt thereof, wherein R² is —C$_{(3-5)}$cycloalkyl, —C$_{(2-3)}$alkyl-O—C$_{(1-3)}$alkyl, or —C$_{(1-3)}$alkyl-O—C$_{(3-5)}$cycloalkyl, wherein the —C$_{(3-5)}$cycloalkyl is unsubstituted or substituted with one —CN group. In some embodiments, disclosed herein is a compound of Formula I, or a pharmaceutically acceptable salt thereof, wherein R² is —C$_{(3-5)}$cycloalkyl or —C$_{(1-3)}$alkyl-O—C$_{(3-5)}$cycloalkyl, wherein the —C$_{(3-5)}$cycloalkyl is unsubstituted or substituted with one —CN group.

In some embodiments, disclosed herein is a compound of Formula I, or a pharmaceutically acceptable salt thereof, wherein R² is H, —C$_{(3-5)}$cycloalkyl, —C$_{(1-3)}$alkyl-O—C$_{(1-3)}$alkyl, or —C$_{(1-3)}$alkyl-O—C$_{(3-5)}$cycloalkyl, wherein the —C$_{(3-5)}$cycloalkyl is unsubstituted or substituted with one —CN group. In some embodiments, disclosed herein is a compound of Formula I, or a pharmaceutically acceptable salt thereof, wherein R² is H, —C$_{(3-5)}$cycloalkyl, —C$_{(1-3)}$alkyl-O—C$_{(1-3)}$alkyl, or —C$_{(1-3)}$alkyl-O—C$_{(3-5)}$cycloalkyl. In some embodiments, disclosed herein is a compound of Formula I, or a pharmaceutically acceptable salt thereof, wherein R² is H, —C$_{(3-5)}$cycloalkyl, or —C$_{(1-3)}$alkyl-O—C$_{(1-3)}$alkyl.

In some embodiments, disclosed herein is a compound of Formula I, or a pharmaceutically acceptable salt thereof, wherein R² is:

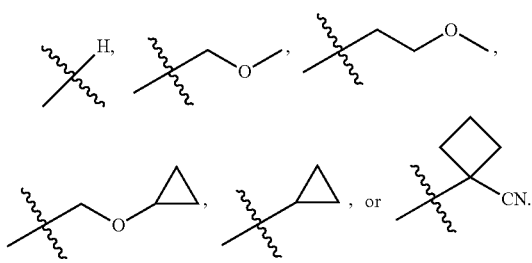

In some embodiments, disclosed herein is a compound of Formula I, or a pharmaceutically acceptable salt thereof, wherein R² is:

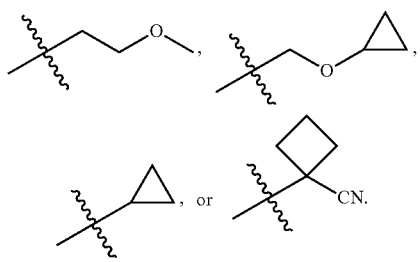

In some embodiments, disclosed herein is a compound of Formula I, or a pharmaceutically acceptable salt thereof, wherein R² is:

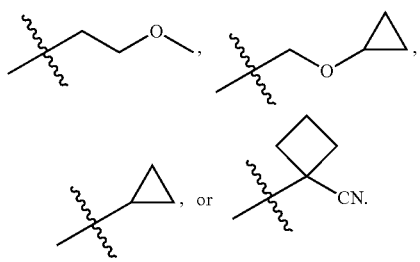

In some embodiments, disclosed herein is a compound of Formula I, or a pharmaceutically acceptable salt thereof, wherein R² is H, —C$_{(3-4)}$cycloalkyl, or —CH$_2$OCH$_3$.

In some embodiments, disclosed herein is a compound of Formula I, or a pharmaceutically acceptable salt thereof, wherein R² is H, —CH$_2$OCH$_3$, —CH$_2$CH$_2$OCH$_3$, or —CH$_2$O-cyclopropyl. In some embodiments, disclosed herein is a compound of Formula I, or a pharmaceutically acceptable salt thereof, wherein R² is H or —CH$_2$OCH$_3$. In some embodiments, disclosed herein is a compound of Formula I, or a pharmaceutically acceptable salt thereof, wherein R² is H. In some embodiments, disclosed herein is a compound of Formula I, or a pharmaceutically acceptable salt thereof, wherein R² is —CH$_2$OCH$_3$. In some embodiments, disclosed herein is a compound of Formula I, or a pharmaceutically acceptable salt thereof, wherein R² is —CH$_2$CH$_2$OCH$_3$. In some embodiments, disclosed herein is a compound of Formula I, or a pharmaceutically acceptable salt thereof, wherein R² is —CH$_2$O-cyclopropyl.

In some embodiments, disclosed herein is a compound of Formula I, or a pharmaceutically acceptable salt thereof, which is a compound of Formula Ia:

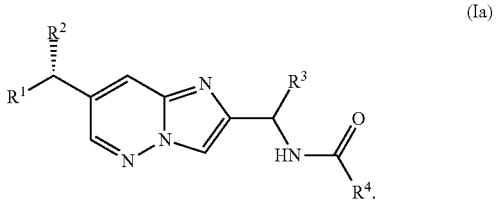

(Ia)

In some embodiments, disclosed herein is a compound of Formula I, or a pharmaceutically acceptable salt thereof, wherein R³ is —C$_{(1-6)}$alkyl, —C$_{(1-6)}$alkyl-O—C$_{(1-6)}$alkyl, or —C$_{(1-6)}$alkyl-O—C$_{(3-5)}$cycloalkyl, each of which is unsubstituted or substituted with one to six fluorine atoms.

In some embodiments, disclosed herein is a compound of Formula I, or a pharmaceutically acceptable salt thereof, wherein R³ is —C$_{(1-6)}$alkyl, —C$_{(1-4)}$alkyl-O—C$_{(1-4)}$alkyl, —C$_{(1-3)}$alkyl-O—C$_{(3-5)}$cycloalkyl, or cyclohexyl, each of which is substituted or unsubstituted with one to six fluorine atoms.

In some embodiments, disclosed herein is a compound of Formula I, or a pharmaceutically acceptable salt thereof, wherein R³ is —C$_{(1-6)}$alkyl, —C$_{(1-6)}$alkyl-O—C$_{(1-5)}$alkyl-CF$_3$ or cyclohexyl, wherein the —C$_{(1-6)}$alkyl is substituted with one to three fluorine atoms and wherein the cyclohexyl is substituted with two fluorine atoms. In some embodiments, disclosed herein is a compound of Formula I, or a pharmaceutically acceptable salt thereof, wherein R³ is —C$_{(1-6)}$alkyl or —C$_{(1-6)}$alkyl-O—C$_{(1-5)}$alkyl-CF$_3$, wherein the —C$_{(1-6)}$alkyl is substituted with one to three fluorine atoms.

In some embodiments, disclosed herein is a compound of Formula I, or a pharmaceutically acceptable salt thereof, wherein R³ is —C$_{(1-5)}$alkyl, —C$_{(1-6)}$alkyl-O—C$_{(1-5)}$alkyl-CF$_3$ or cyclohexyl, wherein the —C$_{(1-5)}$alkyl is substituted with one —CF$_3$ and wherein the cyclohexyl is substituted with two fluorine atoms. In some embodiments, disclosed herein is a compound of Formula I, or a pharmaceutically acceptable salt thereof, wherein R³ is —C$_{(1-5)}$alkyl or —C$_{(1-6)}$alkyl-O—C$_{(1-5)}$alkyl-CF$_3$, wherein the —C$_{(1-5)}$alkyl is substituted with one —CF$_3$.

In some embodiments, disclosed herein is a compound of Formula I, or a pharmaceutically acceptable salt thereof, wherein R³ is —C$_{(1-6)}$alkyl-O—C$_{(1-5)}$alkyl-CF$_3$ or cyclohexyl, wherein the cyclohexyl is substituted with two fluorine atoms.

In some embodiments, disclosed herein is a compound of Formula I, or a pharmaceutically acceptable salt thereof, wherein R³ is —C$_{(1-5)}$alkyl substituted with one —CF$_3$,

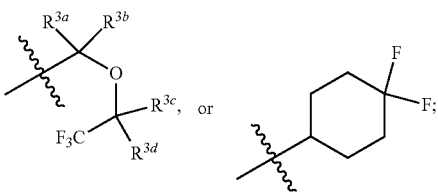

and $R^{3a}$, $R^{3b}$, $R^{3c}$, and $R^{3d}$ are each independently H or —CH$_3$.

In some embodiments, disclosed herein is a compound of Formula I, or a pharmaceutically acceptable salt thereof, wherein R$^3$ is —C$_{(1-5)}$alkyl substituted with one —CF$_3$ or

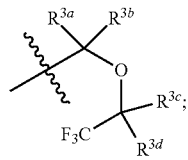

and $R^{3a}$, $R^{3b}$, $R^{3c}$, and $R^{3d}$ are each independently H or —CH$_3$.

In some embodiments, disclosed herein is a compound of Formula I, or a pharmaceutically acceptable salt thereof, wherein R$^3$ is

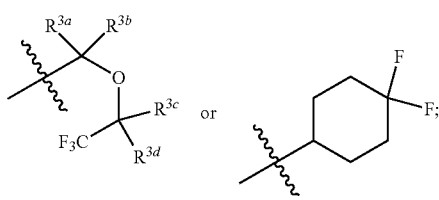

and $R^{3a}$, $R^{3b}$, $R^{3c}$, and $R^{3d}$ are each independently H or —CH$_3$.

In some embodiments, disclosed herein is a compound of Formula I, or a pharmaceutically acceptable salt thereof, wherein R$^3$ is —C$_{(1-5)}$alkyl substituted with one —CF$_3$. In some embodiments, disclosed herein is a compound of Formula I, or a pharmaceutically acceptable salt thereof, wherein R$^3$ is —C$_{(3-5)}$alkyl substituted with one —CF$_3$.

In some embodiments, disclosed herein is a compound of Formula I, or a pharmaceutically acceptable salt thereof, wherein R$^3$ is

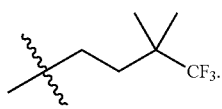 [SMILES: *CCC(C)(C)C(F)(F)F]

In some embodiments, disclosed herein is a compound of Formula I, or a pharmaceutically acceptable salt thereof, wherein R$^3$ is

In some embodiments, disclosed herein is a compound of Formula I, or a pharmaceutically acceptable salt thereof, wherein R$^3$ is:

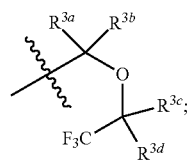

and $R^{3a}$, $R^{3b}$, $R^{3c}$, and $R^{3d}$ are each independently H or —CH$_3$.

In some embodiments, disclosed herein is a compound of Formula I, or a pharmaceutically acceptable salt thereof, wherein R$^3$ is:

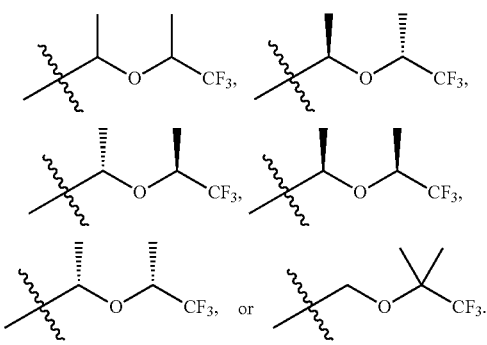

In some embodiments, disclosed herein is a compound of Formula I, or a pharmaceutically acceptable salt thereof, wherein R$^3$ is:

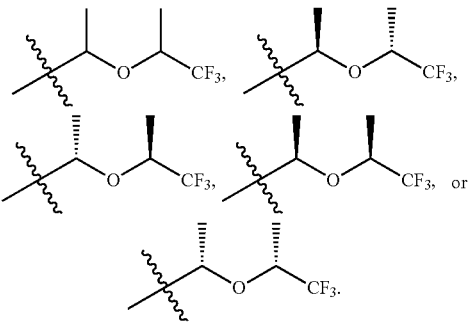

In some embodiments, disclosed herein is a compound of Formula I, or a pharmaceutically acceptable salt thereof, wherein R$^3$ is

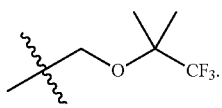 [SMILES: *COC(C)(C)C(F)(F)F]

In some embodiments, disclosed herein is a compound of Formula I, or a pharmaceutically acceptable salt thereof, wherein R³ is

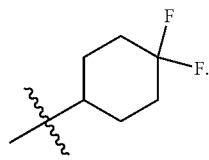 [SMILES: *C1CCC(F)(F)CC1]

In some embodiments, disclosed herein is a compound of Formula I, or a pharmaceutically acceptable salt thereof, which is a compound of Formula Ib:

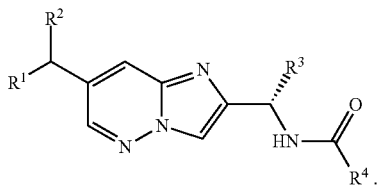
(Ib)

In some embodiments, disclosed herein is a compound of Formula I, or a pharmaceutically acceptable salt thereof, which is a compound of Formula Ib-1:

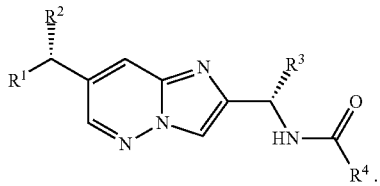
(Ib-1)

In some embodiments, disclosed herein is a compound of Formula I, or a pharmaceutically acceptable salt thereof, which is a compound of Formula Ic:

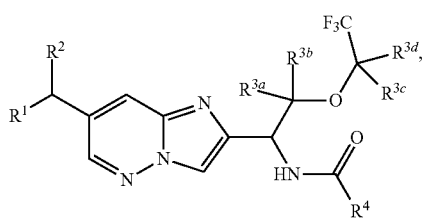
(Ic)

wherein $R^{3a}$, $R^{3b}$, $R^{3c}$, and $R^{3d}$ are each independently H or —CH₃.

In some embodiments, disclosed herein is a compound of Formula I, or a pharmaceutically acceptable salt thereof, which is a compound of Formula Ic-1:

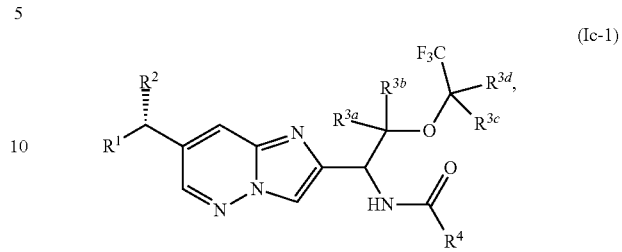
(Ic-1)

wherein $R^{3a}$, $R^{3b}$, $R^{3c}$, and $R^{3d}$ are each independently H or —CH₃.

In some embodiments, disclosed herein is a compound of Formula I, or a pharmaceutically acceptable salt thereof, which is a compound of Formula Ic-2:

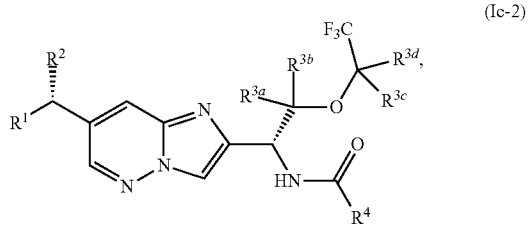
(Ic-2)

wherein $R^{3a}$, $R^{3b}$, $R^{3c}$, and $R^{3d}$ are each independently H or —CH₃.

In some embodiments, disclosed herein is a compound of Formula I, or a pharmaceutically acceptable salt thereof, which is a compound of Formula Id:

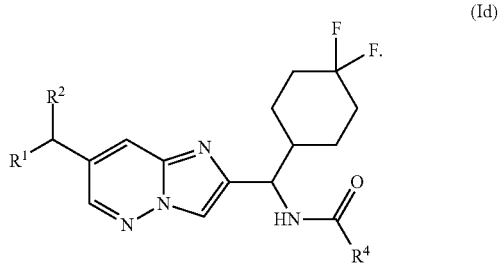
(Id)

In some embodiments, disclosed herein is a compound of Formula I, or a pharmaceutically acceptable salt thereof, which is a compound of Formula Id-1:

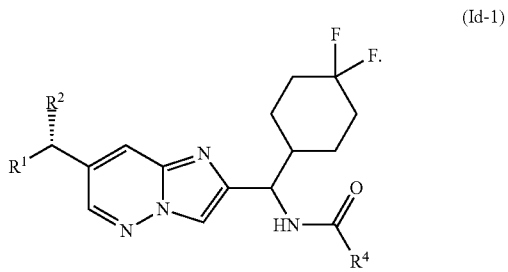
(Id-1)

In some embodiments, disclosed herein is a compound of Formula I, or a pharmaceutically acceptable salt thereof, which is a compound of Formula Id-2:

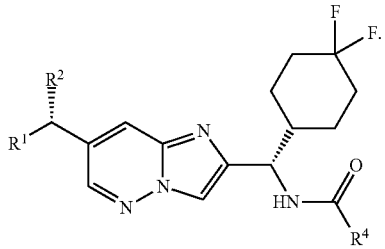

In some embodiments, disclosed herein is a compound of Formula I, or a pharmaceutically acceptable salt thereof, which is a compound of Formula Ie:

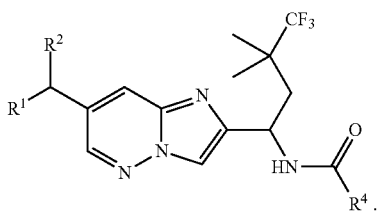

In some embodiments, disclosed herein is a compound of Formula I, or a pharmaceutically acceptable salt thereof, which is a compound of Formula Ie-1:

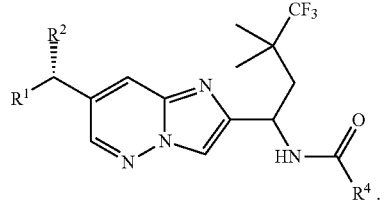

In some embodiments, disclosed herein is a compound of Formula I, or a pharmaceutically acceptable salt thereof, which is a compound of Formula Ie-2:

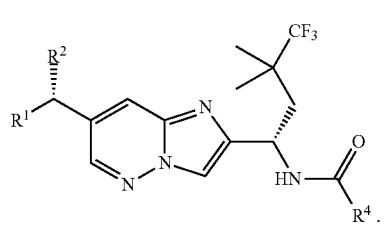

In some embodiments, disclosed herein is a compound of Formula I, or a pharmaceutically acceptable salt thereof, which is a compound of Formula If:

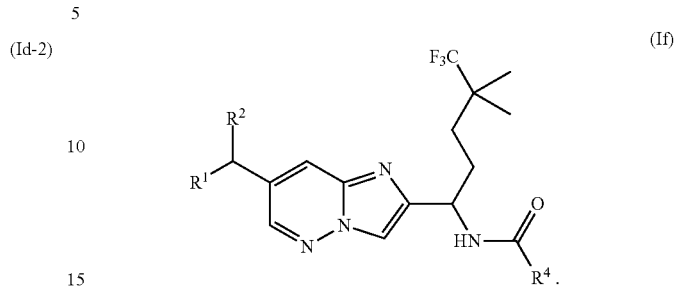

In some embodiments, disclosed herein is a compound of Formula I, or a pharmaceutically acceptable salt thereof, which is a compound of Formula If-1:

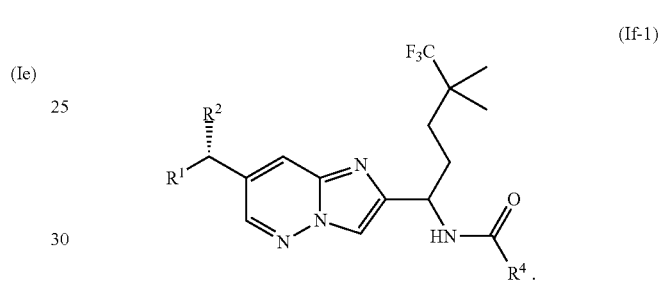

In some embodiments, disclosed herein is a compound of Formula I, or a pharmaceutically acceptable salt thereof, which is a compound of Formula If-2:

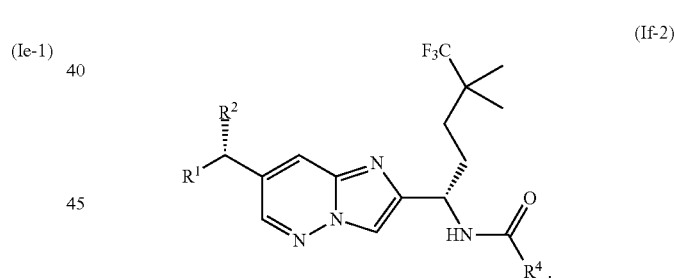

In some embodiments, disclosed herein is a compound of Formula I, or a pharmaceutically acceptable salt thereof, wherein $R^4$ is a 5-membered heteroaryl that is unsubstituted or substituted with one or two $R^{4a}$ groups. In some embodiments, disclosed herein is a compound of Formula I, or a pharmaceutically acceptable salt thereof, wherein $R^4$ is a 5-membered heteroaryl that is substituted with one or two $R^{4a}$ groups.

In some embodiments, disclosed herein is a compound of Formula I, or a pharmaceutically acceptable salt thereof, wherein $R^4$ is a 5-membered heteroaryl comprising one to three heteroatoms selected from O and N, wherein the 5-membered heteroaryl is unsubstituted or substituted with one to two $R^{4a}$ groups.

In some embodiments, disclosed herein is a compound of Formula I, or a pharmaceutically acceptable salt thereof, wherein $R^4$ is pyrrolyl, pyrazolyl, imidazolyl, triazolyl, oxazolyl, isoxazolyl, or oxadiazolyl, each of which is unsubstituted or substituted with one to two R⁴ᵃ groups. In some embodiments, disclosed herein is a compound of Formula I, or a pharmaceutically acceptable salt thereof, wherein R⁴ is pyrazolyl, triazolyl, isoxazolyl, or oxadiazolyl, each of which is unsubstituted or substituted with one to two R⁴ᵃ groups. In some embodiments, disclosed herein is a compound of Formula I, or a pharmaceutically acceptable salt thereof, wherein R⁴ is pyrazolyl, triazolyl, or oxadiazolyl, each of which is unsubstituted or substituted with one to two R⁴ᵃ groups. In some embodiments, disclosed herein is a compound of Formula I, or a pharmaceutically acceptable salt thereof, wherein R⁴ is pyrazolyl or oxadiazolyl, each of which is unsubstituted or substituted with one to two R⁴ᵃ groups.

In some embodiments, disclosed herein is a compound of Formula I, or a pharmaceutically acceptable salt thereof, wherein R⁴ is pyrrolyl, pyrazolyl, imidazolyl, 1,2,3-triazolyl, 1,2,4-triazolyl, oxazolyl, isoxazolyl, 1,2,3-oxadiazolyl, 1,2,4-oxadizaolyl, 1,2,5-oxadiazolyl, or 1,3,4-oxadiazolyl, each of which is unsubstituted or substituted with one to two R⁴ᵃ groups. In some embodiments, disclosed herein is a compound of Formula I, or a pharmaceutically acceptable salt thereof, wherein R⁴ is pyrazolyl, 1,2,3-triazolyl, 1,2,4-triazolyl, isoxazolyl, or 1,2,5-oxadiazolyl, each of which is unsubstituted or substituted with one to two R⁴ᵃ groups. In some embodiments, disclosed herein is a compound of Formula I, or a pharmaceutically acceptable salt thereof, wherein R⁴ is pyrazolyl, 1,2,4-triazolyl, or 1,2,5-oxadiazolyl. In some embodiments, disclosed herein is a compound of Formula I, or a pharmaceutically acceptable salt thereof, wherein R⁴ is pyrazolyl or 1,2,5-oxadiazolyl, each of which is unsubstituted or substituted with one to two R⁴ᵃ groups.

In some embodiments, disclosed herein is a compound of Formula I, or a pharmaceutically acceptable salt thereof, wherein R⁴ is:

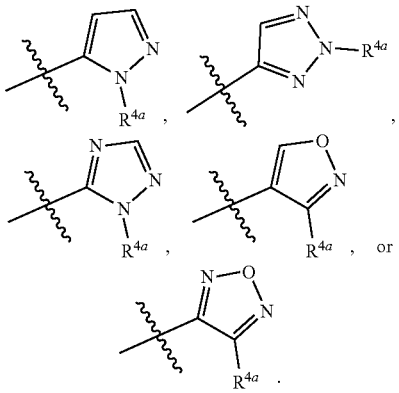

In some embodiments, disclosed herein is a compound of Formula I, or a pharmaceutically acceptable salt thereof, wherein R⁴ is:

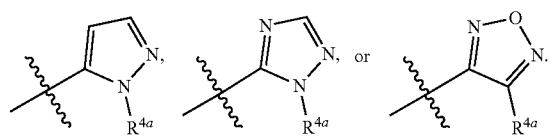

In some embodiments, disclosed herein is a compound of Formula I, or a pharmaceutically acceptable salt thereof, wherein R⁴ is:

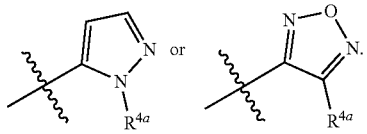

In some embodiments, disclosed herein is a compound of Formula I, or a pharmaceutically acceptable salt thereof, wherein R⁴ᵃ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein R⁴ᵃ is —$C_{(1-6)}$alkyl or —$C_{(0-2)}$alkyl-$C_{(3-6)}$cycloalkyl, each of which are unsubstituted or substituted with one to six substituents independently selected from fluorine, —$CH_3$, —$CD_3$, —$CD_2CD_3$, —$CH_2F$, —$CHF_2$, and —$CF_3$. In some embodiments, disclosed herein is a compound of Formula I, or a pharmaceutically acceptable salt thereof, wherein R⁴ᵃ is —$C_{(1-4)}$alkyl or —$C_{(0-2)}$alkyl-$C_{(3-4)}$cycloalkyl, each of which are unsubstituted or substituted with one to six substituents independently selected from fluorine, —$CH_3$, —$CD_3$, —$CD_2CD_3$, —$CH_2F$, $CHF_2$, and —$CF_3$.

In some embodiments, disclosed herein is a compound of Formula I, or a pharmaceutically acceptable salt thereof, wherein R⁴ᵃ is —$C_{(1-6)}$alkyl, —O—$C_{(1-6)}$alkyl, or —$C_{(0-2)}$alkyl-$C_{(3-6)}$cycloalkyl. In some embodiments, disclosed herein is a compound of Formula I, or a pharmaceutically acceptable salt thereof, wherein R⁴ᵃ is —$C_{(1-4)}$alkyl, —O—$C_{(1-4)}$alkyl, or —$C_{(0-2)}$alkyl-$C_{(3-4)}$cycloalkyl.

In some embodiments, disclosed herein is a compound of Formula I, or a pharmaceutically acceptable salt thereof, wherein R⁴ᵃ is —$C_{(1-6)}$alkyl or —$C_{(0-2)}$alkyl-$C_{(3-6)}$cycloalkyl. In some embodiments, disclosed herein is a compound of Formula I, or a pharmaceutically acceptable salt thereof, wherein R⁴ᵃ is —$C_{(1-4)}$alkyl or —$C_{(0-2)}$alkyl-$C_{(3-6)}$cycloalkyl.

In some embodiments, disclosed herein is a compound of Formula I, or a pharmaceutically acceptable salt thereof, wherein R⁴ᵃ is methyl, isopropyl, —$CD_2CD_3$, —$CH_2CH_2CF_3$, methoxy, —$OCH_2CHF_2$, —$CH_2OCHF_2$, cyclopropyl, or —$CH_2$-cyclopropyl. In some embodiments, disclosed herein is a compound of Formula I, or a pharmaceutically acceptable salt thereof, wherein R⁴ᵃ is methyl, isopropyl, —$CD_2CD_3$, —$CH_2CH_2CF_3$, —$OCH_2CHF_2$, —$CH_2OCHF_2$, cyclopropyl, or —$CH_2$-cyclopropyl.

In some embodiments, disclosed herein is a compound of Formula I, or a pharmaceutically acceptable salt thereof, wherein R⁴ᵃ is methyl, —$CD_2CD_3$, isopropyl, methoxy, or cyclopropyl. In some embodiments, disclosed herein is a compound of Formula I, or a pharmaceutically acceptable salt thereof, wherein R⁴ᵃ is methyl, —$CD_2CD_3$, isopropyl, or cyclopropyl.

In some embodiments, disclosed herein is a compound of Formula I, or a pharmaceutically acceptable salt thereof, wherein $R^4$ is:

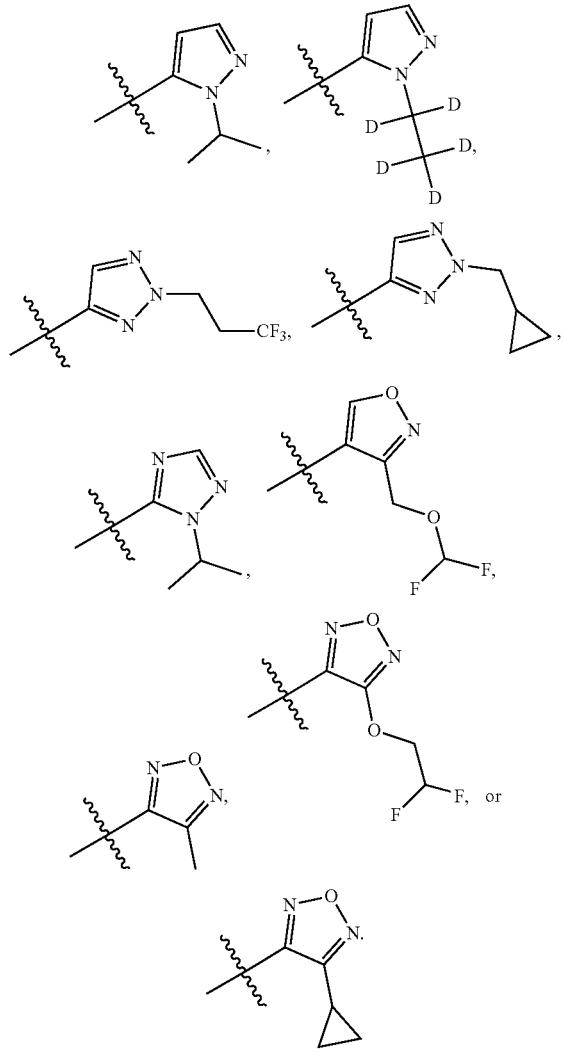

In some embodiments, disclosed herein is a compound of Formula I, or a pharmaceutically acceptable salt thereof, wherein $R^4$ is:

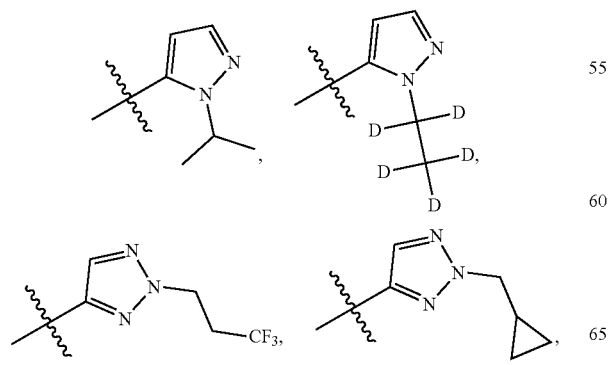

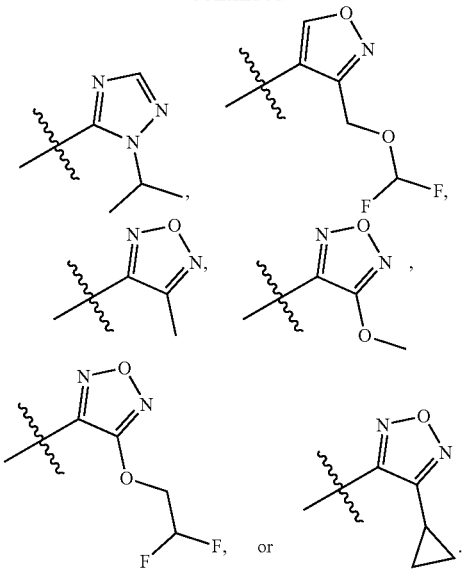

In some embodiments, disclosed herein is a compound of Formula I, or a pharmaceutically acceptable salt thereof, wherein $R^4$ is:

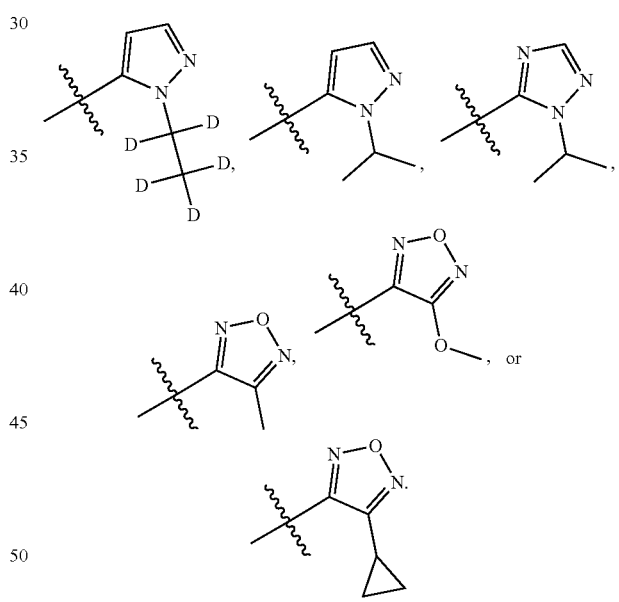

In some embodiments, disclosed herein is a compound of Formula I, or a pharmaceutically acceptable salt thereof, wherein $R^4$ is:

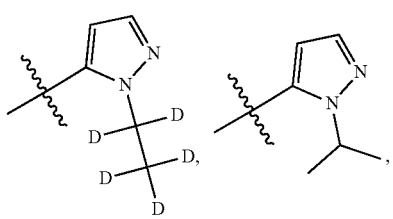

-continued

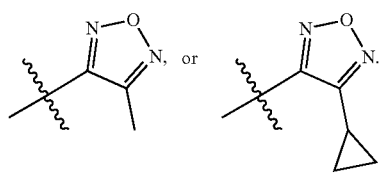

In some embodiments, disclosed herein is a compound of Formula I, or a pharmaceutically acceptable salt thereof, wherein $R^4$ is

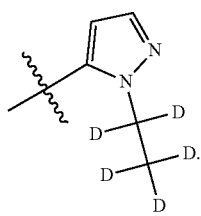

In some embodiments, disclosed herein is a compound of Formula I, or a pharmaceutically acceptable salt thereof, wherein $R^4$ is

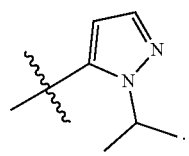 [SMILES: *Cc1ccnn1C(C)C]

In some embodiments, disclosed herein is a compound of Formula I, or a pharmaceutically acceptable salt thereof, wherein $R^4$ is

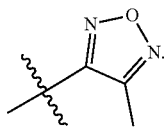

In some embodiments, disclosed herein is a compound of Formula I, or a pharmaceutically acceptable salt thereof, wherein $R^4$ is

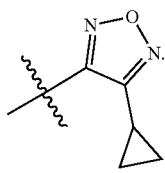 [SMILES: *Cc1nonc1C1CC1]

In some embodiments, disclosed herein is a compound of Formula I, or a pharmaceutically acceptable salt thereof, wherein $R^4$ is

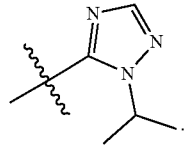

In some embodiments, disclosed herein is a compound of Formula I, or a pharmaceutically acceptable salt thereof, wherein $R^4$ is

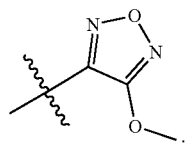 [SMILES: *Cc1nonc1OC]

In some embodiments, disclosed herein is a compound of Formula I, or a pharmaceutically acceptable salt thereof, wherein $R^4$ is a —$C_{(3-5)}$cycloalkyl that is unsubstituted or substituted with one to two $R^{4b}$ groups. In some embodiments, disclosed herein is a compound of Formula I, or a pharmaceutically acceptable salt thereof, wherein $R^4$ is a —$C_{(3-5)}$cycloalkyl that is substituted with one to two $R^{4b}$ groups. In some embodiments, disclosed herein is a compound of Formula I, or a pharmaceutically acceptable salt thereof, wherein $R^4$ is a cyclopropyl that is substituted with one to two $R^{4b}$ groups.

In some embodiments, disclosed herein is a compound of Formula I, or a pharmaceutically acceptable salt thereof, wherein $R^4$ is a —$C_{(3-5)}$cycloalkyl that is unsubstituted or substituted with one —$CF_3$ group.

In some embodiments, disclosed herein is a compound of Formula I, or a pharmaceutically acceptable salt thereof, wherein $R^{4b}$ is —$C_{(1-3)}$alkyl that is unsubstituted or substituted with one to three fluorine atoms. In some embodiments, disclosed herein is a compound of Formula I, or a pharmaceutically acceptable salt thereof, wherein $R^{4b}$ is $CH_3$, $CH_2F$, $CHF_2$, or $CF_3$. In some embodiments, disclosed herein is a compound of Formula I, or a pharmaceutically acceptable salt thereof, wherein $R^{4b}$ is $CF_3$.

In some embodiments, disclosed herein is a compound of Formula I, or a pharmaceutically acceptable salt thereof, wherein $R^4$ is:

In some embodiments, disclosed herein is a compound of Formula I, or a pharmaceutically acceptable salt thereof, that is a deuterated isotope comprising one to thirty deuterium atoms. In some embodiments, disclosed herein is a compound of Formula I, or a pharmaceutically acceptable salt thereof, that is a deuterated isotope comprising one to fifteen deuterium atoms. In some embodiments, disclosed herein is a compound of Formula I, or a pharmaceutically acceptable salt thereof, that is a deuterated isotope comprising one to seven deuterium atoms.
In some embodiments, disclosed herein is a compound of Formula I, or a pharmaceutically acceptable salt thereof, having a structure as shown in Table 1A, 1B, 1C, or 1D.
TABLE 1A
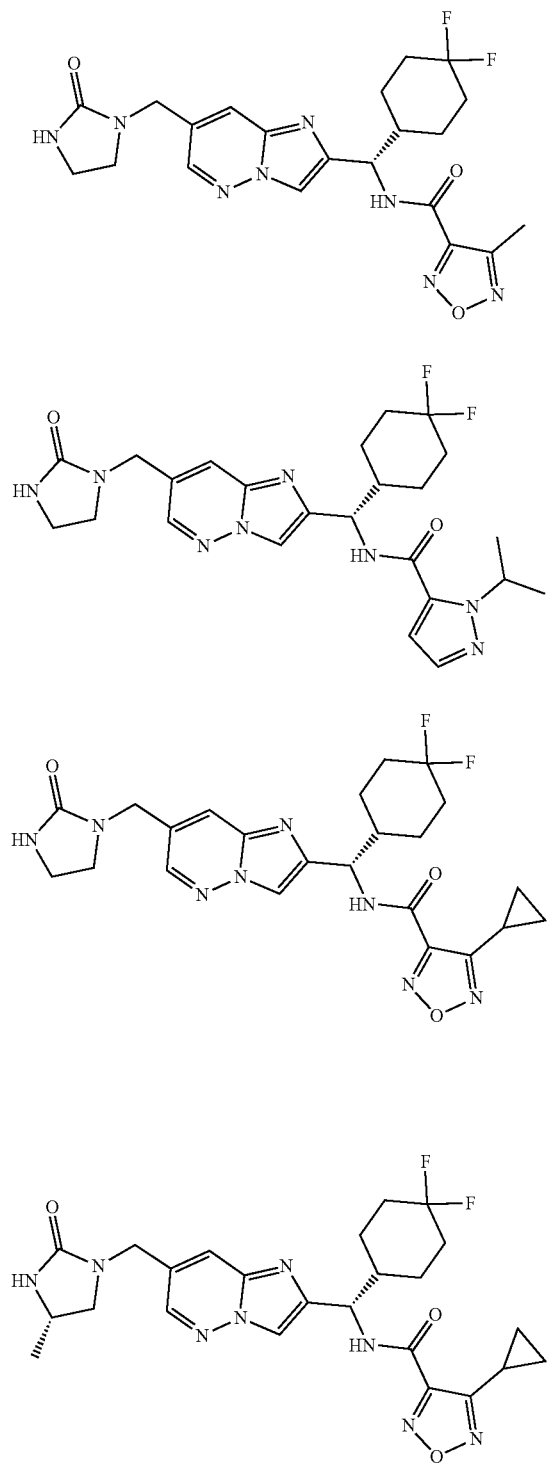
TABLE 1A-continued
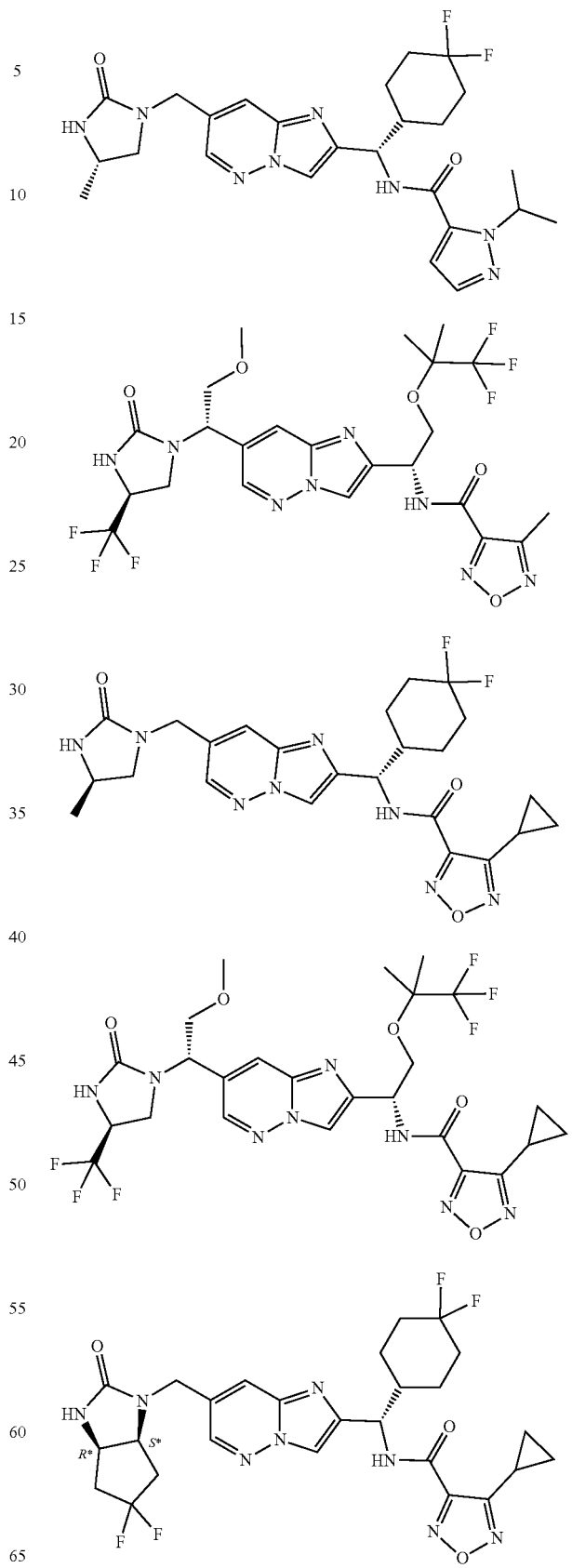

TABLE 1A-continued
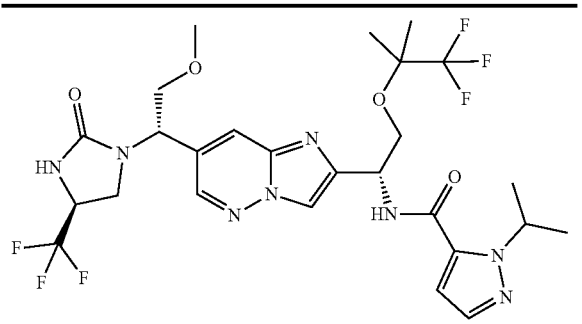
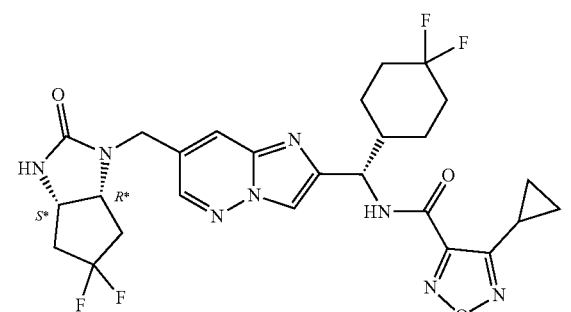
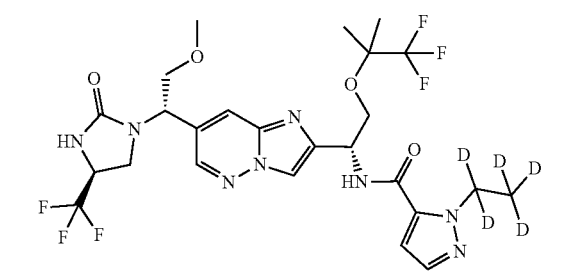 [SMILES: [2H]C([2H])([2H])C([2H])([2H])n1nccc1C(=O)N[C@@H](COC(C)(C)C(F)(F)F)c1cn2ncc([C@@H](COC)N3C[C@@H](C(F)(F)F)NC3=O)cc2n1]
TABLE 1B
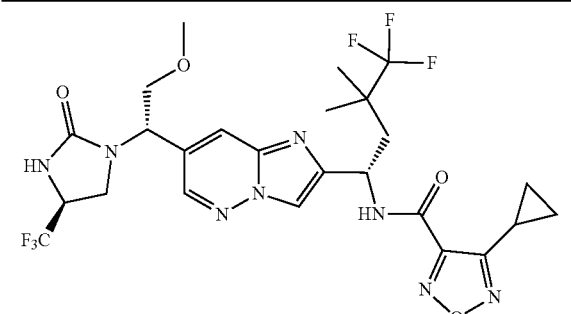
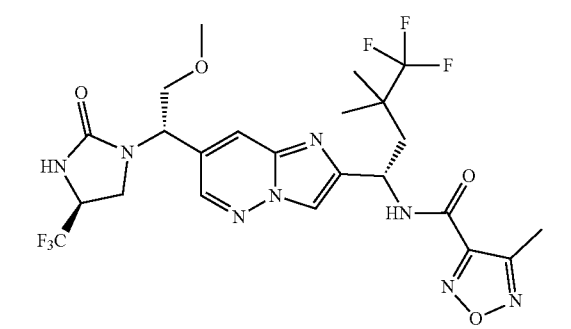 [SMILES: COC[C@H](c1cnn2cc([C@H](CC(C)(C)C(F)(F)F)NC(=O)c3nonc3C)nc2c1)N1C[C@@H](C(F)(F)F)NC1=O]
TABLE 1B-continued
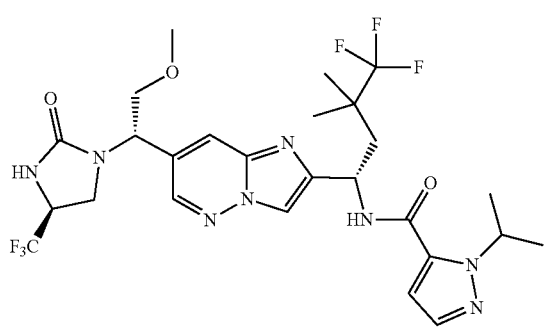 [SMILES: COC[C@H](c1cnn2cc([C@H](CC(C)(C)C(F)(F)F)NC(=O)c3ccnn3C(C)C)nc2c1)N1C[C@@H](C(F)(F)F)NC1=O]
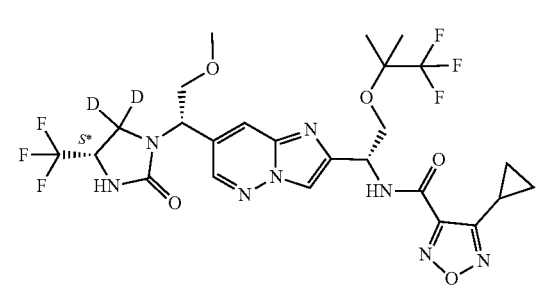 [SMILES: [2H]C1([2H])[C@@H](C(F)(F)F)NC(=O)N1[C@H](COC)c1cnn2cc([C@H](COC(C)(C)C(F)(F)F)NC(=O)c3nonc3C3CC3)nc2c1]
TABLE 1C
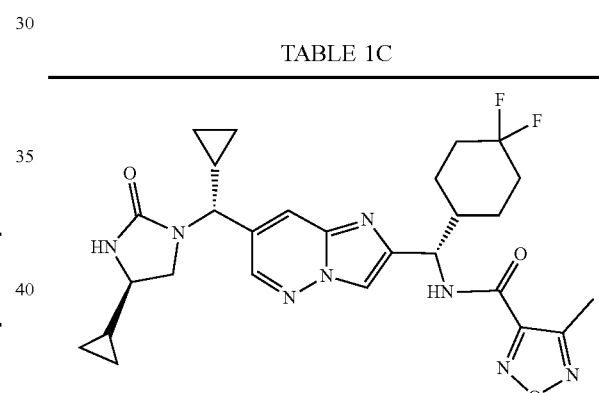
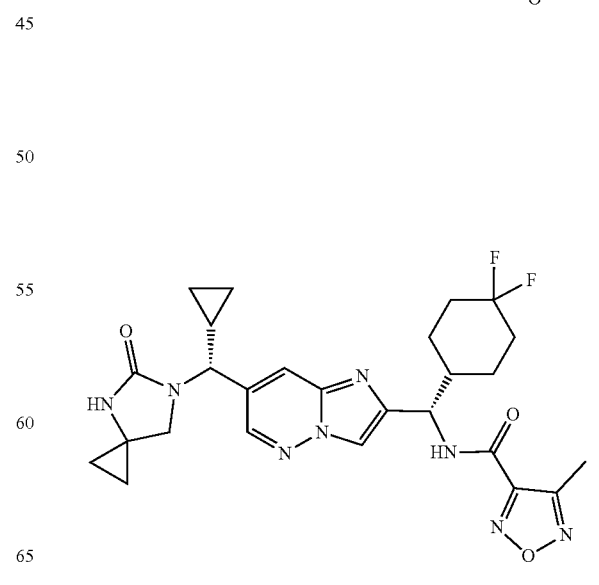

TABLE 1C-continued
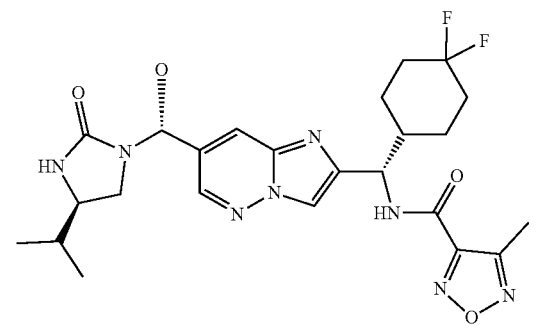
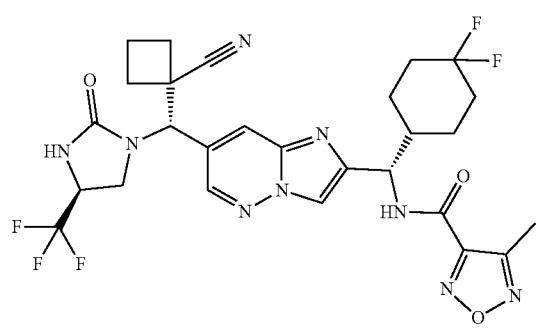 [SMILES: Cc1nonc1C(=O)N[C@H](c1cn2ncc([C@H](N3C[C@@H](C(F)(F)F)NC3=O)C3(C#N)CCC3)cc2n1)C1CCC(F)(F)CC1]
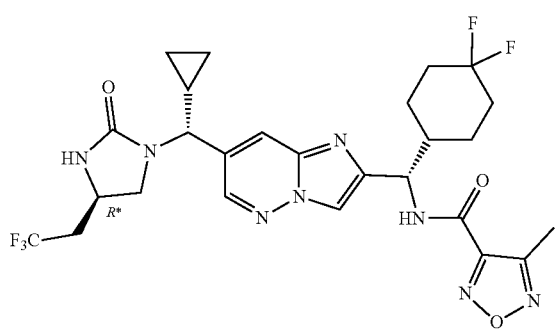 [SMILES: Cc1nonc1C(=O)N[C@H](c1cn2ncc([C@@H](C3CC3)N3C[C@@H](CC(F)(F)F)NC3=O)cc2n1)C1CCC(F)(F)CC1]
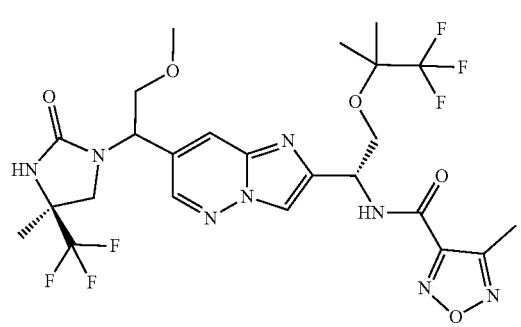
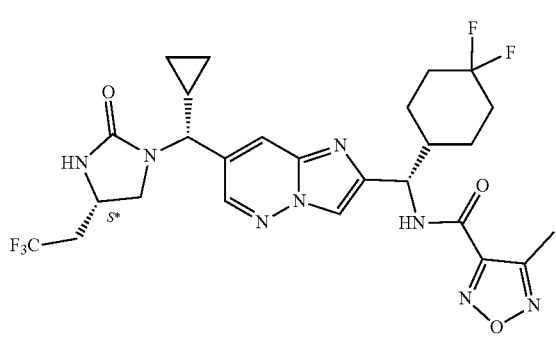 [SMILES: Cc1nonc1C(=O)N[C@H](c1cn2ncc([C@@H](C3CC3)N3C[C@H](CC(F)(F)F)NC3=O)cc2n1)C1CCC(F)(F)CC1]
TABLE 1C-continued
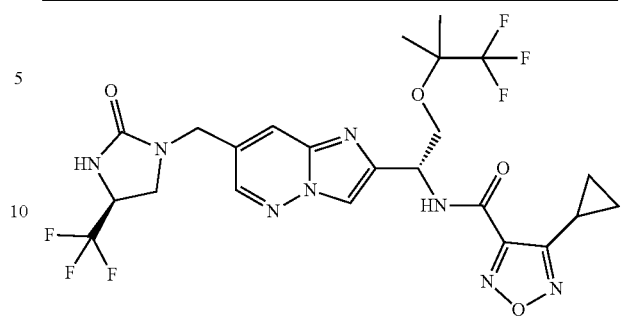
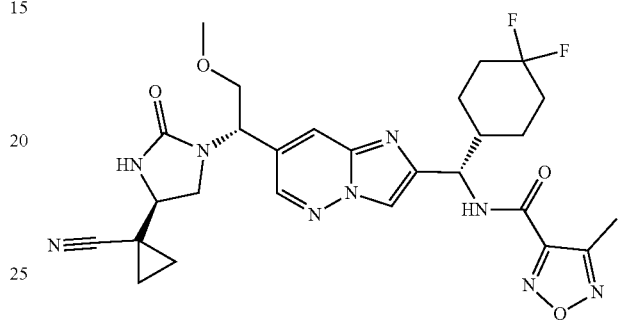
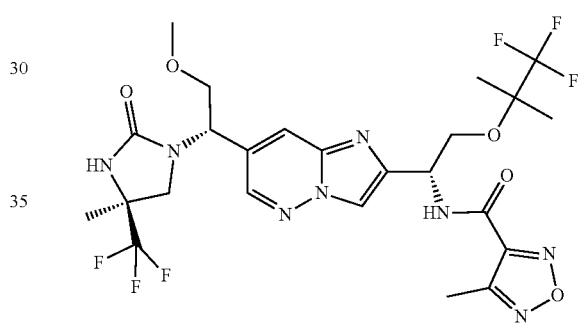
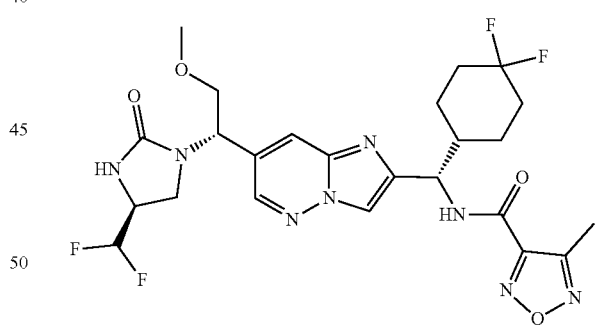
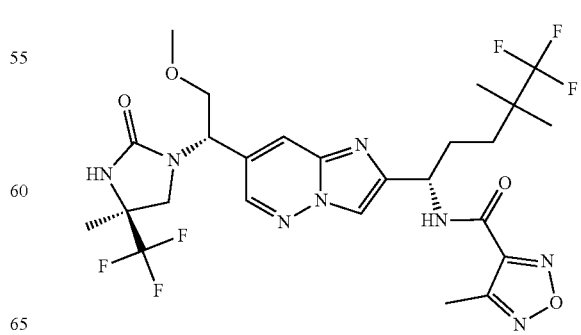

TABLE 1C-continued
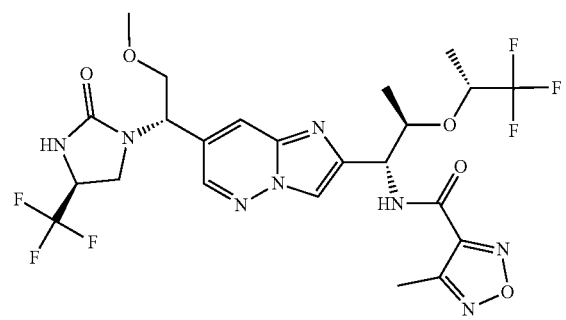 [SMILES: COC[C@H](c1cnn2cc([C@@H](NC(=O)c3nonc3C)[C@@H](C)O[C@H](C)C(F)(F)F)nc2c1)N1C[C@@H](C(F)(F)F)NC1=O]
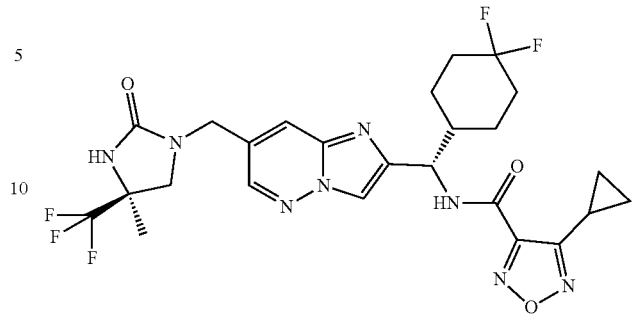
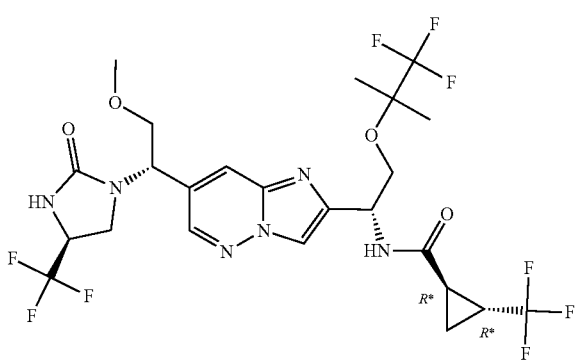 [SMILES: COC[C@H](c1cnn2cc([C@H](COC(C)(C)C(F)(F)F)NC(=O)[C@@H]3C[C@H]3C(F)(F)F)nc2c1)N1C[C@@H](C(F)(F)F)NC1=O]
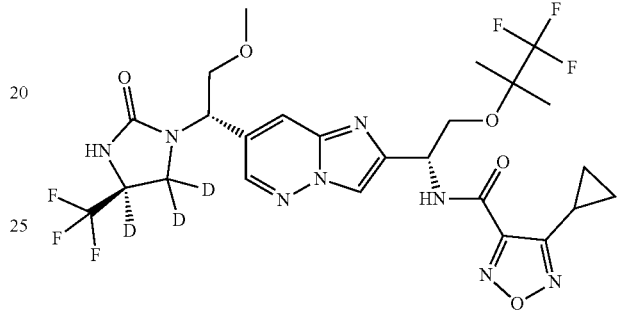
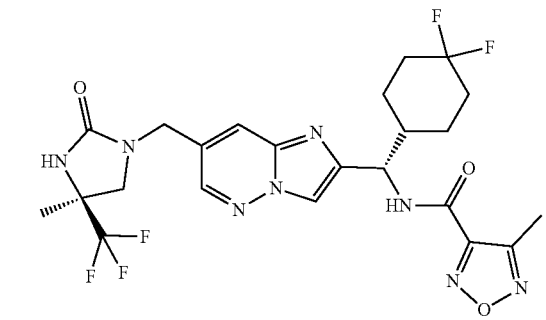
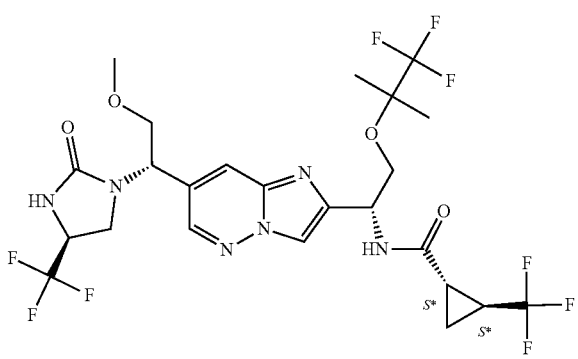 [SMILES: COC[C@H](c1cnn2cc([C@H](COC(C)(C)C(F)(F)F)NC(=O)[C@H]3C[C@@H]3C(F)(F)F)nc2c1)N1C[C@@H](C(F)(F)F)NC1=O]
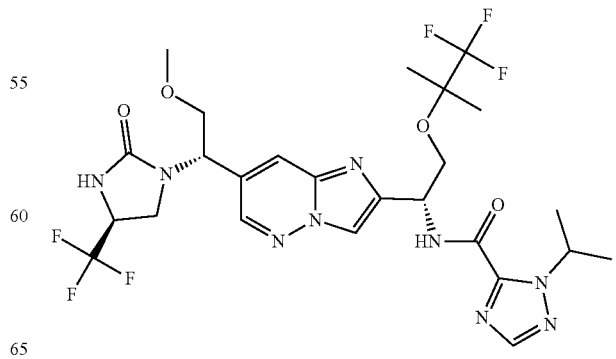

TABLE 1D
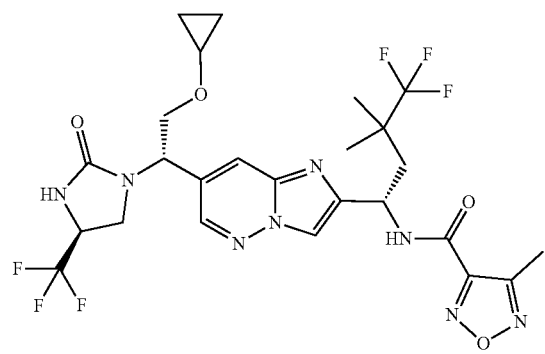 [SMILES: Cc1nonc1C(=O)N[C@@H](CC(C)(C)C(F)(F)F)c1cn2ncc([C@@H](COC3CC3)N3C[C@@H](C(F)(F)F)NC3=O)cc2n1]
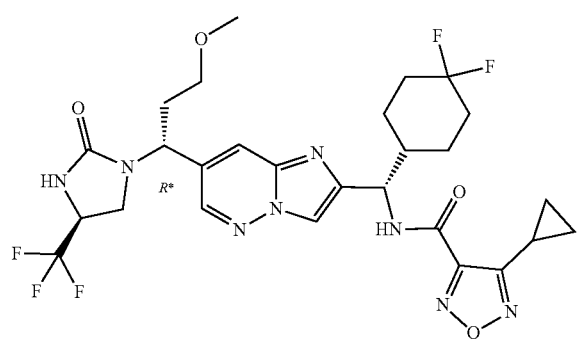 [SMILES: COCC[C@H](c1cnn2cc([C@@H](NC(=O)c3nonc3C3CC3)C3CCC(F)(F)CC3)nc2c1)N1C[C@@H](C(F)(F)F)NC1=O]
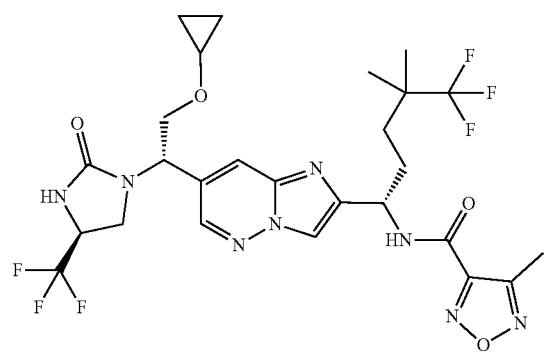 [SMILES: Cc1nonc1C(=O)N[C@@H](CCC(C)(C)C(F)(F)F)c1cn2ncc([C@@H](COC3CC3)N3C[C@@H](C(F)(F)F)NC3=O)cc2n1]
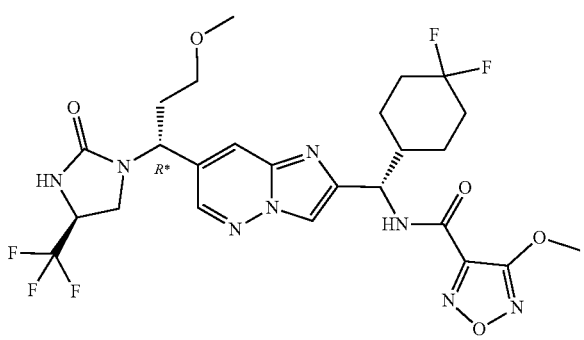 [SMILES: COCC[C@H](c1cnn2cc([C@@H](NC(=O)c3nonc3OC)C3CCC(F)(F)CC3)nc2c1)N1C[C@@H](C(F)(F)F)NC1=O]
TABLE 1D-continued
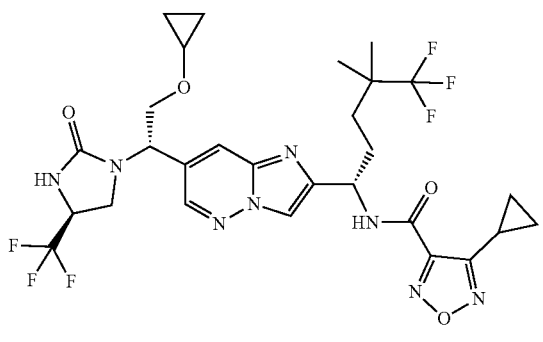 [SMILES: CC(C)(CC[C@H](NC(=O)c1nonc1C1CC1)c1cn2ncc([C@@H](COC3CC3)N3C[C@@H](C(F)(F)F)NC3=O)cc2n1)C(F)(F)F]
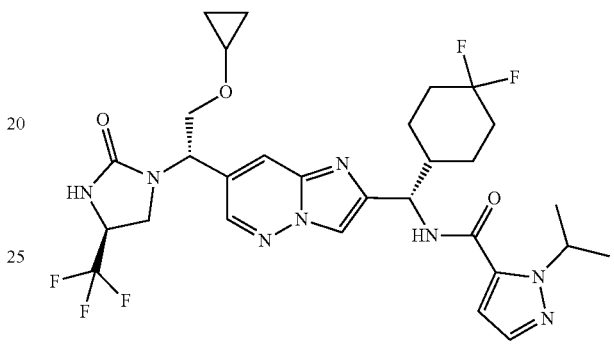
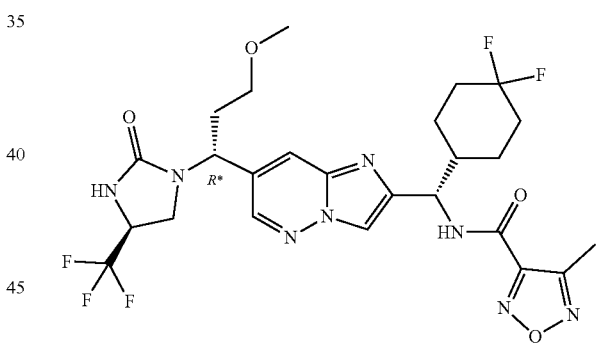
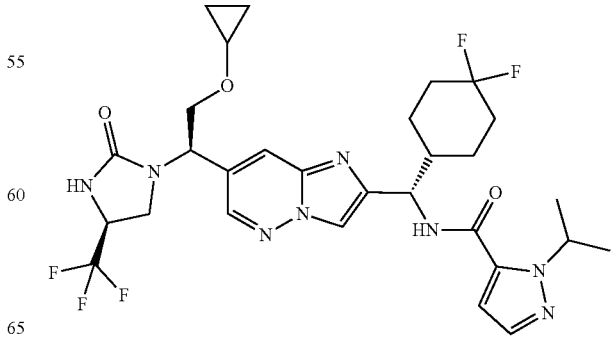

TABLE 1D-continued
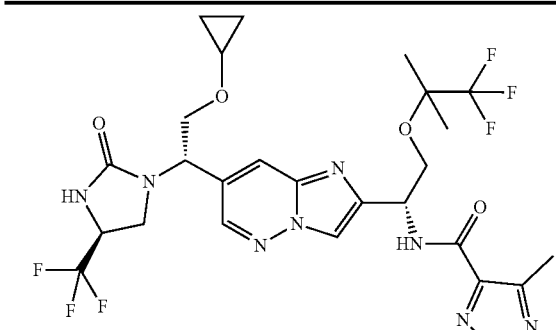
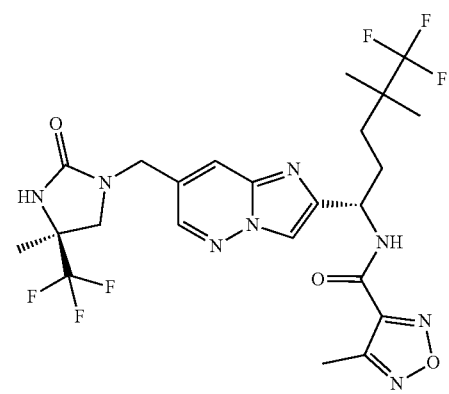 [SMILES: Cc1nonc1C(=O)N[C@@H](CCC(C)(C)C(F)(F)F)c1cn2ncc(CN3C[C@@](C)(C(F)(F)F)NC3=O)cc2n1]
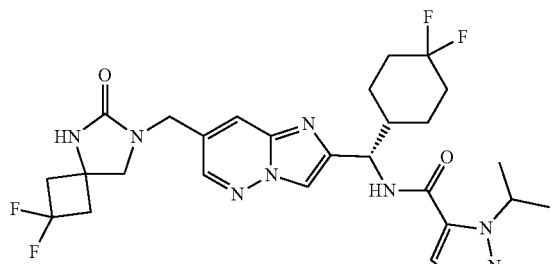
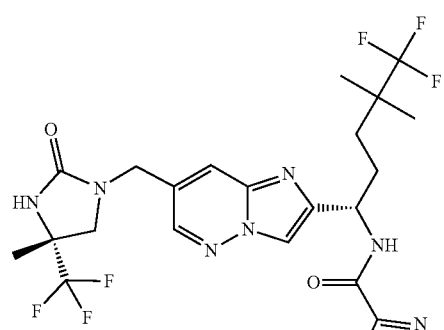
TABLE 1D-continued
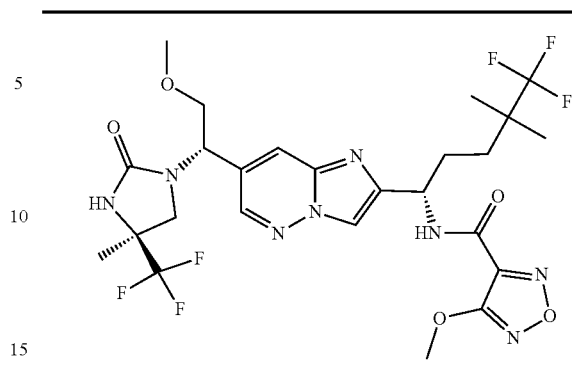
In some embodiments, disclosed herein is a compound of Formula I, or a pharmaceutically acceptable salt thereof, selected from the group consisting of:
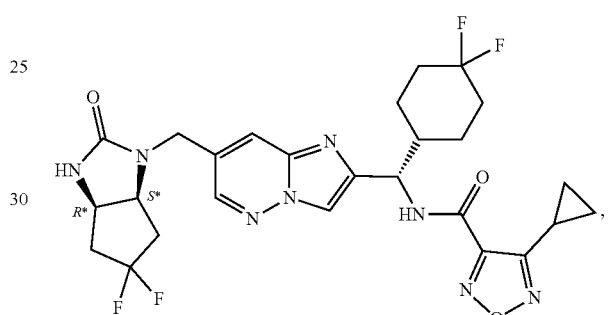
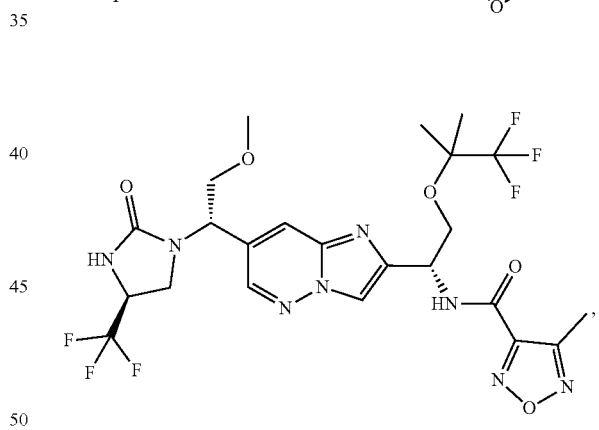
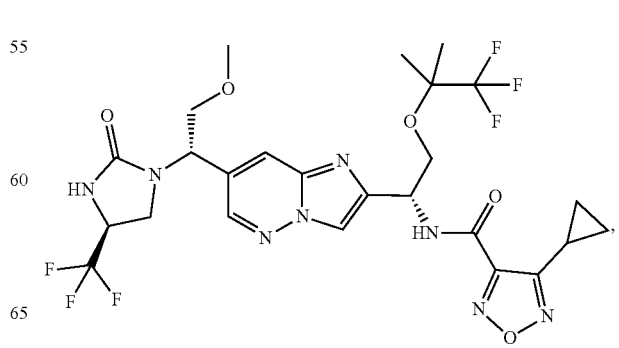

67
-continued
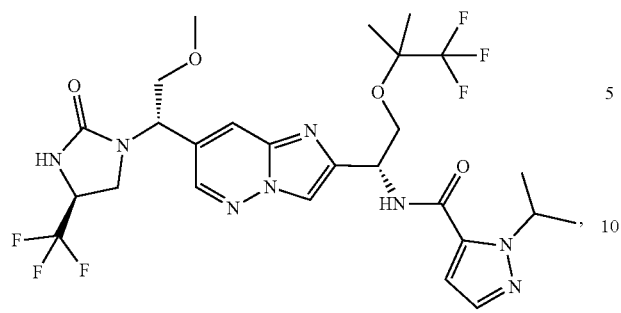
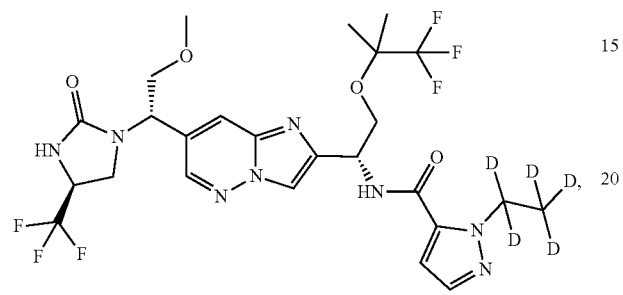
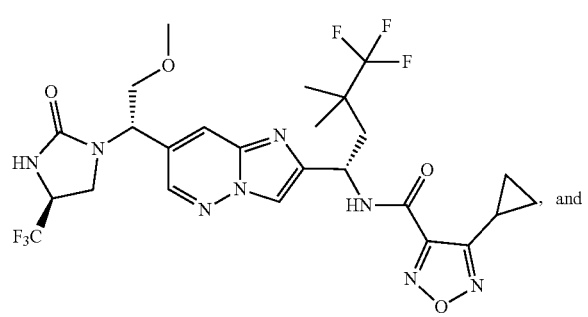, and
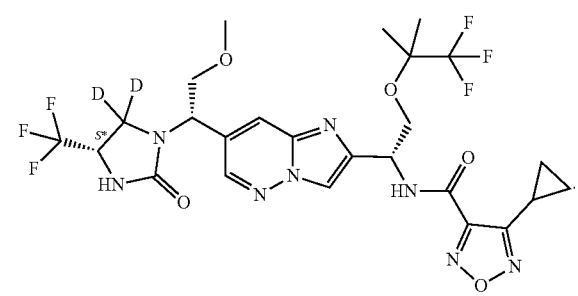
In some embodiments, disclosed herein is a compound of Formula I, or a pharmaceutically acceptable salt thereof, selected from the group consisting of:
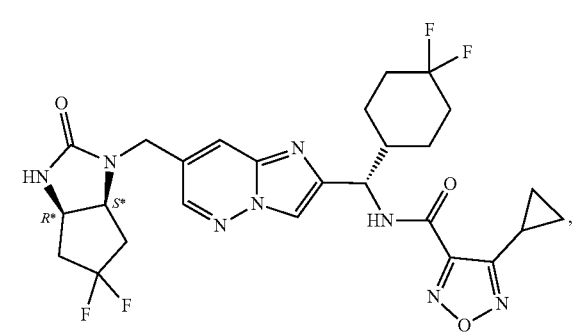
68
-continued
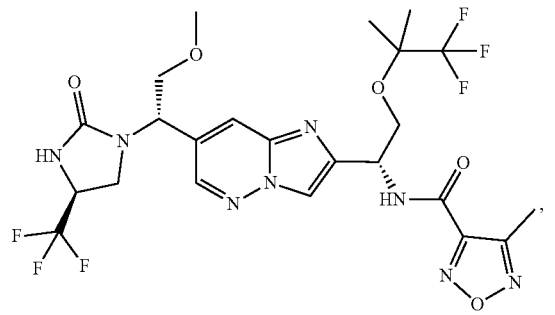 [SMILES: COC[C@H](c1cnn2cc([C@H](COC(C)(C)C(F)(F)F)NC(=O)c3nonc3C)nc2c1)N1C[C@@H](C(F)(F)F)NC1=O]
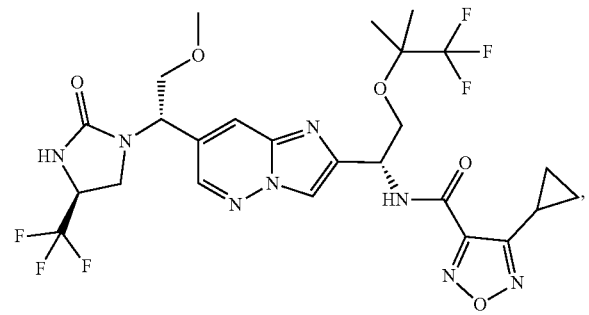 [SMILES: COC[C@H](c1cnn2cc([C@H](COC(C)(C)C(F)(F)F)NC(=O)c3nonc3C3CC3)nc2c1)N1C[C@@H](C(F)(F)F)NC1=O]
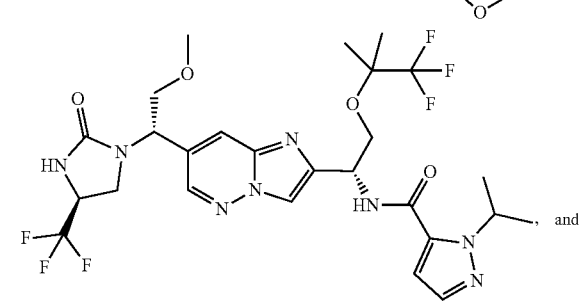, and
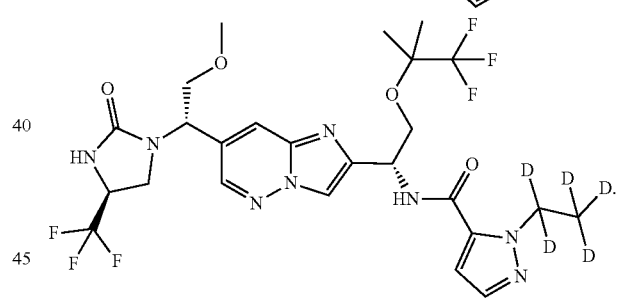
In some embodiments, disclosed herein is a compound of Formula I, or a pharmaceutically acceptable salt thereof, selected from the group consisting of:
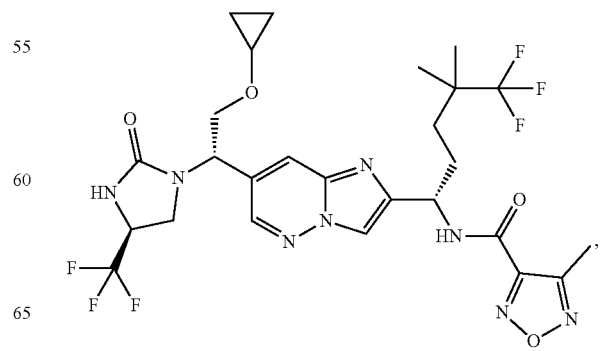

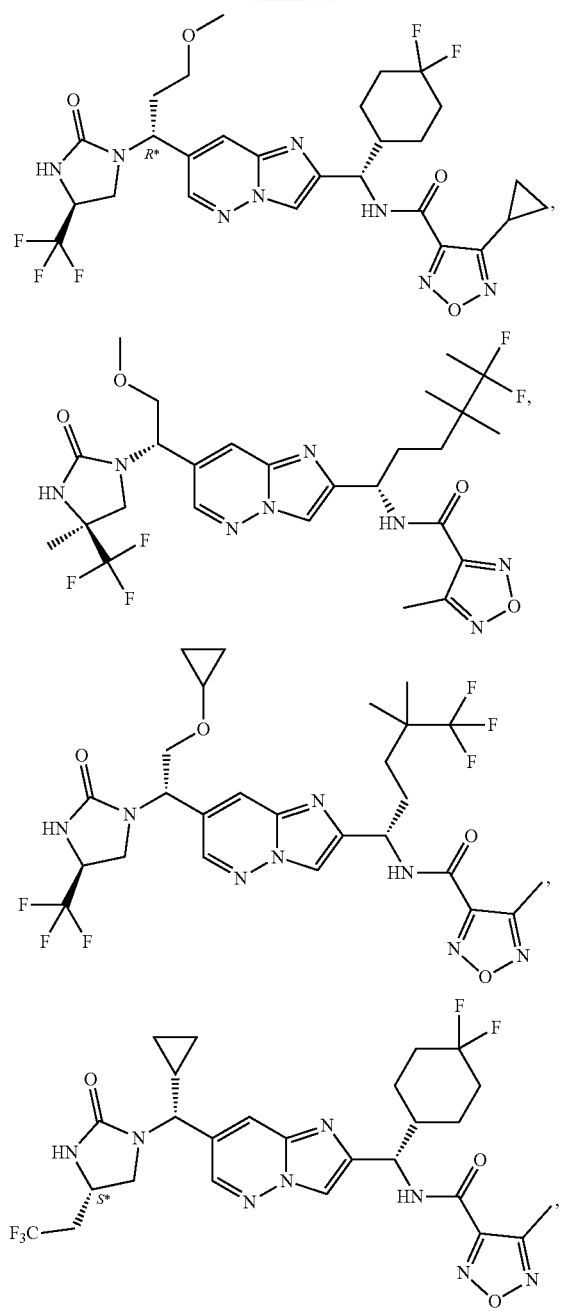
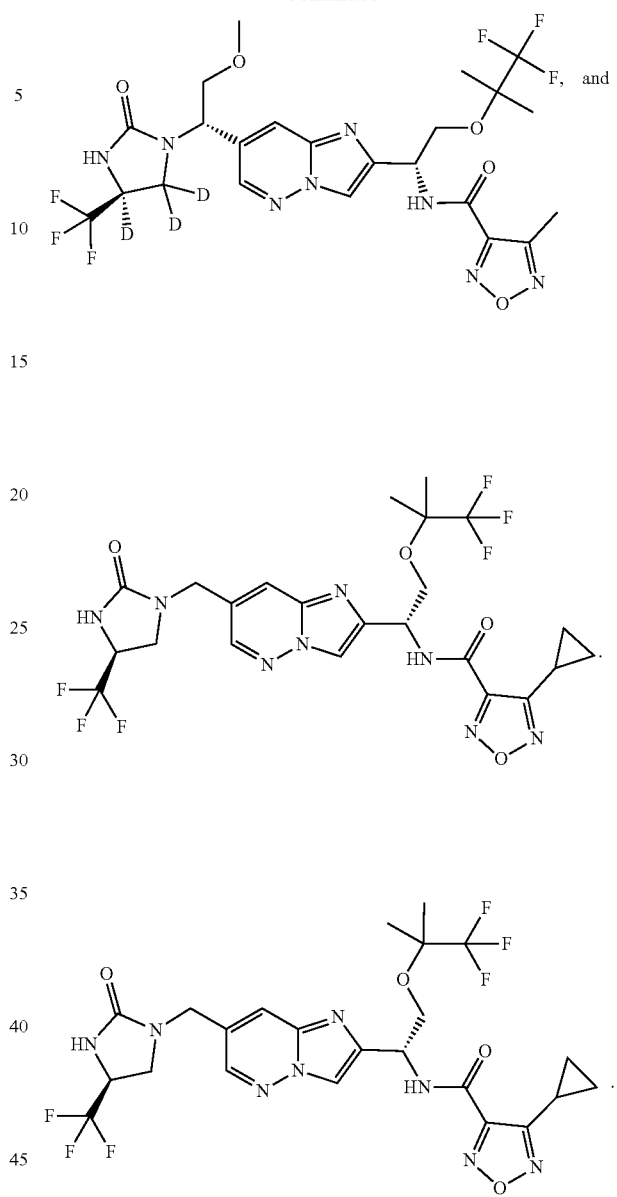
In some embodiments, disclosed herein is a compound of Formula I, or a pharmaceutically acceptable salt thereof, selected from the group consisting of:
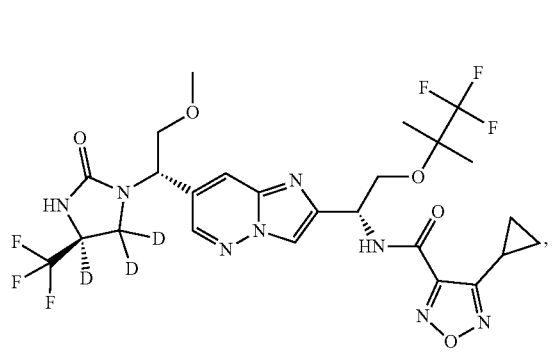
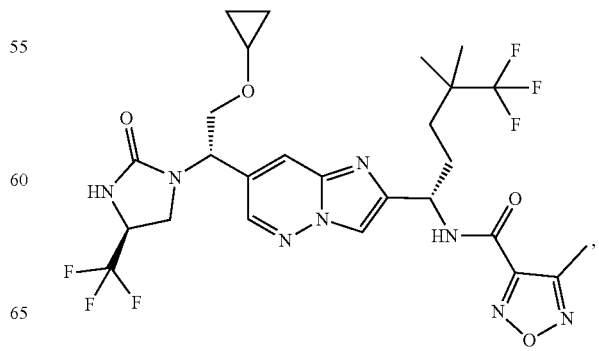

-continued

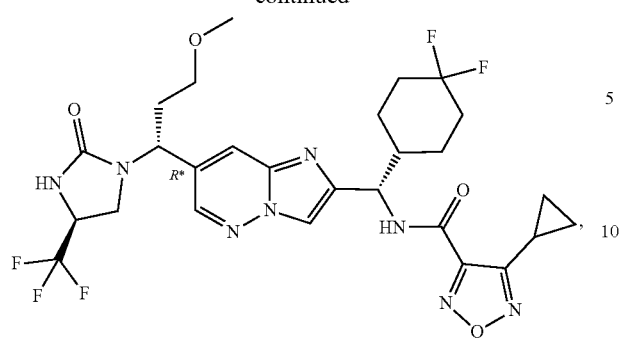

In some embodiments, disclosed herein is a compound of Formula I, or a pharmaceutically acceptable salt thereof, having the following structure:

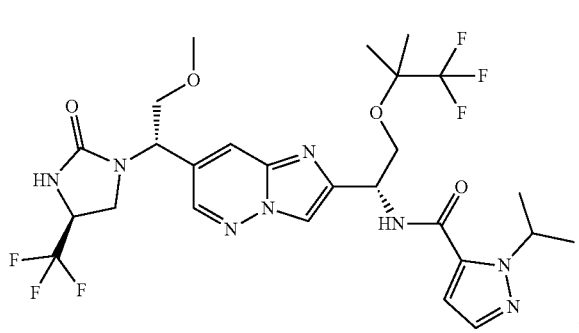

In some embodiments, disclosed herein is a compound of Formula I, or a pharmaceutically acceptable salt thereof, having the following structure:

In some embodiments, disclosed herein is a compound of Formula I, or a pharmaceutically acceptable salt thereof, having the following structure:

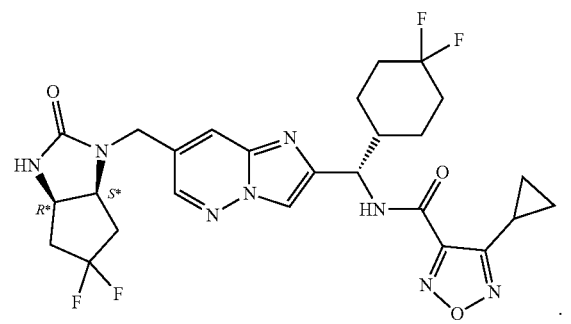

In some embodiments, disclosed herein is a compound of Formula I, or a pharmaceutically acceptable salt thereof, having the following structure:

In some embodiments, disclosed herein is a compound of Formula I, or a pharmaceutically acceptable salt thereof, having the following structure:

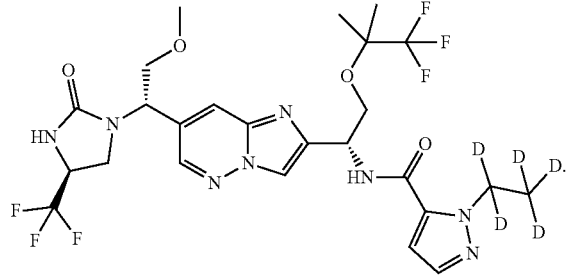

In some embodiments, disclosed herein is a compound of Formula I, or a pharmaceutically acceptable salt thereof, having the following structure:

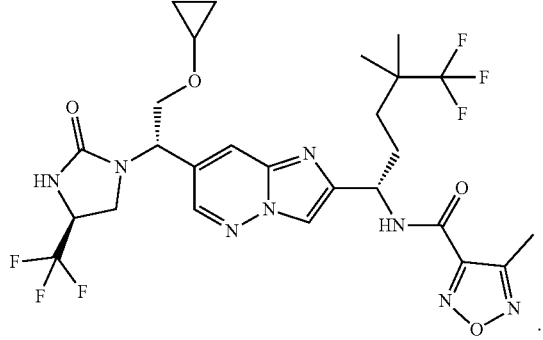

In some embodiments, disclosed herein is a compound of Formula I, or a pharmaceutically acceptable salt thereof, having the following structure:

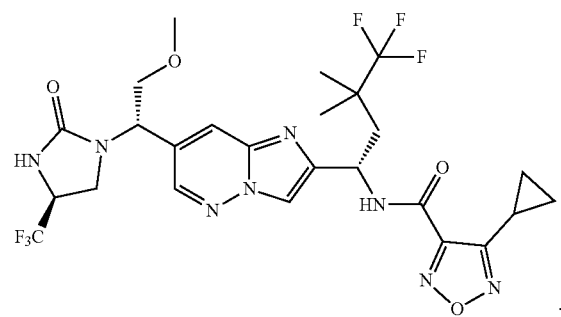 [SMILES: COC[C@H](c1cnn2cc([C@H](CC(C)(C)C(F)(F)F)NC(=O)c3nonc3C3CC3)nc2c1)N1C[C@@H](C(F)(F)F)NC1=O]

In some embodiments, disclosed herein is a compound of Formula I, or a pharmaceutically acceptable salt thereof, having the following structure:

In some embodiments, disclosed herein is a compound of Formula I, or a pharmaceutically acceptable salt thereof, having the following structure:

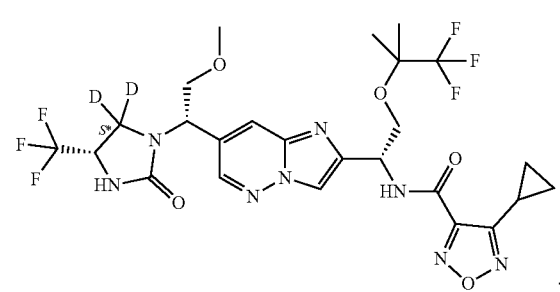 [SMILES: [2H]C1([2H])[C@@H](C(F)(F)F)NC(=O)N1[C@H](COC)c1cnn2cc([C@H](COC(C)(C)C(F)(F)F)NC(=O)c3nonc3C3CC3)nc2c1]

In some embodiments, disclosed herein is a compound of Formula I, or a pharmaceutically acceptable salt thereof, having the following structure:

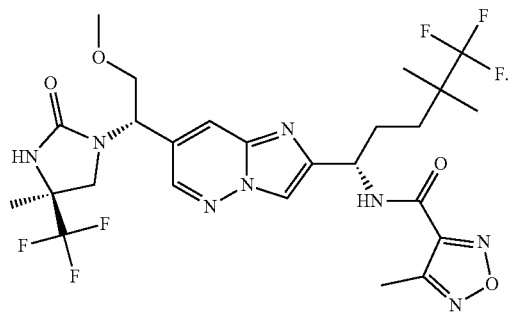 [SMILES: COC[C@H](c1cnn2cc([C@H](CCC(C)(C)C(F)(F)F)NC(=O)c3nonc3C)nc2c1)N1C[C@@](C)(C(F)(F)F)NC1=O]

In some embodiments, disclosed herein is a compound of Formula I, or a pharmaceutically acceptable salt thereof, having the following structure:

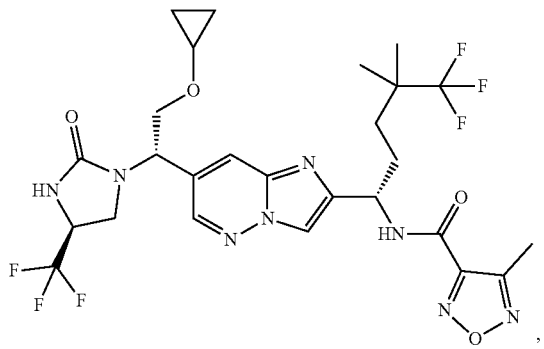 [SMILES: Cc1nonc1C(=O)N[C@@H](CCC(C)(C)C(F)(F)F)c1cn2ncc([C@@H](COC3CC3)N3C[C@@H](C(F)(F)F)NC3=O)cc2n1]

In some embodiments, disclosed herein is a compound of Formula I, or a pharmaceutically acceptable salt thereof, having the following structure:

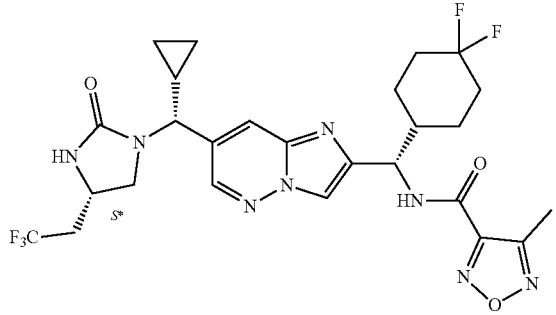

In some embodiments, disclosed herein is a compound of Formula I, or a pharmaceutically acceptable salt thereof, having the following structure:

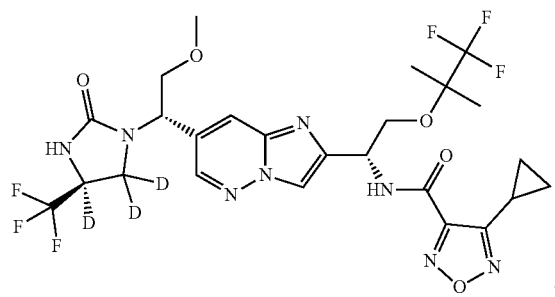 [SMILES: [2H]C1([2H])N([C@H](COC)c2cnn3cc([C@H](COC(C)(C)C(F)(F)F)NC(=O)c4nonc4C4CC4)nc3c2)C(=O)N[C@]1([2H])C(F)(F)F]

In some embodiments, disclosed herein is a compound of Formula I, or a pharmaceutically acceptable salt thereof, having the following structure:

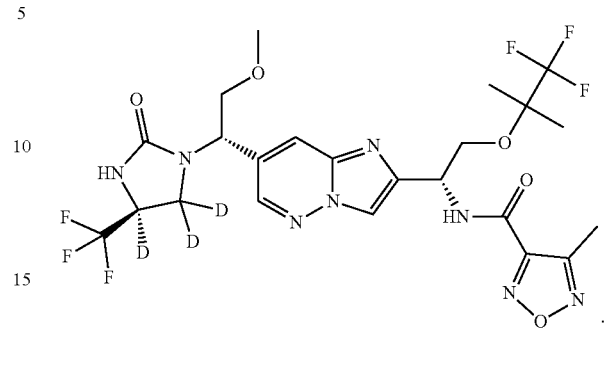

In some embodiments, disclosed herein is a compound of Formula I, or a pharmaceutically acceptable salt thereof, having the following structure:

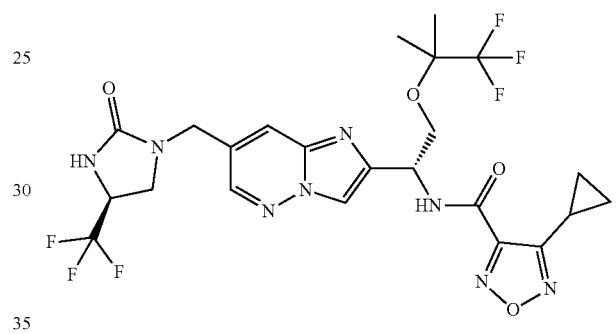

In some embodiments, disclosed herein is a compound of Formula I, or a pharmaceutically acceptable salt thereof, having a structure as shown in Tables 2A, 2B, and 2C.

TABLE 2A

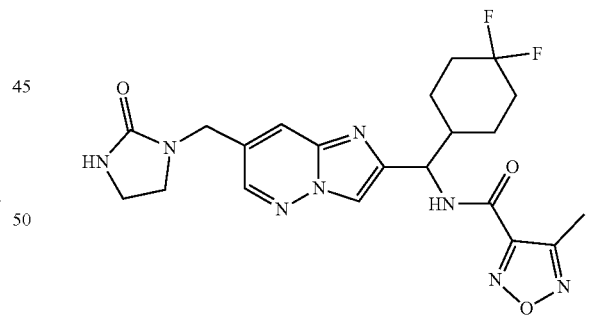

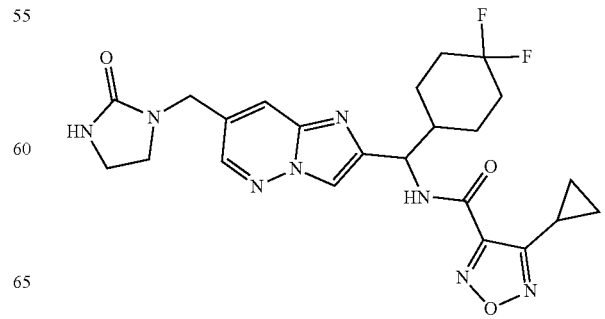

TABLE 2A-continued
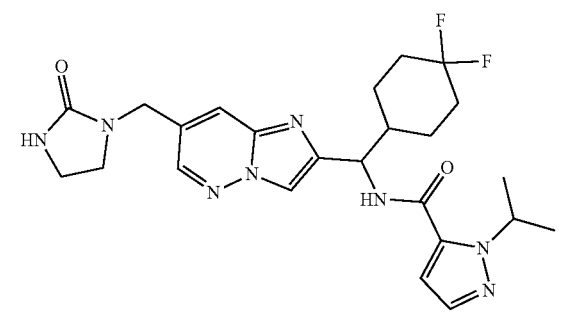 [SMILES: CC(C)n1nccc1C(=O)NC(c1cn2ncc(CN3CCNC3=O)cc2n1)C1CCC(F)(F)CC1]
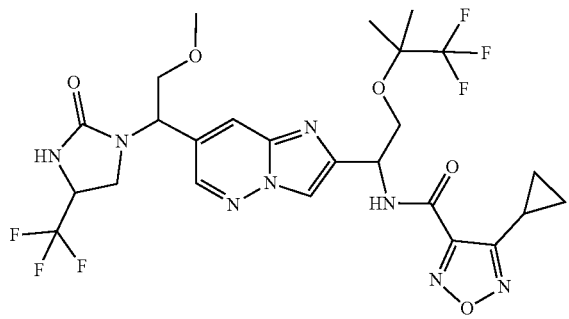 [SMILES: COCC(c1cnn2cc(C(COC(C)(C)C(F)(F)F)NC(=O)c3nonc3C3CC3)nc2c1)N1CC(C(F)(F)F)NC1=O]
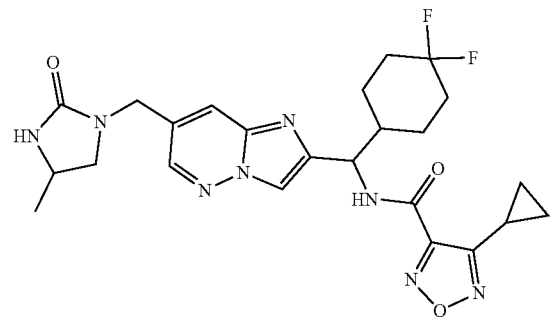 [SMILES: CC1CN(Cc2cnn3cc(C(NC(=O)c4nonc4C4CC4)C4CCC(F)(F)CC4)nc3c2)C(=O)N1]
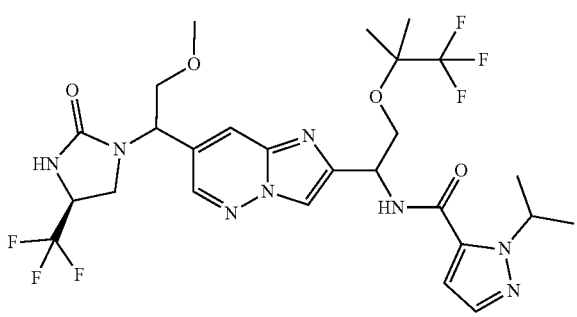 [SMILES: COCC(c1cnn2cc(C(COC(C)(C)C(F)(F)F)NC(=O)c3ccnn3C(C)C)nc2c1)N1C[C@@H](C(F)(F)F)NC1=O]
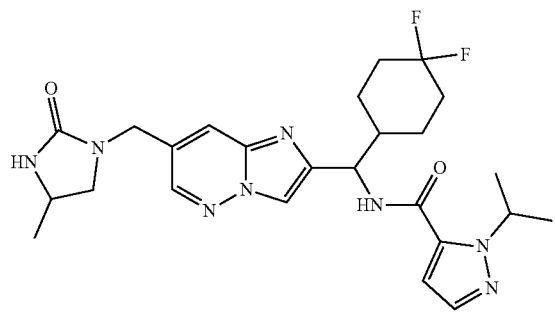 [SMILES: CC1CN(Cc2cnn3cc(C(NC(=O)c4ccnn4C(C)C)C4CCC(F)(F)CC4)nc3c2)C(=O)N1]
TABLE 2A-continued
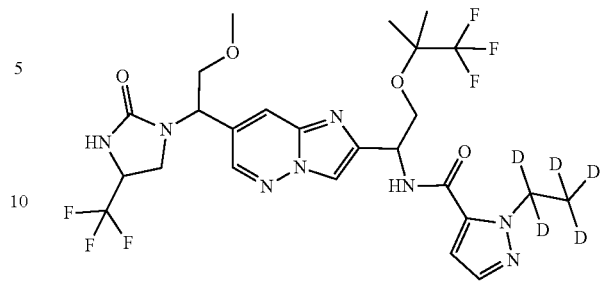
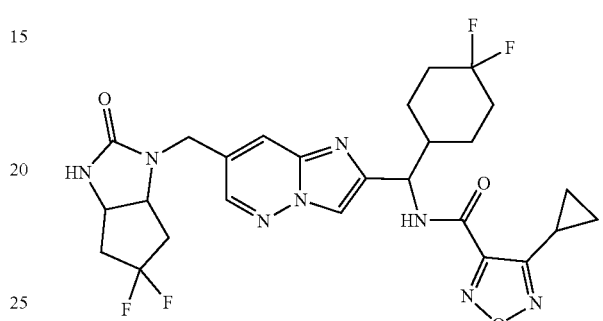
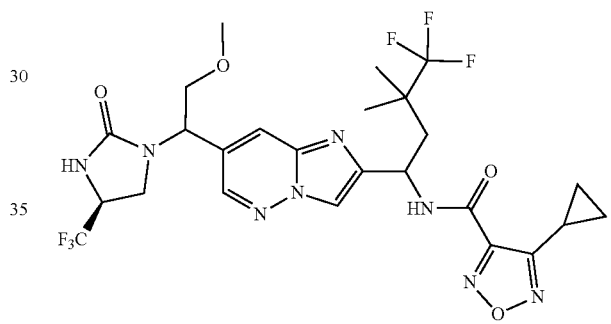
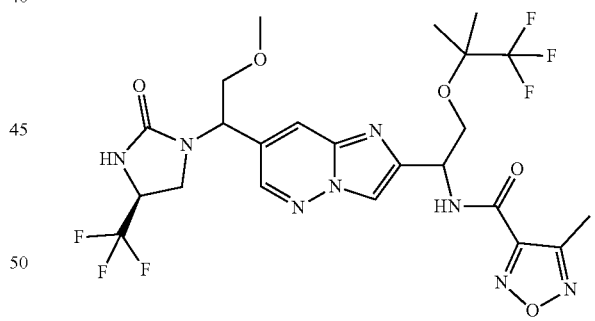
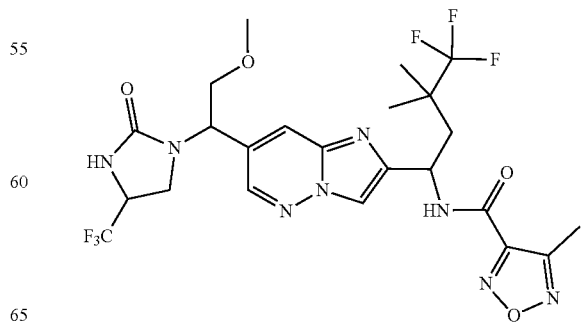

TABLE 2A-continued
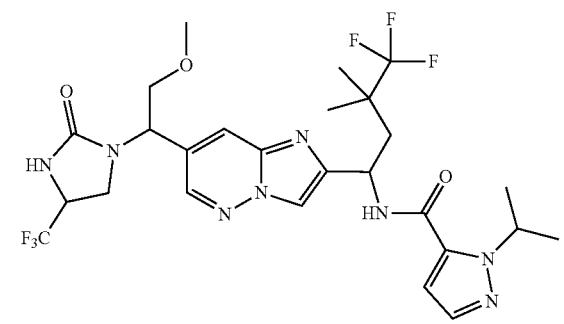 [SMILES: COCC(c1cnn2cc(C(CC(C)(C)C(F)(F)F)NC(=O)c3ccnn3C(C)C)nc2c1)N1CC(C(F)(F)F)NC1=O]
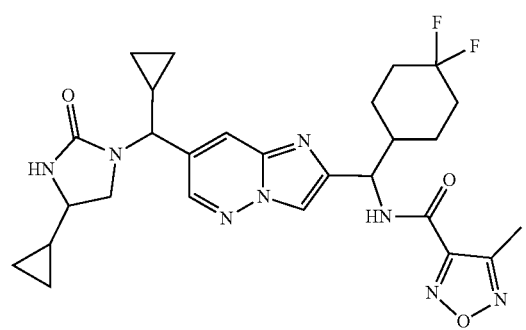 [SMILES: Cc1nonc1C(=O)NC(c1cn2ncc(C(C3CC3)N3CC(C4CC4)NC3=O)cc2n1)C1CCC(F)(F)CC1]
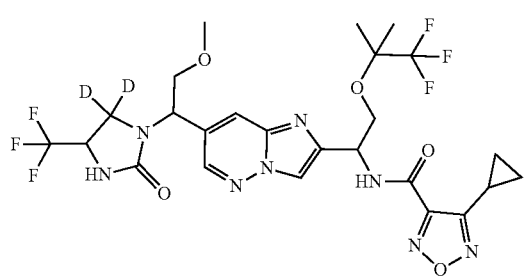 [SMILES: [2H]C1([2H])C(C(F)(F)F)NC(=O)N1C(COC)c1cnn2cc(C(COC(C)(C)C(F)(F)F)NC(=O)c3nonc3C3CC3)nc2c1]
TABLE 2B
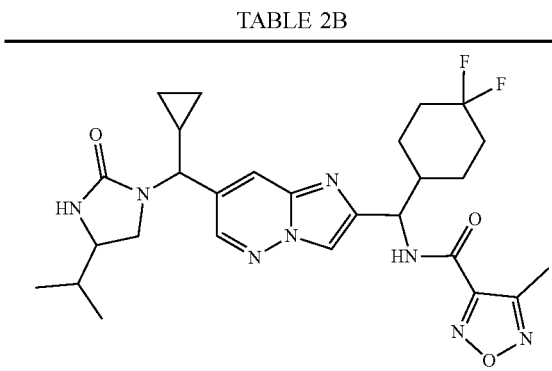
TABLE 2B-continued
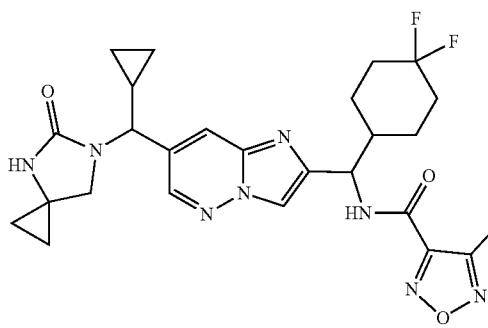
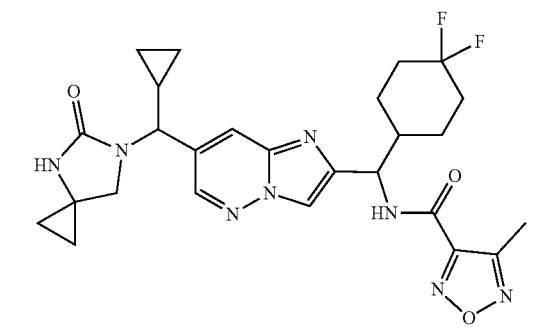 [SMILES: Cc1nonc1C(=O)NC(c1cn2ncc(C(C3CC3)N3CC4(CC4)NC3=O)cc2n1)C1CCC(F)(F)CC1]
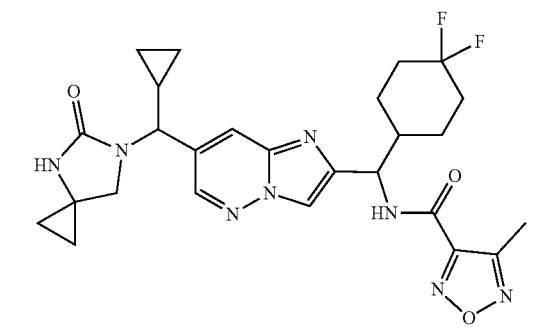 [SMILES: Cc1nonc1C(=O)NC(c1cn2ncc(C(C3CC3)N3CC4(CC4)NC3=O)cc2n1)C1CCC(F)(F)CC1]
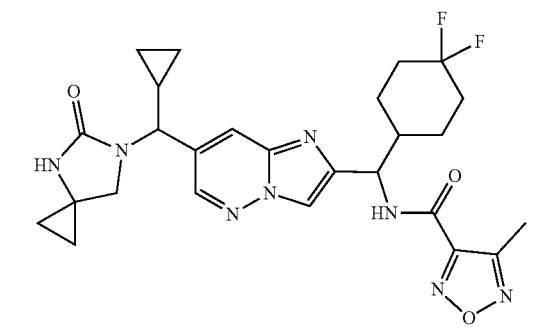 [SMILES: Cc1nonc1C(=O)NC(c1cn2ncc(C(C3CC3)N3CC4(CC4)NC3=O)cc2n1)C1CCC(F)(F)CC1]
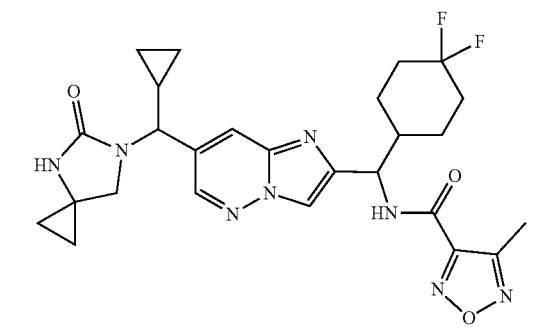 [SMILES: Cc1nonc1C(=O)NC(c1cn2ncc(C(C3CC3)N3CC4(CC4)NC3=O)cc2n1)C1CCC(F)(F)CC1]

TABLE 2B-continued
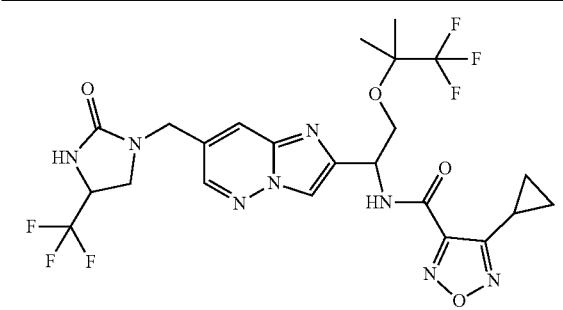
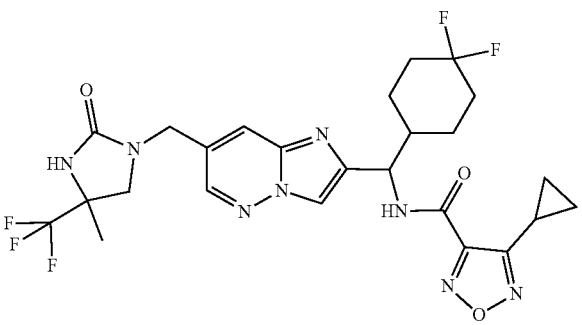 [SMILES: CC1(C(F)(F)F)CN(Cc2cnn3cc(C(NC(=O)c4nonc4C4CC4)C4CCC(F)(F)CC4)nc3c2)C(=O)N1]
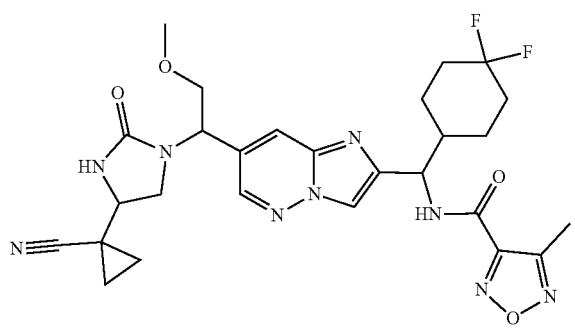 [SMILES: COCC(c1cnn2cc(C(NC(=O)c3nonc3C)C3CCC(F)(F)CC3)nc2c1)N1CC(C2(C#N)CC2)NC1=O]
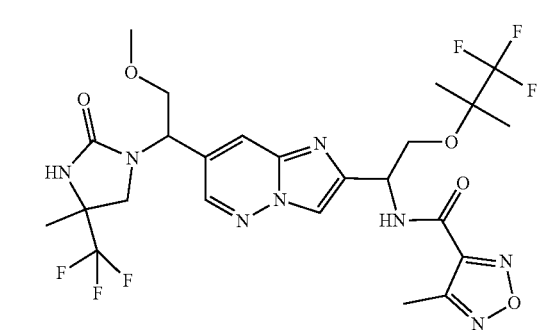 [SMILES: COCC(c1cnn2cc(C(COC(C)(C)C(F)(F)F)NC(=O)c3nonc3C)nc2c1)N1CC(C)(C(F)(F)F)NC1=O]
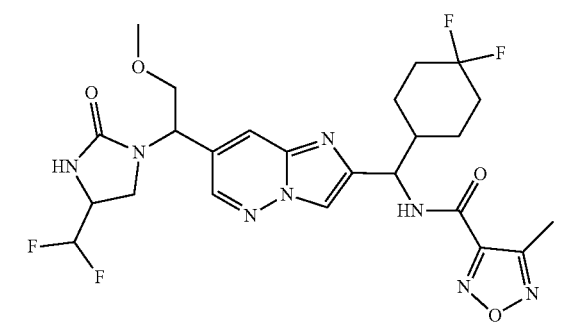 [SMILES: COCC(c1cnn2cc(C(NC(=O)c3nonc3C)C3CCC(F)(F)CC3)nc2c1)N1CC(C(F)F)NC1=O]
TABLE 2B-continued
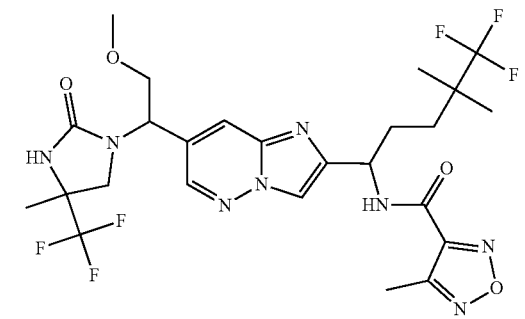 [SMILES: COCC(c1cnn2cc(C(CCC(C)(C)C(F)(F)F)NC(=O)c3nonc3C)nc2c1)N1CC(C)(C(F)(F)F)NC1=O]
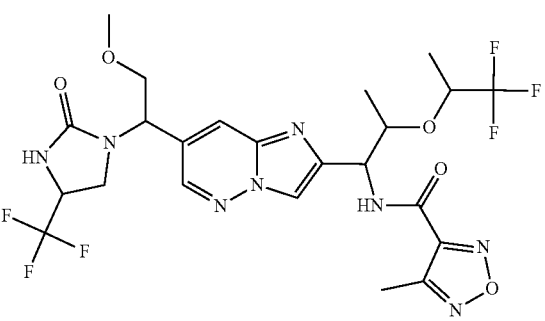 [SMILES: COCC(c1cnn2cc(C(NC(=O)c3nonc3C)C(C)OC(C)C(F)(F)F)nc2c1)N1CC(C(F)(F)F)NC1=O]
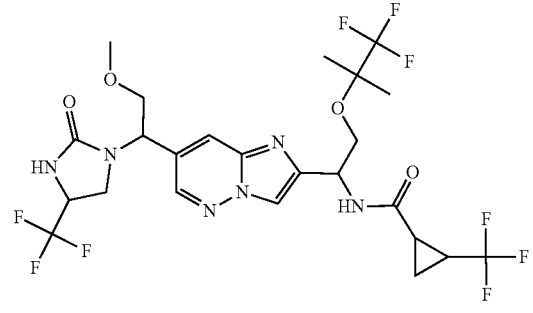 [SMILES: COCC(c1cnn2cc(C(COC(C)(C)C(F)(F)F)NC(=O)C3CC3C(F)(F)F)nc2c1)N1CC(C(F)(F)F)NC1=O]
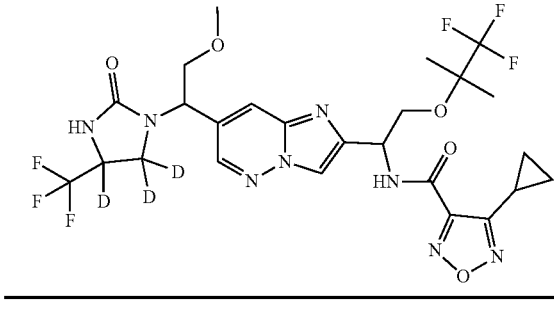
TABLE 2C
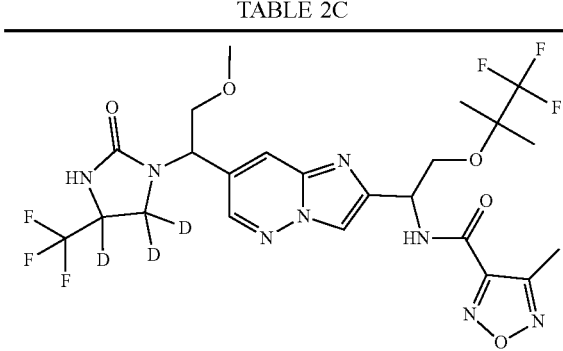

TABLE 2C-continued
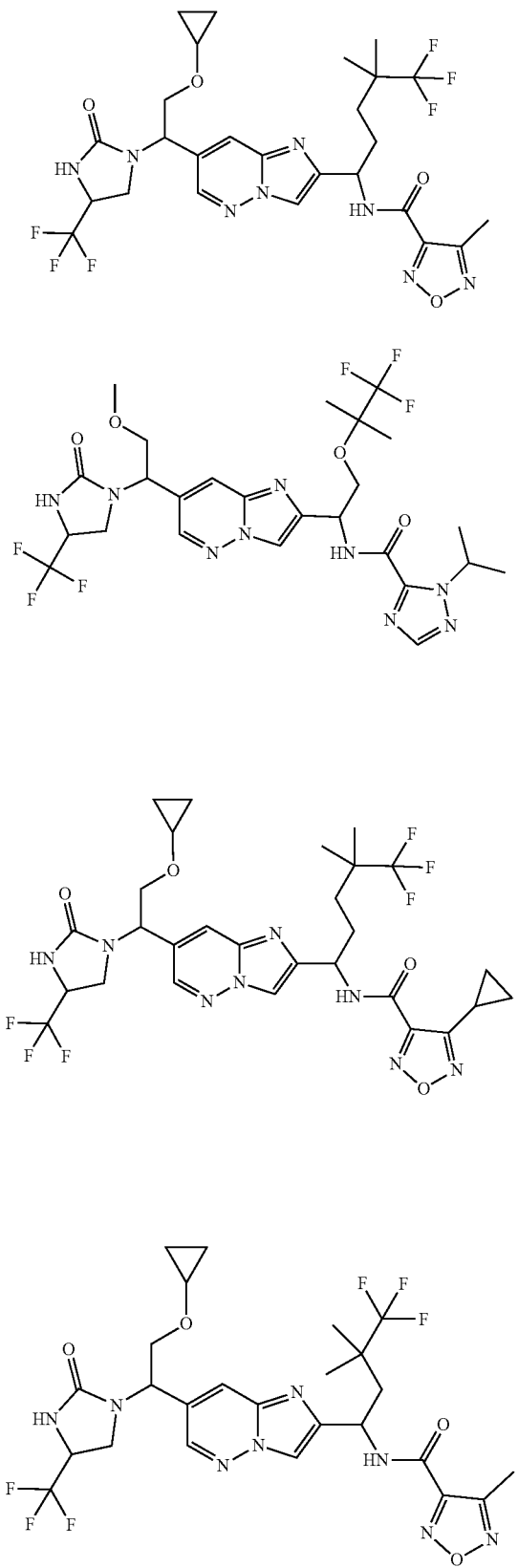
TABLE 2C-continued
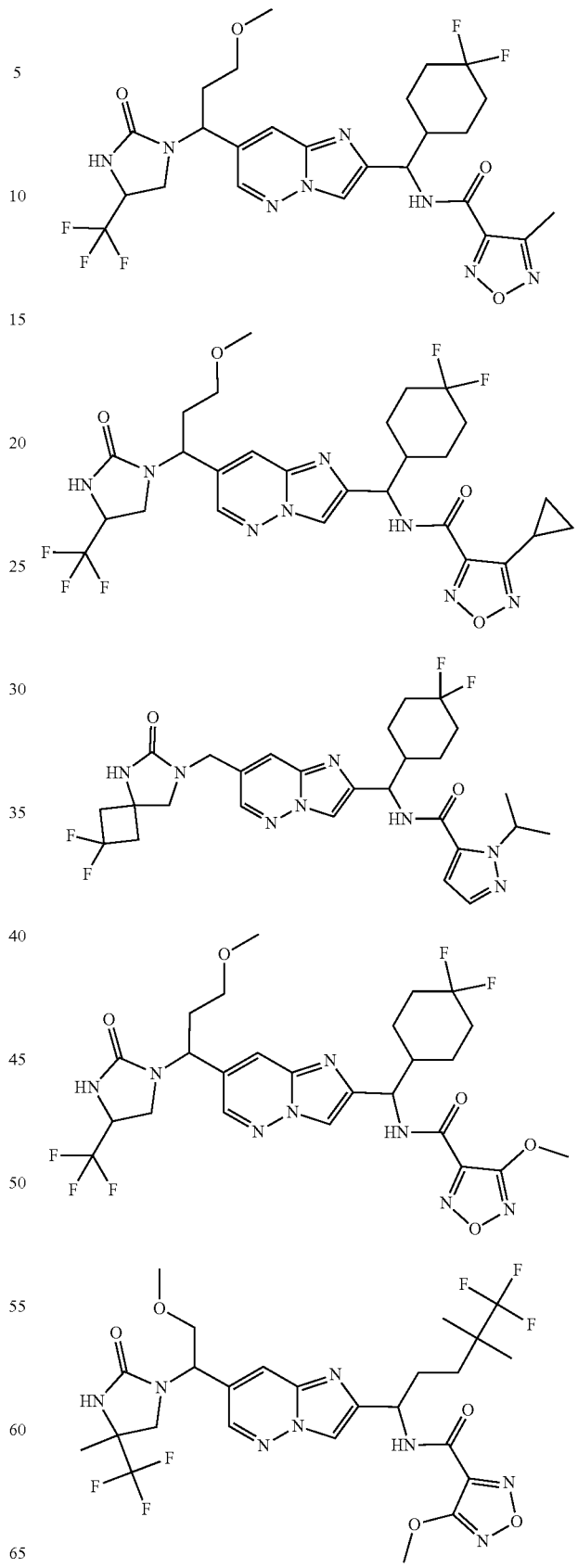

TABLE 2C-continued

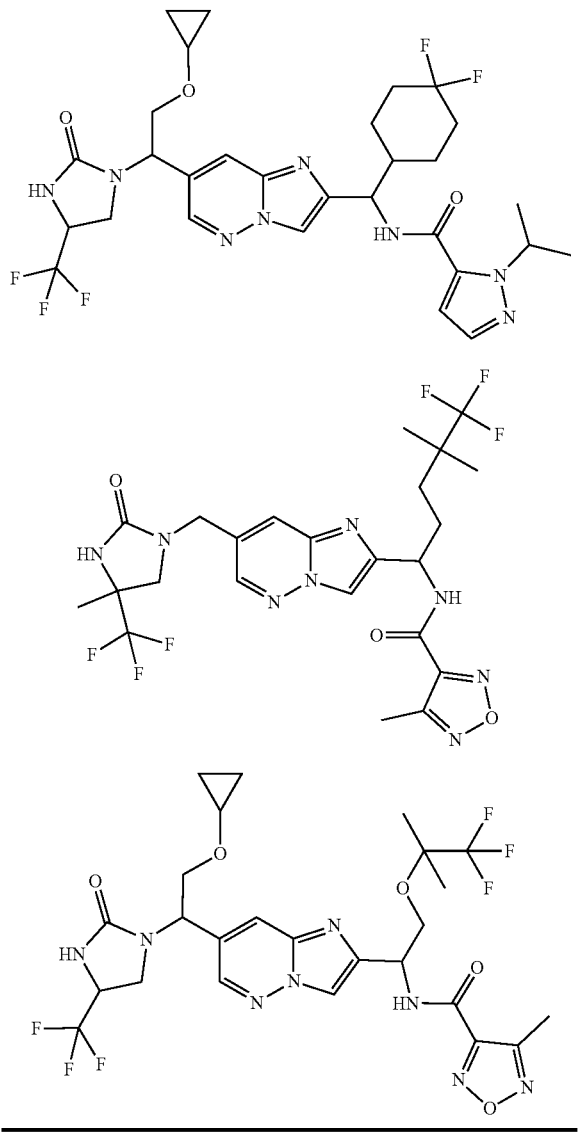

In some embodiments, disclosed herein is a pharmaceutical composition, comprising a compound of Formula I, or a pharmaceutically acceptable salt thereof, and a pharmaceutically acceptable carrier. In some embodiments, the pharmaceutical composition is formulated for oral administration (e.g., a tablet or capsule).

In some embodiments, disclosed herein is a pharmaceutical composition made by mixing a compound of Formula I, or a pharmaceutically acceptable salt thereof, and a pharmaceutically acceptable carrier.

In some embodiments, disclosed herein is a process for making a pharmaceutical composition comprising mixing a compound of Formula I, or a pharmaceutically acceptable salt thereof, and a pharmaceutically acceptable carrier.

III. Therapeutic Use

The present application is also directed to a method for treating and/or ameliorating an IL-17 mediated inflammatory syndrome, disorder or disease comprising administering to a subject in need thereof an effective amount of a compound of Formula I, or pharmaceutically acceptable salt thereof, composition thereof, or medicament thereof.

In some embodiments, disclosed herein is a method for treating or ameliorating an IL-17A mediated inflammatory syndrome, disorder, or disease comprising administering to a subject in need thereof a therapeutically effective amount of a compound of Formula I, or a pharmaceutically acceptable salt thereof.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is psoriasis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is psoriatic arthritis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is rheumatoid arthritis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is ankylosing spondylitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is hidradenitis suppurativa.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is bullous pemphigoid.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is atopic dermatitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is vitiligo.

In some embodiments, disclosed herein is a method for treating or ameliorating and/an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is multiple sclerosis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is asthma.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is uveitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is chronic obstructive pulmonary disorder.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is multiple myeloma.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus, wherein the compound of Formula I or the pharmaceutically acceptable salt thereof is administered orally (e.g., as a tablet or capsule).

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus, wherein the therapeutically effective amount is a dose of about 10 mg to 300 mg QD. In some embodiments, the therapeutically effective amount is a dose of about 20 mg to 200 mg QD. In some embodiments, the therapeutically effective amount is a dose of about 50 mg to 100 mg QD.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus, wherein the therapeutically effective amount is a dose of about 10 mg to 300 mg BID. In some embodiments, the therapeutically effective amount is a dose of about 20 mg to 200 mg BID. In some embodiments, the therapeutically effective amount is a dose of about 50 mg to 100 mg BID.

In some embodiments, disclosed herein is the use of a therapeutically effective amount of compound of Formula I, or a pharmaceutically acceptable salt thereof, for treating and/or ameliorating an IL-17A mediated inflammatory syndrome, disorder, or disease selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus.

In some embodiments, disclosed herein is the use of a compound of Formula I, or pharmaceutically acceptable salt thereof, in the manufacture of a medicament for treating and/or ameliorating an IL-17A mediated inflammatory syndrome, disorder, or disease selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus.

In some embodiments, disclosed herein is a method for treating and/or ameliorating an IL-17 mediated inflammatory syndrome, disorder or disease comprising administering to a subject in need thereof a therapeutically effective amount of a compound of Formula I, or pharmaceutically acceptable salt thereof, a composition thereof, or a medicament thereof.

In some embodiments, disclosed herein is a method of treating and/or ameliorating an IL-17 mediated inflammatory syndrome, disorder or disease, wherein the syndrome, disorder or disease is selected from the group consisting of: psoriasis, psoriatic arthritis, rheumatoid arthritis, ankylosing spondylitis, hidradenitis suppurativa, atopic dermatitis, vitiligo, multiple sclerosis, asthma, allergic asthma, steroid resistant asthma, neutrophilic asthma, chronic obstructive pulmonary disease, uveitis, multiple myeloma, and systemic lupus erythematosus, comprising administering to a subject in need thereof a therapeutically effective amount of a compound of Formula I, or pharmaceutically acceptable salt thereof, a composition thereof, or a medicament thereof.

In some embodiments, disclosed herein is a method of treating or ameliorating an IL-17 mediated inflammatory syndrome, disorder or disease, wherein the syndrome, disorder or disease is selected from the group consisting of: psoriasis, psoriatic arthritis, and ankylosing spondylitis, comprising administering to a subject in need thereof a therapeutically effective amount of a compound of Formula I, or pharmaceutically acceptable salt thereof, a composition thereof, or a medicament thereof.

In some embodiments, disclosed herein are methods of modulating IL-17 activity in a mammal by administration of a therapeutically effective amount of at least one compound of Formula I, or pharmaceutically acceptable salt thereof.

Also disclosed herein is a method of inhibiting production of interleukin-17, comprising administering to a subject in need thereof a therapeutically effective amount of a compound of Formula I, or pharmaceutically acceptable salt thereof.

IV. Combination Therapy

A compound of Formula I, or pharmaceutically acceptable salt thereof, a composition thereof, or a medicament thereof may also be used in combination with one or more additional therapeutic agents.

In some embodiments, the one or more additional therapeutic agents is selected from the group consisting of anti-inflammatory agents, immunomodulatory agents, and immunosuppressive agents.

In some embodiments, the one or more additional therapeutic agents is selected from the group consisting of: anti-TNFalpha agents such as infliximab (Remicade®), adalimumab (Humira®), certolizumab pegol (Cimzia®), golimumab (Simponi®), etanercept (Enbrel®), thalidomide (Immunoprin®), lenalidomide (Revlimid®), and pomalidomide (Pomalyst®/Imnovid®); anti-p40 antibody agents such as ustekinumab (Stelara®); and anti-p19 antibody agents such as guselkumab (Tremfya®), tildrakizumab (Ilumya™/Ilumetri), risankizumab (Skyrizi™), and mirikizumab.

In some embodiments, disclosed herein is a method of treating and/or ameliorating an IL-17 mediated inflammatory syndrome, disorder or disease, in a subject in need thereof comprising administering to the subject a therapeutically effective amount of the compound of Formula I, or pharmaceutically acceptable salt thereof, composition thereof, or medicament thereof in a combination therapy with one or more additional therapeutic agents, such as anti-inflammatory agents, immunomodulatory agents, or immunosuppressive agents, wherein said syndrome, disorder or disease is selected from the group consisting of psoriasis, psoriatic arthritis, rheumatoid arthritis, ankylosing spondylitis, hidradenitis suppurativa, atopic dermatitis, vitiligo, multiple sclerosis, asthma, allergic asthma, steroid resistant asthma, neutrophilic asthma, chronic obstructive pulmonary disease, uveitis, multiple myeloma, and systemic lupus erythematosus.

In some embodiments, disclosed herein is a method of treating and/or ameliorating an IL-17 mediated inflammatory syndrome, disorder or disease, in a subject in need thereof comprising administering to the subject a therapeutically effective amount of the compound of Formula I, or pharmaceutically acceptable salt thereof, composition thereof, or medicament thereof in a combination therapy with one or more additional therapeutic agents, such as anti-inflammatory agents, or immunosuppressive agents, wherein said syndrome, disorder or disease is psoriasis, psoriatic arthritis, ankylosing spondylitis. In some embodiments, the IL-17 mediated inflammatory syndrome, disorder or disease is psoriasis. In some embodiments, the IL-17 mediated inflammatory syndrome, disorder or disease is psoriatic arthritis. In some embodiments, the IL-17 mediated inflammatory syndrome, disorder or disease is ankylosing spondylitis.

Dosage Regimen

When employed as IL-17A modulators, the compounds disclosed herein may be administered in an effective amount within the dosage range of about 0.5 mg to about 1 g, preferably between about 0.5 mg to about 500 mg, in single or divided daily doses. In some embodiments, the dosage amount is about 5 mg to 400 mg. In some embodiments, the dosage amount is about 10 mg to 300 mg. In some embodiments, the dosage amount is about 0.5, 1, 5, 10, 15, 20, 25, 30, 35, 40, 45, 50, 55, 60, 65, 70, 75, 80, 85, 90, 95, or 100 mg of a compound of Formula I, or pharmaceutically acceptable salt thereof. In some embodiments, the dosage amount is about 100, 105, 110, 115, 120, 125, 130, 135, 140, 145, 150, 155, 160, 165, 170, 175, 180, 185, 190, 195, or 200 mg of a compound of Formula I, or pharmaceutically acceptable salt thereof. In some embodiments, the dosage amount is about 200, 205, 210, 215, 220, 225, 230, 235, 240, 245, 250, 255, 260, 265, 270, 275, 280, 285, 290, 295, or 300 mg of a compound of Formula I, or pharmaceutically acceptable salt thereof. In some embodiments, the dosage amount is about 300, 315, 320, 325, 330, 335, 340, 345, 350, 355, 360, 365, 370, 375, 380, 385, 390, 395, or 400 mg of a compound of Formula I, or pharmaceutically acceptable salt thereof. In some embodiments, the dosage amount is about 400, 405, 410, 415, 420, 425, 430, 435, 440, 445, 450, 455, 460, 465, 470, 475, 480, 485, 490, 495, or 500 mg of a compound of Formula I, or pharmaceutically acceptable salt thereof.

In some embodiments, a compound of Formula I, or pharmaceutically acceptable salt thereof, may be administered in an effective amount within the dosage range of about 10 mg to 300 mg QD. In some embodiments, a compound of Formula I, or pharmaceutically acceptable salt thereof, may be administered in an effective amount within the dosage range of about 20 mg to 200 mg QD. In some embodiments, a compound of Formula I, or pharmaceutically acceptable salt thereof, may be administered in an effective amount within the dosage range of about 50 mg to 100 mg QD.

In some embodiments, a compound of Formula I, or pharmaceutically acceptable salt thereof, may be administered in an effective amount within the dosage range of about 10 mg to 300 mg BID. In some embodiments, a compound of Formula I, or pharmaceutically acceptable salt thereof, may be administered in an effective amount within the dosage range of about 20 mg to 200 mg BID. In some embodiments, a compound of Formula I, or pharmaceutically acceptable salt thereof, may be administered in an effective amount within the dosage range of about 50 mg to 100 mg BID.

The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Pharmaceutical Compositions

The compounds of Formula I, or pharmaceutically acceptable salt thereof, may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, topical, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

Also disclosed herein is a method of making a pharmaceutical composition comprising mixing a pharmaceutically acceptable carrier with any of the compounds of Formula I, or pharmaceutically acceptable salt thereof. Additionally, the present application includes pharmaceutical compositions made by mixing a pharmaceutically acceptable carrier with any of the compounds of the present invention.

EXAMPLES

Abbreviations

Herein and throughout the application, the following abbreviations may be used.

Å angstrom
Ac acetyl
atm atmosphere
Boc tert-butoxycarbonyl
CDI 1,1'-carbonyldiimidazole
δ NMR chemical shift in parts per million downfield from a standard
d doublet
DCE 1,2-dichloroethane
DCM dichloromethane
DEAD diethyl azodicarboxylate
DIPEA N,N-diisopropylethylamine (Hünig's base)
DMA N,N-dimethylacetamide
DMAP 4-dimethylaminopyridine
DMF N,N-dimethylformamide
DMSO dimethyl sulfoxide
EDCI 1-ethyl-3-(3-dimethylaminopropyl)carbodiimide
ESI electrospray ionization
Et ethyl
EtOAc ethyl acetate
g gram(s)
h hour(s)
HATU 1-[bis(dimethylamino)methylene]-1H-1,2,3-triazolo[4,5-b]pyridinium 3-oxide hexafluorophosphate
$HOB_t$ 1-hydroxybenzotriazole hydrate
HPLC high pressure liquid chromatography
Hz Hertz IPA isopropanol
J coupling constant (NMR spectroscopy)
L liter(s)
LAH lithium aluminum hydride
LC liquid chromatography
m milli or multiplet
m/z mass-to-charge ratio
M+ parent molecular ion
M molar (moles/liter)
Me methyl
MeCN acetonitrile
min minute(s)
μ micro
MS molecular sieves or mass spectrometry
MOM methoxymethyl
MTBE methyl tert-Butyl ether
N normal (equivalent concentration)
NMP N-methylpyrrolidine
NMR nuclear magnetic resonance
Pearlman's catalyst palladium hydroxide on activated charcoal
PPTS pyridinium p-toluenesulfonate
Pr propyl
rac racemic
rt room temperature
RuPhos Pd G3 (2-dicyclohexylphosphino-2',6'-diisopropoxy-1,1'-biphenyl)[2-(2'-amino-1,1'-biphenyl)]palladium(II) methanesulfonate
s singlet
SFC supercritical fluid chromatography
spt septet
t triplet
$T_3P$ 1-propanephosphonic anhydride
TEA triethylamine
tert tertiary
Tf trifluoromethanesulfonate
TFA trifluoroacetic acid
TFE 2,2,2-trifluoroethanol
THF tetrahydrofuran
TMP 2,2,6,6-tetramethylpiperidine
TMS trimethylsilyl
wt weight In some embodiments, provided herein are processes and intermediates disclosed herein that are useful for preparing a compound of the disclosure or pharmaceutically acceptable salts thereof.

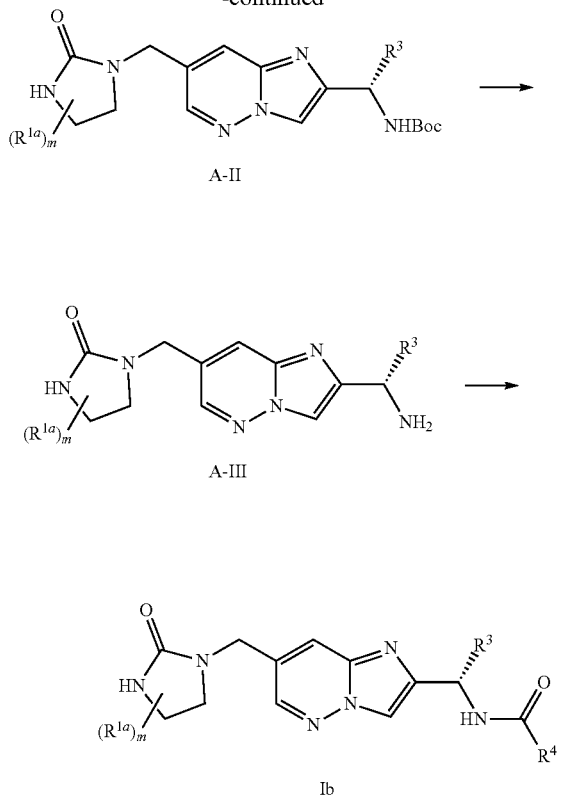

Compounds of formula I can be prepared as shown in Scheme 1. Aldehydes A-I can undergo reductive amination with diamines C-Ia. Aldehydes A-I can be treated with diamines C-Ia, such as ethylene diamine, and a reducing agent such as $NaCNBH_3$ in a solvent such as methanol in the presence of additives such as acetic acid. The resulting adducts (structures not shown) are treated with a reagent such as triphosgene or CDI in a solvent such as DCM or THF to afford the corresponding cyclic ureas A-II. Alternatively, Boc protected diamines C-Ib, such as tert-Butyl (S)-(1-aminopropan-2-yl)carbamate, can undergo reductive amination using the conditions listed above. In a second step, cyclization of the resulting reductive amination adducts (structure not shown) to the urea using reagents such as potassium tert-pentoxide in solvents such as tert-amyl alcohol affords the corresponding ureas A-II. Compounds A-II can be treated with an acid such as TFA in a solvent such as DCM to afford compounds A-III. These conditions are herein known as "Boc deprotection conditions". Amide bond formation between amines A-III and carboxylic acids ($R^4CO_2H$) can be achieved through the use of a coupling agent, such as HATU or EDCI, in the presence of a base, such as DIPEA, in a solvent, such as DMF, MeCN, or DCM, with or without an additive, such as HOBt and DIPEA, to yield compounds I. Alternatively, amide bond formation can be achieved by treatment of amines A-III with a reagent such as a carboxylic acid chloride ($R^4CO_2Cl$) in the presence of additives such as DIPEA or DMAP in solvents such as DCM or THF to yield compounds of formula I. In addition, amines A-III can be treated with N-hydroxysuccinate esters in the presence of reagents such as DIPEA in a solvent such as acetonitrile to provide compounds of formula I. These conditions are herein known as "amide bond formation conditions".

Scheme 2

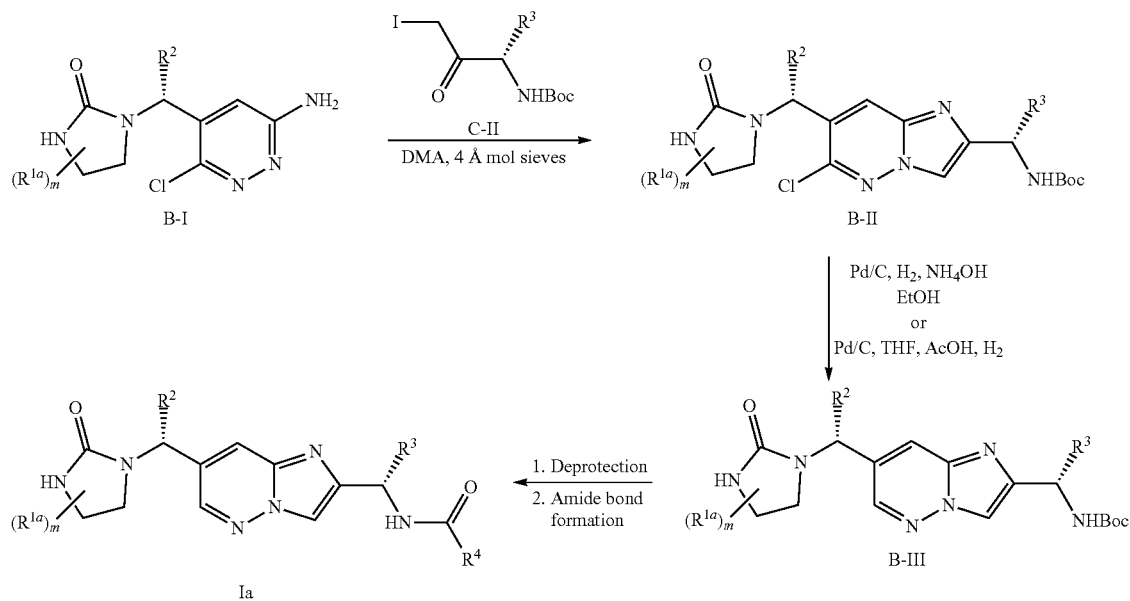

Compounds Ia may be prepared as shown in Scheme 2. Cyclocondensation of aminopyridazines B—I with iodoketones C-II in a solvent such as DMA in the presence of 4 Å molecular sieves affords compounds B-II. Hydrogenation using palladium catalysis in the presence of hydrogen gas and ammonium hydroxide in ethanol, or in the presence of hydrogen gas and acetic acid in a solvent such as THF then yields compounds B—III. Deprotection of compound B—III using "Boc deprotection conditions" and subsequent amide bond formation using amide bond formation conditions yields compounds Ia.

Scheme 3

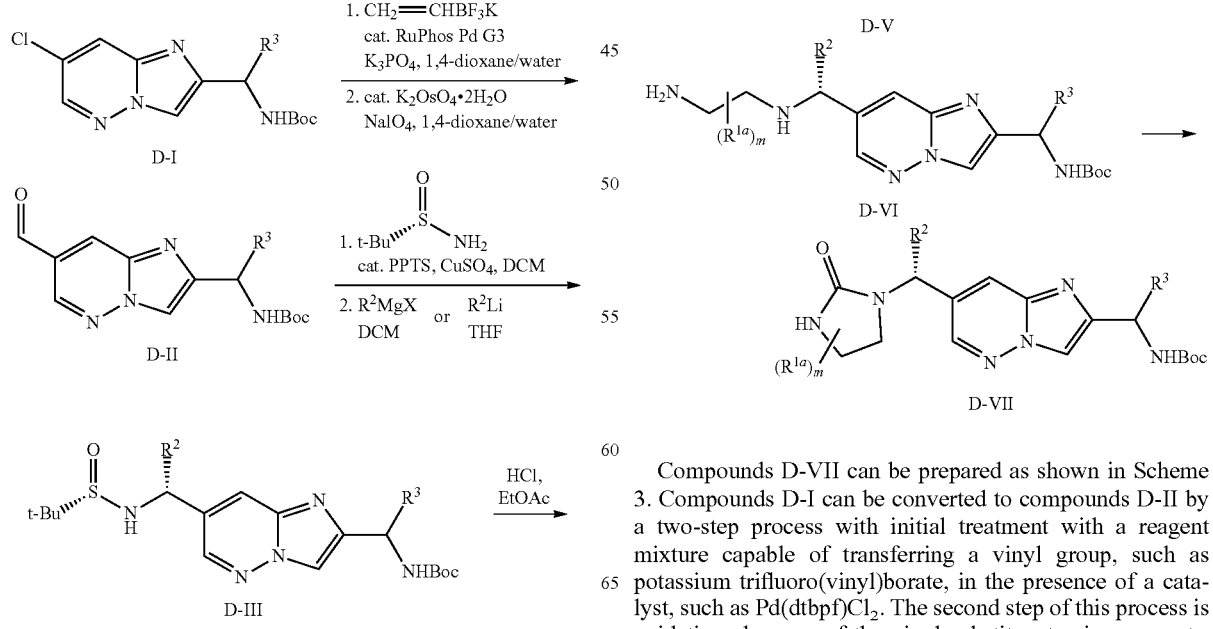

Compounds D-VII can be prepared as shown in Scheme 3. Compounds D-I can be converted to compounds D-II by a two-step process with initial treatment with a reagent mixture capable of transferring a vinyl group, such as potassium trifluoro(vinyl)borate, in the presence of a catalyst, such as Pd(dtbpf)Cl$_2$. The second step of this process is oxidative cleavage of the vinyl substituent using reagents, such as sodium periodate, in the presence of a catalyst, such as potassium osmate, in a solvent, such as aqueous 1,4-dioxane. Subsequent condensation of compounds D-II with (S)-(−)-2-methyl-2-propanesulfinamide gives the corresponding sulfinimide, that upon addition of nucleophilic carbon-containing reagents, such as alkyl magnesium halides, alkyl lithiums or metalated alkyl nitriles, yields sulfinamides Conversion of compounds D-III to D-IV can be accomplished by treatment with an acid such as aqueous hydrochloric acid. Compounds D-IV are converted to compounds D-V by treatment with compounds such as D-VIII in the presence of a base such as DIPEA or TEA in a solvent such as ACN, DCM or THF. Alternatively, compounds D-IV can be converted to compounds D-V by reductive amination using a catalyst such as tetraethoxytitanium with a reducing agent such as NaCNBH$_3$, in a solvent such as MeOH with an aldehyde such as CbzNH(C)(R$^{1a}$)$_m$CHO. Compounds D-V are converted to compounds D-VI by treating with H$_2$ in the presence of a palladium catalyst such as Pd/C in a solvent such as methanol. Compounds D-VI can be converted to compounds D-VII by treating with a reagent such as triphosgene or CDI in a solvent such as DCM or THF. Compounds D-VII can be converted to compounds Ia as shown in Scheme 2 employing methods analogous to those describing the conversion of compounds B—III to compounds Ia.

Compounds D-VIa can be prepared as shown in Scheme 4. Compounds D-Ia can be converted to compounds D-IX by treatment with D-XI, in the presence of a catalyst, such as RuPhos Pd G3, with an additive such as K$_3$PO$_4$ and in a solvent such as aqueous 1,4-dioxane. Compounds D-IX can be converted to compounds D-X by treatment with potassium osmate and sodium periodate, in a solvent, such as aqueous 1,4-dioxane. Conversion of compounds D-X to compounds D-VIa can be accomplished by titanium isopropoxide-mediated imine formation with diamines C-Ia followed by reduction with a reducing agent such as NaCNBH$_3$ in a solvent such as methanol in the presence of an additive such as acetic acid. Compounds D-VIa can be converted to compounds such as D-VII as shown in Scheme 3.

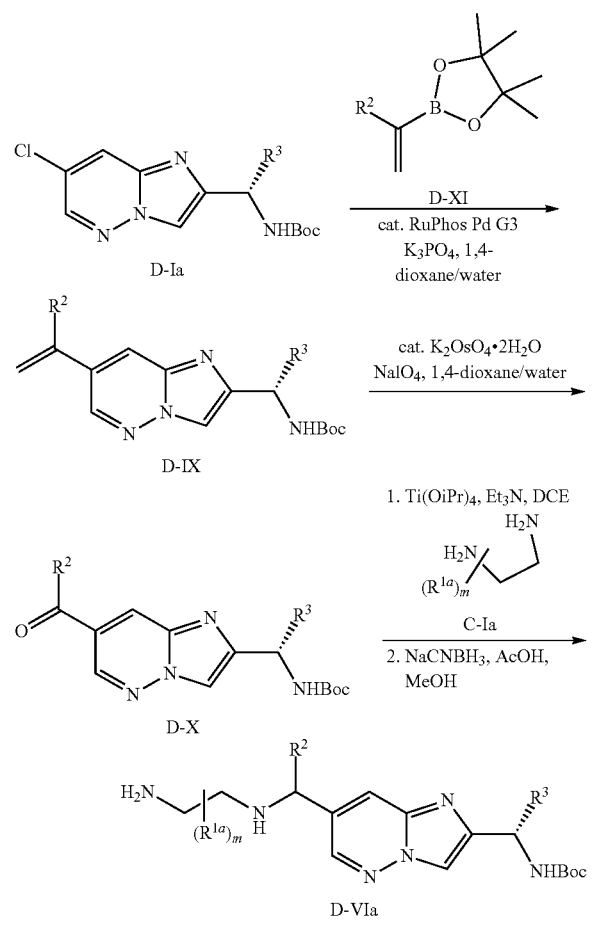

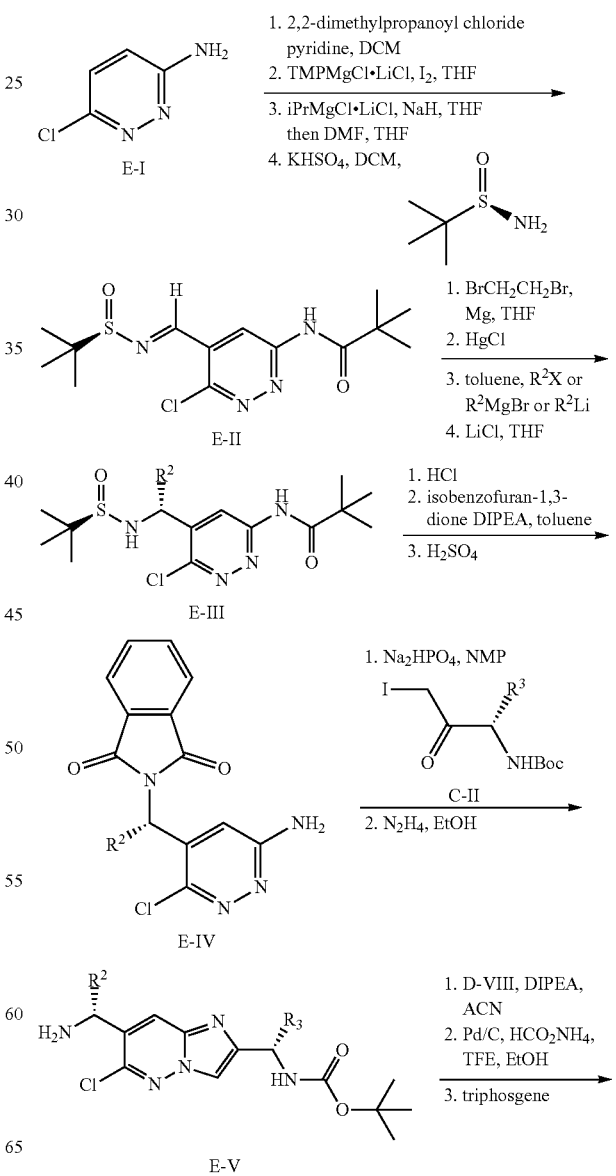

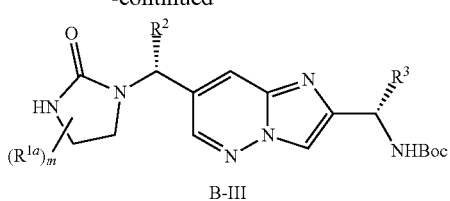

B-III

Compounds B—III may also be prepared as shown in Scheme 5. Protection of the amine in aminochloropyridazine E-I with a protecting group such as 2,2-dimethylpropanamide followed by metalation, formylation and treatment of the resulting aldehyde (structure not shown) with (S)-(−)-2-methyl-2-propanesulfinamide provides compound E-II. Compound E-II can be converted to compounds E-III by a four-step procedure as shown above. Compounds E-III can be converted to compounds E-IV by sulfoxamine deprotection using reagents such as HCl in solvents such as EtOAc, phthalimide formation as shown above and amine deprotection using reagents such as sulfuric acid in solvents such as 1,4-dioxane or MeOH. Treatment of compounds E-IV with compounds C-II using a base such as Na$_2$HPO$_4$ in a solvent such as NMP followed by phthalimide removal using reagents such as hydrazine in solvents such as EtOH provides imidazopyridazines E-V. Compounds E-V are converted to compounds B—III by a three-step process shown above. Initial treatment of compounds E-V with compounds D-VIII in a solvent such as ACN with a base such as DIPEA provides an intermediate (structure not shown). Then, chlorine hydrogenolysis of this intermediate with reagents such as ammonium formate and TFE in the presence of a palladium catalyst such as Pd/C in a solvent such as ethanol followed by cyclization using reagents such as triphosgene or CDI provides compounds Scheme 6

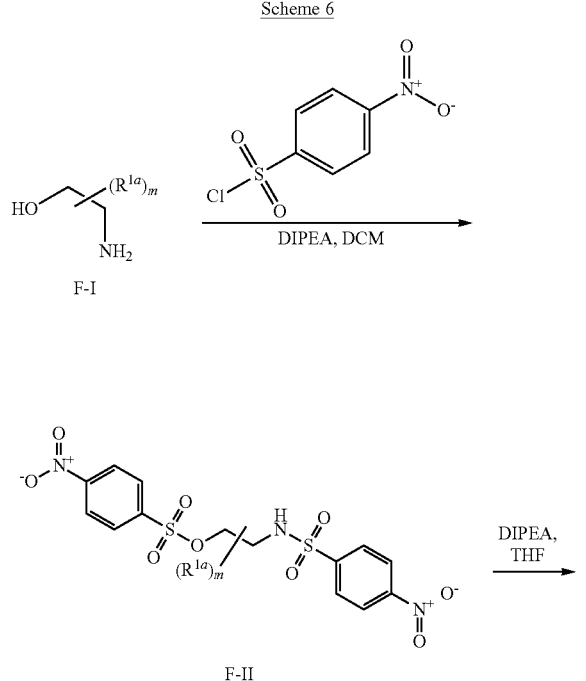

F-I

F-II

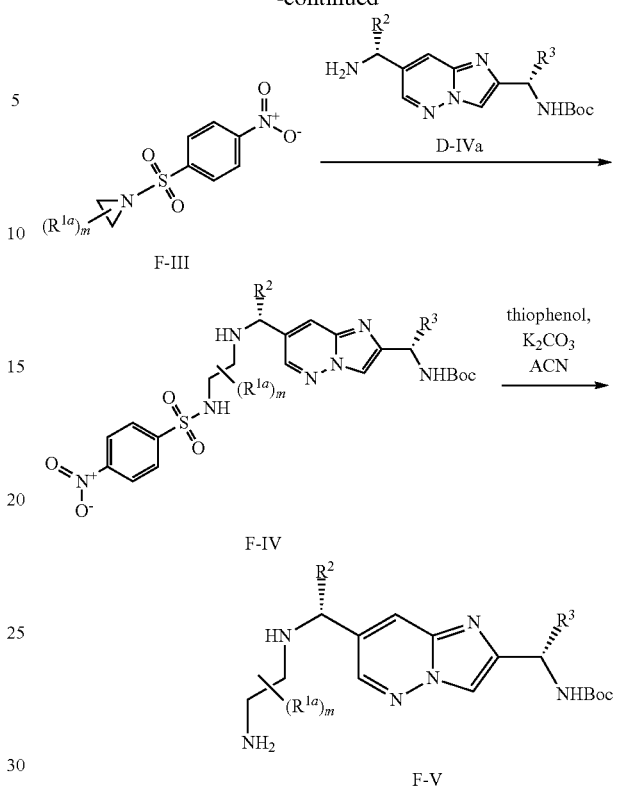

F-III

F-IV

F-V

Compounds F—V can be prepared as shown in Scheme 6. Treatment of amino alcohols F—I with 4-nitrobenzenesulfonyl chloride in the presence of a base such as DIPEA in a solvent such as DCM provides compounds F-II. Treatment of compounds F-II with a base, such as DIPEA, in a solvent, such as THF, provides aziridines F—III Reaction of aziridines F—III with amines D-IVa provides compounds F—IV. Deprotection of the protecting/activating group can be accomplished by treatment with reagents such as thiophenol with a base such as K$_2$CO$_3$ in a solvent such as ACN, thereby providing diamines F—V.

Scheme 7

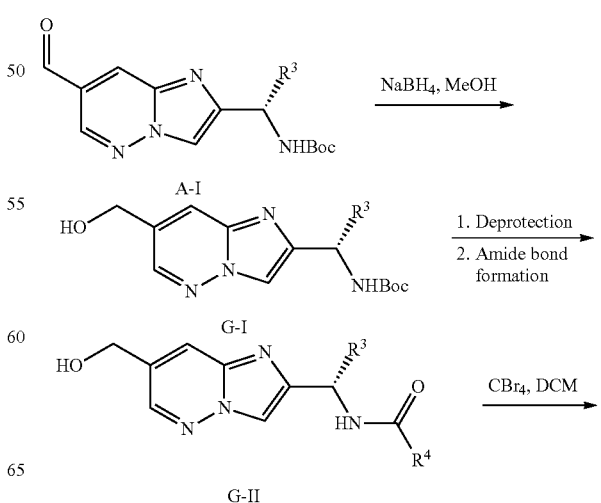

A-I

G-I

G-II

101
-continued

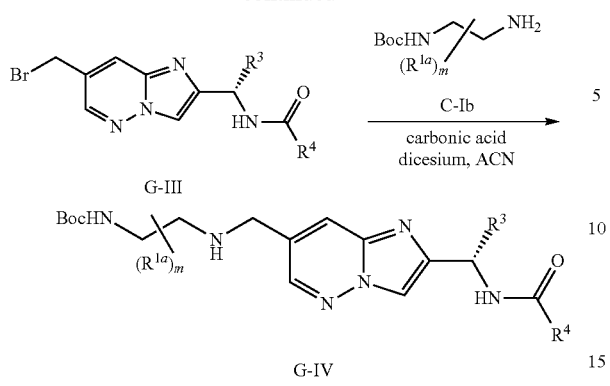

Compounds G-IV can be prepared as shown in Scheme 7. Treatment of aldehydes A-I with a reducing agent such as sodium borohydride in a solvent such as MeOH affords the corresponding alcohols G-I. Compounds G-I can be converted to compounds G-II by a two-step process comprising deprotection of compounds G-I using "Boc deprotection conditions" and subsequent amide bond formation using "amide bond formation" conditions with either $R^4CO_2H$ or $R^4CO_2Cl$. Treatment of alcohols G-II with reagents such as carbon tetrabromide in solvents such as DCM with additives such as 1H-imidazole affords compounds G-III. Reaction of compounds G-III with diamines C-Ib using reagents such as carbonic acid dicesium in solvents such as ACN or DCM provides compounds G-IV. Compounds G-IV can then be elaborated into compounds of formula Ia as described in the schemes above.

Scheme 8

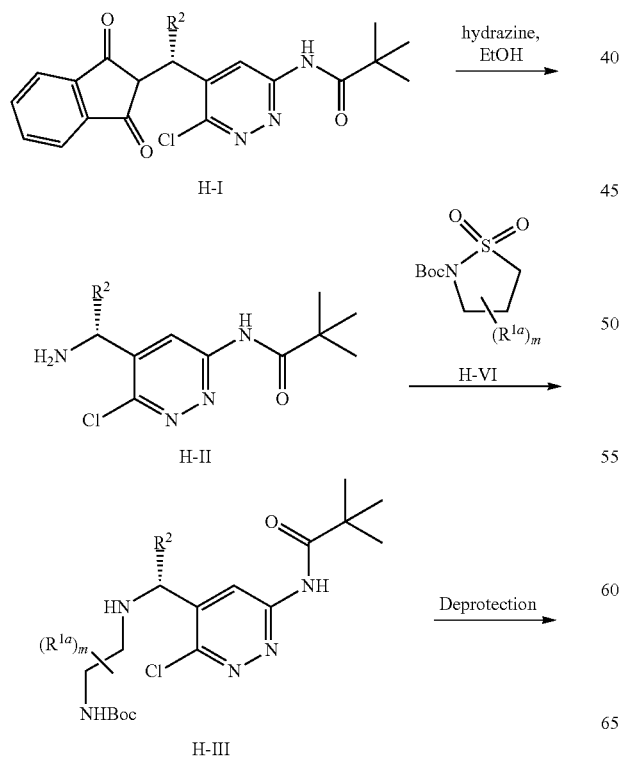

102
-continued

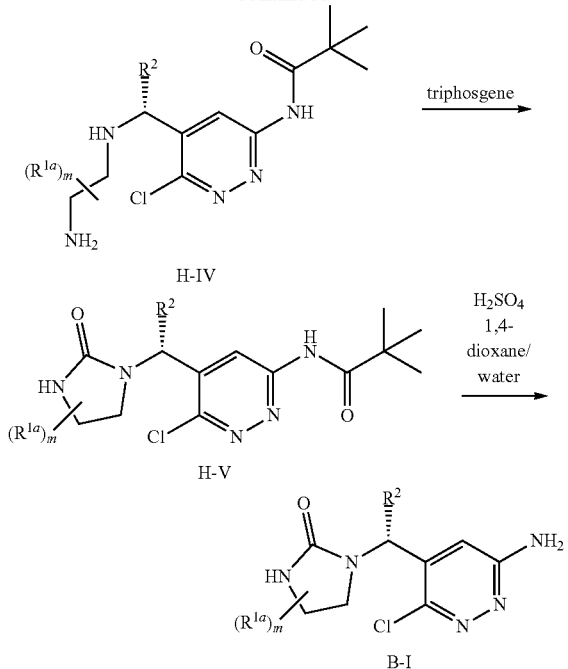

Compounds B—I may also be prepared as shown in Scheme 8. Aminopyridazines H—I can be prepared by protection of amines E-IV as the 2,2-dimethylpropanamide. Treatment of aminopyridazines H—I with reagents such as hydrazine in solvents such as EtOH affords amines H-II. Reaction of compounds H-II with oxathiazolidine dioxides H—VI using a base such as DIPEA or TEA in solvents such as ACN provides diamines H—III. Compounds H—III can then undergo deprotection using "Boc deprotection conditions" followed by cyclization using reagents such as triphosgene or CDI in a solvent such as DCM or THF to afford cyclic ureas H—V. Treatment of compounds H—V with reagents such as sulfuric acid in solvents such as 1,4-dioxane and water affords aminopyridazines B—I.

Scheme 9

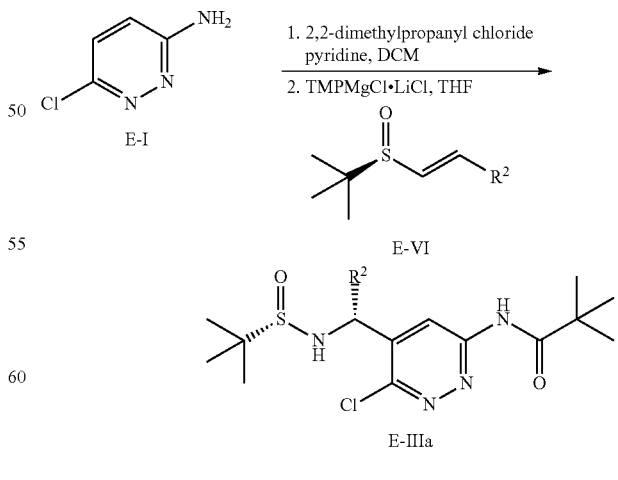

Compounds E-IIIa may be prepared as shown in Scheme 9. Protection of the amine in aminochloropyridazine E-I with a protecting group such as 2,2-dimethylpropanamide followed by metalation with a reagent such as TMPMgCl·LiCl in a solvent such as THF and treatment with vinyl sulfinyl reagents E-VI provides compounds E-IIIa.

Intermediate 1

(S)-1-((2-(Amino(4,4-difluorocyclohexyl)methyl)imidazo[1,2-b]pyridazin-7-yl)methyl)imidazolidin-2-one

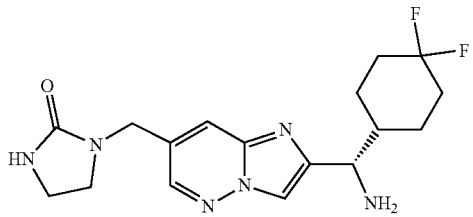 [SMILES: N[C@H](c1cn2ncc(CN3CCNC3=O)cc2n1)C1CCC(F)(F)CC1]

Step A: tert-Butyl (S)-((7(2-aminoethyl)amino)methyl)imidazo[1,2-b]pyridazin-2-yl)(4,4-difluorocyclohexyl)methyl)carbamate. A solution of tert-Butyl (S)-((4,4-difluorocyclohexyl)(7-formylimidazo[1,2-b]pyridazin-2-yl)methyl)carbamate (350 mg, 0.89 mmol), ethylene diamine (161 mg, 2.66 mmol), and triethylamine (0.271 mL, 1.95 mmol) in DCM (10 mL) was stirred at rt. After 2 h, acetic acid (0.305 mL, 5.32 mmol) and MeOH (1.5 mL) were added. After a further 45 min at rt, sodium cyanoborohydride (195 mg, 3.10 mmol) was added and the heterogenous reaction mixture was stirred at rt for 12 h. The reaction mixture was diluted with DCM (40 mL) and saturated aqueous sodium bicarbonate (60 mL). The layers were separated, and the aqueous layer was extracted with DCM (×20 mL). The combined organic layers were dried over anhydrous Na$_2$SO$_4$, filtered, and concentrated to a gum that was used directly in the next step without further purification.

Step B: tert-Butyl (S)-((4,4-difluorocyclohexyl)((7-((2-oxoimidazolidin-1-yl)methyl)imidazo[1,2-b]pyridazin-2-yl)methyl)carbamate. tert-Butyl (S)-((7-(((2-aminoethyl)amino)methyl)imidazo[1,2-b]pyridazin-2-yl)(4,4-difluorocyclohexyl)methyl)carbamate (0.89 mmol, Step A) was diluted with THF (10 mL), treated with CDI (432 mg, 2.66 mmol) and the mixture stirred at rt. After 30 min, the reaction mixture was warmed to 60° C. for 1 h. The reaction mixture was cooled to rt and treated with aqueous 3 M sodium hydroxide (2 mL). After 30 min at rt, the reaction mixture was diluted with half saturated brine (100 mL) and EtOAc (50 mL), and the layers were separated. The aqueous layer was extracted with EtOAc (3×30 mL). The combined organic layers were dried over anhydrous Na$_2$SO$_4$, filtered, and concentrated to a gum that was used directly in the next step without further purification.

Step C: (S)-1-((2-(Amino(4,4-difluorocyclohexyl)methyl)imidazo[1,2-b]pyridazin-7-yl)methyl)imidazolidin-2-one. To a cooled (0° C.) solution of tert-Butyl (S)-((4,4-difluorocyclohexyl)(7-((2-oxoimidazolidin-1-yl)methyl)imidazo[1,2-b]pyridazin-2-yl)methyl)carbamate (0.89 mmol, Step B) in DCM (5.0 mL) was added TFA (3.7 mL, 65 mmol). After 1.5 h, the reaction mixture was concentrated to dryness, and diluted with EtOAc (20 mL), brine (30 mL), aqueous 3 M sodium hydroxide (5 mL), and saturated aqueous sodium bicarbonate (35 mL). The layers were separated, and the aqueous layer was extracted with. EtOAc (2×20 mL). The combined extracts were dried over anhydrous Na$_2$SO$_4$, filtered, and concentrated to give the title compound as a yellow film (60.7%, over three steps) that was used without further purification.

Intermediate 2

(S)-1-((2-((S)-Amino(4,4-difluorocyclohexyl)methyl)imidazo[1,2-b]pyridazin-7-yl)methyl)-4-methylimidazolidin-2-one

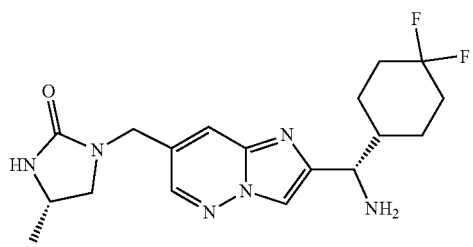 [SMILES: C[C@H]1CN(Cc2cnn3cc([C@@H](N)C4CCC(F)(F)CC4)nc3c2)C(=O)N1]

Step A: tert-Butyl ((S)-(7-(((((S)-2-((tert-butoxycarbonyl)amino)propyl)amino)methyl)imidazo[1,2-b]pyridazin-2-yl)(4,4-difluorocyclohexyl)methyl)carbamate. The title compound was synthesized in a manner analogous to Intermediate 1 Step A using tert-Butyl (S)-(1-aminopropan-2-yl)carbamate in place of ethylene diamine.

Step B: tert-Butyl ((S)-(4,4-difluorocyclohexyl)(7-(((S)-4-methyl-2-oxoimidazolidin-1-yl)methyl)imidazo[1,2-b]pyridazin-2-yl)methyl)carbamate. tert-Butyl ((S)-(7-(((((S)-2-((tert-butoxycarbonyl)amino)propyl)amino)methyl)imidazo[1,2-b]pyridazin-2-yl)(4,4-difluorocyclohexyl)methyl)carbamate (0.76 mmol, Step A) was diluted with THF (12 mL), treated with potassium tert-pentoxide (0.57 mL, 2 M in tert-amyl alcohol), and warmed to 60° C. After 2.5 h, the reaction mixture was cooled to rt and diluted with EtOAc (30 mL) and saturated aqueous NaHCO$_3$ (30 mL). The layers were separated, and the aqueous layer was extracted with EtOAc (3×20 mL). The combined organic layers were washed with aqueous 0.1 M HCl (3×15 mL) and brine (20 mL), dried over anhydrous Na$_2$SO$_4$, filtered, and concentrated to dryness to give an oil which was used in the next step without further purification.

Step C: (S)-1-((2-((S)-Amino(4,4-difluorocyclohexyl)methyl)imidazo[1,2-b]pyridazin-7-yl)methyl)-4-methylimidazolidin-2-one. The title compound was synthesized in a manner analogous to Intermediate 1 Step C using tert-Butyl ((S)-(4,4-difluorocyclohexyl)(7-(((S)-4-methyl-2-oxoimidazolidin-1-yl)methyl)imidazo[1,2-b]pyridazin-2-yl)methyl)carbamate generated above (Step B) in place of tert-Butyl (S)-((4,4-difluorocyclohexyl)(7-((2-oxoimidazolidin-1-yl)methyl)imidazo[1,2-b]pyridazin-2-yl)methyl)carbamate. The title compound (53.9% yield, over three steps) was used without further purification.

Intermediate 3

(R)-1-((2-((S)-Amino(4,4-difluorocyclohexyl)methyl)imidazo[1,2-b]pyridazin-7-yl)methyl)-4-methylimidazolidin-2-one

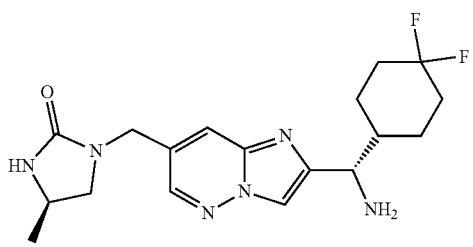 [SMILES: C[C@@H]1CN(Cc2cnn3cc([C@@H](N)C4CCC(F)(F)CC4)nc3c2)C(=O)N1]

The title compound (44.7% yield) was prepared by an analogous three step sequence as described for Intermediate 2 using tert-Butyl (R)-(1-aminopropan-2-yl)carbamate in place of tert-butyl (S)-(1-aminopropan-2-yl)carbamate in Step A.

Intermediate 4

(S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one

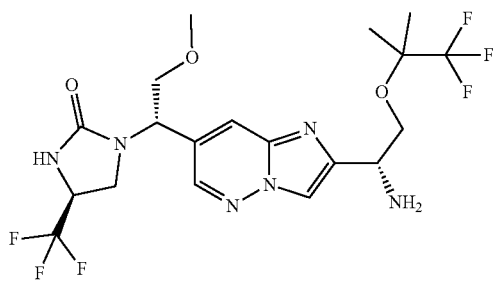 [SMILES: COC[C@H](c1cnn2cc([C@@H](N)COC(C)(C)C(F)(F)F)nc2c1)N1C[C@@H](C(F)(F)F)NC1=O]

Step A: tert-Butyl ((R)-1-(6-chloro-7-((S)-2-methoxy-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)carbamate. A 100 mL round bottom flask was charged with (S)-1-((S)-1-(6-amino-3-chloropyridazin-4-yl)-2-methoxyethyl)-4-(trifluoromethyl)imidazolidin-2-one (450 mg, 1.33 mmol), tert-Butyl (S)-(4-iodo-3-oxo-1-((1,1,1-trifluoro-2-methylpropan-2-yl)oxy)butan-2-yl)carbamate (808 mg, 1.84 mmol), 4 Å MS and DMA (14 mL) and the reaction mixture was heated to 50° C. for 21 h. The reaction mixture was then diluted with 5% aqueous LiCl (about 30 mL) and extracted with EtOAc (3×30 mL). The combined organic layers were concentrated and purified by silica gel chromatography (0-100% EtOAc/hexanes) to provide the title compound as a brown solid (65.2% yield).

Step B: tert-Butyl ((R)-1-(7-((S)-2-methoxy-1-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)carbamate. A 50 mL round bottom flask was charged with tert-butyl ((R)-1-(6-chloro-7-((S)-2-methoxy-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)carbamate (35 mg, 0.055 mmol, Step A), palladium (11.8 mg, 0.096 mmol, 10 wt % on activated carbon), ethanol (5.5 mL), and NH₄OH (7 M, 0.150 mL, 1.15 mmol). The flask was then evacuated and backfilled with hydrogen four times before being allowed to stir at rt for 54 h. Once LCMS analysis indicated the complete consumption of the starting material, the reaction mixture was filtered through a pad of diatomaceous earth (e.g., Celite®) and the filtrate was concentrated to yield the title compound as an off white solid (99% yield), which was used without further purification.

Step C: (S)-1-((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one. A solution of tert-Butyl ((R)-1-(7-((S)-2-methoxy-1-((S)-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)carbamate (40.7 mg, 0.068 mmol, Step B) in dry DCM (2 mL) was cooled to 0° C. in an ice bath under a nitrogen atmosphere and TFA (6 mL, 78.4 mmol) was then added slowly. The reaction was stirred at 0° C. for 30 min before the cooling bath was removed and the reaction was allowed to warm to rt over 3 h. Once LCMS analysis indicated the complete consumption of the starting material, the reaction was concentrated to remove most of the TFA and the resulting residue was dissolved in DCM and washed with saturated aqueous NaHCO₃. The aqueous layer was extracted with DCM and the combined organic layers were dried over anhydrous Na₂SO₄, filtered, and concentrated to provide the title compound as a brown solid (99% yield) which was used without further purification.

Intermediate 5

2,5-Dioxopyrrolidin-1-yl 4-cyclopropyl-1,2,5-oxadiazole-3-carboxylate

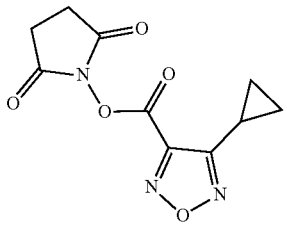 [SMILES: O=C(ON1C(=O)CCC1=O)c1nonc1C1CC1]

Step A: 4-Cyclopropyl-1,2,5-oxadiazole-3-carbonyl chloride. A flask was charged with 4-cyclopropyl-1,2,5-oxadiazole-3-carboxylic acid (200 mg, 1.30 mmol) and DCM (2.6 mL). The solution was cooled to 0° C. and then oxalyl chloride (0.224 mL, 2.60 mmol) was added dropwise followed by 1 drop of DMF. The mixture was stirred for 3 h as it warmed to rt. The reaction mixture was concentrated under reduced pressure into a yellow oil and dissolved in DCM to result in a 2 M solution of 4-cyclopropyl-1,2,5-oxadiazole-3-carbonyl chloride that was used without further purification.

Step B: 2,5-Dioxopyrrolidin-1-yl 4-cyclopropyl-1,2,5-oxadiazole-3-carboxylate. A flask was charged with N-hydroxysuccinimide (231 mg, 1.95 mmol), DCM (3.25 mL) and DIPEA (0.336 mL, 1.95 mmol). The reaction mixture was cooled to 0° C. and 4-cyclopropyl-1,2,5-oxadiazole-3-carbonyl chloride (2 M in DCM, 0.649 mL, 1.30 mmol, Step A) was then added dropwise. The reaction mixture was stirred for 1 h as it warmed to rt. The reaction mixture was then washed with water and brine, dried over anhydrous MgSO$_4$, filtered and concentrated. The material was purified by silica gel chromatography (0-100% ethyl acetate (with 10% MeOH): hexane) to afford the title compound as a clear oil (39% yield).

Intermediate 6

(S)-1-((S)-1-(2-((S)-1-Amino-4,4,4-trifluoro-3,3-dimethylbutyl)imidazo[1,2-b]pyridazin-7-yl)-2-methoxyethyl)-4-(trifluoromethyl)imidazolidin-2-one

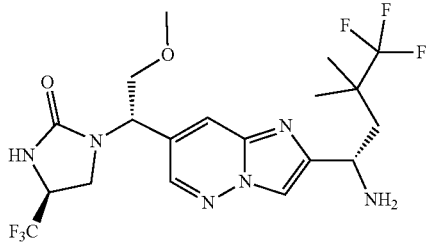 [SMILES: COC[C@H](c1cnn2cc([C@@H](N)CC(C)(C)C(F)(F)F)nc2c1)N1C[C@@H](C(F)(F)F)NC1=O]

Step A: tert-Butyl ((S)-1-(6-chloro-7-((S)-2-methoxy-((S)-2-oxo-4-(trifluoromethyl)imidazolidin-1-yl)ethyl)imidazo[1,2-b]pyridazin-2-yl)-4,4,4-trifluoro-3,3-dimethylbutyl)carbamate. To an oven dried N$_2$ flushed vial was added oven dried 4 Å molecular sieves (2.5 g), (S)-1-((S)-1-(6-amino-3-chloropyridazin-4-yl)-2-methoxyethyl)-4-(trifluoromethyl)imidazolidin-2-one (407 mg, 1.2 mmol), tert-Butyl (S)-(6,6,6-trifluoro-1-iodo-5,5-dimethyl-2-oxohexan-3-yl)carbamate (703 mg, 1.66 mmol) and dimethyl acetamide (12.5 mL). The reaction mixture was heated at 45° C. for 36 h, at which time an additional portion of tert-Butyl (S)-(6,6,6-trifluoro-1-iodo-5,5-dimethyl-2-oxohexan-3-yl)carbamate (649 mg, 1.59 mmol) was added and heated at 45° C. for an additional 72 h. The reaction mixture was cooled to rt, filtered over a pad of diatomaceous earth (e.g. Celite®), and the solids were washed with EtOAc and DCM. The filtrate was diluted with 5% aqueous LiCl, and the layers were separated. The aqueous layer was extracted with EtOAc (3×) and the combined organic layers were dried over anhydrous Na$_2$SO$_4$, filtered, concentrated, and purified by silica gel chromatography (0-100% EtOAc (with 10% MeOH)/hexanes) to give the title compound (22% yield).

Step B: tert-Butyl ((S)-4,4,4-trifluoro-1-(7-((S)-2-methoxy-1-((S)-2-oxo-4-(trifluoromethyl)imidazolidin-1-yl)ethyl)imidazo[1,2-b]pyridazin-2-yl)-3,3-dimethylbutyl)carbamate. To a suspension of ammonium formate (241 mg, 3.82 mmol) and 10% Pd/C (156 mg, dry) in EtOH (26 mL) was added tert-Butyl ((S)-1-(6-chloro-7-((S)-2-methoxy-((S)-2-oxo-4-(trifluoromethyl)imidazolidin-1-yl)ethyl)imidazo[1,2-b]pyridazin-2-yl)-4,4,4-trifluoro-3,3-dimethylbutyl)carbamate (157 mg, 0.25 mmol, Step A). The reaction mixture was heated at 80° C. for 1 h. The reaction mixture was cooled to rt, filtered over a pad of diatomaceous earth (e.g., Celite®), and the pad was washed with EtOH. The combined filtrates were concentrated and purified by silica gel chromatography (10% MeOH/DCM) to give the title compound (92.4% yield).

Step C: (S)-1-((S)-1-(2-((S)-1-Amino-4,4,4-trifluoro-3,3-dimethylbutyl)imidazo[1,2-b]pyridazin-7-yl)-2-methoxy-ethyl)-4-(trifluoromethyl)imidazolidin-2-one. The title compound was prepared as described for the synthesis of Intermediate 1 Step C, using tert-Butyl ((S)-4,4,4-trifluoro-1-(7-((S)-2-methoxy-((S)-2-oxo-4-(trifluoromethyl)imidazolidin-1-yl)ethyl)imidazo[1,2-b]pyridazin-2-yl)-3,3-dimethylbutyl)carbamate (Step B) in place of tert-butyl (S)-((4,4-difluorocyclohexyl)(7-((2-oxoimidazolidin-1-yl)methyl)imidazo[1,2-b]pyridazin-2-yl)methyl)carbamate to afford the title compound that was used without further purification (assume 100% yield).

Intermediate 7

2,5-Dioxopyrrolidin-1-yl 1-isopropyl-1H-pyrazole-5-carboxylate

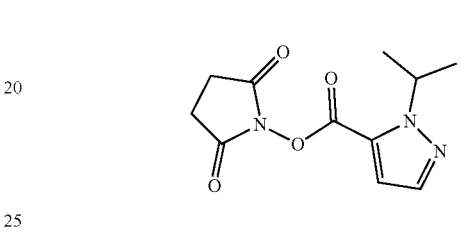

Step A. 1-Isopropyl-1H-pyrazole-5-carbonyl chloride. A round bottom flask was charged with a 1-isopropyl-1H-pyrazole-5-carboxylic acid (1 g, 6.5 mmol), DCM (13 mL) and was cooled to 0° C. under a nitrogen atmosphere. To the solution was added oxalyl chloride (1.1 mL, 13.0 mmol) followed by DMF (0.05 mL, 0.65 mmol) dropwise. The reaction mixture was slowly warmed to rt. Once the gas evolution ceased, the reaction mixture was condensed into a yellow oil that was then dissolved in 12 mL of dry DCM and stored as a 2 M solution.

Step B. 2,5-Dioxopyrrolidin-1-yl 1-isopropyl-1H-pyrazole-5-carboxylate. A round bottom flask was charged with N-hydroxysuccinimide (1.1 g, 9.7 mmol), DCM (25 mL), and DIPEA (16 mL, 6.5 mmol), and cooled to 0° C. under a nitrogen atmosphere. To the solution was added a solution of 1-isopropyl-1H-pyrazole-5-carbonyl chloride (13 mL, 6.5 mmol, 2 M in DCM, Step A). The resulting solution was allowed to warm to rt over 1 h. The solution was washed with water and then with brine, dried over anhydrous MgSO$_4$, filtered, and concentrated. The material was purified by silica gel chromatography (0-100% EtOAc (with 10% MeOH)/hexanes) to afford the title compound as an off white solid.

Intermediate 8

(R,E)-N-(5-(((tert-Butylsulfinyl)imino)methyl)-6-chloropyridazin-3-yl)pivalamide

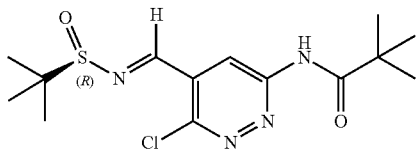

Step A: N-(6-Chloropyridazin-3-yl)pivalamide. To a stirred solution of 6-chloropyridazin-3-amine (350 g, 2.70 mol) and pyridine (427 g, 5.40 mol) in DCM (5000 mL) was added 2,2-dimethylpropanoyl chloride (814 g, 6.75 mol)

dropwise at 0° C. under a nitrogen atmosphere. The resulting mixture was stirred for 2 h at rt under a nitrogen atmosphere. The pH of the mixture was adjusted to pH 7-8 using saturated aqueous NaHCO₃ solution and the resulting mixture was extracted with DCM (3×3 L). The combined organic layers were washed with brine (1×2 L) and water (1×2 L), and dried over anhydrous Na₂SO₄. After filtration, the filtrate was concentrated under reduced pressure and the residue was purified by trituration with petroleum ether (2 L). The precipitated solids were collected by filtration affording the title compound in 87% yield.

Step B: N-(6-Chloro-5-iodopyridazin-3-yl)pivalamide. To a stirred solution of TMPMgCl·LiCl (6.8 L, 6.8 mol, 1 M in THF) was added N-(6-chloropyridazin-3-yl)pivalamide (560 g, 2.62 mol, Step A) in THF (5.0 L) dropwise at −60° C. under a nitrogen atmosphere. The resulting mixture was stirred for 2.5 h at −55° C. under a nitrogen atmosphere. Then the reaction mixture was cooled to −60° C. and iodine (998 g, 3.93 mol) in THF (3.0 L) was added dropwise at −60° C. The temperature of the resulting mixture was adjusted to −55° C. and the reaction mixture was stirred for an additional 1 h at −55° C. and the reaction was then quenched by the addition of saturated aqueous NH₄Cl (2 L) at −40° C. The resulting mixture was extracted with EtOAc (3×3 L) and the combined organic layers were washed with saturated aqueous Na₂S₂O₃ (1×2 L) and brine (1×2 L), dried over anhydrous Na₂SO₄, and filtered. The filtrate was concentrated under reduced pressure and the residue was purified by silica gel chromatography (33% EtOAc/petroleum ether) to afford the title compound in 69% yield.

Step C: N-(6-Chloro-5-formylpyridazin-3-yl)pivalamide. To a stirred solution of N-(6-chloro-5-iodopyridazin-3-yl)pivalamide (607 g, 1.79 mol, Step B) in THF (6.0 L) was added a 60% dispersion of NaH in mineral oil (93.0 g, 2.32 mol) in portions at 0° C. under a nitrogen atmosphere. The resulting mixture was stirred for 30 min at rt under a nitrogen atmosphere and isopropylmagnesium chloride lithium chloride complex (1.99 L, 2.59 mol, 1.3 M in THF) was added dropwise at −60° C. The resulting mixture was stirred for additional 1.5 h at −55° C. and then dimethylformamide (653 g, 8.94 mol) in THF (700 mL) was added dropwise at −60° C. The resulting mixture was stirred for additional 1 h at rt and then quenched by the addition of saturated aqueous NH₄Cl (2 L) at 0° C. The resulting mixture was extracted with EtOAc (3×3 L). The combined organic layers were washed with brine (1×2 L) and water (1×2 L), dried over anhydrous Na₂SO₄, and filtered. The filtrate was concentrated under reduced pressure to afford the title compound that was used without further purification.

Step D: (R,E)-N-(5-(((tert-Butylsulfinyl)imino)methyl)-6-chloropyridazin-3-yl)pivalamide. To a stirred solution of N-(6-chloro-5-formylpyridazin-3-yl)pivalamide (372 g, 1.54 mol, Step C) and (R)-2-methylpropane-2-sulfinamide (243 g, 2.00 mol) in DCM (2.20 L) was added potassium bisulfate (272 g, 2.00 mol) in portions at rt. The resulting mixture was stirred overnight at rt and then quenched with water (2 L) at rt. The mixture was extracted with DCM (3×1.5 L), and the combined organic layers were washed with water (1×1 L), dried over anhydrous Na₂SO₄, and filtered. The filtrate was concentrated under reduced pressure and purified by silica gel chromatography (25% EtOAc/petroleum ether) to afford the title compound in 60% yield over 2 steps (Steps C and D).

Intermediate 9

N-(5-((S)-1-(((R)-tert-Butylsulfinyl)amino)-2-methoxyethyl)-6-chloropyridazin-3-yl)pivalamide

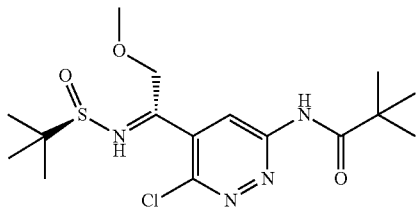

To a stirred solution of magnesium (47.4 g, 1.95 mol) in THF (360 mL) was added dibromoethane (13.7 g, 74.0 mmol) dropwise at rt under a nitrogen atmosphere. The resulting mixture was stirred for 30 min at rt under a nitrogen atmosphere and additional dibromoethane (60.0 g, 222 mmol) was added. Then the reaction mixture was heated to 40° C. and mercuric chloride (4.72 g, 17.4 mmol) was added in portions and the reaction mixture was stirred for an additional 20 min at rt. MOMBr (22.1 g, 177 mmol) in toluene (30 mL) was then added dropwise at rt and stirred for an additional 20 min. The reaction mixture was then cooled to −15° C. followed by the addition of more MOMBr (200 g, 1.60 mol) in toluene (270 mL) dropwise and the resulting mixture was stirred for 40 min at −15° C. To the mixture was added LiCl (74.0 g, 1.74 mol) in portions and the resulting mixture was stirred for 30 min at −15° C. To the mixture was added (R,E)-N-(5-(((tert-butylsulfinyl)imino)methyl)-6-chloropyridazin-3-yl)pivalamide (60.0 g, 174 mmol, Intermediate 8) in THF (360 mL) dropwise at −20° C. The resulting mixture was stirred for an additional 30 min at −10° C. The reaction was quenched by the addition of saturated aqueous NH₄Cl (5 L) at 0° C. The mixture was extracted with EtOAc (3×2 L) and the combined organic layers were washed with water (1×2 L), dried over anhydrous Na₂SO₄, and filtered. The filtrate was concentrated under reduced pressure and purified sequentially by silica gel chromatography (50% EtOAc/petroleum ether), reverse phase chromatography (40% MeCN/(water (0.1% NH₄HCO₃))), and chiral SFC (CHIRAL ART Cellulose-SC, 5 μm, 5×25 cm, 30% MeOH/CO₂) to afford the title compound as the second eluting isomer in 21% yield.

Intermediate 10 tert-Butyl ((R)-1-(7-((S)-1-amino-2-methoxyethyl)-6-chloroimidazo[1,2-b]pyridazin-2-yl)-2-((1,1,1-trifluoro-2-methylpropan-2-yl)oxy)ethyl)carbamate

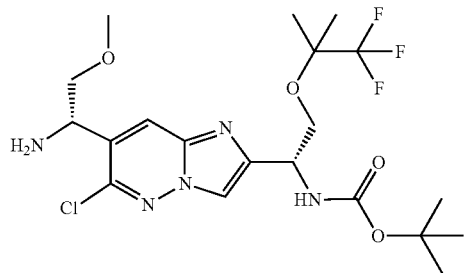 [SMILES: COC[C@@H](N)c1cc2nc([C@H](COC(C)(C)C(F)(F)F)NC(=O)OC(C)(C)C)cn2nc1Cl]

Step A: (S)—N-(5-(1-Amino-2-methoxy ethyl)-6-chloropyridazin-3-yl)pivalamide. To a stirred solution of N-(5-((S)-1-(((R)-tert-butylsulfinyl)amino)-2-methoxyethyl)-6-chloropyridazin-3-yl)pivalamide (8.00 g, 20.5 mmol, Intermediate 9) in EtOAc (102 mL) at rt was added a solution of HCl in 1,4-dioxane (4 M, 20.5 mL, 81.9 mmol). After 5 h, the reaction mixture was diluted with hexanes (150 mL) and water (200 mL). The layers were separated, and the organic layer was extracted with aqueous HCl (0.05 M, 2×50 mL). The combined aqueous layers were diluted with EtOAc (50 mL) and the pH of the solution was adjusted to pH 11 with aqueous 3 M NaOH. The layers were separated, and the aqueous layers were extracted with EtOAc (4×50 mL). The combined organic layers were dried over anhydrous $Na_2SO_4$, filtered and concentrated to give the title compound as a solid (>99% yield, trace EtOAc was present), which was used without further purification.

Step B: (S)—N-(6-Chloro-5-(1-(1,3-dioxoisoindolin-2-yl)-2-methoxyethyl)pyridazin-3-yl)pivalamide. To a stirred solution of (S)—N-(5-(1-amino-2-methoxyethyl)-6-chloropyridazin-3-yl)pivalamide (1.17 g, 4.07 mmol, Step A) and isobenzofuran-1,3-dione (0.81 g, 5.48 mmol) in toluene (25 mL) was added DIPEA (1.1 mL, 6.3 mmol) and the resulting solution was heated at 100° C. for 17 h. The reaction mixture was cooled to rt and concentrated to a residue, then purified by silica gel chromatography (0-100% EtOAc in hexanes) to give the title compound (89.5% yield).

Step C: (S)-2-(1-(6-Amino-3-chloropyridazin-4-yl)-2-methoxyethyl)isoindoline-1,3-dione. A pear shaped flask was charged with (S)—N-(6-chloro-5-(1-(1,3-dioxoisoindolin-2-yl)-2-methoxyethyl)pyridazin-3-yl)pivalamide (1.2 g, 2.9 mmol, Step B), 1,4-dioxane (7.2 mL) and 6 M $H_2SO_4$ (4.8 mL, 28.8 mmol) and the resulting yellow solution was heated at 60° C. for 11 h. Then this solution was cooled to 0° C. and the pH was adjusted to pH 8 by the slow addition of 58.7 mL of saturated aqueous sodium bicarbonate. The aqueous portion of this mixture was extracted with EtOAc (3×25 mL). The combined organic layers were dried over anhydrous $Na_2SO_4$, filtered, and concentrated to give a brown oil. The product was purified by silica gel chromatography (0-100% EtOAc in hexanes) to give the title compound as a white foam (74.1% yield).

Step D: tert-Butyl ((R)-1-(6-chloro-7-((S)-1-(1,3-dioxoisoindolin-2-yl)-2-methoxyethyl)imidazo[1,2-b]pyridazin-2-yl)-2-((1,1,1-trifluoro-2-methylpropan-2-yl)oxy)ethyl)carbamate. The title compound was prepared as described for the synthesis of Intermediate 4 Step A using (S)-2-(1-(6-amino-3-chloropyridazin-4-yl)-2-methoxyethyl)isoindoline-1,3-dione (Step C) in place of (S)-1-((S)-1-(6-amino-3-chloropyridazin-4-yl)-2-methoxyethyl)-4-(trifluoromethyl)imidazolidin-2-one to provide the title compound (32.8% yield) as a brown oil.

Step E: tert-Butyl ((R)-1-(7-((S)-1-amino-2-methoxyethyl)-6-chloroimidazo[1,2-b]pyridazin-2-yl)-2-(1,1,1-trifluoro-2-methylpropan-2-yl)oxy)ethyl)carbamate. To tert-Butyl ((R)-1-(6-chloro-7-((S)-1-(1,3-dioxoisoindolin-2-yl)-2-methoxyethyl)imidazo[1,2-b]pyridazin yl)-2-((1,1,1-trifluoro-2-methylpropan-2-yl)oxy)ethyl)carbamate (473 mg, 0.756 mmol, Step D) in EtOH (5 mL) was added hydrazine monohydrate (565 μL, 7.56 mmol) and the resulting red-brown solution was stirred at rt for 4 h. The mixture was concentrated to a residue that was then diluted with $H_2O$ (5 mL) and was extracted with EtOAc (3×5 mL). NaCl (solid) was added to this mixture to facilitate separation of the aqueous and organic layers. The organic layer was dried over anhydrous $MgSO_4$, filtered, concentrated, and purified by silica gel chromatography (0-5% (2 M $NH_3$ in MeOH)/DCM) to give the title compound (95% yield) as a brown oil.

Intermediate 11

Benzyl (S*)-4-(trifluoromethyl)-1,2,3-oxathiazolidine-3-carboxylate-5,5-$d_2$ 2,2-dioxide

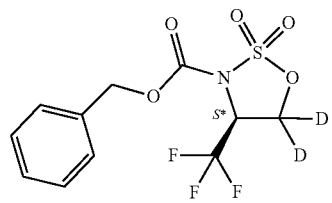 [SMILES: [2H]C1([2H])OS(=O)(=O)N(C(=O)OCc2ccccc2)[C@@H]1C(F)(F)F]

Step A: Methyl 2-(((benzyloxy)carbonyl)amino)-3,3,3-trifluoropropanoate. A round-bottom flask was charged with $NaHCO_3$ (55 g, 650 mmol) and water (100 mL) and was cooled to 0° C. THF (200 mL) was then added followed by the portion-wise addition of methyl 2-amino-3,3,3-trifluoropropanoate hydrochloride (25 g, 130 mmol). After 5 min, benzyl chloroformate (36.5 mL, 259 mmol) was added dropwise. After 1 h at 0° C., the reaction mixture was diluted with. EtOAc and the biphasic solution was separated. The aqueous layer was extracted three times with EtOAc. The combined organic layers were washed with brine, dried over anhydrous $MgSO_4$, filtered, and concentrated to dryness to afford a colorless solid. The product was purified by silica gel chromatography (0-30% EtOAc/hexanes) to afford the title compound in 40% yield as a white solid.

Step B: Benzyl (S*)-(1,1,1-trifluoro-3-hydroxypropan-2-yl-3,3-$d_2$)carbamate. A round-bottom flask was charged with methyl 2-(((benzyloxy)carbonyl)amino)-3,3,3-trifluoropropanoate (2.3 g, 7.8 mmol, Step A) and MeOH (30 mL) and cooled to 0° C. $NaBD_4$ (1.0 g, 24 mmol) was added portionwise, and the sides of the flask were rinsed with MeOH (5 mL). After 1.5 h at 0° C., the reaction mixture was quenched with a small amount of water and then poured into brine.

This solution was extracted three times with EtOAc, and the combined organic layers were washed with brine, dried over anhydrous $MgSO_4$, filtered, and concentrated to produce a colorless oil that solidified over time. The product was purified by silica gel chromatography (0-50%, EtOAc/hexanes) to afford the racemic title compound in 90% yield. The racemic mixture was separated by SFC using the following conditions: Stationary phase: Lux Cellulose 2, 5 μm, 250×21 Mm, Mobile phase: 15% methanol:isopropanol (1:1), 85% $CO_2$, flow rate 96 mL/min. The retention time of the title compound was 1.66 min and it is the first eluting peak.

Step C: Benzyl (4S*)-4-(trifluoromethyl)-1,2,3-oxathiazolidine-3-carboxylate-5,5-$d_2$ 2-oxide. A stir bar, $CH_3CN$ (39 mL), and $SOCl_2$ (2.0 mL, 27 mmol) were added to a dry round-bottom flask under nitrogen, and the resulting solution cooled to −48° C. A solution of benzyl (S*)-(1,1,1-trifluoro-3-hydroxypropan-2-yl-3,3-$d_2$)carbamate (2.8 g, 11 mmol, Step B) and $CH_3CN$ (17 mL) was then added dropwise to the reaction vessel over 10 min, followed by dropwise addition of pyridine (4.5 mL, 56 mmol). The mixture was stirred for 15 min at −45° C. and an additional 2 h at −35° C. The reaction mixture was then poured over crushed ice (100 g) and diluted with $CH_2Cl_2$ (50 mL). The aqueous layer was saturated with solid NaCl, the layers were separated, and the organic layer was concentrated to a residue. The residue was redissolved in EtOAc (30 mL), washed with 0.1 N aqueous HCl, dried over anhydrous Na$_2$SO$_4$, filtered, and concentrated under reduced pressure to afford the product in 99% yield as a colorless oil that was used without further purification.

Step D: Benzyl (S*)-4-(trifluoromethyl)-1,2,3-oxathiazolidine-3-carboxylate-5,5-d$_2$,2,2-dioxide. A round-bottom flask was charged with benzyl (4S*)-4-(trifluoromethyl)-1,2,3-oxathiazolidine-3-carboxylate-5,5-d$_2$ 2-oxide (1.25 g, 4.0 mmol, Step C), MeCN (4.3 mL), CCl$_4$ (4.3 mL) and H$_2$O (8.7 mL) and cooled to 0° C. Then NaIO$_4$ (1.1 g, 5.2 mmol) and RuCl$_3$·3H$_2$O (15.8 mg, 0.060 mmol) were sequentially added and the reaction mixture was stirred for 1 h at 0° C. After full consumption of benzyl (4S*)-4-(trifluoromethyl)-1,2,3-oxathiazolidine-3-carboxylate-5,5-d$_2$ 2-oxide was observed by LCMS analysis, the reaction mixture was diluted with additional water (10 mL). The biphasic solution was separated, and the aqueous layer was extracted with EtOAc (3×25 mL). The combined organic layers were dried over anhydrous. Na$_2$SO$_4$, filtered, and concentrated under reduced pressure. The residue was purified by silica gel chromatography (0-50% EtOAc/hexanes) to afford the title compound in 81% yield as a white solid.

Intermediate 12

(S*)-1-((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one-5,5-d$_2$

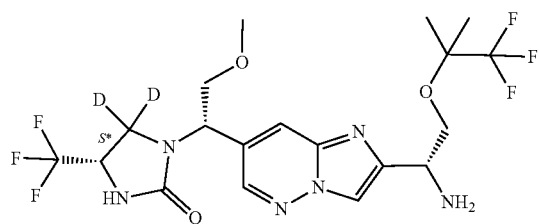 [SMILES: [2H]C1([2H])[C@@H](C(F)(F)F)NC(=O)N1[C@H](COC)c1cnn2cc([C@@H](N)COC(C)(C)C(F)(F)F)nc2c1]

Step A: tert-Butyl ((R)-1-(6-chloro-7-((5S*,8S)-3-oxo-1-phenyl-5-(trifluoromethyl)-2,10-dioxa-4,7-diazaundecan-8-yl-6,6-d$_2$)imidazo[1,2-b]pyridazin-2-yl)-2-(1,1,1-trifluoro-2-methylpropan-2-yl)oxy)ethyl)carbamate. To a solution of tert-Butyl ((R)-1-(7-((S)-1-amino-2-methoxyethyl)-6-chloroimidazo[1,2-b]pyridazin-2-yl)-2-(1,1,1-trifluoro-2-methylpropan-2-yl)oxy)ethyl)carbamate (227 mg, 0.412 mmol, Intermediate 10) and benzyl (S*)-4-(trifluoromethyl)-1,2,3-oxathiazolidine-3-carboxylate-5,5-d$_2$ 2,2-dioxide (202 mg, 0.618 mmol, Intermediate 11) in CH$_3$CN (4.1 mL) was added DIPEA (106 μL, 0.618 mmol) and the resulting brown solution was stirred at 35° C. for 18 h. The reaction mixture was concentrated and purified initially by silica gel chromatography (0-100% EtOAc/DCM, then further purified by silica gel chromatography (0-5% (2 M NH$_3$ in MeOH)/DCM) to afford the title compound as a brown oil (55.5% yield).

Step B: tert-Butyl ((R)-1-(7-((S)-1-(((S*)-2-amino-3,3,3-trifluoropropyl-1,1-d$_2$)amino)-2-methoxy ethyl)imidazo[1,2-b]pyridazin-2-yl)-2-((1,1,1-trifluoro-2-methylpropan-2-yl)oxy)ethyl)carbamate. tert-Butyl ((R)-1-(6-chloro-7-((5S*,8S)-3-oxo-1-phenyl-5-(trifluoromethyl)-2,10-dioxa-4,7-diazaundecan-8-yl-6,6-d$_2$)imidazo[1,2-b]pyridazin-2-yl)-2-((1,1,1-trifluoro-2-methylpropan-2-yl)oxy)ethyl)carbamate (155 mg, 0.209 mmol, Step A), MeOH (7.5 mL) and 10% Pd/C (89 mg, 0.83 mmol) were added to a hydrogenation flask. The reaction mixture was placed under 3 atm of H$_2$ for 2 h. The reaction mixture was filtered through diatomaceous earth (e.g. Celite®), and the solids were washed with MeOH. The filtrate was concentrated to give the title compound as a brownish foam (approximately 80% pure, 93% yield).

Step C: tert-Butyl ((R)-1-(7-((S)-2-methoxy-1-((S*)-2-oxo-4-(trifluoromethyl)imidazolidin-1-yl-5,5-d$_2$)ethyl)imidazo[1,2-b]pyridazin-2-yl)-2-(1,1,1-trifluoro-2-methylpropan-2-yl)oxy)ethyl)carbamate. tert-Butyl ((R)-1-(7-((S)-1-(((S*)-2-amino-3,3,3-trifluoropropyl-1,1-d$_2$)amino)-2-methoxyethyl)imidazo[1,2-b]pyridazin-2-yl)-2-(1,1,1-trifluoro-2-methylpropan-2-yl)oxy)ethyl)carbamate (120 mg, 0.209 mmol, Step B) was dissolved in DCM (2 mL). DIPEA (108 μL, 0.627 mmol) was added and the resulting solution was cooled to 0° C. A solution of triphosgene (21 mg, 0.069 mmol) in DCM (2 mL) was then added and the resulting mixture was stirred at 0° C. for 10 min, then was quenched with water (5 mL). The aqueous portion was extracted with DCM (3×5 mL) and the combined organic layers were dried over anhydrous Na$_2$SO$_4$, filtered and concentrated to give the title compound as a brown oil (80% pure, 76% yield).

Step D: (S*)-1-((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one-5,5-d$_2$. tert-Butyl ((R)-1-(7-((S)-2-methoxy-1-((S*)-2-oxo-4-(trifluoromethyl)imidazolidin-1-yl-5,5-d$_2$)ethyl)imidazo[1,2-b]pyridazin-2-yl)-2-((1,1,1-trifluoro-2-methylpropan-2-yl)oxy)ethyl)carbamate (144 mg, 80% pure, 0.192 mmol, Step C) was dissolved in DCM (1.6 mL) and cooled to 0° C. TFA (1.6 mL) was then added and the resulting mixture was stirred at 0° C. for 30 min then warmed to rt over 1.5 h. The reaction mixture was then concentrated to a residue and 2 N NH$_3$ in MeOH (2 mL, 4 mmol) was added to adjust the pH of solution to pH 8. Purification by reverse phase basic HPLC (X-Bridge Prep C18 5 μm column 50×250 mm, 5-100% acetonitrile/water (with 20 mM NH$_4$OH)) afforded the title compound as a brown film (50% yield).

Intermediate 13

Benzyl (R)-4-cyclopropyl-1,2,3-oxathiazolidine-3-carboxylate 2,2-dioxide

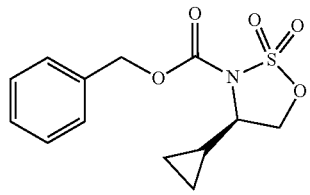 [SMILES: O=C(OCc1ccccc1)N1[C@H](C2CC2)COS1(=O)=O]

The title compound was prepared as described for the synthesis of Intermediate 11 Steps A, C and D, using (R)-2-amino-2-cyclopropylethanol hydrochloride in place of methyl 2-amino-3,3,3-trifluoropropanoate hydrochloride in Step A. In Step A, the mixture was heated at 30° C. for 16 h instead of 0° C. for 1 h and the residue was purified by silica gel chromatography (0-50% EtOAc/petroleum ether). In Step D, no CCl₄ was added and the mixture was stirred for an additional 4 h at rt.

Intermediate 14

Benzyl (R)-4-isopropyl-1,2,3-oxathiazolidine-3-carboxylate 2,2-dioxide

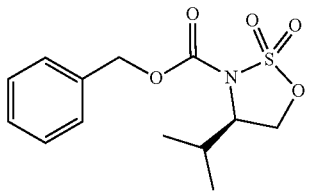 [SMILES: CC(C)[C@@H]1COS(=O)(=O)N1C(=O)OCc1ccccc1]

The title compound was prepared as described for the synthesis of Intermediate 11 Steps A, C and D, using (R)-2-amino-3-methylbutan-1-ol in place of methyl 2-amino-3,3,3-trifluoropropanoate hydrochloride in Step A. In Step A, the mixture was heated at 30° C. for 16 h instead of 0° C. for 1 h. In Step D, no CCl₄ was added and the mixture was stirred for an additional 4 h at rt.

Intermediate 15

Benzyl 4-(2,2,2-trifluoroethyl)-1,2,3-oxathiazolidine-3-carboxylate 2,2-dioxide

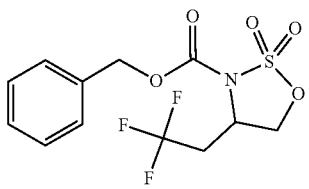 [SMILES: O=C(OCc1ccccc1)N1C(CC(F)(F)F)COS1(=O)=O]

The title compound was prepared as described for Intermediate 11 Steps A, C and D, using 2-amino-4,4,4-trifluorobutan-1-ol in place of methyl 2-amino-3,3,3-trifluoropropanoate hydrochloride in Step A. In Step A, the residue was purified by silica gel chromatography (0-25% EtOAc/petroleum ether). In Step C, the mixture was stirred for 3 h at −30° C. instead of −35° C. for 2 h, and the oxathiazolidine oxide stereoisomers were separated by silica gel chromatography (0-30% EtOAc/petroleum ether). In Step D, the benzyl (2R*)-4-(2,2,2-trifluoroethyl)-1,2,3-oxathiazolidine-3-carboxylate 2-oxide isomer was utilized, and the residue was purified by silica gel chromatography (0-13% EtOAc/petroleum ether) to provide the title compound as a white solid.

Intermediate 16 tert-Butyl ((S)-(7-((R)—(((R*)-2-amino-4,4,4-trifluorobutyl)amino)(cyclopropyl)methyl)imidazo[1,2-b]pyridazin-2-yl)(4,4-difluorocyclohexyl)methyl)carbamate

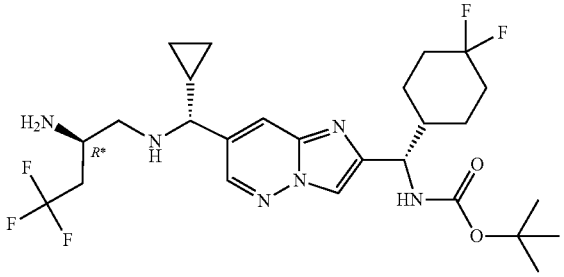 [SMILES: CC(C)(C)OC(=O)N[C@H](c1cn2ncc([C@H](NC[C@H](N)CC(F)(F)F)C3CC3)cc2n1)C1CCC(F)(F)CC1]

Intermediate 17 tert-Butyl ((S)-(7-((R)—(((S*)-2-amino-4,4,4-trifluorobutyl)amino)(cyclopropyl)methyl)imidazo[1,2-b]pyridazin-2-yl)(4,4-difluorocyclohexyl)methyl)carbamate

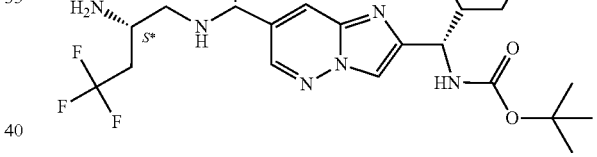

Step A: Benzyl (1-(((R)-(2-((S)-((tert-butoxycarbonyl)amino)(4,4-difluorocyclohexyl)methyl)imidazo[1,2-b]pyridazin-7-yl)(cyclopropyl)methyl)amino)-4,4,4-trifluorobutan-2-yl)carbamate. A mixture of tert-Butyl ((S)-(7-((R)-amino(cyclopropyl)methyl)imidazo[1,2-b]pyridazin-2-yl)(4,4-difluorocyclohexyl)methyl)carbamate (200 mg, 0.46 mmol), benzyl 4-(2,2,2-trifluoroethyl)-1,2,3-oxathiazolidine-3-carboxylate 2,2-dioxide (234 mg, 0.69 mmol, Intermediate 15) and sodium carbonate (146 mg, 1.38 mmol) in ACN (4 mL) was heated to 60° C. for 2 h. The reaction mixture was concentrated and the residue purified by silica gel chromatography (0-10% MeOH/DCM) to provide the title compound as a light-yellow solid (81% yield).

Step B: tert-Butyl ((1S)-(7-((1R)-((2-amino-4,4,4-trifluorobutyl)amino)(cyclopropyl)methyl)imidazo[1,2-b]pyridazin-2-yl)(4,4-difluorocyclohexyl)methyl)carbamate. The title compound was prepared as described for the synthesis of Intermediate 12 Step B using benzyl (1-(((R)-(2-((S)-((tert-butoxycarbonyl)amino)(4,4-difluorocyclohexyl)methyl)imidazo[1,2-b]pyridazin-7-yl)(cyclopropyl)methyl)amino)-4,4,4-trifluorobutan-2-yl)carbamate (Step A) in place of tert-butyl ((R)-1-(6-chloro-7-((5S*,8S)-3-oxo-1-phenyl-5-(trifluoromethyl)-2,10-dioxa-4,7-diazaundecan-8-yl-6,6-d₂)imidazo[1,2-b]pyridazin-2-yl)-2-((1,1,1-trifluoro-2-methylpropan-2-yl)oxy)ethyl)carbamate and 10% wet Pd/C in place of 10% Pd/C. The residue was purified by silica gel chromatography (0-15% MeOH/DCM) to provide the racemic title compound as a white solid (56% yield).

The (R) and (S) diastereomers of tert-Butyl ((S)-(7-((R)—(((R,S)-2-amino-4,4,4-trifluorobutyl)amino)(cyclopropyl)methyl)imidazo[1,2-b]pyridazin-2-yl)(4,4-difluorocyclohexyl)methyl)carbamate (Step B) were separated by SFC (DAICEL CHIRALPAK AD column, 10 μm, 250×30 mm, 40% IPA (with 0.1% NH$_4$OH)/CO$_2$). The first eluting diastereomer was designated R* (Intermediate 16), and was isolated as a white solid (40% yield). The second eluting diastereomer was designated S* (Intermediate 17), and was isolated as a white solid (39% yield).

Intermediate 18

Benzyl (1-formylcyclopropyl)carbamate

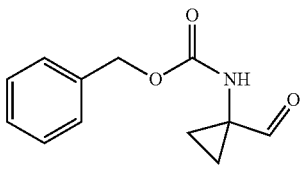 [SMILES: O=CC1(NC(=O)OCc2ccccc2)CC1]

A mixture of benzyl (1-(hydroxymethyl)cyclopropyl)carbamate (500 mg, 2.26 mmol) and pyridinium chlorochromate (0.97 g, 4.5 mmol) in DCM (10 mL) was stirred at rt for 2 h. Then, the reaction mixture was filtered and concentrated to dryness. The residue was purified by silica gel chromatography (0-50% EtOAc/petroleum ether) to provide the title compound as a white solid (80% yield).

Intermediate 19

1-((S)-(2-((S)-Amino(4,4-difluorocyclohexyl)methyl)imidazo[1,2-b]pyridazin-7-yl)((S)-2-oxo-4-(trifluoromethyl)imidazolidin-1-yl)methyl)cyclobutane-1-carbonitrile

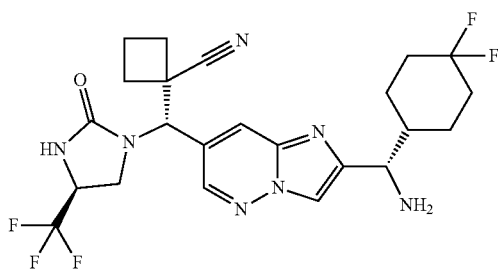 [SMILES: N#CC1([C@H](c2cnn3cc([C@@H](N)C4CCC(F)(F)CC4)nc3c2)N2C[C@@H](C(F)(F)F)NC2=O)CCC1]

Step A: tert-Butyl ((S)-(7-((S)—(((R)-tert-butylsulfinyl)amino)(1-cyanocyclobutyl)methyl)imidazo[1,2-b]pyridazin-2-yl)(4,4-difluorocyclohexyl)methyl)carbamate. To a solution of cyclobutanecarbonitrile (4.65 mL, 48.2 mmol) in THF (140 mL) cooled to 0° C. was added LiHMDS (49.8 mL, 49.8 mmol, 1 M in THF) and the resulting solution was stirred at 0° C. for 2 h to prepare the reaction mixture. Then, a solution of tert-Butyl ((S)-(7-((E)-(((R)-tert-butylsulfinyl)imino)methyl)imidazo[1,2-b]pyridazin-2-yl)(4,4-difluorocyclohexyl)methyl)carbamate (8.00 g, 16.1 mmol) in THF (40 mL) was added dropwise to the reaction mixture. The resulting solution was stirred for 3 h while warming to rt and then was quenched by the addition of saturated aqueous NH$_4$Cl (20 mL). This mixture was then diluted with half-saturated brine (200 mL) and EtOAc (100 mL) and transferred to a separatory funnel where the layers were separated. The aqueous layer was extracted with EtOAc (3×100 mL), and the combined organic layers were washed with brine, dried over anhydrous Na$_2$SO$_4$, filtered, and concentrated to dryness. The residue was initially purified by silica gel chromatography (10-60% acetone/hexanes (with 0.1% TEA)) and then further purified by SFC (Chiralpak IC3, 3 μm, 100×4.6 mm, Mobile phase: 20% methanol, 80% CO$_2$) to afford the title compound (37% yield).

Step B: tert-Butyl ((S)-(7-((S)-amino(1-cyanocyclobutyl)methyl)imidazo[1,2-b]pyridazin-2-yl)(4,4-difluorocyclohexyl)methyl)carbamate. The title compound (96% yield) was prepared as described for the synthesis of Intermediate 10 Step A using tert-Butyl ((S)-(7-((S)—(((R)-tert-butylsulfinyl)amino)(1-cyanocyclobutyl)methyl)imidazo[1,2-b]pyridazin-2-yl)(4,4-difluorocyclohexyl)methyl)carbamate (Step A) in place of N-(5-((S)-1-(((R)-tert-butylsulfinyl)amino)-2-methoxyethyl)-6-chloropyridazin-3-yl)pivalamide.

Step C: tert-Butyl ((S)-(7-((S)—(((S)-2-(((benzyloxy)carbonyl)amino)-3,3,3-trifluoropropyl)amino)(1-cyanocyclobutyl)methyl)imidazo[1,2-b]pyridazin-2-yl)(4,4-difluorocyclohexyl)methyl)carbamate. To a mixture of tert-Butyl ((S)-(7-((S)-amino(1-cyanocyclobutyl)methyl)imidazo[1,2-b]pyridazin-2-yl)(4,4-difluorocyclohexyl)methyl)carbamate (410 mg, 0.865 mmol, Step B) and DIPEA (0.17 mL, 0.95 mmol) in ACN (4.3 mL) was added benzyl (S)-4-(trifluoromethyl)-1,2,3-oxathiazolidine-3-carboxylate 2,2-dioxide (510 mg, 1.33 mmol, Intermediate SALT). The reaction mixture was heated at 45° C. for 24 h. The mixture was then concentrated and purified by silica gel chromatography (15-65% EtOAc (with 10% MeOH)/hexanes) to afford the title compound (52% yield).

Step D: tert-Butyl ((S)-(7-((S)—(((S)-2-amino-3,3,3-trifluoropropyl)amino)(1-cyanocyclobutyl)methyl)imidazo[1,2-b]pyridazin-2-yl)(4,4-difluorocyclohexyl)methyl)carbamate. A solution of tert-Butyl ((S)-(7-((S)—(((S)-2-(((benzyloxy)carbonyl)amino)-3,3,3-trifluoropropyl)amino)(1-cyanocyclobutyl)methyl)imidazo[1,2-b]pyridazin-2-yl)(4,4-difluorocyclohexyl)methyl)carbamate (324 mg, 0.45 mmol, Step C) in EtOH (92.0 mL) was transferred to a Parr shaker. Then, 10% Pd/C (479 mg, 0.45 mmol) was added and the resulting mixture was placed under 40 bar of H$_2$ for 90 min. The mixture was then filtered through diatomaceous earth (e.g. Celite®) and the filtrate was concentrated to dryness to provide the title compound that was used without further purification.

Step E: tert-Butyl ((S)-(7-((S)—(1-cyanocyclobutyl)((S)-2-oxo-4-(trifluoromethyl)imidazolidin-1-yl)methyl)imidazo[1,2-b]pyridazin-2-yl)(4,4-difluorocyclohexyl)methyl)carbamate. The title compound (47% yield over Steps D and E) was prepared as described for the synthesis of Intermediate 2 Step B using tert-Butyl ((S)-(7-((S)—(((S)-2-amino-3,3,3-trifluoropropyl)amino)(1-cyanocyclobutyl)methyl)imidazo[1,2-b]pyridazin-2-yl)(4,4-difluorocyclohexyl)methyl)carbamate (Step D) in place of tert-Butyl (S)—((7-(((2-aminoethyl)amino)methyl)imidazo[1,2-b]pyridazin-2-yl)(4,4-difluorocyclohexyl)methyl)carbamate.

Step F: 1-((S)—(2-((S)-Amino(4,4-difluorocyclohexyl)methyl)imidazo[1,2-b]pyridazin-7-yl)((S)-2-oxo-4-(trifluoromethyl)imidazolidin-1-yl)methyl)cyclobutane-1-carbonitrile. The title compound (99% yield) was prepared as described for the synthesis of Intermediate 1 Step C using tert-Butyl ((S)-(7-((S)—(1-cyanocyclobutyl)((S)-2-oxo-4-(trifluoromethyl)imidazolidin-1-yl)methyl)imidazo[1,2-b]pyridazin-2-yl)(4,4-difluorocyclohexyl)methyl)carbamate (Step E) in place of tert-Butyl (S)—((4,4-difluorocyclohexyl)((7-((2-oxoimidazolidin-1-yl)methyl)imidazo[1,2-b]pyridazin-2-yl)methyl)carbamate.

Intermediate 20

(4S)-1-(1-(2-((R)-1-Amino-2-((1,1,1-trifluoro-2-methylpropan-2-yl)oxy)ethyl)imidazo[1,2-b]pyridazin-7-yl)-2-methoxyethyl)-4-methyl-4-(trifluoromethyl)imidazolidin-2-one

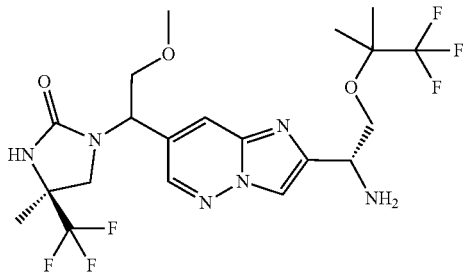 [SMILES: COCC(c1cnn2cc([C@@H](N)COC(C)(C)C(F)(F)F)nc2c1)N1C[C@@](C)(C(F)(F)F)NC1=O]

Step A: tert-Butyl (R)-(1-(7-chloroimidazo[1,2-b]pyridazin-2-yl)-2-((1,1,1-trifluoro-2-methylpropan-2-yl)oxy)ethyl)carbamate. An oven dried round-bottom flask was charged with 5-chloropyridazin-3-amine (4.45 g, 34.3 mmol), tert-Butyl (S)—(4-(dimethyl(oxo)-l$^6$-sulfaneylidene)-3-oxo-1-((1,1,1-trifluoro-2-methylpropan-2-yl)oxy)butan-2-yl)carbamate (12.7 g, 32.6 mmol), chlorocyclopentadienylbis(triphenylphosphine)ruthenium (II) (630 mg, 0.868 mmol), sodium trifluoromethanesulfonate (313 mg, 1.82 mmol) and 4 Å molecular sieves (8.9 g). Anhydrous toluene (110 mL) was added under an atmosphere of $N_2$ and then the reaction mixture was heated at 90° C. for 24 h. The mixture was allowed to cool to rt then filtered through diatomaceous earth (e.g., Celite®). The filter cake was washed with EtOAc and then the filtrate was concentrated to dryness. The residue was purified by silica gel chromatography (0-40%. EtOAc/hexanes) to provide the title compound in 28% yield.

Step B: tert-Butyl (R)-(1-(7-(3-methoxyprop-1-en-2-yl)imidazo[1,2-b]pyridazin-2-yl)-2-((1,1,1-trifluoro-2-methylpropan-2-yl)oxy)ethyl)carbamate. To a solution of tert-Butyl (R)-(1-(7-chloroimidazo[1,2-b]pyridazin-2-yl)-2-((1,1,1-trifluoro-2-methylpropan-2-yl)oxy)ethyl)carbamate (600 mg, 1.42 mmol, Step A) and 2-(3-methoxyprop-1-en-2-yl)-4,4,5,5-tetramethyl-1,3,2-dioxaborolane (562 mg, 2.84 mmol) in 1,4-dioxane (12 mL) was added a solution of $K_3PO_4$ (932 mg, 4.26 mmol) in $H_2O$ (3 mL) then the resulting mixture was degassed by $N_2$ sparging. After 5 min, RuPhos Pd G3 (30 mg, 0.036 mmol) was added and the reaction mixture was sparged with $N_2$ for an additional 5 min. The vessel was sealed, and the reaction heated at 100° C. under microwave irradiation for 30 min. The reaction mixture was diluted with brine and extracted with EtOAc. The combined organics were dried over anhydrous $Na_2SO_4$, filtered, concentrated to dryness and used without further purification.

Step C: tert-Butyl (R)-(1-(7-(2-methoxyacetyl)imidazo[1,2-b]pyridazin-2-yl)-2-(1,1,1-trifluoro-2-methylpropan-2-yl)oxy)ethyl)carbamate. To a solution of tert-Butyl (R)-(1-(7-(3-methoxyprop-1-en-2-yl)imidazo[1,2-b]pyridazin-2-yl)-2-(1,1,1-trifluoro-2-methylpropan yl)oxy)ethyl)carbamate (600 mg, 1.31 mmol, Step B) in 1,4-dioxane (11 mL) was added potassium osmate dihydrate (24 mg, 0.065 mmol). A suspension of sodium periodate (1.12 g, 5.24 mmol) in $H_2O$ (12 mL) was then added. The mixture was stirred at rt overnight then diluted with $H_2O$ and extracted with EtOAc. The combined organics were washed with saturated sodium thiosulfate and brine, dried over anhydrous $Na_2SO_4$, filtered, and concentrated to dryness. Purification by silica gel chromatography (5-40% acetone/hexanes) provided the title compound in 66% yield.

Step D: tert-Butyl ((1R)-1-(7-(1-(((S)-2-amino-3,3,3-trifluoro-2-methylpropyl)amino)-2-methoxyethyl)imidazo[1,2-b]pyridazin-2-yl)-2-(1,1,1-trifluoro-2-methylpropan-2-yl)oxy)ethyl)carbamate. To a mixture of tert-Butyl (R)-(1-(7-(2-methoxyacetyl)imidazo[1,2-b]pyridazin-2-yl)-2-(1,1,1-trifluoro-2-methylpropan-2-yl)oxy)ethyl)carbamate (0.35 g, 0.76 mmol, Step C) and (S)-3,3,3-trifluoro-2-methylpropane-1,2-diamine dihydrochloride (0.20 g, 0.91 mmol) in DCE (8 mL) was added triethylamine (0.32 mL, 2.3 mmol) and Ti(OiPr)$_4$ (0.45 mL, 1.5 mmol) and the reaction was heated at 50° C. for 24 h. MeOH (0.85 mL) was added and the resulting mixture stirred for 30 min followed by the addition of AcOH (0.22 mL, 3.8 mmol) and sodium cyanoborohydride (0.14 g, 2.3 mmol). The reaction mixture was heated at 50° C. for 30 min then another portion of sodium cyanoborohydride (0.14 g, 2.3 mmol) was added. The reaction was heated at 50° C. for 2 h, then additional portions of sodium cyanoborohydride (0.14 g, 2.3 mmol) and AcOH (0.22 mL, 3.8 mmol) were added. The reaction was heated for 1 h at 50° C. then allowed to cool to rt, diluted with saturated aqueous NaHCO$_3$ and EtOAc, and filtered through diatomaceous earth (e.g. Celite®). The layers were separated then the organics washed with brine, dried over anhydrous Na$_2$SO$_4$, filtered, concentrated to dryness and was used without further purification.

Step E: tert-Butyl ((1R)-1-(7-(2-methoxy-((S)-4-methyl-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)carbamate. A solution of tert-Butyl ((1R)-1-(7-(1-(((S)-2-amino-3,3,3-trifluoro-2-methylpropyl)amino)-2-methoxyethyl)imidazo[1,2-b]pyridazin-2-yl)-2-(1,1,1-trifluoro-2-methylpropan-2-yl)oxy)ethyl)carbamate (0.44 g, 0.75 mmol, Step D) and DIPEA (0.28 mL, 1.7 mmol) in CH$_2$Cl$_2$ (30 mL) was cooled to 0° C. then triphosgene (89 mg, 0.30 mmol) was added as a solution in CH$_2$Cl$_2$ (8 mL). The reaction mixture was stirred at rt overnight then cooled to 0° C. and additional portions of DIPEA (0.13 mL, 0.83 mmol) and triphosgene (89 mg, 0.30 mmol) were added. After stirring for 1 h at 0° C., the reaction was quenched with H$_2$O and allowed to warm to rt. The mixture was concentrated to dryness then purified by silica gel chromatography (10-100% (10% MeOH/EtOAc)/(0.1% TEA/hexanes)) to afford the title compound in 59% yield.

Step F: (4S)-1-(1-(2-((R)-1-Amino-2-((1,1,1-trifluoro-2-methylpropan-2-yl)oxy)ethyl)imidazo[1,2-b]pyridazin-7-yl)-2-methoxyethyl)-4-methyl-4-(trifluoromethyl)imidazolidin-2-one. A solution of tert-Butyl ((1R)-1-(7-(2-methoxy-((S)-4-methyl-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)carbamate (270 mg, 0.441 mmol, Step E) in CH$_2$Cl$_2$ (0.3 mL) was treated with TFA (0.675 mL, 8.82 mmol) and stirred at rt for 15 min. The mixture was diluted with CH$_2$Cl$_2$ and quenched with NaOH (441 mg, 11.0 mmol) in H$_2$O, then diluted with saturated aqueous NaHCO$_3$. The mixture was extracted with CH$_2$Cl$_2$ Intermediate 21

(S)-1-((2-((R)-1-amino-2-((1,1,1-trifluoro-2-methyl-propan-2-yl)oxy)ethyl)imidazo[1,2-b]pyridazin-7-yl)methyl)-4-(trifluoromethyl)imidazolidin-2-one

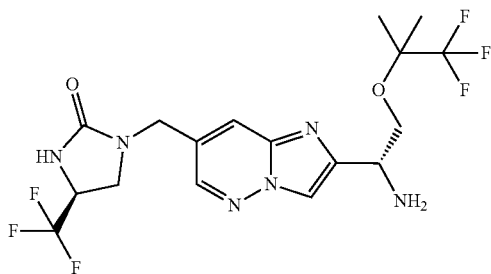 [SMILES: CC(C)(OC[C@H](N)c1cn2ncc(CN3C[C@@H](C(F)(F)F)NC3=O)cc2n1)C(F)(F)F]

Step A: (S)—N-(5-(((2-Amino-3,3,3-trifluoropropyl)amino)methyl)-6-chloropyridazin-3-yl)pivalamide. A mixture of N-(6-chloro-5-formylpyridazin-3-yl)pivalamide (1.00 g, 3.43 mmol, Intermediate 8 Step C), (2S)-3,3,3-trifluoropropane-1,2-diamine dihydrochloride (778 mg, 3.77 mmol), and DIPEA (2.08 mL, 12.0 mmol) in DCM (31 mL) was stirred at rt. After 2 h, acetic acid (0.882 mL, 15.4 mmol), MeOH (5.6 mL) and sodium cyanoborohydride (754 mg, 12.0 mmol) were added. The heterogenous reaction mixture was stirred at rt for 2 h. The reaction mixture was concentrated then saturated aqueous sodium bicarbonate (25 mL) was added and the mixture extracted with DCM (3×25 mL). The combined organic layers were dried over anhydrous $Na_2SO_4$, filtered, concentrated to dryness and purified by silica gel chromatography (0-100% EtOAc/DCM) to give the title compound (99% yield).

Step B: (S)—N-(6-Chloro-5-((2-oxo-4-(trifluoromethyl)imidazolidin-1-yl)methyl)pyridazin-3-yl)pivalamide. A mixture of (S)—N-(5-(((2-amino-3,3,3-trifluoropropyl)amino)methyl)-6-chloropyridazin-3-yl)pivalamide (1.20 g, 3.39 mmol, Step A) in DIPEA (1.75 mL, 10.2 mmol) was cooled to 0° C. Then, the mixture was treated with a solution of triphosgene (403 mg, 1.36 mmol) in DCM (30 mL) in one portion, and the resulting solution was stirred at 0° C. for 15 min. The mixture was quenched by the addition of $H_2O$ (45 mL) and extracted with DCM (3×25 mL). The combined organic extracts were dried over anhydrous $Na_2SO_4$, filtered and concentrated to dryness. The residue was purified by silica gel chromatography (0-100% EtOAc/hexanes) to give the title compound (19% yield).

Step C: (S)-1-((6-Amino-3-chloropyridazin-4-yl)methyl)-4-(trifluoromethyl)imidazolidin-2-one. To a mixture of (S)—N-(6-chloro-5-((2-oxo-4-(trifluoromethyl)imidazolidin-1-yl)methyl)pyridazin-3-yl)pivalamide (245 mg 0.645 mmol, Step B) in i-PrOH (2.6 mL) was added 5 N HCl in i-PrOH (2.6 mL, 13 mmol) and the resulting yellow mixture was heated at 85° C. After 1.5 h, the reaction mixture was cooled to rt and concentrated to dryness. The residue was diluted with EtOAc (5 mL) then the pH of the solution was adjusted to pH 7 by the addition of aqueous 1.0 M NaOH (5.2 mL). The layers were separated and then the aqueous layer was further extracted with EtOAc (2×5 mL) and 4:1 DCM:IPA (2×5 mL). The combined organic layers were dried over anhydrous $MgSO_4$, filtered and concentrated to dryness to give the title compound (100% yield) as a brown solid that was used without further purification.

Step D: tert-Butyl ((R)-1-(6-chloro-7-(((S)-2-oxo-4-(trifluoromethyl)imidazolidin-1-yl)methyl)imidazo[1,2-b]pyridazin-2-yl)-2-(1,1,1-trifluoro-2-methylpropan-2-yl)oxy)ethyl)carbamate. To a solution of (S)-1-((6-amino-3-chloropyridazin-4-yl)methyl)-4-(trifluoromethyl)imidazolidin-2-one (209 mg, 0.643 mmol, Step C) in DMA (6.7 mL) were added tert-Butyl (S)—(4-iodo-3-oxo-1-((1,1,1-trifluoro-2-methylpropan-2-yl)oxy)butan-2-yl)carbamate (645 mg, 1.35 mmol) and molecular sieves (4 Å, oven-dried, 0.63 g). The resulting mixture was then heated to 50° C. for 4 d. The reaction mixture was cooled to rt, filtered and the solids rinsed with EtOAc. The organic layer was washed with 5% aqueous LiCl (15 mL) and the aqueous portion was further extracted with EtOAc (2×15 mL). The combined organic layers were dried over anhydrous $Na_2SO_4$, filtered and concentrated to dryness. The residue was purified by silica gel chromatography twice (0-50% EtOAc/hexanes) followed by (50-100%. EtOAc/DCM) to give the title compound (16% yield).

Step E: tert-Butyl ((R)-1-(7-(((S)-2-oxo-4-(trifluoromethyl)imidazolidin-1-yl)methyl)imidazo[1,2-b]pyridazin-2-yl)-2-(1,1,1-trifluoro-2-methylpropan-2-yl)oxy)ethyl)carbamate. To a solution of tert-Butyl ((R)-1-(6-chloro-7-(((S)-2-oxo-4-(trifluoromethyl)imidazolidin-1-yl)methyl)imidazo[1,2-b]pyridazin-2-yl)-2-((1,1,1-trifluoro-2-methylpropan-2-yl)oxy)ethyl)carbamate (43 mg, 0.073 mmol, Step D) in MeOH (2.9 mL) was added 10% Pd/C (31 mg, 0.29 mmol) in a Parr bottle and the reaction mixture was placed under 3 atm of $H_2$ for 2 h. The reaction mixture was filtered through diatomaceous earth (e.g. Celite®), the filter cake rinsed with MeOH, and the filtrate concentrated to dryness to give the title compound (91% yield) that was used without further purification.

Step F: (S)-1-((2-((R)-1-Amino-2-((1,1,1-trifluoro-2-methylpropan-2-yl)oxy)ethyl)imidazo[1,2-b]pyridazin-7-yl)methyl)-4-(trifluoromethyl)imidazolidin-2-one. To a solution of tert-Butyl ((R)-1-(7-(((S)-2-oxo-4-(trifluoromethyl)imidazolidin-1-yl)methyl)imidazo[1,2-b]pyridazin-2-yl)-2-(1,1,1-trifluoro-2-methylpropan-2-yl)oxy)ethyl)carbamate (41 mg, 0.074 mmol, Step E) in DCM (1.0 mL) that had been cooled to 0° C., was added TFA (1.0 mL) and the resulting solution was stirred at 0° C. for 30 min. The reaction mixture was then warmed to rt over 30 min. The reaction mixture was concentrated and the pH was adjusted to pH 8 by the addition of 2 M $NH_3$ in MeOH (1.0 mL). Then the material was purified by preparative HPLC (10-100% $CH_3CN$/(20 mM $NH_4OH$ in $H_2O$)) to give the title compound (36% yield) as a brown film.

123

Intermediate 22 tert-Butyl ((S)-(7-((S)-1-amino-2-methoxyethyl)imidazo[1,2-b]pyridazin-2-yl)(4,4-difluorocyclohexyl)methyl)carbamate

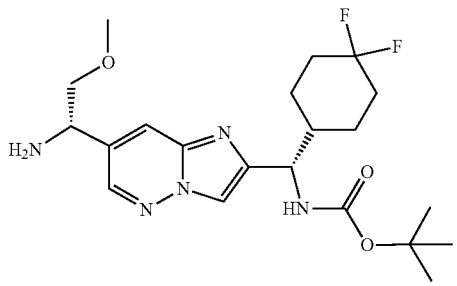 [SMILES: COC[C@@H](N)c1cnn2cc([C@@H](NC(=O)OC(C)(C)C)C3CCC(F)(F)CC3)nc2c1]

Step A: tert-Butyl ((S)-(7-((S)-1-(((R)-tert-butylsulfinyl)amino)-2-methoxyethyl)imidazo[1,2-b]pyridazin-2-yl)(4,4-difluorocyclohexyl)methyl)carbamate. To an oven-dried, $N_2$ flushed flask was added tributyl(methoxymethyl)stannane (1.41 g, 4.22 mmol) and THF (20.1 mL). This mixture was cooled to −78° C. and n-butyllithium (1.76 mL, 4.22 mmol, 2.4 M in hexanes) was added in a dropwise manner. After a further 15 min at −78° C., the reaction mixture was treated with a solution of tert-Butyl ((S)-(7-((E)-(((R)-tert-butylsulfinyl)imino)methyl)imidazo[1,2-b]pyridazin-2-yl)(4,4-difluorocyclohexyl)methyl)carbamate (1.00 g, 2.01 mmol) in THF (5 mL) in a dropwise manner. Upon stirring at −78° C. for an additional 2 h, the reaction mixture was quenched with EtOH (0.35 mL), allowed to warm to rt, and diluted with saturated aqueous $NaHCO_3$ and EtOAc. The layers were separated and the aqueous layer was further extracted with EtOAc. The combined organic layers were dried over anhydrous $Na_2SO_4$, filtered, and concentrated to dryness. The residue was purified by silica gel chromatography (40-100% acetone/hexanes) to give the title compound (39% yield) as the second eluting isomer. The absolute stereochemistry was confirmed via. Mosher analysis of tert-butyl ((S)-(7-((S)-1-amino-2-methoxyethyl)imidazo[1,2-b]pyridazin-2-yl)(4,4-difluorocyclohexyl)methyl)carbamate. A small amount of the diastereomer, tert-Butyl ((S)-(7-((R)-1-(((R)-tert-butylsulfinyl)amino)-2-methoxy ethyl)imidazo[1,2-b]pyridazin-2-yl)(4,4-difluorocyclohexyl)methyl)carbamate, was also formed in the reaction but was not used.

Step B: tert-Butyl ((S)-(7-((S)-1-amino-2-methoxyethyl)imidazo[1,2-b]pyridazin-2-yl)(4,4-difluorocyclohexyl)methyl)carbamate. The title compound (100% yield) was prepared as described for the synthesis of Intermediate 10 Step A using tert-butyl ((S)-(7-((S)-1-(((R)-tert-butylsulfinyl)amino)-2-methoxyethyl)imidazo[1,2-b]pyridazin-2-yl)(4,4-difluorocyclohexyl)methyl)carbamate (Step A) in place of N-(5-((S)-1-(((R)-tert-butylsulfinyl)amino)-2-methoxyethyl)-6-chloropyridazin-3-yl)pivalamide.

124

Intermediate 23

Benzyl (R)-4-(1-cyanocyclopropyl)-1,2,3-oxathiazolidine-3-carboxylate 2,2-dioxide

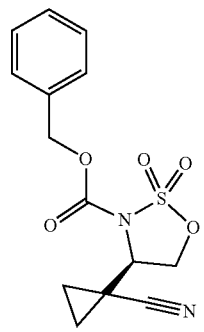 [SMILES: N#CC1([C@@H]2COS(=O)(=O)N2C(=O)OCc2ccccc2)CC1]

Step A: (R)—N—((R)-2-((tert-Butyldiphenylsilyl)oxy)-1-(1-cyanocyclopropyl)ethyl)-2-methylpropane-2-sulfinamide. Cyclopropanecarbonitrile (670 mg, 10.0 mmol) was dissolved in THF (18 mL) and the solution was cooled to −40° C. a 1 M THF solution of LiTMP (17 mL, 17 mmol) was added dropwise over 5 min and the resulting mixture was stirred for 3 h at −40° C. (R,E)-N-(2-((tert-Butyldiphenylsilyl)oxy)ethylidene)-2-methylpropane-2-sulfinamide (2.0 g, 5.0 mmol) in THF (2.0 mL) was added dropwise and the reaction mixture was allowed to gradually warm to rt and stir for 16 h. The reaction mixture was then poured into water (30 mL) and saturated aqueous $NH_4Cl$ (10 mL) and extracted with EtOAc (3×30 mL). The combined organic layers were washed with brine (30 mL), dried over anhydrous $Na_2SO_4$, filtered, and concentrated to dryness. The residue was then purified by silica gel chromatography (0-30% EtOAc/petroleum ether) to afford the title compound in 42% yield.

Step B: (R)-1-(1-Amino-2-((tert-butyldiphenylsilyl)oxy)ethyl)cyclopropane-1-carbonitrile. (R)—N—((R)-2-((tert-butyldiphenylsilyl)oxy)-1-(1-cyanocyclopropyl)ethyl)-2-methylpropane-2-sulfinamide (1.00 g, 2.13 mmol, Step A) was dissolved in THF (50 mL) and water (10 mL). Then, 12 (271 mg, 1.07 mmol) was added and the solution was heated at 60° C. and stirred for 16 h. The reaction mixture was then poured into ice water (50 mL) and extracted with EtOAc (50 mL×3). The combined organic layers were washed with brine (30 mL), dried over anhydrous $Na_2SO_4$, filtered, and concentrated to dryness. This mixture was then purified by silica gel chromatography (0-100% EtOAc/petroleum ether) to afford the title compound in 64% yield.

Step C: Benzyl (R)-(2-((tert-butyldiphenylsilyl)oxy)-1-(1-cyanocyclopropyl)ethyl)carbamate. (R)-1-(1-Amino-2-((tert-butyldiphenylsilyl)oxy)ethyl)cyclopropane-1-carbonitrile (500 mg, 1.37 mmol, Step B) was dissolved in $CHCl_3$ (5.0 mL) and the solution was cooled to 0° C. DIPEA (319 mg, 2.47 mmol) and benzyl chloroformate (0.235 mL, 1.65 mmol) were sequentially added dropwise and the reaction was allowed to gradually warm to rt while stirring for 1 h. The reaction was then poured into water (10 mL) and was extracted with EtOAc (10 mL×3). The combined organic layers were washed with brine (10 mL), dried over anhydrous $Na_2SO_4$, filtered, and concentrated to dryness. The resultant oil was then purified by silica gel chromatography (0-30% EtOAc/petroleum ether) to afford the title compound in 73% yield.

Step D: Benzyl (R)-(1-(1-cyanocyclopropyl)-2-hydroxyethyl)carbamate. Benzyl (R)-(2-((tert-butyldiphenylsilyl)oxy)-1-(1-cyanocyclopropyl)ethyl)carbamate (2.00 g, 4.01 mmol, Step C) was dissolved in MeCN (10 mL) and then CsF (30.5 g, 201 mmol) and water (0.2 mL) were added sequentially. The reaction was heated at 40° C. for 16 h, after which time, the reaction was poured into water (20 mL). The solution was extracted with EtOAc (20 mL×3) and the combined organic layers were washed with brine (20 mL), dried over anhydrous Na$_2$SO$_4$, filtered, and concentrated to dryness. The resultant oil was purified by silica gel chromatography (0-50% EtOAc/petroleum ether) to afford the title compound in 20% yield.

Step E: Benzyl (4R)-4-(1-cyanocyclopropyl)-1,2,3-oxathiazolidine-3-carboxylate 2-oxide. The title compound (100% yield) was synthesized in a manner analogous to Intermediate 11 Step C using benzyl (R)-(1-(1-cyanocyclopropyl)-2-hydroxyethyl)carbamate (Step D) in place of benzyl (S*)-(1,1,1-trifluoro-3-hydroxypropan-2-yl-3,3-d$_2$)carbamate and was used without further purification.

Step F: Benzyl (R)-4-(1-cyanocyclopropyl)-1,2,3-oxathiazolidine-3-carboxylate 2,2-dioxide. The title compound (80% yield) was synthesized in a manner analogous to Intermediate 11 Step D using benzyl (4R)-4-(1-cyanocyclopropyl)-1,2,3-oxathiazolidine-3-carboxylate 2-oxide (Step E) in place of benzyl (4S*)-4-(trifluoromethyl)-1,2,3-oxathiazolidine-3-carboxylate-5,5-d$_2$ 2-oxide and was used without further purification.

Intermediate 24

(S)-(7-((S)—((R)-4-(1-Cyanocyclopropyl)-2-oxoimidazolidin-1-yl)-2-methoxyethyl)imidazo[1,2-b]pyridazin-2-yl)(4,4-difluorocyclohexyl)methanaminium 2,2,2-trifluoroacetate

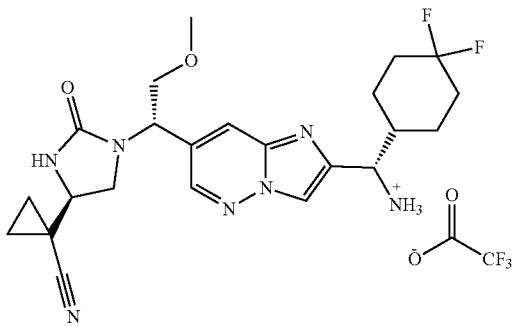

Step A: tert-Butyl ((S)-(7-((5R,8S)-5-(1-cyanocyclopropyl)-3-oxo-1-phenyl-2,10-dioxa-4,7-diazaundecan-8-yl)imidazo[1,2-b]pyridazin-2-yl)(4,4-difluorocyclohexyl)methyl)carbamate. The title compound was synthesized in a manner analogous to Intermediate 12 Step A using tert-butyl ((S)-(7-((S)-1-amino-2-methoxyethyl)imidazo[1,2-b]pyridazin-2-yl)(4,4-difluorocyclohexyl)methyl)carbamate (Intermediate 22) in place of tert-Butyl ((R)-1-(7-((S)-1-amino-2-methoxyethyl)-6-chloroimidazo[1,2-b]pyridazin-2-yl)-2-((1,1,1-trifluoro-2-methylpropan-2-yl)oxy)ethyl)carbamate and benzyl (R)-4-(1-cyanocyclopropyl)-1,2,3-oxathiazolidine-3-carboxylate 2,2-dioxide (Intermediate 23) in place of benzyl (S*)-4-(trifluoromethyl)-1,2,3-oxathiazolidine-3-carboxylate-5,5-d$_2$ 2-dioxide. The residue was purified by silica gel chromatography (0-20% MeOH/DCM) to provide the title compound in 70% yield.

Step B: tert-Butyl ((S)-(7-((S)-1-(((R)-2-amino-2-(1-cyanocyclopropyl)ethyl)amino)-2-methoxyethyl)imidazo[1,2-b]pyridazin-2-yl)(4,4-difluorocyclohexyl)methyl)carbamate. The title compound (100% yield) was synthesized in a manner analogous to Intermediate 12 Step B using tert-Butyl ((S)-(7-((5R,8S)-5-(1-cyanocyclopropyl)-3-oxo-1-phenyl-2,10-dioxa-4,7-diazaundecan-8-yl)imidazo[1,2-b]pyridazin-2-yl)(4,4-difluorocyclohexyl)methyl)carbamate (Step A) in place of tert-Butyl ((R)-1-(6-chloro-7-((5S*,8S)-3-oxo-1-phenyl-5-(trifluoromethyl)-2,10-dioxa-4,7-diazaundecan-8-yl-6,6-d$_2$)imidazo[1,2-b]pyridazin-2-yl)-2-((1,1,1-trifluoro-2-methylpropan-2-yl)oxy)ethyl)carbamate and was used without further purification.

Step C: tert-Butyl ((S)-(7-((S)-1-((R)-4-(1-cyanocyclopropyl)-2-oxoimidazolidin-1-yl)-2-methoxyethyl)imidazo[1,2-b]pyridazin-2-yl)(4,4-difluorocyclohexyl)methyl)carbamate. The title compound was synthesized in a manner analogous to Intermediate 12 Step C using tert-Butyl ((S)-(7-((S)-1-(((R)-2-amino-2-(1-cyanocyclopropyl)ethyl)amino)-2-methoxyethyl)imidazo[1,2-b]pyridazin-2-yl)(4,4-difluorocyclohexyl)methyl)carbamate (Step B) in place of tert-Butyl ((R)-1-(7-((S)-1-(((S*)-2-amino-3,3,3-trifluoropropyl-1,1-d$_2$)amino)-2-methoxyethyl)imidazo[1,2-b]pyridazin-2-yl)-2-(1,1,1-trifluoro-2-methylpropan-2-yl)oxy)ethyl)carbamate. The residue was purified by silica gel chromatography (0-100% acetone/hexanes (0.1% TEA)) to provide the title compound in 39% yield.

Step D: (S)-(7-((S)-1-((R)-4-(1-Cyanocyclopropyl)-2-oxoimidazolidin-1-yl)-2-methoxyethyl)imidazo[1,2-b]pyridazin-2-yl)(4,4-difluorocyclohexyl)methanaminium 2,2,2-trifluoroacetate. tert-Butyl ((S)-(7-((S)-1-((R)-4-(1-cyanocyclopropyl)-2-oxoimidazolidin-1-yl)-2-methoxyethyl)imidazo[1,2-b]pyridazin-2-yl)(4,4-difluorocyclohexyl)methyl)carbamate (78.5 mg, 0.137 mmol, Step C) was dissolved in DCM (4.4 mL) and the solution was cooled to 0° C. TFA (4.4 mL) was then added and the reaction was allowed to stir at 0° C. for 40 min. The solution was concentrated to dryness and used without further purification (100% yield).

Intermediate 25

Benzyl (S)-4-(difluoromethyl)-1,2,3-oxathiazolidine-3-carboxylate 2,2-dioxide

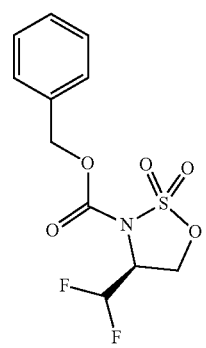 [SMILES: O=C(OCc1ccccc1)N1[C@H](C(F)F)COS1(=O)=O]

Step A: Benzyl (S)—(1,1-difluoro-3-hydroxypropan-2-yl)carbamate. The title compound was synthesized in a manner analogous to Intermediate 11 Step A using (S)-2-amino-3,3-difluoropropan-1-ol hydrochloride in place of methyl 2-amino-3,3,3-trifluoropropanoate hydrochloride. The residue was purified by silica gel chromatography (0-18% EtOAc/petroleum ether) to provide the title compound in 46% yield.

Step B: Benzyl (4S)-4-(difluoromethyl)-1,2,3-oxathiazolidine-3-carboxylate 2-oxide. The title compound was synthesized in a manner analogous to Intermediate 11 Step C using benzyl (S)—(1,1-difluoro-3-hydroxypropan-2-yl)carbamate (Step A) in place of benzyl (S*)-(1,1,1-trifluoro-3-hydroxypropan-2-yl-3,3-$d_2$)carbamate. The residue was purified by silica gel chromatography (0-22% EtOAc/petroleum ether) to provide the title compound in 85% yield.

Step C: Benzyl (S)-4-(difluoromethyl)-1,2,3-oxathiazolidine-3-carboxylate 2,2-dioxide. The title compound was synthesized in a manner analogous to Intermediate 11 Step D using benzyl (4S)-4-(difluoromethyl)-1,2,3-oxathiazolidine-3-carboxylate 2-oxide (Step B) in place of benzyl (4S*)-4-(trifluoromethyl)-1,2,3-oxathiazolidine-3-carboxylate-5,5-$d_2$-oxide. The residue was purified by silica gel chromatography (0-17% EtOAc/petroleum ether) to provide the title compound in 44% yield.

Intermediate 26

(S)—(4,4-Difluorocyclohexyl)(7-((S)-1-((S)-4-(difluoromethyl)-2-oxoimidazolidin-1-yl)-2-methoxyethyl)imidazo[1,2-b]pyridazin-2-yl)methanaminium chloride

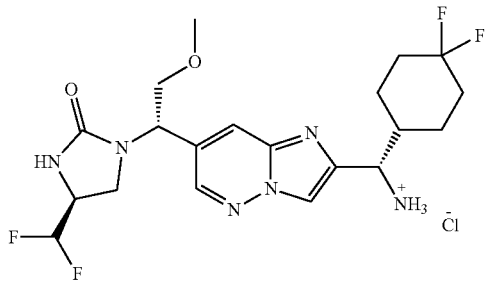 [SMILES: COC[C@H](c1cnn2cc([C@@H](N)C3CCC(F)(F)CC3)nc2c1)N1C[C@@H](C(F)F)NC1=O ; Cl]

Step A: tert-Butyl ((S)—(4,4-difluorocyclohexyl)(7-((5S,8S)-5-(difluoromethyl)-3-oxo-1-phenyl-2,10-dioxa-4,7-diazaundecan-8-yl)imidazo[1,2-b]pyridazin-2-yl)methyl)carbamate. The title compound was synthesized in a manner analogous to Intermediate 12 Step A using tert-butyl ((S)-(7-((S)-1-amino-2-methoxyethyl)imidazo[1,2-b]pyridazin-2-yl)(4,4-difluorocyclohexyl)methyl)carbamate (Intermediate 22) in place of tert-Butyl ((R)-1-(7-((S)-1-amino-2-methoxyethyl)-6-chloroimidazo[1,2-b]pyridazin-2-yl)-2-((1,1,1-trifluoro-2-methylpropan-2-yl)oxy)ethyl)carbamate and benzyl (S)-4-(difluoromethyl)-1,2,3-oxathiazolidine-3-carboxylate 2,2-dioxide (Intermediate 25) in place of benzyl (S*)-4-(trifluoromethyl)-1,2,3-oxathiazolidine-3-carboxylate-5,5-$d_2$ 2,2-dioxide. The residue was purified by silica gel chromatography (0-20% MeOH/DCM) to provide the title compound in 79% yield.

Step B: tert-Butyl ((S)-(7-((S)-1-(((S)-2-amino-3,3-difluoropropyl)amino)-2-methoxyethyl)imidazo[1,2-b]pyridazin-2-yl)(4,4-difluorocyclohexyl)methyl)carbamate. The title compound (100% yield) was synthesized in a manner analogous to Intermediate 12 Step B using tert-Butyl ((S)—(4,4-difluorocyclohexyl)(7-((5S,8S)-5-(difluoromethyl)-3-oxo-1-phenyl-2,10-dioxa-4,7-diazaundecan-8-yl)imidazo[1,2-b]pyridazin-2-yl)methyl)carbamate (Step A) in place of tert-Butyl ((R)-1-(6-chloro-7-((5S*,8S)-3-oxo-1-phenyl-5-(trifluoromethyl)-2,10-dioxa-4,7-diazaundecan-8-yl-6,6-$d_2$)imidazo[1,2-b]pyridazin-2-yl)-2-((1,1,1-trifluoro-2-methylpropan-2-yl)oxy)ethyl)carbamate and was used without further purification.

Step C: tert-Butyl ((S)—(4,4-difluorocyclohexyl)(7-((S)-1-((S)-4-(difluoromethyl)-2-oxoimidazolidin-1-yl)-2-methoxyethyl)imidazo[1,2-b]pyridazin-2-yl)methyl)carbamate. The title compound was synthesized in a manner analogous to Intermediate 12 Step C using tert-Butyl ((S)-(7-((S)-1-(((S)-2-amino-3,3-difluoropropyl)amino)-2-methoxyethyl)imidazo[1,2-b]pyridazin-2-yl)(4,4-difluorocyclohexyl)methyl)carbamate (Step B) in place of tert-Butyl ((R)-1-(7-((S)-1-(((S*)-2-amino-3,3,3-trifluoropropyl-1,1-$d_2$)amino)-2-methoxyethyl)imidazo[1,2-b]pyridazin-2-yl)-2-(1,1,1-trifluoro-2-methylpropan-2-yl)oxy)ethyl)carbamate. The residue was purified by silica gel chromatography (0-100% acetone/hexanes (0.1% TEA)) to provide the title compound in 6% yield.

Step D: (S)—(4,4-Difluorocyclohexyl)(7-((S)—((S)-4-(difluoromethyl)-2-oxoimidazolidin-1-yl)-2-methoxyethyl)imidazo[1,2-b]pyridazin-2-yl)methanaminium chloride. tert-Butyl ((S)—(4,4-difluorocyclohexyl)(7-((S)-1-((S)-4-(difluoromethyl)-2-oxoimidazolidin-1-yl)-2-methoxyethyl)imidazo[1,2-b]pyridazin-2-yl)methyl)carbamate (14.5 mg, 26.0 mmol, Step C) was dissolved in DCM (0.26 mL) and then a 4 M solution of HCl in 1,4-dioxane (64.9 mL, 0.26 mmol) was added dropwise. The reaction mixture was allowed to stir at rt for 40 min and was then concentrated to dryness and used without further purification (92% yield).

Intermediate 27 tert-Butyl ((3S,4R)-1-iodo-2-oxo-4-(((R)-1,1,1-trifluoropropan-2-yl)oxy)pentan-3-yl)carbamate

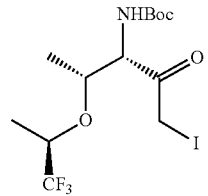 [SMILES: C[C@@H](O[C@H](C)C(F)(F)F)[C@H](NC(=O)OC(C)(C)C)C(=O)CI]

Step A: (R)-2-(((R)-1,1,1-Trifluoropropan-2-yl)oxy)propanoic acid. Sodium hydride (3.5 g, 88 mmol, 60% dispersion in mineral oil) was added in portions to a solution of (R)-1,1,1-trifluoropropan-2-ol (5.0 g, 44 mmol) in DMF (70 mL) at 0° C. The resultant mixture was stirred for 30 min at rt before recooling the reaction mixture to 0° C. A solution of (S)-2-bromopropanoic acid (6.0 g, 40 mmol) in DMF (5 mL) was added to the reaction mixture at 0° C. and the resulting mixture was allowed to warm to rt and stir for 12 h. After this time, the reaction mixture was poured into ice chilled water (100 mL) and extracted with MTBE (25 mL). The pH of the aqueous layer was adjusted to pH 5-6 by the addition of 2 N aqueous HCl (15 mL). The aqueous layer was then extracted with MTBE (80 mL×3). The combined organic layers were washed with brine, dried over anhydrous $Na_2SO_4$, filtered, and concentrated to dryness to afford the title compound as a yellow oil (93% yield) that was used without further purification.

Step B: (R)—N-Methoxy-N-methyl-2-(((R)-1,1,1-trifluoropropan-2-yl)oxy)propanamide. A flask was charged with (R)-2-(((R)-1,1,1-trifluoropropan-2-yl)oxy)propanoic acid (7.6 g, 41 mmol, Step A), DMF (70 mL), HATU (20 g, 53 mmol), and DIPEA (18 mL, 102 mmol). The mixture was stirred for 5 min before the addition of N,O-dimethylhydroxylamine hydrochloride (6.0 g, 61 mmol). The resulting solution was stirred for 12 h. After which time, the reaction was quenched with water (30 mL) and diluted with MTBE (50 mL). The organic layer was separated, and the aqueous layer was extracted with MTBE (80 mL×2). The combined organic layers were washed with water and brine, dried over anhydrous $Na_2SO_4$, filtered, and concentrated to dryness. The residue was purified by silica gel chromatography (9-17% EtOAc/petroleum ether) to afford the title compound as a yellow oil (58% yield).

Step C: (R)-2-(((R)-1,1,1-Trifluoropropan-2-yl)oxy)propanal. A flask was charged with (R)—N-methoxy-N-methyl-2-(((R)-1,1,1-trifluoropropan-2-yl)oxy)propanamide (5.4 g, 24 mmol, Step B) and THF (300 mL). The mixture was cooled to −78° C. and then LAH (4.5 g, 120 mmol) was added portion wise. The resulting mixture was stirred for about 1 h at −78° C. and was subsequently quenched with water (20 mL) dropwise at −78° C. A saturated aqueous solution of sodium potassium tartrate (120 mL) was added, and the solution was stirred at rt for 30 min and then extracted with MTBE (120 mL×3). The combined organic layers were washed with brine, dried over anhydrous $Na_2SO_4$, filtered, and concentrated to dryness to afford the title compound (100% yield) that was used without further purification.

Step D: (S)-2-Methyl-N—((R,E)-2-(((R)-1,1,1-trifluoropropan-2-yl)oxy)propylidene)propane-2-sulfinamide. A flask was charged with (R)-2-(((R)-1,1,1-trifluoropropan-2-yl)oxy)propanal (7.4 g, 44 mmol, Step C), THF (250 mL), $CuSO_4$ (28 g, 174 mmol), (S)-2-methylpropane-2-sulfinamide (7.9 g, 65 mmol), and PPTS (2.2 g, 8.7 mmol), and the resulting mixture was heated at 30° C. for 16 h. The suspension was filtered through diatomaceous earth (e.g., Celite®), and the filtrate was concentrated to dryness. The residue was purified by silica gel chromatography (0-50% EtOAc/petroleum ether) to afford the title compound as a colorless oil (73% yield).

Step E: (S)—N-((1R,2R)-1-Cyano-2-(((R)-1,1,1-trifluoropropan-2-yl)oxy)propyl)-2-methylpropane-2-sulfinamide. A mixture of (S)-2-methyl-N—((R,E)-2-(((R)-1,1,1-trifluoropropan-2-yl)oxy)propylidene)propane-2-sulfinamide (8.7 g, 32 mmol, Step D), TMSCN (5.5 mL, 44 mmol), $Sc(OTf)_3$ (3.1 g, 6.4 mmol), and 4 Å molecular sieves (5 g) in DCM (100 mL) was stirred at rt for 16 h. The reaction mixture was then filtered and concentrated to dryness. Purification by silica gel chromatography (0-60% EtOAc/petroleum ether) provided the title compound as a colorless oil in 79% yield.

Step F: O—((R)-1,1,1-Trifluoropropan-2-yl)-L-threonine hydrochloride. (S)—N-((1R,2R)-1-Cyano-2-(((R)-1,1,1-trifluoropropan-2-yl)oxy)propyl)-2-methylpropane-2-sulfinamide (7.6 g, 25 mmol, Step E) was dissolved in 4 M HCl in 1,4-dioxane (120 mL) and water (20 mL). The resulting mixture was heated at 80° C. for 16 h. The reaction mixture was then cooled to rt and concentrated to dryness to afford the title compound as a brown oil, which was used without further purification (100% yield). The absolute stereochemistry of the title compound was confirmed by Mosher analysis.

Step G: N-(tert-Butoxycarbonyl)-O—((R)-1,1,1-trifluoropropan-2-yl)-L-threonine. A flask was charged with O—((R)-1,1,1-trifluoropropan-2-yl)-L-threonine hydrochloride (7.3 g, 25 mmol, Step F), THF (100 mL), and 1 M aqueous NaOH (101 mL) and the mixture was allowed to stir at rt for 0.5 h. $Boc_2O$ (5.5 g, 25 mmol) was then added in one portion and the reaction was allowed to stir for 16 h at rt. The reaction mixture was poured into water (100 mL) and the biphasic mixture was extracted with EtOAc (3×100 mL). The pH of the aqueous layer was then adjusted to pH 3-4 by the addition of citric acid. The acidic aqueous layer was then extracted with EtOAc (3×100 mL) and the combined organic layers were washed with brine, dried over anhydrous $MgSO_4$, filtered, and concentrated to dryness to afford the title compound in 88% yield, which was used without further purification.

Step H: tert-Butyl ((3S,4R)-1-(dimethyl(oxo)-$\lambda^6$-sulfaneylidene)-2-oxo-4-(((R)-1,1,1-trifluoropropan-2-yl)oxy)pentan-3-yl)carbamate. To a suspension of trimethylsulfoxonium iodide (15.5 g, 49.2 mmol) in THF (250 mL) was added a 1 M THF solution of potassium tert-butoxide (73.7 mL, 73.7 mmol). The resulting mixture was stirred at rt for 2 h. In a separate flask a solution of N-(tert-butoxycarbonyl)-O—((R)-1,1,1-trifluoropropan-2-yl)-L-threonine (15.5 g, 49.2 mmol, Step G) in THF (250 mL) was cooled to 0° C., charged with CDI (9.57 g, 59.0 mmol) in one portion, and stirred for 2 h at 0° C. The CDI solution was then added dropwise to the trimethylsulfoxonium iodide solution and the resulting mixture was allowed to stir for 2 h at 25° C. The reaction mixture was then poured into water (200 mL) and extracted with EtOAc (100 mL×3). The combined organic layers were washed with brine, dried over anhydrous $MgSO_4$, filtered, and concentrated to dryness. The residue was initially purified by silica gel chromatography (0-100% EtOAc/petroleum ether) and then subsequently purified by chiral SFC (DAICEL CHIRALPAK AD, 10 μm, 50×250 mm, 20% EtOH (with 0.1% of 25% aqueous $NH_3$)/$CO_2$) to afford the title compound in 21% yield as the first eluting fraction.

Step I: tert-Butyl ((3S,4R)-1-chloro-2-oxo-4-(((R)-1,1,1-trifluoropropan-2-yl)oxy)pentan-3-yl)carbamate. An oven dried round bottom flask was charged with anhydrous lithium chloride (120 mg, 2.85 mmol) and tert-Butyl ((3S, 4R)-1-(dimethyl(oxo)-$\lambda^6$-sulfaneylidene)-2-oxo-4-(((R)-1, 1,1-trifluoropropan-2-yl)oxy)pentan-3-yl)carbamate (400 mg, 1.03 mmol, Step H) under an $N_2$ atmosphere. Anhydrous THF (7.2 mL) was added, the reaction mixture was cooled to 0° C., then methanesulfonic acid (71.5 μL, 1.01 mmol) was added dropwise. The reaction mixture was maintained at 0° C. for 10 min then heated at 60° C. for 3 h. After this time, the mixture was cooled to rt, diluted with $H_2O$, and extracted with 1:1 EtOAc:hexanes. The combined organic extracts were washed with brine, dried over anhydrous $Na_2SO_4$, filtered, and concentrated to dryness to provide the title compound that was used without further purification.

Step J: tert-Butyl ((3S,4R)-1-iodo-2-oxo-4-(((R)-1,1,1-trifluoropropan-2-yl)oxy)pentan-3-yl)carbamate. A mixture of tert-Butyl ((3S,4R)-1-chloro-2-oxo-4-(((R)-1,1,1-trifluoropropan-2-yl)oxy)pentan-3-yl)carbamate (354 mg, 1.02 mmol, Step I) and NaI (1.53 g, 10.2 mmol) in acetone was stirred at rt for 1 h then diluted with EtOAc and filtered. The filtrate was washed with saturated aqueous sodium thiosulfate then dried over anhydrous $Na_2SO_4$, filtered, and concentrated to dryness to afford the title compound that was used without further purification.

Intermediate 28

Benzyl (S)-4-(trifluoromethyl)-1,2,3-oxathiazolidine-3-carboxylate 2,2-dioxide

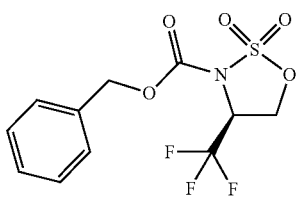 [SMILES: O=C(OCc1ccccc1)N1[C@H](C(F)(F)F)COS1(=O)=O]

Step A: Benzyl (S)—(1,1,1-trifluoro-3-hydroxypropan-2-yl)carbamate. The title compound was synthesized in a manner analogous to Intermediate 11 Step A using (S)-2-amino-3,3,3-trifluoropropan-1-ol hydrochloride in place of methyl 2-amino-3,3,3-trifluoropropanoate hydrochloride. The residue was purified by silica gel chromatography (40-50% EtOAc/petroleum ether) to provide the title compound in 85% yield.

Step B: Benzyl (4S)-4-(trifluoromethyl)-1,2,3-oxathiazolidine-3-carboxylate 2-oxide. The title compound was synthesized in a manner analogous to Intermediate 11 Step C using benzyl (S)—(1,1,1-trifluoro-3-hydroxypropan-2-yl)carbamate (Step A) in place of benzyl (S*)-(1,1,1-trifluoro-3-hydroxypropan-2-yl-3,3-d$_2$)carbamate and was used without further purification.

Step C: Benzyl (S)-4-(trifluoromethyl)-1,2,3-oxathiazolidine-3-carboxylate 2,2-dioxide. The title compound was synthesized in a manner analogous to Intermediate 11 Step D using benzyl (4S)-4-(trifluoromethyl)-1,2,3-oxathiazolidine-3-carboxylate 2-oxide (Step B) in place of benzyl (4S*)-4-(trifluoromethyl)-1,2,3-oxathiazolidine-3-carboxylate-5,5-d$_2$ 2-oxide. The residue was purified by silica gel chromatography (20-30% EtOAc/petroleum ether) to provide the title compound in 42% yield.

Intermediate 29

(1R,2R)-1-(7-((S)-2-Methoxy-1-((S)-2-oxo-4-(trifluoromethyl)imidazolidin-1-yl)ethyl)imidazo[1,2-b]pyridazin-2-yl)-2-(((R)-1,1,1-trifluoropropan-2-yl)oxy)propan-1-aminium 2,2,2-trifluoroacetate

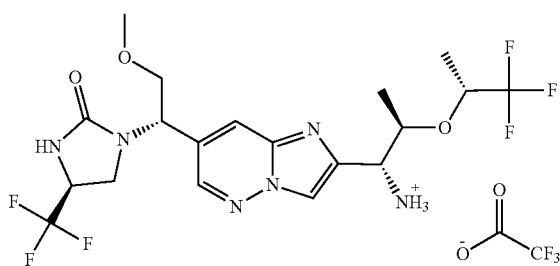

Step A: tert-Butyl ((1R,2R)-1-(6-chloro-7-((S)-1-(1,3-dioxoisoindolin-2-yl)-2-methoxyethyl)imidazo[1,2-b]pyridazin-2-yl)-2-(((R)-1,1,1-trifluoropropan-yl)oxy)propyl)carbamate. (S)-2-(1-(6-Amino-3-chloropyridazin-4-yl)-2-methoxyethyl)isoindoline-1,3-dione (150 mg, 0.451 mmol, Intermediate 10 Step C), tert-Butyl ((3S,4R)-1-iodo-2-oxo-4-(((R)-1,1,1-trifluoropropan-2-yl)oxy)pentan-3-yl)carbamate (297 mg, 0.676 mmol, Intermediate 27) and sodium phosphate dibasic (83.5 mg, 0.588 mmol) were dissolved in NMP (0.33 mL) and the resulting mixture was heated at 40° C. for 18 h. After this time, additional tert-Butyl ((3S,4R)-1-iodo-2-oxo-4-(((R)-1,1,1-trifluoropropan-2-yl)oxy)pentan-3-yl)carbamate (297 mg, Intermediate 27) was added and the reaction mixture was heated for an additional 20 h at 40° C. The reaction mixture was then diluted with water (10 mL) and EtOAc (10 mL) and the biphasic mixture was extracted with EtOAc (3×10 mL). The combined organic layers were washed with brine, dried over anhydrous Na$_2$SO$_4$, filtered, and concentrated to dryness. The residue was then purified by silica gel chromatography (0-100% acetone/hexanes (0.1% TEA)) to afford the title compound in 53% yield.

Step B: tert-Butyl ((1R,2R)-1-(7-((S)-1-amino-2-methoxyethyl)-6-chloroimidazo[1,2-b]pyridazin-2-yl)-2-((R)-1,1,1-trifluoropropan-2-yl)oxy)propyl)carbamate. The title compound was synthesized in a manner analogous to Intermediate 10 Step E using tert-Butyl ((1R,2R)-1-(6-chloro-7-((S)-1-(1,3-dioxoisoindolin-2-yl)-2-methoxyethyl)imidazo[1,2-b]pyridazin-2-yl)-2-(((R)-1,1,1-trifluoropropan-2-yl)oxy)propyl)carbamate (Step A) in place of tert-Butyl ((R)-1-(6-chloro-7-((S)-1-(1,3-dioxoisoindolin-2-yl)-2-methoxyethyl)imidazo[1,2-b]pyridazin-2-yl)-2-((1,1,1-trifluoro-2-methylpropan-2-yl)oxy)ethyl)carbamate and was used without further purification.

Step C: tert-Butyl ((1R,2R)-1-(6-chloro-7-((5S,8S)-3-oxo-1-phenyl-5-(trifluoromethyl)-2,10-dioxa-4,7-diazaundecan-8-yl)imidazo[1,2-b]pyridazin-2-yl)-2-(((R)-1,1,1-trifluoropropan-2-yl)oxy)propyl)carbamate. The title compound (90% yield over Steps B and C) was synthesized in a manner analogous to Intermediate 12 Step A using tert-Butyl ((1R,2R)-1-(7-((S)-1-amino-2-methoxyethyl)-6-chloroimidazo[1,2-b]pyridazin-2-yl)-2-(((R)-1,1,1-trifluoropropan-2-yl)oxy)propyl)carbamate (Step B) in place of tert-Butyl ((R)-1-(7-((S)-1-amino-2-methoxyethyl)-6-chloroimidazo[1,2-b]pyridazin-2-yl)-2-(1,1,1-trifluoro-2-methylpropan-2-yl)oxy)ethyl)carbamate and benzyl (S)-4-(trifluoromethyl)-1,2,3-oxathiazolidine-3-carboxylate 2,2-dioxide (Intermediate 28) in place of benzyl (S*)-4-(trifluoromethyl)-1,2,3-oxathiazolidine-3-carboxylate-5,5-d$_2$ 2,2-dioxide.

Step D: tert-Butyl ((1R,2R)-1-(7-((S)-1-(((S)-2-amino-3,3,3-trifluoropropyl)amino)-2-methoxyethyl)imidazo[1,2-b]pyridazin-2-yl)-2-(((R)-1,1,1-trifluoropropan-2-yl)oxy)propyl)carbamate. tert-Butyl ((1R,2R)-1-(6-chloro-7-((5S,8S)-3-oxo-1-phenyl-5-(trifluoromethyl)-2,10-dioxa-4,7-diazaundecan-8-yl)imidazo[1,2-b]pyridazin-2-yl)-2-(((R)-1,1,1-trifluoropropan-2-yl)oxy)propyl)carbamate (161 mg, 0.217 mmol, Step C) was dissolved in EtOH (17 mL) and then TFE (8 mL), ammonium formate (205 mg, 3.25 mmol) and 10% wt Pd/C (132 mg) were sequentially added. The resulting heterogenous solution was heated at 85° C. for 1 h under a N$_2$ atmosphere. The reaction mixture was then filtered through diatomaceous earth (e.g., Celite®), concentrated to dryness, and purified by silica gel chromatography (0-100% acetone/hexanes (0.1% TEA)) to afford the title compound in 46% yield.

Step E: tert-Butyl ((1R,2R)-1-(7-((S)-2-methoxy-1-((S)-2-oxo-4-(trifluoromethyl)imidazolidin-1-yl)ethyl)imidazo[1,2-b]pyridazin-2-yl)-2-(((R)-1,1,1-trifluoropropan-2-yl)oxy)propyl)carbamate. The title compound was synthesized in a manner analogous to Intermediate 12 Step C using tert-Butyl ((1R,2R)-1-(7-((S)—((S)-2-amino-3,3,3-trifluoropropyl)amino)-2-methoxyethyl)imidazo[1,2-b]pyridazin- 2-yl)-2-(((R)-1,1,1-trifluoropropan-2-yl)oxy)propyl)carbamate (Step D) in place of tert-Butyl ((R)-1-(7-((S)-1-(((S*)-2-amino-3,3,3-trifluoropropyl-1,1-d₂)amino)-2-methoxyethyl)imidazo[1,2-b]pyridazin-2-yl)-2-((1,1,1-trifluoro-2-methylpropan-2-yl)oxy)ethyl)carbamate. The residue was purified by silica gel chromatography (0-100% acetone/hexanes (0.1% TEA)) to provide the title compound in 50% yield.

Step F: (1R,2R)-1-(7-((S)-2-Methoxy-((S)-2-oxo-4-(trifluoromethyl)imidazolidin-1-yl)ethyl)imidazo[1,2-b]pyridazin-2-yl)-2-(((R)-1,1,1-trifluoropropan-2-yl)oxy)propan-1-aminium 2,2,2-trifluoroacetate. The title compound was synthesized in a manner analogous to Intermediate 24 Step D using tert-Butyl ((1R,2R)-1-(7-((S)-2-methoxy-1-((S)-2-oxo-4-(trifluoromethyl)imidazolidin-1-yl)ethyl)imidazo[1,2-b]pyridazin-2-yl)-2-(((R)-1,1,1-trifluoropropan-2-yl)oxy)propyl)carbamate (Step E) in place of tert-Butyl ((S)-(7-((S)-1-((R)-4-(1-cyanocyclopropyl)-2-oxoimidazolidin-1-yl)-2-methoxyethyl)imidazo[1,2-b]pyridazin-2-yl)(4,4-difluorocyclohexyl)methyl)carbamate and was used without further purification.

Intermediate 30

(S)-2-Methyl-1-((4-nitrophenyl)sulfonyl)-2-(trifluoromethyl)aziridine

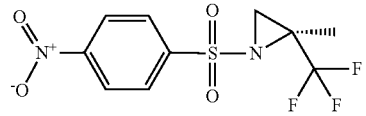

Step A: Ethyl (4S)-4-phenyl-2-(trifluoromethyl)oxazolidine-2-carboxylate. To ethyl 3,3,3-trifluoro-2-oxopropanoate (3.0 g, 17.6 mmol) dissolved in toluene (176 mL) was added (S)-2-amino-2-phenylethan-1-ol (2.42 g, 17.6 mmol) and pyridinium p-toluenesulfonate (1.11 g, 4.41 mmol). The reaction mixture was heated to reflux at 112° C. for 18 h. The reaction was then cooled to rt and then to 0° C. using an ice-water bath. The reaction mixture was then concentrated to dryness and purified by silica gel chromatography (0-40% EtOAc/hexanes) to afford the title compound (38% yield).

Step B: ((4S)-4-Phenyl-2-(trifluoromethyl)oxazolidin-2-yl)methanol. In a flask under an atmosphere of N₂ was added ethyl (4S)-4-phenyl-2-(trifluoromethyl)oxazolidine-2-carboxylate (11.7 g, 40.6 mmol, Step A) and MeOH (162 mL). The mixture was cooled to 0° C. using an ice-water bath and then sodium borohydride (1.55 g, 40.6 mmol) was added in portions. The reaction was stirred for 2 h while the ice-water bath slowly warmed to rt. The reaction was then quenched with saturated aqueous NH₄Cl (25 mL). The reaction was concentrated under reduced pressure and EtOAc (30 mL) was added to the aqueous solution. The layers were separated and the aqueous layer was extracted with EtOAc (2×30 mL). The combined organic layer was washed with brine, dried over anhydrous Na₂SO₄, filtered, and concentrated to dryness to give a white solid. The solid was washed with pentane and filtered to give the title compound as a white solid (56% yield).

Step C: (S)-3,3,3-Trifluoro-2-(((S)-2-hydroxy-1-phenylethyl)amino)-2-methylpropan-1-ol. To an oven dried flask was added ((4S)-4-phenyl-2-(trifluoromethyl)oxazolidin-2-yl)methanol (5.14 g, 20.8 mmol, Step B) in THF (200 mL). The mixture was cooled to −78° C. and then methyllithium (36.9 mL, 114 mmol) was added slowly. After 10 min at −78° C., the acetone-dry ice bath was removed, and the reaction stirred at rt for 2.5 h. The reaction was quenched with saturated aqueous NH₄Cl solution (150 mL). The layers were separated and the aqueous layer was extracted with EtOAc (3×75 mL). The combined organic layers were washed with brine, dried over anhydrous MgSO₄, filtered, and concentrated to dryness. The residue obtained was purified by silica gel chromatography (0-60% EtOAc/hexanes) to provide a 2.5 to 1 Mixture of (S)-3,3,3-trifluoro-2-(((S)-2-hydroxy-1-phenylethyl)amino)-2-methylpropan-1-ol to (R)-3,3,3-trifluoro-2-(((S)-2-hydroxy-1-phenylethyl)amino)-2-methylpropan-1-ol. This mixture was used in the next step without separation and further purification.

Step D: (S)-2-Amino-3,3,3-trifluoro-2-methylpropan-1-ol hydrochloride. (S)-3,3,3-Trifluoro-2-(((S)-2-hydroxy-1-phenylethyl)amino)-2-methylpropan-1-ol (4.0 g, 15.2 mmol, Step C), palladium hydroxide on carbon (1.07 g, 7.60 mmol), and HCl in water (2 M, 11.4 mL, 22.8 mmol) were added sequentially to a Parr shaker containing MeOH (23 mL). The vessel was then pressurized to 50 psi of H₂ and shaken for about 18 h. After this time, the reaction vessel was depressurized, and the reaction mixture was filtered and concentrated to dryness. The residue was dissolved in aqueous 2 M HCl and the aqueous layer was washed with MTBE (2×20 mL). The aqueous layer was concentrated to dryness to provide the title compound that was used without further purification (100% yield).

Step E: (S)-3,3,3-Trifluoro-2-methyl-2-((4-nitrophenyl)sulfonamido)propyl 4-nitrobenzenesulfonate. (S)-2-Amino-3,3,3-trifluoro-2-methylpropan-1-ol hydrochloride (1.0 g, 6.99 mmol, Step D) in DCM (35 mL) was cooled to 0° C. and then DIPEA (3.61 mL, 21.0 mmol) and 4-nitrobenzenesulfonyl chloride (3.43 g, 15.0 mmol) were added. The reaction mixture was allowed to warm to rt and stirred for 18 h. The reaction was quenched with aqueous 2 M HCl and the aqueous layer was extracted with DCM (2×30 mL). The combined organic layers were washed with 5% aqueous NaCO₃, dried over anhydrous MgSO₄, filtered, and concentrated to dryness. The residue was purified by silica gel chromatography (0-50% EtOAc/hexanes) to provide the title compound (50% yield).

Step F: (S)-2-Methyl-1-((4-nitrophenyl)sulfonyl)-2-(trifluoromethyl)aziridine. To a mixture of (S)-3,3,3-trifluoro-2-methyl-2-((4-nitrophenyl)sulfonamido)propyl 4-nitrobenzenesulfonate (93.0 mg, 0.184 mmol, Step E) in THF (3.6 mL) was added DIPEA (37.5 µL, 0.217 mmol). The resulting mixture was heated at 60° C. for 2 h. The reaction was quenched with water (1 mL) and extracted with EtOAc (3×4 mL). The combined organic layers were dried over anhydrous Na₂SO₄, filtered, and concentrated to dryness. The residue was purified by silica gel chromatography (0-50% EtOAc/hexanes) to provide the title compound (82% yield).

Intermediate 31 tert-Butyl ((S)-(7-((((S)-2-amino-3,3,3-trifluoro-2-methylpropyl)amino)methyl)imidazo[1,2-b]pyridazin-2-yl)(4,4-difluorocyclohexyl)methyl)carbamate

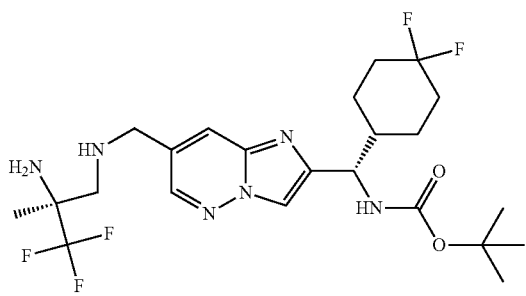 [SMILES: CC(C)(C)OC(=O)N[C@H](c1cn2ncc(CNC[C@](C)(N)C(F)(F)F)cc2n1)C1CCC(F)(F)CC1]

To tert-Butyl (S)—((4,4-difluorocyclohexyl)(7-formylimidazo[1,2-b]pyridazin-2-yl)methyl)carbamate (250 mg, 0.634 mmol) dissolved in DCE (6.34 mL) were added (S)-3,3,3-trifluoro-2-methylpropane-1,2-diamine dihydrochloride (164 mg, 0.761 mmol), Et₃N (0.264 mL, 1.90 mmol) and tetraisopropoxytitanium (0.371 mL, 1.27 mmol). The resulting mixture was heated at 50° C. for 3 h. The reaction mixture was then cooled to rt and AcOH (0.181 mL, 3.17 mmol), MeOH (0.71 mL) and sodium cyanoborohydride (119 mg, 1.90 mmol) were added. The mixture was heated at 50° C. for 30 min. The reaction mixture was then cooled to rt, diluted with saturated aqueous NaHCO₃ and EtOAc, and filtered through diatomaceous earth (e.g., Celite®). The filtrate was concentrated to remove the MeOH. To the aqueous solution was added EtOAc (15 mL) and the layers were separated. The aqueous was further extracted with EtOAc (3×15 mL), the organic layers combined, washed with brine, dried over anhydrous Na₂SO₄, filtered and concentrated to dryness to provide the title compound which was used without further purification (94% yield).

Intermediate 32

(S)-1-((2-((S)-Amino(4,4-difluorocyclohexyl)methyl)imidazo[1,2-b]pyridazin-7-yl)methyl)-4-methyl-4-(trifluoromethyl)imidazolidin-2-one

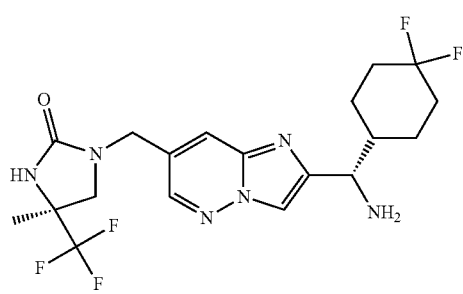 [SMILES: C[C@@]1(C(F)(F)F)CN(Cc2cnn3cc([C@@H](N)C4CCC(F)(F)CC4)nc3c2)C(=O)N1]

Step A: tert-Butyl ((S)—(4,4-difluorocyclohexyl)(7-((S)-4-methyl-2-oxo-4-(trifluoromethyl)imidazolidin-1-yl)methyl)imidazo[1,2-b]pyridazin-2-yl)methyl)carbamate. The title compound (68% yield) was synthesized in a manner analogous to Intermediate 12 Step C using tert-Butyl ((S)-(7-((((S)-2-amino-3,3,3-trifluoro-2-methylpropyl)amino)methyl)imidazo[1,2-b]pyridazin-2-yl)(4,4-difluorocyclohexyl)methyl)carbamate (Intermediate 31) in place of tert-Butyl ((R)-1-(7-((S)-1-(((S*)-2-amino-3,3,3-trifluoropropyl-1,1-d₂)amino)-2-methoxyethyl)imidazo[1,2-b]pyridazinyl)-2-((1,1,1-trifluoro-2-methylpropan-2-yl)oxy)ethyl)carbamate.

Step B: (S)-1-((2-((S)-Amino(4,4-difluorocyclohexyl)methyl)imidazo[1,2-b]pyridazin-7-yl)methyl)-4-methyl-4-(trifluoromethyl)imidazolidin-2-one. The title compound was synthesized in a manner analogous to Intermediate 12 Step D using tert-Butyl ((S)—(4,4-difluorocyclohexyl)(7-((S)-4-methyl-2-oxo-4-(trifluoromethyl)imidazolidin-1-yl)methyl)imidazo[1,2-b]pyridazin-2-yl)methyl)carbamate (Step A) in place of tert-Butyl ((R)-1-(7-((S)-2-methoxy-1-((S*)-2-oxo-4-(trifluoromethyl)imidazolidin-1-yl-5,5-d₂)ethyl)imidazo[1,2-b]pyridazin-2-yl)-2-(1,1,1-trifluoro-2-methylpropan-2-yl)oxy)ethyl)carbamate and was used without further purification.

Intermediate 33

(S)—((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-methyl-4-(trifluoromethyl)imidazolidin-2-one

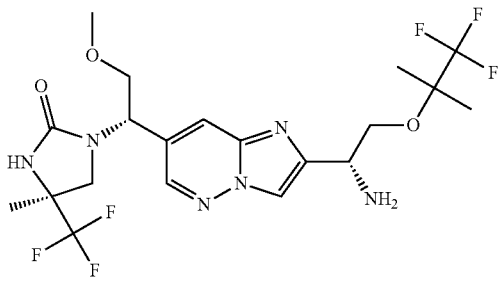 [SMILES: COC[C@H](c1cnn2cc([C@@H](N)COC(C)(C)C(F)(F)F)nc2c1)N1C[C@@](C)(C(F)(F)F)NC1=O]

Step A: tert-Butyl ((R)-1-(7-((S)-2-methoxy-((S)-3,3,3-trifluoro-2-methyl-2-((4-nitrophenyl)sulfonamido)propyl)amino)ethyl)imidazo[1,2-b]pyridazin-2-yl)-2-(1,1,1-trifluoro-2-methylpropan-2-yl)oxy)ethyl)carbamate. A mixture of tert-Butyl ((R)-1-(7-((S)-1-amino-2-methoxyethyl)imidazo[1,2-b]pyridazin-2-yl)-2-(1,1,1-trifluoro-2-methylpropan-2-yl)oxy)ethyl)carbamate (110 mg, 0.24 mmol, Intermediate 36 Step B), (S)-2-methyl-1-((4-nitrophenyl)sulfonyl)-2-(trifluoromethyl)aziridine (88.7 mg, 0.29 mmol, Intermediate 30) and MeCN (5 mL) was heated at 85° C. for 18 h. After this time, additional (S)-2-methyl-1-((4-nitrophenyl)sulfonyl)-2-(trifluoromethyl)aziridine (40 mg, 0.13 mmol, Intermediate 30) was added and the mixture was heated at 85° C. for 7 h. The reaction was then quenched with water (5 mL) and the aqueous layer was extracted with EtOAc (3×15 mL). The organic layers were combined, dried over anhydrous Na₂SO₄, filtered, and concentrated to dryness. The residue was purified by silica gel chromatography (0-60% EtOAc/hexanes) to afford the title compound in 58% yield.

Step B: tert-Butyl ((R)-1-(7-((S)-1-(((S)-2-amino-3,3,3-trifluoro-2-methylpropyl)amino)-2-methoxyethyl)imidazo[1,2-b]pyridazin-2-yl)-2-((1,1,1-trifluoro-2-methylpropan-2-yl)oxy)ethyl)carbamate. Thiophenol (15.7 µL, 0.15 mmol) in MeCN (0.5 mL) was cooled to 0° C. in an ice-water bath. Then, potassium carbonate (28.7 mg, 0.207 mmol) was slowly added. After stirring for 5 min, the ice-water bath was removed and to the mixture was added tert-Butyl ((R)-1-(7-((S)-2-methoxy-1-(((S)-3,3,3-trifluoro-2-methyl-2-((4-nitrophenyl)sulfonamido)propyl)amino)ethyl)imidazo[1,2-b]pyridazin-2-yl)-2-(1,1,1-trifluoro-2-methylpropan-2-yl)oxy)ethyl)carbamate (107 mg, 0.14 mmol, Step A) in MeCN (1 mL) dropwise. The reaction was heated at 50° C. for 4 h. Then, additional thiophenol (5.7 µL, 0.055 mmol) was added and the mixture was stirred for 18 h at 50° C. Another aliquot of thiophenol (7.1 µL, 0.069 mmol) and potassium carbonate (9.6 mg, 0.069 mmol) were added and the mixture was stirred for 18 h at 50° C. The reaction was cooled to rt, diluted with water (5 mL), and extracted with DCM (3×15 mL). The combined organic layer was washed with brine, dried over anhydrous MgSO₄, filtered and concentrated to dryness. Purification by preparative HPLC (X-Bridge Prep C18 5 µm column 50×250 mm, 5-100% acetonitrile/water (with 20 mM NH₄OH)) afforded the title compound (74% yield).

Step C: tert-Butyl ((R)-1-(7-((S)-2-methoxy-((S)-4-methyl-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)carbamate. The title compound was synthesized in a manner analogous to Intermediate 12 Step C using tert-Butyl ((R)-1-(7-((S)-1-(((S)-2-amino-3,3,3-trifluoro-2-methylpropyl)amino)-2-methoxyethyl)imidazo[1,2-b]pyridazin-2-yl)-2-((1,1,1-trifluoro-2-methylpropan-2-yl)oxy)ethyl)carbamate (Step B) in place of tert-Butyl ((R)-1-(7-((S)-1-(((S*)-2-amino-3,3,3-trifluoropropyl-1,1-d₂)amino)-2-methoxyethyl)imidazo[1,2-b]pyridazin-2-yl)-2-((1,1,1-trifluoro-2-methylpropan-2-yl)oxy)ethyl)carbamate. In addition, the residue was purified by silica gel chromatography (10-100% EtOAc/hexanes) and used without further purification to afford the title compound in 100% yield.

Step D: (S)-1-((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-4-methyl-4-(trifluoromethyl)imidazolidin-2-one. A mixture of tert-Butyl ((R)-1-(7-((S)-2-methoxy-1-((S)-4-methyl-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)carbamate (69 mg, 0.113 mmol, Step C) and HCl in 1,4-dioxane (4 M, 0.42 mL, 1.7 mmol) was stirred at rt for 1 h. Then, DCM (0.25 mL) was added and the mixture stirred for 3 h at rt. Additional HCl in 1,4-dioxane (4 M, 0.42 mL, 1.7 mmol) was added and the mixture was stirred at rt for 1 h. The reaction was then concentrated and the residue was dissolved in EtOAc and washed with saturated aqueous NaHCO₃, washed with brine, dried over anhydrous Na₂SO₄, filtered, and concentrated to dryness to provide the title compound (73% yield) that was used without further purification.

Intermediate 34 tert-Butyl ((S)-1-(7-((S)-1-amino-2-methoxyethyl)imidazo[1,2-b]pyridazin-2-yl)-5,5,5-trifluoro-4,4-dimethylpentyl)carbamate

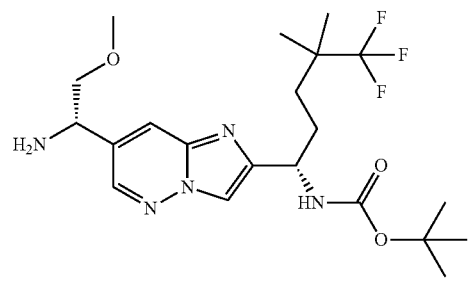 [SMILES: COC[C@@H](N)c1cnn2cc([C@H](CCC(C)(C)C(F)(F)F)NC(=O)OC(C)(C)C)nc2c1]

Step A: tert-Butyl ((S)-1-(6-chloro-7-((S)-1-(1,3-dioxoisoindolin-2-yl)-2-methoxyethyl)imidazo[1,2-b]pyridazin-2-yl)-5,5,5-trifluoro-4,4-dimethylpentyl)carbamate. (S)-2-(1-(6-Amino-3-chloropyridazin-4-yl)-2-methoxyethyl)isoindoline-1,3-dione (970 mg, 2.91 mmol, Intermediate 10 Step C), tert-Butyl (S)-(7,7,7-trifluoro-1-iodo-6,6-dimethyl-2-oxoheptan-3-yl)carbamate (850 mg, 1.94 mmol, Intermediate 45), and sodium phosphate dibasic (360 mg, 2.53 mmol) were combined with 1-methylpyrrolidin-2-one (1.5 mL) and the resulting mixture was heated at 40° C. for 18 h. After this time, the reaction mixture was diluted with EtOAc and water. The layers were separated and the aqueous layer was extracted with EtOAc. The combined organic layers were washed with brine, dried over anhydrous Na₂SO₄, filtered and concentrated to dryness. The residue was purified by silica gel chromatography (0-100% acetone/hexanes (0.1% TEA)) to provide the title compound (48% yield).

Step B: tert-Butyl ((S)-1-(7-((S)-1-(1,3-dioxoisoindolin-2-yl)-2-methoxyethyl)imidazo[1,2-b]pyridazin-2-yl)-5,5,5-trifluoro-4,4-dimethylpentyl)carbamate. The title compound was made in a manner analogous to Intermediate 36 Step A using tert-Butyl ((S)-1-(6-chloro-7-((S)-1-(1,3-dioxoisoindolin-2-yl)-2-methoxyethyl)imidazo[1,2-b]pyridazin-2-yl)-5,5,5-trifluoro-4,4-dimethylpentyl)carbamate (Step A) in place of tert-Butyl ((R)-1-(6-chloro-7-((S)-1-(1,3-dioxoisoindolin-2-yl)-2-methoxyethyl)imidazo[1,2-b]pyridazin-2-yl)-2-((1,1,1-trifluoro-2-methylpropan-2-yl)oxy)ethyl)carbamate. The residue was purified by silica gel chromatography (0-100% acetone/hexanes (0.1% TEA)) to provide the title compound (91% yield).

Step C: tert-Butyl ((S)-1-(7-((S)-1-amino-2-methoxyethyl)imidazo[1,2-b]pyridazin-2-yl)-5,5,5-trifluoro-4,4-dimethylpentyl)carbamate. To tert-Butyl ((S)-1-(7-((S)-1-(1,3-dioxoisoindolin-2-yl)-2-methoxyethyl)imidazo[1,2-b]pyridazin-2-yl)-5,5,5-trifluoro-4,4-dimethylpentyl)carbamate (506 mg, 0.86 mmol, Step B) in EtOH (3 mL) was added hydrazine monohydrate (0.13 mL, 2.58 mmol) and the resulting mixture was stirred at rt for 1 h. Then, the reaction was heated at 40° C. for 3.5 h. The reaction mixture was diluted with EtOAc, filtered through a pad of diatomaceous earth (e.g., Celite®) and the filtrate was concentrated to dryness. The residue was purified by silica gel chromatography (0-100% acetone/hexanes (0.1% TEA)) to provide the title compound (76% yield).

Intermediate 35

(S)-1-((S)-1-(2-((S)-1-Amino-5,5,5-trifluoro-4,4-dimethylpentyl)imidazo[1,2-b]pyridazin-7-yl)-2-methoxyethyl)-4-methyl-4-(trifluoromethyl)imidazolidin-2-one

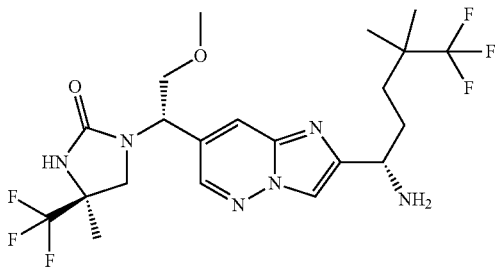 [SMILES: COC[C@H](c1cnn2cc([C@@H](N)CCC(C)(C)C(F)(F)F)nc2c1)N1C[C@@](C)(C(F)(F)F)NC1=O]

The title compound was synthesized in a manner analogous to Intermediate 33 using tert-Butyl ((S)-1-(7-((S)-1-amino-2-methoxyethyl)imidazo[1,2-b]pyridazin-2-yl)-5,5,5-trifluoro-4,4-dimethylpentyl)carbamate (Intermediate 34) in place of tert-Butyl ((R)-1-(7-((S)-1-amino-2-methoxyethyl)imidazo[1,2-b]pyridazin-2-yl)-2-((1,1,1-trifluoro-2-methylpropan-2-yl)oxy)ethyl)carbamate.

Intermediate 36

(S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one-4,5,5-$d_3$

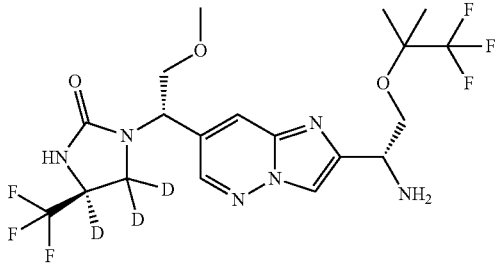 [SMILES: [2H]C1([2H])N([C@H](COC)c2cnn3cc([C@@H](N)COC(C)(C)C(F)(F)F)nc3c2)C(=O)N[C@]1([2H])C(F)(F)F]

Step A: tert-Butyl ((R)-1-(7-((S)-1-(1,3-dioxoisoindolin-2-yl)-2-methoxyethyl)imidazo[1,2-b]pyridazin-2-yl)-2-(1,1,1-trifluoro-2-methylpropan-2-yl)oxy)ethyl)carbamate. A flask was charged with tert-Butyl ((R)-1-(6-chloro-7-((S)-1-(1,3-dioxoisoindolin-2-yl)-2-methoxyethyl)imidazo[1,2-b]pyridazin-2-yl)-2-(1,1,1-trifluoro-2-methylpropan-2-yl)oxy)ethyl)carbamate (260 mg, 0.415 mmol, Intermediate 10 Step D), 2-methyl-2-butanol (20 mL), 2,2,2-trifluoroethanol (10 mL), Pd/C (254 mg, 2.10 mmol, 10 wt % Pd), and ammonium formate (916 mg, 14.5 mmol). The mixture was heated at 90° C. for 1 h, then cooled to rt. The reaction mixture was then filtered through a pad of diatomaceous earth (e.g., Celite®), and the solids were washed with ethanol. The combined organic layers were concentrated to provide the title compound as a yellow solid in 100% yield.

Step B: tert-Butyl ((R)-1-(7-((S)-1-amino-2-methoxyethyl)imidazo[1,2-b]pyridazin-2-yl)-2-(1,1,1-trifluoro-2-methylpropan-2-yl)oxy)ethyl)carbamate. The title compound was synthesized in a manner analogous to Intermediate 10 Step E using tert-Butyl ((R)-1-(7-((S)-1-(1,3-dioxoisoindolin-2-yl)-2-methoxyethyl)imidazo[1,2-b]pyridazin-2-yl)-2-((1,1,1-trifluoro-2-methylpropan-2-yl)oxy)ethyl)carbamate (Step A) in place of tert-Butyl ((R)-1-(6-chloro-7-((S)-1-(1,3-dioxoisoindolin-2-yl)-2-methoxyethyl)imidazo[1,2-b]pyridazin-2-yl)-2-(1,1,1-trifluoro-2-methylpropan-2-yl)oxy)ethyl)carbamate. Purification by silica gel chromatography (0-100% (10% MeOH in EtOAc)/(0.5% $Et_3N$ in hexanes)) provided the title compound in 78% yield.

Step C: tert-Butyl ((R)-1-(74*5S,8S)-3-oxo-1-phenyl-5-(trifluoromethyl)-2,10-dioxa-4,7-diazaundecan-8-yl-5,6,6-$d_3$)imidazo[1,2-b]pyridazin-2-yl)-2-(1,1,1-trifluoro-2-methylpropan-2-yl)oxy)ethyl)carbamate. A vial was charged with tert-Butyl ((R)-1-(7-((S)-1-amino-2-methoxyethyl)imidazo[1,2-b]pyridazin-2-yl)-2-(1,1,1-trifluoro-2-methylpropan-2-yl)oxy)ethyl)carbamate (159 mg, 0.345 mmol, Step B), benzyl (S)-4-(trifluoromethyl)-1,2,3-oxathiazolidine-3-carboxylate-4,5,5-$d_3$ 2,2-dioxide (147 mg, 0.448 mmol, Intermediate 37), N,N-diisopropylethylamine (0.090 mL, 0.517 mmol) and acetonitrile (2.5 mL) and the reaction mixture was allowed to stir at rt for 18 h. The mixture was concentrated to dryness and then purified by silica gel chromatography (0-100% (10% MeOH in EtOAc)/(0.5% $Et_3N$ in hexanes)) to provide the title compound in 98% yield.

Step D: tert-Butyl ((R)-1-(7-((S)-1-(((S)-2-amino-3,3,3-trifluoropropyl-1,1,2-$d_3$)amino)-2-methoxyethyl)imidazo[1,2-b]pyridazin-2-yl)-2-((1,1,1-trifluoro-2-methylpropan-2-yl)oxy)ethyl)carbamate. A Parr flask was charged with tert-Butyl ((R)-1-(7-((5S,8S)-3-oxo-1-phenyl-5-(trifluoromethyl)-2,10-dioxa-4,7-diazaundecan-8-yl-5,6,6-$d_3$)imidazo[1,2-b]pyridazin-2-yl)-2-(1,1,1-trifluoro-2-methylpropan-2-yl)oxy)ethyl)carbamate (130 mg, 183 mmol, Step C), N,N-diisopropylethylamine (0.150 mL, 0.874 mmol), Pd/C (92.1 mg, 0.886 mmol, 10 wt % Pd) and methanol (6.28 mL, 0.176 mmol) and was then placed under a $H_2$ atmosphere (40 atm) for 1 h. The reaction mixture was filtered through a pad of diatomaceous earth (e.g., Celite®), and the solids were washed with ethanol. The combined organic layers were concentrated to provide the title compound as a yellow solid that was used without further purification.

Step E: tert-Butyl ((R)-1-(7-((S)-2-methoxy-((S)-2-oxo-4-(trifluoromethyl)imidazolidin-1-yl-4,5,5-$d_3$)ethyl)imidazo[1,2-b]pyridazin-2-yl)-2-((1,1,1-trifluoro-2-methylpropan-2-yl)oxy)ethyl)carbamate. A vial was charged with tert-Butyl ((R)-1-(7-((S)-1-(((S)-2-amino-3,3,3-trifluoropropyl-1,1,2-$d_3$)amino)-2-methoxyethyl)imidazo[1,2-b]pyridazin-2-yl)-2-(1,1,1-trifluoro-2-methylpropan-2-yl)oxy)ethyl)carbamate (200 mg, 0.347 mmol, Step D), N,N-diisopropylethylamine (0.180 mL, 1.04 mmol), and DCM (3.1 mL). The vial was cooled to 0° C. under an atmosphere of $N_2$ and stirred for 10 min before triphosgene (33 mg, 0.112 mmol) was added dropwise as a solution in DCM (1.1 mL). Water was added and the mixture was extracted with DCM, dried over anhydrous $Na_2SO_4$, filtered, concentrated to dryness and used without further purification.

Step F: (S)-1-((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one-4,5,5-$d_3$. A vial was charged with tert-Butyl ((R)-1-(7-((S)-2-methoxy-1-((S)-2-oxo(trifluoromethyl)imidazolidin-1-yl-4,5,5-$d_3$)ethyl)imidazo[1,2-b]pyridazin-2-yl)-2-((1,1,1-trifluoro-2-methylpropan-2-yl)oxy)ethyl)carbamate (200 mg, 0.332 mmol, Step E) and DCM (2 mL). Then TFA (2 mL, 26.1 mmol) was added dropwise and the mixture was

Intermediate 37

Benzyl (S)-4-(trifluoromethyl)-1,2,3-oxathiazolidine-3-carboxylate-4,5,5-d₃ 2,2-dioxide

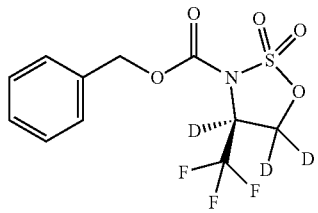 [SMILES: [2H]C1([2H])OS(=O)(=O)N(C(=O)OCc2ccccc2)[C@]1([2H])C(F)(F)F]

Step A: Benzyl (S)—(1,1,1-trifluoro-3-hydroxypropan-2-yl-2,3,3-d₃)carbamate. To a stirred solution of (S)-2-amino-3,3,3-trifluoropropan-1,1,2-d₃-1-ol hydrochloride (48 g, 285 mmol, Intermediate 38) and DIPEA (110.4 g, 854 mmol) in DCM (500 mL) was added benzyl chloroformate (72.9 g, 427 mmol) dropwise at 0° C. under a nitrogen atmosphere. The resulting mixture was stirred overnight at rt. The reaction was quenched by the addition of water/ice (2 L) at rt. The resulting mixture was extracted with CH₂Cl₂ (3×1 L). The combined organic layers were washed with brine (1×1 L) and water (1×1 L), dried over anhydrous Na₂SO₄, filtered, and concentrated to dryness. Purification by silica gel chromatography (5/1 petroleum ether/EtOAc) provided the title compound as an off-white solid in 82% yield.

Step B: Benzyl (4S)-4-(trifluoromethyl)-1,2,3-oxathiazolidine-3-carboxylate-4,5,5-d₃ 2-oxide. To a stirred solution of thionyl chloride (68.5 g, 576 mmol) in acetonitrile (800 mL) that had been cooled to −40° C. was added a solution of benzyl (S)—(1,1,1-trifluoro-3-hydroxypropan-2-yl-2,3,3-d₃)carbamate (59 g, 221 mmol, Step A) in acetonitrile (400 mL) dropwise over 40 min under a nitrogen atmosphere. The resulting mixture was stirred for 30 min at −40° C. Then, pyridine (92.9 g, 1200 mmol) was added dropwise at −40° C. and the resulting mixture was stirred for 2 h at −30° C. The reaction was quenched by the addition of water/ice (3 L) at rt. The resulting mixture was extracted with CH₂Cl₂ (3×2 L). The combined organic layers were washed sequentially with aqueous HCl (0.1 N, 1 L) and water (1 L), dried over anhydrous Na₂SO₄, filtered, and concentrated to dryness to afford the title compound (73% yield) that was used without further purification.

Step C: Benzyl (S)-4-(trifluoromethyl)-1,2,3-oxathiazolidine-3-carboxylate-4,5,5-d₃ 2,2-dioxide. To a stirred solution of benzyl (4S)-4-(trifluoromethyl)-1,2,3-oxathiazolidine-3-carboxylate-4,5,5-d₃ 2-oxide (65 g, Step B), CCl₄ (200 mL), water (400 mL) and acetonitrile (200 mL) at 0° C. were added sodium periodate (57.9 g, 271 mmol) and RuCl₃·3H₂O (0.81 g, 3.12 mmol) in portions. The resulting mixture was stirred for 1 h at 0° C. The reaction was quenched with water/ice (1 L) at rt. The resulting mixture was extracted with EtOAc (3×1 L). The combined organic layers were washed with brine (1×1 L) and water (1×1 L), dried over anhydrous Na₂SO₄, filtered, and concentrated to dryness. The residue was purified by silica gel chromatography (5:1 petroleum ether/EtOAc) to afford the title compound as a white solid in 71% yield.

Intermediate 38

(S)-2-Amino-3,3,3-trifluoropropan-1,1,2-d₃-1-ol hydrochloride

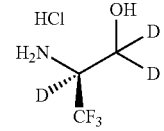

Step A: (S)-2-((tert-Butyldimethylsilyl)oxy)-1-phenylethan-1-amine. To a mixture of (S)-2-amino-2-phenylethan-1-ol (500 g, 3.64 mol), DMAP (89.1 g, 729 mmol) and TEA (1.01 L, 7.29 mol) in CH₂Cl₂ (3500 mL) was added a solution of tert-butylchlorodimethylsilane (447 mL, 3.64 mol) in CH₂Cl₂ (1500 mL) at 0° C., then the mixture was stirred at 20° C. for 12 h. Water (2 L) was added and the mixture was extracted with CH₂Cl₂ (1 L×2). The combined organic layers were washed with brine (1000 mL), dried over anhydrous Na₂SO₄, filtered, and concentrated to dryness. The residue was purified by silica gel chromatography (0-50% EtOAc/petroleum ether) to give the title compound as a yellow oil in 80.3% yield.

Step B: Ethyl (S,Z)-3,3,3-trifluoro-2-((2-hydroxy-1-phenylethyl)imino)propanoate. A mixture of (S)-2-((tert-Butyldimethylsilyl)oxy)-1-phenylethan-1-amine (640 g, 2.55 mol, Step A), ethyl 3,3,3-trifluoro-2-oxopropanoate (423 mL, 3.20 mol) and PPTS (96 g, 382 mmol) in toluene (4000 mL) was heated at 130° C. for 24 h with a Dean-Stark trap attached. The mixture was concentrated to dryness and the residue was triturated with MTBE (200 mL) at 20° C. The mixture was filtered and the filtrate was concentrated to dryness to give a brown oil. The oil was purified by silica gel chromatography (0-10% EtOAc/petroleum ether) to provide the title compound as a red oil in 35.7% yield.

Step C: (S)-3,3,3-Trifluoro-2-(((S)-2-hydroxy-1-phenylethyl)amino)propan-1,1,2-d₃-1-ol. To a mixture of ethyl (S,Z)-3,3,3-trifluoro-2-((2-hydroxy-1-phenylethyl)imino) propanoate (300 g, 1.04 mol, Step B) in THF (500 mL) at 0° C. was added LiAlD₄ (59.1 g, 1.6 mol) and the resulting mixture was stirred at 20° C. for 16 h. Then, the mixture was cooled to 0° C. and water (60 mL), 15% aqueous NaOH (60 mL) and H₂O (180 mL) were added to the mixture sequentially. The mixture was filtered and the filter cake was washed with EtOAc (1000 mL×3). The filtrate was concentrated to dryness and the residue was purified by silica gel chromatography (0-50% EtOAc/petroleum ether) to provide the title compound as a yellow solid in 37.1% yield.

Step D: (S)-2-Amino-3,3,3-trifluoropropan-1,1,2-d₃-1-ol hydrochloride. A mixture of (S)-3,3,3-trifluoro-2-(((S)-2-hydroxy-1-phenylethyl)amino)propan-1,1,2-d₃-1-ol (89.0 g, 353 mmol, Step C) and Pearlman's catalyst (14.8 g, 21.2 mmol) in MeOH (1000 mL) was heated at 50° C. under H₂ (40 psi) for 12 h. The mixture was filtered and the filtrate was concentrated to dryness.

To the residue was added 4 M HCl in MeOH (400 mL) and the resulting mixture was stirred at 20° C. for 2 h. Then, the mixture was filtered and the filtrate was concentrated to dryness. The residue was triturated in EtOAc (200 mL) at 20° C. to provide the title compound as a white solid in 84.1% yield.

Intermediate 39

N-(5-((R*)-1-(((S)-tert-Butyl sulfinyl)amino)-3-methoxypropyl)-6-chloropyridazin-3-yl)pivalamide

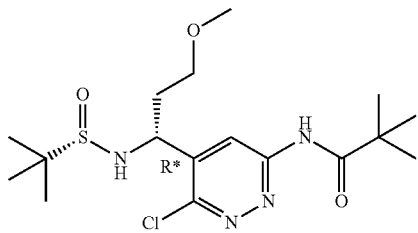 [SMILES: COCC[C@@H](N[S@@](=O)C(C)(C)C)c1cc(NC(=O)C(C)(C)C)nnc1Cl]

To a stirred solution of N-(6-chloropyridazin-3-yl)pivalamide (2.43 g, 11.36 mol, Intermediate 8 Step A) in THF (24.5 mL) was added 2,2,6,6-tetramethylpiperidinylmagnesium chloride lithium chloride complex (25 mL, 1 M in THF/toluene, 25 mmol) dropwise at −78° C. under a nitrogen atmosphere. The resulting solution was warmed to −40° C. and stirred at this temperature for 3 h. After this time, neat (S,E/Z)-1-(tert-Butylsulfinyl)-4-methoxybut-1-ene (2.65 g, 13.83 mmol) was added, and the solution was removed from the cold bath and allowed to warm to rt and stirred for 18 h. The reaction was quenched by the addition of saturated aqueous NH$_4$Cl and diluted with EtOAc. The mixture was separated and the aqueous layer further extracted with EtOAc. The combined organic layers were washed with brine, dried over anhydrous Na$_2$SO$_4$, and filtered.

The filtrate was concentrated to dryness and purified sequentially by silica gel chromatography (20-50% acetone/hexanes) and chiral SFC (Chiralpak IF, 5 μm, 250×21 cm, 15% MeOH:isopropanol with 0.2% isopropylamine/85% CO$_2$) to afford the title compound as the first eluting isomer in 8% yield.

Intermediate 40

(S)-1-((S)-1-(2-((S)-1-Amino-4,4,4-trifluoro-3,3-dimethylbutyl)imidazo[1,2-b]pyridazin-7-yl)-2-cyclopropoxyethyl)-4-(trifluoromethyl)imidazolidin-2-one

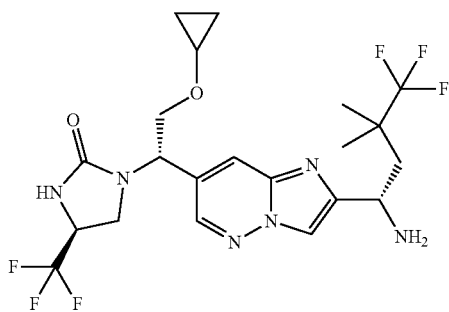 [SMILES: CC(C)(C[C@H](N)c1cn2ncc([C@@H](COC3CC3)N3C[C@@H](C(F)(F)F)NC3=O)cc2n1)C(F)(F)F]

Step A: tert-Butyl ((S)-1-(6-chloro-7-((S)-2-cyclopropoxy-1-(1,3-dioxoisoindolin-2-yl)ethyl)imidazo[1,2-b]pyridazin-2-yl)-4,4,4-trifluoro-3,3-dimethylbutyl)carbamate. The title compound was synthesized in a manner analogous to Intermediate 47 Step F using tert-Butyl (S)—(6,6,6-trifluoro-1-iodo-5,5-dimethyl-2-oxohexan-3-yl)carbamate in place of tert-Butyl (S)—(4-iodo-3-oxo-1-((1,1,1-trifluoro-2-methylpropan-2-yl)oxy)butan-2-yl)carbamate and tert-Butyl (S)-4-(trifluoromethyl)-1,2,3-oxathiazolidine-3-carboxylate 2,2-dioxide (Intermediate 48) in place of tert-Butyl (S)—(4-iodo-3-oxo-1-((1,1,1-trifluoro-2-methylpropan-2-yl)oxy)butan-2-yl)carbamate. Purification by silica gel chromatography (0-100% ethyl acetate (with 10% MeOH)/hexanes) afforded the title compound (84% yield).

Step B: tert-Butyl ((S)-1-(7-((S)-1-amino-2-cyclopropoxyethyl)-6-chloroimidazo[1,2-b]pyridazin-2-yl)-4,4,4-trifluoro-3,3-dimethylbutyl)carbamate. The title compound was synthesized in a manner analogous to Intermediate 47 Step A using tert-Butyl ((S)-1-(6-chloro-7-((S)-2-cyclopropoxy-1-(1,3-dioxoisoindolin-2-yl)ethyl)imidazo[1,2-b]pyridazin-2-yl)-4,4,4-trifluoro-3,3-dimethylbutyl)carbamate (Step A) in place of (S)—N-(5-(1-amino-2-cyclopropoxyethyl)-6-chloropyridazin-3-yl)pivalamide.

Step C: tert-Butyl ((S)-1-(7-((S)—((S)-2-(((benzyloxy)carbonyl)amino)-3,3,3-trifluoropropyl)amino)-2-cyclopropoxyethyl)-6-chloroimidazo[1,2-b]pyridazin-2-yl)-4,4,4-trifluoro-3,3-dimethylbutyl)carbamate. The title compound was synthesized in a manner analogous to Intermediate 19 Step C using tert-Butyl ((S)-1-(7-((S)-1-amino-2-cyclopropoxyethyl)-6-chloroimidazo[1,2-b]pyridazin-2-yl)-4,4,4-trifluoro-3,3-dimethylbutyl)carbamate (Step B) in place of tert-Butyl ((S)-(7-((S)-amino(1-cyanocyclobutyl)methyl)imidazo[1,2-b]pyridazin-2-yl)(4,4-difluorocyclohexyl)methyl)carbamate. The material was purified by silica gel chromatography (0-10% (2 M NH$_3$ in MeOH)/DCM) to afford the title compound as a white foam (95% yield).

Step D: tert-Butyl ((S)-1-(7-((S)-1-(((S)-2-amino-3,3,3-trifluoropropyl)amino)-2-cyclopropoxyethyl)imidazo[1,2-b]pyridazin-2-yl)-4,4,4-trifluoro-3,3-dimethylbutyl)carbamate. The title compound was synthesized in a manner analogous to Intermediate DAG Step G using tert-Butyl ((S)-1-(7-((S)-1-(((S)-2-(((benzyloxy)carbonyl)amino)-3,3,3-trifluoropropyl)amino)-2-cyclopropoxyethyl)-6-chloroimidazo[1,2-b]pyridazin-2-yl)-4,4,4-trifluoro-3,3-dimethylbutyl)carbamate (Step C) in place of tert-Butyl ((R)-1-(7-((S)-2-cyclopropoxy-1-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)carbamate, EtOH in place of MeOH and purification by silica gel chromatography (0-10% (2 M NH$_3$ in MeOH)/DCM) to afford the title compound (92% yield).

Step E: tert-Butyl ((S)-1-(7-((S)-2-cyclopropoxy-1-((S)-2-oxo-4-(trifluoromethyl)imidazolidin-1-yl)ethyl)imidazo[1,2-b]pyridazin-2-yl)-4,4,4-trifluoro-3,3-dimethylbutyl)carbamate. The title compound was synthesized in a manner analogous to Intermediate 12 Step C using tert-Butyl ((S)-1-(7-((S)-1-(((S)-2-amino-3,3,3-trifluoropropyl)amino)-2-cyclopropoxyethyl)imidazo[1,2-b]pyridazin-2-yl)-4,4,4-trifluoro-3,3-dimethylbutyl)carbamate (Step D) in place of tert-Butyl ((R)-1-(7-((S)-1-(((S*)-2-amino-3,3,3-trifluoropropyl-1,1-d$_2$)amino)-2-methoxyethyl)imidazo[1,2-b]pyridazin-2-yl)-2-(1,1,1-trifluoro-2-methylpropan-2-yl)oxy)ethyl)carbamate, an additional 0.68 equivalents of triphosgene was added and purification by silica gel chromatography (0-100% EtOAc (with 10% MeOH)/hexanes) to afford the title compound (49% yield).

Step F: (S)-1-((S)-1-(2-((S)-1-Amino-4,4,4-trifluoro-3,3-dimethylbutyl)imidazo[1,2-b]pyridazin-7-yl)-2-cyclopropoxyethyl)-4-(trifluoromethyl)imidazolidin-2-one. The title compound was synthesized in a manner analogous to Intermediate 20 Step F using tert-Butyl ((S)-1-(7-((S)-2-cyclopropoxy-((S)-2-oxo-4-(trifluoromethyl)imidazolidin-1-yl)ethyl)imidazo[1,2-b]pyridazin-2-yl)-4,4,4-trifluoro-3, 3-dimethylbutyl)carbamate (Step E) in place of tert-Butyl ((1R)-1-(7-(2-methoxy-((S)-4-methyl-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)carbamate. The material was used without further purification.

Intermediate 41

(S)-1-((S)-1-(2-((S)-1-Amino-5,5,5-trifluoro-4,4-dimethylpentyl)imidazo[1,2-b]pyridazin-7-yl)-2-cyclopropoxyethyl)-4-(trifluoromethyl)imidazolidin-2-one

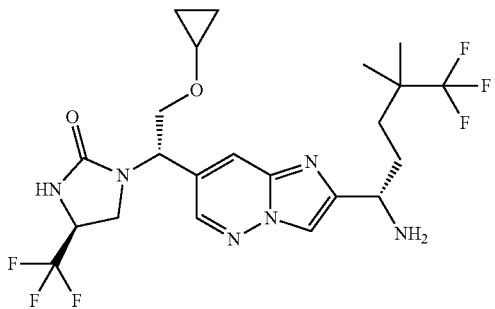 [SMILES: CC(C)(CC[C@H](N)c1cn2ncc([C@@H](COC3CC3)N3C[C@@H](C(F)(F)F)NC3=O)cc2n1)C(F)(F)F]

Step A: tert-Butyl ((S)-1-(6-chloro-7-((S)-2-cyclopropoxy-1-((S)-2-oxo-4-(trifluoromethyl)imidazolidin-1-yl)ethyl)imidazo[1,2-b]pyridazin-2-yl)-5,5,5-trifluoro-4,4-dimethylpentyl)carbamate. The title compound was synthesized in a manner analogous to Intermediate 47 Step F using tert-Butyl (S)-(7,7,7-trifluoro-1-iodo-6,6-dimethyl-2-oxoheptan-3-yl)carbamate (Intermediate 45) in place of tert-Butyl (S)—(4-iodo-3-oxo-1-((1,1,1-trifluoro-2-methylpropan-2-yl)oxy)butan-2-yl)carbamate and purification by silica gel chromatography (0-100% EtOAc (with 10% MeOH)/hexanes) to afford the title compound (39% yield).

Step B: tert-Butyl ((S)-1-(7-((S)-2-cyclopropoxy-1-((S)-2-oxo-4-(trifluoromethyl)imidazolidin-1-yl)ethyl)imidazo[1,2-b]pyridazin-2-yl)-5,5,5-trifluoro-4,4-dimethylpentyl)carbamate. The title compound was synthesized in a manner analogous to Intermediate 47 Step G using tert-Butyl ((S)-1-(6-chloro-7-((S)-2-cyclopropoxy-1-((S)-2-oxo-4-(trifluoromethyl)imidazolidin-1-yl)ethyl)imidazo[1,2-b]pyridazin-2-yl)-5,5,5-trifluoro-4,4-dimethylpentyl)carbamate (Step A) in place of tert-Butyl ((R)-1-(7-((S)-2-cyclopropoxy-1-((S)-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)carbamate, EtOH in place of MeOH and purification by silica gel chromatography (0-10% (2 M NH₃ in MeOH)/DCM) to afford the title compound as a white foam (93% yield).

Step C: (S)—((S)-1-(2-((S)-1-Amino-5,5,5-trifluoro-4,4-dimethylpentyl)imidazo[1,2-b]pyridazin-7-yl)-2-cyclopropoxyethyl)-4-(trifluoromethyl)imidazolidin-2-one. The title compound was synthesized in a manner analogous to Intermediate 20 Step F using tert-Butyl ((S)-1-(7-((S)-2-cyclopropoxy-1-((S)-2-oxo-4-(trifluoromethyl)imidazolidin-1-yl)ethyl)imidazo[1,2-b]pyridazin-2-yl)-5,5,5-trifluoro-4,4-dimethylpentyl)carbamate (Step B) in place of tert-Butyl ((1R)-1-(7-(2-methoxy-1-((S)-4-methyl-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)carbamate. The material was used without further purification.

Intermediate 42

(S)-1-((R*)-1-(6-Amino-3-chloropyridazin-4-yl)-3-methoxypropyl)-4-(trifluoromethyl)imidazolidin-2-one

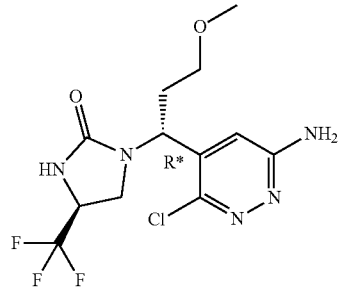 [SMILES: COCC[C@H](c1cc(N)nnc1Cl)N1C[C@@H](C(F)(F)F)NC1=O]

Step A: (R*)—N-(5-(1-Amino-3-methoxypropyl)-6-chloropyridazin-3-yl)pivalamide. The title compound was synthesized in a manner analogous to Intermediate 10 Step A using N-(5-((R*)-1-(((S)-tert-butyl sulfinyl)amino)-3-methoxypropyl)-6-chloropyridazin-3-yl)pivalamide (Intermediate 39) in place of N-(5-((S)-1-(((R)-tert-butylsulfinyl)amino)-2-methoxyethyl)-6-chloropyridazin-3-yl) pivalamide. The material was used without further purification.

Step B: tert-Butyl ((S)-3-(((R*)-1-(3-chloro-6-pivalamidopyridazin-4-yl)-3-methoxypropyl)amino)-1,1,1-trifluoropropan-2-yl)carbamate. The title compound was synthesized in a manner analogous to Intermediate 47 Step B using (R*)—N-(5-(1-amino-3-methoxypropyl)-6-chloropyridazin-3-yl)pivalamide (Step A) in place of (S)—N-(5-(1-amino-2-cyclopropoxyethyl)-6-chloropyridazin-3-yl) pivalamide. The material was purified by silica gel chromatography (0-100% EtOAc (with 10% MeOH)/hexanes) to afford the title compound that was used without further purification.

Step C: N-(5-((R*)-1-(((S)-2-Amino-3,3,3-trifluoropropyl)amino)-3-methoxypropyl)-6-chloropyridazin-3-yl)pivalamide. A solution of tert-Butyl ((S)-3-(((R*)-1-(3-chloro-6-pivalamidopyridazin-4-yl)-3-methoxypropyl)amino)-1,1,1-trifluoropropan-2-yl)carbamate (685 mg, 1.34 mmol, Step B) in 1,4-dioxane (6.7 mL) was treated with a 4 M solution of HCl in 1,4-dioxane (6.7 mL, 26.76 mmol) and stirred at rt for 1 h. The mixture was diluted with CH₂Cl₂ and quenched with saturated aqueous NaHCO₃ (pH>10). The aqueous layer was removed and was further extracted with CH₂Cl₂, then the combined organic layers were dried over anhydrous Na₂SO₄, filtered, and concentrated to dryness. Purification by silica gel chromatography (0-10% (2 M NH₃ in MeOH)/DCM) afforded the title compound (60% yield).

Step D: N-(6-Chloro-5-((R*)-3-methoxy-1-((S)-2-oxo-4-(trifluoromethyl)imidazolidin-1-yl)propyl)pyridazin-3-yl) pivalamide. The title compound (59% yield) was synthesized in a manner analogous to Intermediate 47 Step D using N-(5-((R*)-1-(((S)-2-amino-3,3,3-trifluoropropyl)amino)-3-methoxypropyl)-6-chloropyridazin-3-yl)pivalamide (Step C) in place of N-(5-((S)-1-(((S)-2-amino-3,3,3-trifluoropropyl)amino)-2-cyclopropoxyethyl)-6-chloropyridazin-3-yl) pivalamide.

Step E: (S)-1-((R*)-1-(6-Amino-3-chloropyridazin-4-yl)-3-methoxypropyl)-4-(trifluoromethyl)imidazolidin-2-one. To a stirred solution of N-(6-chloro-5-((R*)-3-methoxy-1-

((S)-2-oxo-4-(trifluoromethyl)imidazolidin-1-yl)propyl) pyridazin-3-yl)pivalamide (210 mg, 0.48 mmol, Step D) in MeOH (3.6 mL) was added aqueous $H_2SO_4$ (3 M, 3.6 mL, 10.8 mmol) and the reaction mixture was heated at 55° C. for 18 h. The reaction mixture was cooled to rt, diluted with EtOAc and treated with aqueous 3 M NaOH until the pH of the mixture was pH>12. The aqueous layer was extracted three times with EtOAc, twice with DCM, and the combined organic layers were dried over anhydrous $Na_2SO_4$, filtered, and concentrated to dryness to give the title compound that was used without further purification.

Intermediate 43

(S)-1-((R*)-1-(2-((S)-Amino(4,4-difluorocyclohexyl)methyl)imidazo[1,2-b]pyridazin-7-yl)-3-methoxypropyl)-4-(trifluoromethyl)imidazolidin-2-one

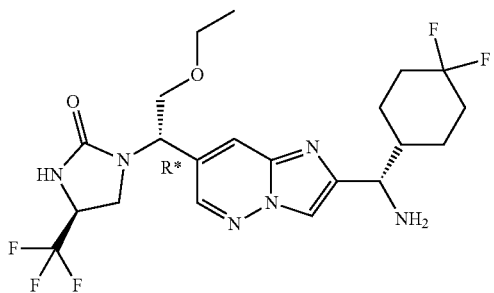 [SMILES: CCOC[C@H](c1cnn2cc([C@@H](N)C3CCC(F)(F)CC3)nc2c1)N1C[C@@H](C(F)(F)F)NC1=O]

Step A: tert-Butyl ((S)—(6-chloro-7-((R*)-3-methoxy-1-((S)-2-oxo-4-(trifluoromethyl)imidazolidin-1-yl)propyl) imidazo[1,2-b]pyridazin-2-yl)(4,4-difluorocyclohexyl) methyl)carbamate. The title compound was synthesized in a manner analogous to Intermediate 47 Step F using (S)-1-((R*)-1-(6-amino-3-chloropyridazin-4-yl)-3-methoxypropyl)-4-(trifluoromethyl)imidazolidin-2-one (Intermediate 42) in place of (S)—((S)-1-(6-amino-3-chloropyridazin-4-yl)-2-cyclopropoxyethyl)-4-(trifluoromethyl)imidazolidin-2-one and tert-Butyl (S)—(1-(4,4-difluorocyclohexyl)-3-iodo-2-oxopropyl)carbamate in place of tert-butyl (S)—(4-iodo-3-oxo-((1,1,1-trifluoro-2-methylpropan-2-yl)oxy) butan-2-yl)carbamate. Purification by silica gel chromatography (0-100% EtOAc (with 10% MeOH)/hexanes) followed by a subsequent purification by silica gel chromatography (0-10% MeOH/DCM) afforded the title compound (61% yield).

Step B: tert-Butyl ((S)—(4,4-difluorocyclohexyl)(7-((R*)-3-methoxy-1-((S)-2-oxo-4-(trifluoromethyl)imidazolidin-1-yl)propyl)imidazo[1,2-b]pyridazin-2-yl)methyl)carbamate. The title compound was synthesized in a manner analogous to Intermediate 47 Step G using tert-butyl ((S)—(6-chloro-7-((R*)-3-methoxy-1-((S)-2-oxo-4-(trifluoromethyl)imidazolidin-1-yl)propyl)imidazo[1,2-b]pyridazin-2-yl)(4,4-difluorocyclohexyl)methyl)carbamate (Step A) in place of tert-Butyl ((R)-1-(7-((S)-2-cyclopropoxy-1-((S)-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)carbamate and EtOH in place of MeOH. The residue was purified by silica gel chromatography (0-10% MeOH/DCM) to afford the title compound as a white foam (93% yield).

Step C: (S)-1-((R*)-1-(2-((S)-Amino(4,4-difluorocyclohexyl)methyl)imidazo[1,2-b]pyridazin-7-yl)-3-methoxypropyl)-4-(trifluoromethyl)imidazolidin-2-one. The title compound was synthesized in a manner analogous to Intermediate 20 Step F using tert-Butyl ((S)—(4,4-difluorocyclohexyl)(7-((R*)-3-methoxy-1-((S)-2-oxo-4-(trifluoromethyl)imidazolidin-1-yl)propyl)imidazo[1,2-b]pyridazin-2-yl)methyl)carbamate (Step B) in place of tert-Butyl ((1R)-1-(7-(2-methoxy-((S)-4-methyl-2-oxo-4-(trifluoromethyl) imidazolidin-1-yl)ethyl)imidazo[1,2-b]pyridazin-2-yl)-2-((1,1,1-trifluoro-2-methylpropan-2-yl)oxy)ethyl)carbamate. The material was used without further purification.

Intermediate 44 tert-Butyl (S)—(1-(dimethyl(oxo)-$\lambda^6$-sulfanylidene)-7,7,7-trifluoro-6,6-dimethyl-2-oxoheptan-3-yl)carbamate

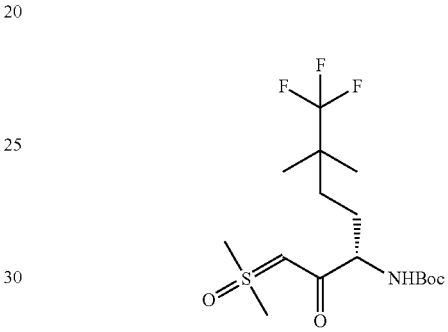

Step A: 1,1,1-Trifluoro-4-iodo-2,2-dimethylbutane. To a solution of 4,4,4-trifluoro-3,3-dimethylbutan-1-ol (9.75 g, 62.5 mmol) in DCM (125 mL) was added triphenylphosphine (24.6 g, 93.7 mmol) and imidazole (5.53 g, 81.2 mmol), and the resulting mixture was cooled to 0° C. Iodine (23.8 g, 93.7 mmol) was then added portion-wise and the mixture was allowed to warm to rt and stirred for 24 h at which time it was quenched with saturated aqueous $NaHCO_3$ and stirred for 15 min. The organic layer was removed and washed sequentially with half-saturated aqueous $NaHCO_3$ and brine, dried over anhydrous $MgSO_4$, filtered, and concentrated to a residue. To the residue was added chilled hexanes (50 mL), and the mixture was stirred vigorously for 10 min during which time a white precipitated formed. The white solid was removed by filtration through a pad of silica and the solids were washed with a second portion of chilled hexanes. The filtrates were concentrated to afford the title compound as a clear, colorless oil (66% yield) that was used without further purification.

Step B: (2R,5S)-2-Isopropyl-3,6-dimethoxy-5-(4,4,4-trifluoro-3,3-dimethylbutyl)-2,5-dihydropyrazine. To a stirred solution of (R)-2-isopropyl-3,6-dimethoxy-2,5-dihydropyrazine (0.66 g, 3.59 mmol) in THF (7 mL) at −78° C. was added t-BuLi (2.33 mL, 3.95 mmol, 1.7 M in pentane), and the reaction was allowed to stir at −78° C. After 1 h, a solution of 1,1,1-trifluoro-4-iodo-2,2-dimethylbutane (1.05 g, 3.95 mmol, Step A) in THF (6 mL) was added dropwise, and the reaction mixture was stirred for 24 h at rt. The reaction was quenched by the addition of aqueous phosphate buffer (50 mL, 0.1 M, pH 7) and was diluted with diethyl ether. The organic layer was removed, and the aqueous layer was extracted with diethyl ether (2×50 mL). The combined organic layers were dried over anhydrous $MgSO_4$, filtered, and concentrated to give an oil. LC/MS of this oil revealed a mixture of diastereomers in approximately a 1.5:1 ratio. This mixture was separated by silica gel chromatography (0-30% EtOAc/hexanes) to afford the first-eluting isomer (50% yield), which was designated as the R,S diastereomer, (2R,5S)-2-isopropyl-3,6-dimethoxy-5-(4,4,4-trifluoro-3,3-dimethylbutyl)-2,5-dihydropyrazine, as a yellow oil. The second-eluting isomer, designated as the R,R diastereomer, (2R,5R)-2-isopropyl-3,6-dimethoxy-5-(4,4,4-trifluoro-3,3-dimethylbutyl)-2,5-dihydropyrazine, was isolated in 28% yield.

Step C: Methyl (S)-2-amino-6,6,6-trifluoro-5,5-dimethylhexanoate. To a stirred solution of (2R,5S)-2-isopropyl-3,6-dimethoxy-5-(4,4,4-trifluoro-3,3-dimethylbutyl)-2,5-dihydropyrazine (1.15 g, 3.57 mmol, Step B) in ACN (14.3 mL) at rt was added aqueous HCl (14.3 mL, 1 M). After stirring for 2 h, the reaction mixture was poured onto saturated aqueous NaHCO$_3$ at 0° C. and was then extracted with EtOAc (3×150 mL). The combined organic layers were washed with brine, dried over anhydrous MgSO$_4$, filtered, and concentrated to give an oil that was used without further purification.

Step D: Methyl (S)-2-((tert-butoxycarbonyl)amino)-6,6,6-trifluoro-5,5-dimethylhexanoate. To a stirred solution of methyl (S)-2-amino-6,6,6-trifluoro-5,5-dimethylhexanoate (810.6 mg, 3.57 mmol, Step C) in DCM (15.1 mL) was added Boc$_2$O (1.56 g, 7.14 mmol). After 24 h, the reaction was quenched with aqueous HCl (10 mL, 1 M), and the layers were separated. The organic layer was washed with aqueous HCl (10 mL, 1 M), water, brine, dried over anhydrous MgSO$_4$, filtered, and concentrated to give an oil that was used in the next step without further purification.

Step E: (S)-2-((tert-Butoxycarbonyl)amino)-6,6,6-trifluoro-5,5-dimethylhexanoic acid. To a stirred solution of methyl (S)-2-((tert-butoxycarbonyl)amino)-6,6,6-trifluoro-5,5-dimethylhexanoate (925 mg, 2.83 mmol, Step D) in THF (22.4 mL) at 0° C. was added aqueous. LiOH (8.50 mL, 1 M) and the resulting mixture was stirred for 2 h. The pH of the reaction mixture was then adjusted to pH 2 using aqueous HCl (1 M). The mixture was extracted with EtOAc (3×60 mL). The combined organic layers were washed with brine, dried over anhydrous MgSO$_4$, filtered, and concentrated to give a clear oil that was used in the next step without further purification.

Step F: tert-Butyl (S)—(1-(dimethyl(oxo)-λ$^6$-sulfaneylidene)-7,7,7-trifluoro-6,6-dimethyl-2-oxoheptan-3-yl)carbamate. To a suspension of trimethylsulfoxonium chloride (0.581 g, 4.52 mmol) in THF (7 mL) was added a solution of t-BuOK (4.24 mL, 4.24 mmol, 1 M in THF) and the resulting solution was allowed to stir for 2 h. Separately, (S)-2-((tert-butoxycarbonyl)amino)-6,6,6-trifluoro-5,5-dimethylhexanoic acid (885 mg, 2.83 mmol, Step E) in THF (7 mL) was cooled to 0° C., CDI (550 mg, 3.39 mmol) was subsequently added and the resulting mixture was stirred for 2 h at 0° C. This mixture was then added via cannula to the trimethylsulfoxonium derived suspension, and the resulting mixture was stirred at rt. After 2 h, the reaction mixture was filtered through diatomaceous earth (e.g., Celite®), concentrated, and purified via silica gel chromatography (0-100% EtOAc/hexanes) to afford the title compound (56% yield) as a white foam. The absolute configuration of the title compound was confirmed by Mosher analysis of a derivative made from the title compound.

Intermediate 45 tert-Butyl (S)-(7,7,7-trifluoro-1-iodo-6,6-dimethyl-2-oxoheptan-3-yl)carbamate

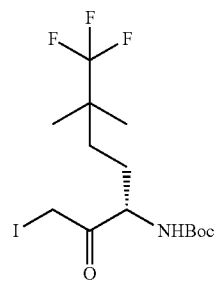 [SMILES: CC(C)(C)OC(=O)N[C@@H](CCC(C)(C)C(F)(F)F)C(=O)CI]

Step A: tert-Butyl (S)—(1-chloro-7,7,7-trifluoro-6,6-dimethyl-2-oxoheptan-3-yl)carbamate. An oven dried round bottom flask was charged with anhydrous lithium chloride (296 mg, 6.98 mmol) and tert-Butyl (S)—(1-(dimethyl(oxo)-λ$^6$-sulfaneylidene)-7,7,7-trifluoro-6,6-dimethyl-2-oxoheptan-3-yl)carbamate (Intermediate 44) under an N$_2$ atmosphere. Anhydrous. THF (17.0 mL) was added, the reaction mixture was cooled to 0° C., then methanesulfonic acid (164 µL, 2.53 mmol) was added dropwise. The reaction mixture was maintained at 0° C. for 10 min then heated at 60° C. for 18 h. After this time, the mixture was cooled to rt, diluted with H$_2$O, and extracted with 1:1 EtOAc. The organic extracts were washed with brine, dried over anhydrous Na$_2$SO$_4$, filtered, and concentrated to dryness to provide the title compound that was used without further purification.

Step B: tert-Butyl (S)-(7,7,7-trifluoro-1-iodo-6,6-dimethyl-2-oxoheptan-3-yl)carbamate. A mixture of tert-Butyl (S)—(1-chloro-7,7,7-trifluoro-6,6-dimethyl-2-oxoheptan-3-yl)carbamate (779 mg, 2.25 mmol, Step A) and NaI (3.38 g, 22.5 mmol) in acetone (11.5 mL) was stirred at rt for 18 h then diluted with EtOAc and filtered. The filtrate was washed with saturated aqueous sodium thiosulfate then dried over anhydrous Na$_2$SO$_4$, filtered, and concentrated to dryness to afford the title compound that was used without further purification.

Intermediate 46

(S)—N-(6-Chloro-5-(2-cyclopropoxy-1-(1,3-dioxoisoindolin-2-yl)ethyl)pyridazin-3-yl)pivalamide

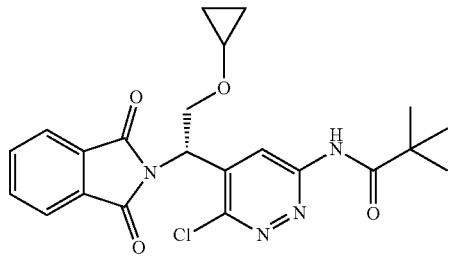 [SMILES: CC(C)(C)C(=O)Nc1cc([C@@H](COC2CC2)N2C(=O)c3ccccc3C2=O)c(Cl)nn1]

Step A: N-(6-Chloro-5-methylpyridazin-3-yl)pivalamide. 6-Chloro-5-methylpyridazin-3-amine (25.0 g, 174 mmol), pyridine (28 mL), and NMP (115 mL) were added to an oven-dried and nitrogen-purged three-neck round-bottomed flask equipped with a thermometer. This mixture was subsequently cooled to 0° C. in an ice/water bath, and the resulting mixture treated with pivaloyl chloride (27.8 mL, 226 mmol) at a rate such that the temperature did not exceed 10° C. (20 min). After this addition, the reaction vessel was removed from the ice bath and allowed to gradually warm to rt over the course of 30 min, after which time stirring was continued for 1 h. The reaction vessel was then placed in an ice bath, treated with water (100 mL) portion-wise over 10 min and some solids were separated out. The suspension was stirred for 30 min at 0° C. and then filtered, the filter cake was washed with water (100 mL) and concentrated to dryness to afford the title compound in 83% yield.

Step B: (E)-N-(6-Chloro-5-(2-(dimethylamino)vinyl) pyridazin-3-yl)pivalamide. N-(6-Chloro-5-methylpyridazin-3-yl)pivalamide (29.9 g, 131 mmol, Step A), 1,1-diethoxy-N,N-dimethylmethanamine (98.6 mL, 591 mmol), and DMF (10.2 mL) were added to an oven-dried and nitrogen-purged round-bottomed flask fitted with a reflux condenser, which was subsequently evacuated and refilled with $N_2$ three times, and the resulting mixture heated at 120° C. for 10 h. The reaction mixture was allowed to cool to rt overnight. During that time, some solids precipitated and were then removed by filtration, and the filter cake was washed with hexanes (150 mL). The combined filtrates were concentrated to dryness to afford the title compound in 42% yield.

Step C: N-(6-Chloro-5-formylpyridazin-3-yl)pivalamide. (E)-N-(6-Chloro-5-(2-(dimethylamino)vinyl)pyridazin-3-yl)pivalamide (15.8 g, 55.7 mmol, Step B), THF (150 mL) and water (150 mL) were added to a round-bottomed flask, and the resulting mixture was treated with $NaIO_4$ (41.7 g, 195 mmol) in one portion. The mixture was then stirred at rt for 2 h. The reaction mixture was filtered, and the filter cake was washed with EtOAc (100 mL×2). The filtrate layers were separated, and the aqueous layer was extracted with EtOAc (100 mL×2). The combined organic extracts were washed with brine (100 mL), dried over anhydrous $Na_2SO_4$, filtered, and concentrated to dryness to afford the title compound which was used without further purification.

Step D: N-(6-Chloro-5-(2-cyclopropoxy-1-hydroxyethyl) pyridazin-3-yl)pivalamide. Tributyl(cyclopropoxymethyl) stannane (12.0 g, 33.1 mmol, Intermediate 49) and THF (50 mL) were added to an oven-dried and nitrogen-purged three-neck round-bottomed flask fitted with a thermometer, which was subsequently cooled to −65° C. Then, n-BuLi (13.2 mL, 33.1 mmol, 2.5 M in hexanes) was added dropwise over 30 min and the resulting mixture was stirred for 1 h at −65° C. Then a solution of N-(6-chloro-5-formylpyridazin-3-yl)pivalamide (2.0 g, 8.3 mmol, Step C) in THF (10 mL) was added dropwise over 80 min into the mixture. The resulting mixture was stirred for 1 h at −65° C. The reaction mixture was then treated with saturated aqueous $NH_4Cl$ solution (50 mL), extracted with EtOAc (100 mL×3), and the combined organic extracts were washed with brine (100 mL), dried over anhydrous $Na_2SO_4$, filtered, and concentrated to dryness. The material was purified by silica gel chromatography (0-10% methanol/DCM) to afford the title compound in 82% yield.

Step E: (S)—N-(6-Chloro-5-(2-cyclopropoxy-1-(1,3-dioxoisoindolin-2-yl)ethyl)pyridazin-3-yl)pivalamide. N-(6-Chloro-5-(2-cyclopropoxy-1-hydroxyethyl)pyridazin-3-yl) pivalamide (3.80 g, 12.1 mmol, Step D), phthalimide (3.56 g, 24.2 mmol), $Ph_3P$ (15.9 g, 60.6 mmol) and THF (160 mL) were added to an oven-dried and nitrogen-purged three-necked round-bottomed flask with a thermometer. The resulting mixture was cooled to 0° C. then treated with DEAD (9.54 mL, 60.6 mmol) dropwise via syringe over 15 min at 0° C. The resulting mixture was allowed to warm to rt, then heated to 30° C. and stirred for 16 h. The reaction mixture was then diluted with water (150 mL) and extracted with EtOAc (100 mL×3). The organic layers were combined, washed with brine (200 mL), dried over anhydrous $Na_2SO_4$, filtered, and concentrated to dryness to give a yellow oil. The oil was initially purified by silica gel chromatography (0-50% EtOAc/petroleum ether) and then further purified by SFC (DAICEL CHIRALPAK IG 10 mm, 250×50 mm, isocratic elution: 35% (0.1% $NH_3H_2O$ in IPA)/65% $CO_2$) to afford the title compound as the first eluting isomer in 41% yield. The absolute configuration of the title compound was confirmed by Mosher analysis of a derivative made from the title compound.

Intermediate 47

(S)-1-((S)-1-(2-((R)-1-amino-2-((1,1,1-trifluoro-2-methylpropan-2-yl)oxy)ethyl)imidazo[1,2-b] pyridazin-7-yl)-2-cyclopropoxyethyl)-4-(trifluoromethyl)imidazolidin-2-one

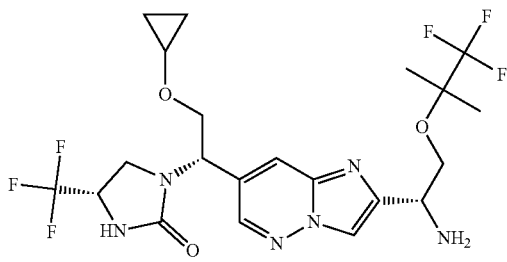 [SMILES: CC(C)(OC[C@H](N)c1cn2ncc([C@@H](COC3CC3)N3C[C@@H](C(F)(F)F)NC3=O)cc2n1)C(F)(F)F]

Step A: (S)—N-(5-(1-Amino-2-cyclopropoxyethyl)-6-chloropyridazin-3-yl)pivalamide. To a solution of (S)—N-(6-chloro-5-(2-cyclopropoxy-1-(1,3-dioxoisoindolin-2-yl) ethyl)pyridazin-3-yl)pivalamide (425 mg, 0.960 mmol, Intermediate 46) in EtOH (12 mL) was added hydrazine monohydrate (0.460 mL, 9.56 mmol). The resulting solution was allowed to stir at rt for 3 h, then the reaction mixture was diluted with water and brine and this mixture was extracted with EtOAc three times. The combined organic layers were dried over anhydrous $MgSO_4$, filtered, and concentrated to dryness to afford the title compound that was used without further purification.

Step B: tert-Butyl ((S)-3-(((S)-1-(3-chloro-6-pivalamidopyridazin-4-yl)-2-cyclopropoxyethyl)amino)-1,1,1-trifluoropropan-2-yl)carbamate. To a solution of (S)—N-(5-(1-amino-2-cyclopropoxyethyl)-6-chloropyridazin-3-yl) pivalamide (300 mg, 0.959 mmol, Step A) in $CH_3CN$ (4.8 mL) were added DIPEA (0.496 mL, 2.88 mmol) and tert-Butyl (S)-4-(trifluoromethyl)-1,2,3-oxathiazolidine-3-carboxylate 2,2-dioxide (335 mg, 1.15 mmol, Intermediate 48) sequentially. The resulting mixture was heated at 65° C. for 18 h. The reaction was then diluted with water and extracted with EtOAc (×4). The combined organic layers were washed with brine, dried over anhydrous $Na_2SO_4$, filtered and concentrated to dryness. The residue was purified by silica gel chromatography (0-10% (2 M $NH_3$ in MeOH)/DCM) to provide the title compound in 66% yield.

Step C: N-(5-((S)-1-(((S)-2-Amino-3,3,3-trifluoropropyl) amino)-2-cyclopropoxyethyl)-6-chloropyridazin-3-yl)pivalamide. To a solution of tert-Butyl ((S)-3-(((S)-1-(3-chloro-6-pivalamidopyridazin-4-yl)-2-cyclopropoxyethyl)amino)-

1,1,1-trifluoropropan-2-yl)carbamate (332 mg, 0.634 mmol, Step B) in DCM (3 mL) was added TFA (3.00 mL, 39.2 mmol). The resulting solution was allowed to stir at rt for 1 h and then was concentrated to dryness. The residue was purified by silica gel chromatography (0-10% (2 M NH₃ in MeOH)/DCM) to provide the title compound in 53% yield.

Step D: N-(6-Chloro-5-((S)-2-cyclopropoxy-1-((S)-2-oxo-4-(trifluoromethyl)imidazolidin-1-yl)ethyl)pyridazin-3-yl)pivalamide. To a stirred solution of N-(5-((S)-1-(((S)-2-amino-3,3,3-trifluoropropyl)amino)-2-cyclopropoxyethyl)-6-chloropyridazin-3-yl)pivalamide (193 mg, 0.455 mmol, Step C) in THF (2.3 mL) was added CDI (148 mg, 0.911 mmol). The resulting mixture was heated at 65° C. for 1 h. The mixture was then cooled to rt, diluted with water and extracted with EtOAc (×4). The organic layers were combined, washed with brine, dried over anhydrous Na₂SO₄, filtered, and concentrated to dryness to afford a yellow oil. The oil was purified by silica gel chromatography (0-10% (2 M NH₃ in MeOH)/DCM) to provide the title compound in 64% yield.

Step E: (S)-1-((S)-1-(6-Amino-3-chloropyridazin-4-yl)-2-cyclopropoxyethyl)-4-(trifluoromethyl)imidazolidin-2-one. To a stirred solution N-(6-chloro-5-((S)-2-cyclopropoxy-1-((S)-2-oxo-4-(trifluoromethyl)imidazolidin-1-yl)ethyl)pyridazin-3-yl)pivalamide (618 mg, 1.03 mmol, Step D) in 1,4-dioxane (4 mL) was added aqueous H₂SO₄ (3 M, 3.4 mL, 10.3 mmol) and the reaction mixture was heated at 60° C. for 6 h. The reaction mixture was cooled to rt, diluted with EtOAc (80 mL) and water (80 mL) and then cooled to 0° C. The mixture was then treated with NaHCO₃ (40 g) in a portion wise manner with stirring. (Gas evolution was observed.) The resulting mixture was diluted with saturated aqueous NaHCO₃ (100 mL), and the layers were separated. The aqueous layer was extracted with EtOAc (4×100 mL), and the combined organic layers were dried over anhydrous Na₂SO₄, filtered and concentrated to dryness to give the title compound which was used without further purification.

Step F: tert-Butyl ((R)-1-(6-chloro-7-((S)-2-cyclopropoxy-1-((S)-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)carbamate. A mixture of (S)—((S)-1-(6-amino-3-chloropyridazin-4-yl)-2-cyclopropoxyethyl)-4-(trifluoromethyl)imidazolidin-2-one (167 mg, 0.457 mmol, Step E), tert-Butyl (S)—(4-iodo-3-oxo-1-((1,1,1-trifluoro-2-methylpropan-2-yl)oxy)butan-2-yl)carbamate (290 mg, 0.66 mmol), NMP (0.334 mL, 3.47 mmol) and sodium phosphate dibasic (84.6 mg, 0.596 mmol) was heated at 40° C. for 18 h. The reaction mixture was then diluted with. EtOAc, water and saturated aqueous NaS₂O₃. The layers were separated, and the aqueous phase was further extracted with EtOAc (×3). The combined organic extracts were washed with brine, dried over anhydrous Na₂SO₄ filtered and concentrated to dryness. The residue was purified by silica gel chromatography (0-100% acetone/hexanes (0.1% TEA)) to afford the title compound in 70% yield.

Step G: tert-Butyl ((R)-1-(7-((S)-2-cyclopropoxy-1-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)carbamate. A round bottom flask was charged with tert-butyl ((R)-1-(6-chloro-7-((S)-2-cyclopropoxy-1-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)carbamate (274 mg, 0.416 mmol, Step F), MeOH (5 mL), TEA (0.185 mL, 1.33 mmol) and palladium (221 mg, 0.208 mmol, 10 wt % on activated carbon). The flask was then evacuated and backfilled with hydrogen four times before being allowed to stir at rt for 1.5 h. The reaction mixture was filtered through a pad of diatomaceous earth (e.g., Celite®) and the filtrate was concentrated to dryness to provide the title compound which was used without further purification.

Step H: (S)-1-((S)-1-(2-((R)-1-Amino-2-((1,1,1-trifluoro-2-methylpropan-2-yl)oxy)ethyl)imidazo[1,2-b]pyridazin-7-yl)-2-cyclopropoxyethyl)-4-(trifluoromethyl)imidazolidin-2-one. To a solution of tert-Butyl ((R)-1-(7-((S)-2-cyclopropoxy-1-((S)-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)carbamate (274 mg, 0.439 mmol, Step G) in 1,4-dioxane (2.2 mL) was added HCl (4 M in 1,4-dioxane, 2.2 mL, 0.774 mmol). The resulting solution was allowed to stir at rt for 1 h, then the mixture was concentrated to dryness and was used without further purification.

Intermediate 48 tert-Butyl (S)-4-(trifluoromethyl)-1,2,3-oxathiazolidine-3-carboxylate 2,2-dioxide

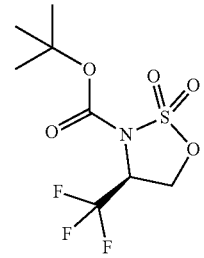 [SMILES: CC(C)(C)OC(=O)N1[C@H](C(F)(F)F)COS1(=O)=O]

Step A: tert-Butyl (S)—(1,1,1-trifluoro-3-hydroxypropan-2-yl)carbamate. To a solution of (S)-2-amino-3,3,3-trifluoropropan-1-ol hydrochloride (500 mg, 3.02 mmol) and Et₃N (0.92 mL, 6.7 mmol) in THF (10 mL) at 0° C., was added Boc₂O (801 mg, 3.67 mmol). The reaction mixture was warmed to rt and stirred for 1.5 h. The mixture was concentrated to dryness and the residue dissolved in EtOAc (50 mL), then washed with water (2×50 mL) and brine (50 mL). The organic layer was dried over anhydrous MgSO₄, filtered and concentrated to dryness to provide the title compound as a colorless solid that was used without further purification.

Step B: tert-Butyl (4S)-4-(trifluoromethyl)-1,2,3-oxathiazolidine-3-carboxylate 2-oxide. An oven dried round bottom flask was cooled and backfilled with N₂, then a solution of SOCl₂ (0.56 mL, 7.7 mmol) in CH₃CN (15 mL) was added. The solution was cooled to −45° C., then a solution of tert-Butyl (S)—(1,1,1-trifluoro-3-hydroxypropan-2-yl)carbamate (681 mg, 2.97 mmol, Step A) in CH₃CN (4 mL) was added dropwise over 10 min. Pyridine (1.30 mL, 15.7 mmol) was then added dropwise over 5 min and the resulting mixture was warmed to −35° C. and then maintained at a temperature between −35° C. to −25° C. for 2 h. The reaction was then quenched by the addition of crushed ice (20 g). Then, DCM (50 mL) was added followed by brine. The layers were separated and the organic layer was concentrated to dryness. The residue was then dissolved in EtOAc (30 mL) and washed with 0.1 N aqueous HCl (10 mL). The organic layer was dried over anhydrous MgSO₄, filtered, then concentrated to dryness to afford the title compound that was used without further purification.

Step C: tert-Butyl (S)-4-(trifluoromethyl)-1,2,3-oxathiazolidine-3-carboxylate 2,2-dioxide. A mixture of tert-Butyl (4S)-4-(trifluoromethyl)-1,2,3-oxathiazolidine-3-carboxylate 2-oxide (1.2 g, 4.36 mmol, Step B) in CH₃CN (4.7 mL), CCl₄ (4.7 mL) and water (9.5 mL) was cooled to 0° C. NaIO₄ (1.35 g, 6.3 mmol) and RuCl₃·4H₂O (11.4 mg, 0.04 mmol) were added sequentially and the resulting brown solution was stirred at 0° C. for 2 h. The brown reaction mixture was extracted with EtOAc (4×20 mL). Brine was added to the separatory funnel to break up any emulsion that formed. The light green organic layer was removed then dried over anhydrous Na₂SO₄, covered with parafilm, and then allowed to sit overnight, during which time a precipitate formed. The solids were filtered off and the filtrate was concentrated to dryness to afford the title compound in 75% yield over three steps (A-C).

Intermediate 49

Tributyl(cyclopropoxymethyl)stannane

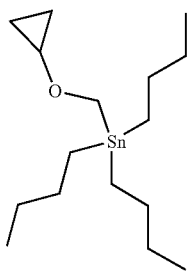 [SMILES: CCC[CH2][Sn]([CH2]CCC)([CH2]CCC)[CH2]OC1CC1]

To a reaction vial containing NaH (0.500 g, 12.5 mmol, 60% in mineral oil) under N₂ was added DMF (40 mL). The resulting suspension was cooled to 0° C. then cyclopropanol (0.789 mL, 12.5 mmol) was added dropwise. The reaction was stirred at 0° C. for 10 min then tributyl(iodomethyl)stannane (3.32 mL, 10.0 mmol) was added. The reaction mixture was allowed to warm to rt and stirred for 1 h. The reaction was then quenched with H₂O and diluted with aqueous 5% LiCl. The resulting mixture was extracted with CH₂Cl₂ (3×25 mL) then the combined organics were washed with brine, dried over anhydrous Na₂SO₄, filtered, and concentrated to dryness. The residue was purified by silica gel chromatography (0-20% EtOAc/hexanes) to provide the title compound in 100% yield.

Intermediate 50 tert-Butyl ((S)-(7-((S)-1-(((R)-tert-butyl sulfinyl)amino)-2-cyclopropoxyethyl)imidazo[1,2-b]pyridazin-2-yl)(4,4-difluorocyclohexyl)methyl)carbamate

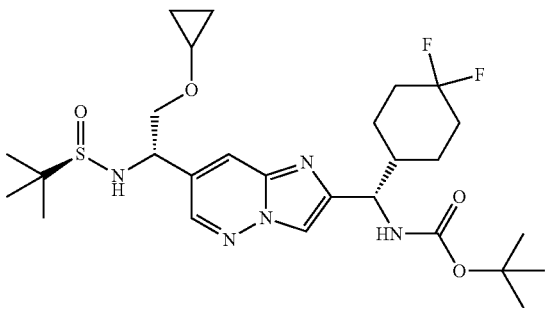 [SMILES: CC(C)(C)OC(=O)N[C@H](c1cn2ncc([C@@H](COC3CC3)N[S@](=O)C(C)(C)C)cc2n1)C1CCC(F)(F)CC1]

A solution of tributyl(cyclopropoxymethyl)stannane (800 mg, 2.22 mmol, Intermediate 49) in THF (10 mL) was cooled to −78° C. then n-butyllithium (1.4 mL, 1.6 M in hexanes, 2.2 mmol) was added dropwise. The reaction was stirred at −78° C. for 20 min then a solution of tert-Butyl ((S)-(7-((E)-(((R)-tert-butylsulfinyl)imino)methyl)imidazo[1,2-b]pyridazin-2-yl)(4,4-difluorocyclohexyl)methyl)carbamate (525 mg, 1.06 mmol) in THF (5 mL) was added slowly over a period of 10 min. The reaction was stirred at −78° C. for 30 min then quenched with EtOH (0.19 mL) and allowed to warm to rt. The resulting mixture was diluted with EtOAc, washed sequentially with saturated aqueous NaHCO₃ and brine, dried over anhydrous Na₂SO₄, filtered, and concentrated to dryness. The residue was purified by silica gel chromatography (10-60% acetone/hexanes (0.1% TEA)) to provide the title compound in 48% yield.

Intermediate 51 tert-Butyl ((S)-(7-((S)-1-amino-2-cyclopropoxyethyl)imidazo[1,2-b]pyridazin-2-yl)(4,4-difluorocyclohexyl)methyl)carbamate

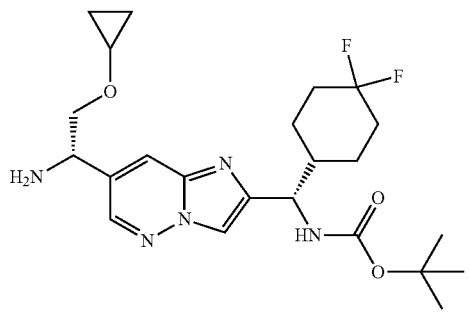 [SMILES: CC(C)(C)OC(=O)N[C@H](c1cn2ncc([C@H](N)COC3CC3)cc2n1)C1CCC(F)(F)CC1]

To a solution of tert-Butyl ((S)-(7-((S)-1-(((R)-tert-butylsulfinyl)amino)-2-cyclopropoxyethyl)imidazo[1,2-b]pyridazin-2-yl)(4,4-difluorocyclohexyl)methyl)carbamate (300 mg, 0.527 mmol, Intermediate 50) in EtOAc (3.5 mL) was added HCl (0.33 mL, 1.3 mmol, 4 M in 1,4-dioxane). The reaction was stirred at rt for 1 h then diluted with H₂O. The resulting solution was washed twice with hexanes and these extracts were discarded. The pH of the aqueous mixture was adjusted by the addition of 3 M aqueous NaOH (0.7 mL) then the mixture was extracted with EtOAc (×3). The combined organic layers were dried over anhydrous Na₂SO₄, filtered, and concentrated to dryness to provide the title compound that was used without further purification. The stereochemistry at the aminostereocenter was assigned by Mosher analysis.

Intermediate 52

(S)-1-((S)-1-(2-((S)-Amino(4,4-difluorocyclohexyl) methyl)imidazo[1,2-b]pyridazin-7-yl) cyclopropoxyethyl)-4-(trifluoromethyl)imidazolidin-2-one

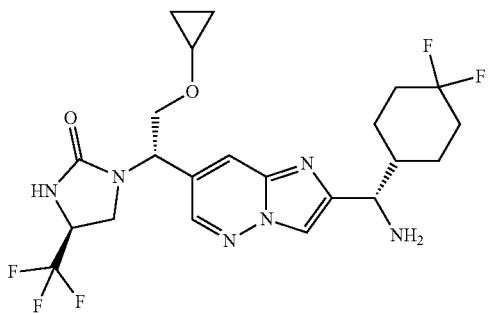 [SMILES: N[C@H](c1cn2ncc([C@@H](COC3CC3)N3C[C@@H](C(F)(F)F)NC3=O)cc2n1)C1CCC(F)(F)CC1]

Step A: Benzyl ((S)-3-(((S)-1-(2-((S)—((tert-butoxycarbonyl)amino)(4,4-difluorocyclohexyl)methyl)imidazo[1,2-b]pyridazin-7-yl)-2-cyclopropoxyethyl)amino)-1,1,1-trifluoropropan-2-yl)carbamate. The title compound (85% yield) was synthesized in a manner analogous to Intermediate 12 Step A using tert-Butyl ((S)-(7-((S)-1-amino-2-cyclopropoxyethyl)imidazo[1,2-b]pyridazin-2-yl)(4,4-difluorocyclohexyl)methyl)carbamate (Intermediate 51) in place of tert-Butyl ((R)-1-(7-((S)-1-amino-2-methoxyethyl)-6-chloroimidazo[1,2-b]pyridazin-2-yl)-2-((1,1,1-trifluoro-2-methylpropan-2-yl)oxy)ethyl)carbamate and benzyl (S)-4-(trifluoromethyl)-1,2,3-oxathiazolidine-3-carboxylate 2,2-dioxide (Intermediate 28) in place of (S*)-4-(trifluoromethyl)-1,2,3-oxathiazolidine-3-carboxylate-5,5-d₂ 2,2-dioxide.

Step B: tert-Butyl ((S)-(7-((S)-1-(((S)-2-amino-3,3,3-trifluoropropyl)amino)-2-cyclopropoxyethyl)imidazo[1,2-b] pyridazin-2-yl)(4,4-difluorocyclohexyl)methyl)carbamate. The title compound (95% yield) was synthesized in a manner analogous to Intermediate 12 Step B using benzyl ((S)-3-(((S)-1-(2-((S)—((tert-butoxycarbonyl)amino)(4,4-difluorocyclohexyl)methyl)imidazo[1,2-b]pyridazin-7-yl)-2-cyclopropoxyethyl)amino)-1,1,1-trifluoropropan-2-yl) carbamate (Step A) in place of tert-Butyl ((R)-1-(6-chloro-7-((5S*,8S)-3-oxo-1-phenyl-5-(trifluoromethyl)-2,10-dioxa-4,7-diazaundecan-8-yl-6,6-d₂)imidazo[1,2-b] pyridazin-2-yl)-2-(1,1,1-trifluoro-2-methylpropan-2-yl) oxy)ethyl)carbamate.

Step C: tert-Butyl ((S)-(7-((S)-2-cyclopropoxy-1-((S)-2-oxo-4-(trifluoromethyl)imidazolidin-1-yl)ethyl)imidazo[1,2-b]pyridazin-2-yl)(4,4-difluorocyclohexyl)methyl)carbamate. The title compound (12% yield) was synthesized in a manner analogous to Intermediate 12 Step C using tert-Butyl ((S)-(7-((S)-1-(((S)-2-amino-3,3,3-trifluoropropyl)amino)-2-cyclopropoxyethyl)imidazo[1,2-b]pyridazin-2-yl)(4,4-difluorocyclohexyl)methyl)carbamate (Step B) in place of tert-Butyl ((R)-1-(7-((S)-1-(((S*)-2-amino-3,3,3-trifluoropropyl-1,1-d₂)amino)-2-methoxyethyl)imidazo[1,2-b] pyridazin-2-yl)-2-((1,1,1-trifluoro-2-methylpropan-2-yl) oxy)ethyl)carbamate.

Step D: (S)-1-((S)-1-(2-((S)-Amino(4,4-difluorocyclohexyl)methyl)imidazo[1,2-b]pyridazin-7-yl)-2-cyclopropoxyethyl)-4-(trifluoromethyl)imidazolidin-2-one. The title compound was synthesized in a manner analogous to Intermediate 12 Step D using tert-Butyl ((S)-(7-((S)-2-cyclopropoxy-1-((S)-2-oxo-4-(trifluoromethyl)imidazolidin-1-yl)ethyl)imidazo[1,2-b]pyridazin-2-yl)(4,4-difluorocyclohexyl)methyl)carbamate (Step C) in place of tert-Butyl ((R)-1-(7-((S)—((S)-2-amino-3,3,3-trifluoropropyl-1,1-d₂) amino)-2-methoxyethyl)imidazo[1,2-b]pyridazin-2-yl)-2-(1,1,1-trifluoro-2-methylpropan-2-yl)oxy)ethyl)carbamate and was used without further purification.

Intermediate 53 tert-Butyl (S)—(1-(dimethyl(oxo)-λ⁶-sulfanylidene)-7,7,7-trifluoro-6,6-dimethyl-2-oxoheptan-3-yl)carbamate

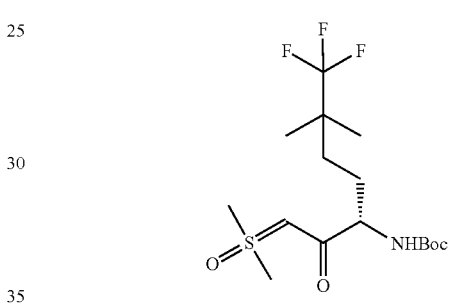

Step A: 1,1,1-Trifluoro-4-iodo-2,2-dimethylbutane. To a stirred solution of 4,4,4-trifluoro-3,3-dimethylbutan-1-ol (9.75 g, 62.5 mmol) in DCM (125 mL) were added triphenylphosphine (24.6 g, 93.7 mmol) and imidazole (5.53 g, 81.2 mmol), and the resulting mixture was cooled to 0° C. Iodine (23.8 g, 93.7 mmol) was then added portion-wise and the mixture was stirred for 24 h while warming to rt. The reaction mixture was quenched with saturated aqueous NaHCO₃ and stirred for 15 min. The organic layer was removed and washed sequentially with half-saturated aqueous NaHCO₃ and brine, dried over anhydrous MgSO₄, filtered, and concentrated to a residue. To the residue was added chilled hexanes (50 mL), and the mixture was stirred vigorously for 10 min at which time a white precipitated formed. The white solid was removed by filtration through a pad of silica and the solids were washed with a second portion of chilled hexanes. The filtrates were concentrated to dryness to afford the title compound as a clear, colorless oil (66% yield) that was used without further purification.

Step B: (2R,5S)-2-Isopropyl-3,6-dimethoxy-5-(4,4,4-trifluoro-3,3-dimethylbutyl)-2,5-dihydropyrazine. To a stirred solution of (R)-2-isopropyl-3,6-dimethoxy-2,5-dihydropyrazine (0.66 g, 3.59 mmol) in THF (7 mL) at −78° C. was added t-BuLi (2.33 mL, 3.95 mmol, 1.7 M in pentane), and the reaction mixture was allowed to stir at −78° C. After 1 h, a solution of 1,1,1-trifluoro-4-iodo-2,2-dimethylbutane (1.05 g, 3.95 mmol, Step A) in THF (6 mL) was added dropwise, and the resulting mixture was stirred for 24 h at rt. The reaction was quenched by the addition of aqueous phosphate buffer (50 mL, 0.1 M, pH 7) and then diluted with diethyl ether.

The organic layer was removed, and the aqueous layer was extracted with diethyl ether (2×50 mL). The combined organic layers were dried over anhydrous MgSO₄, filtered, and concentrated to give an oil. LC/MS of this oil revealed a mixture of diastereomers in ~1.5:1 ratio. This mixture was separated by silica gel chromatography (0-30% EtOAc/hexanes) to afford the first-eluting isomer (50% yield), which was designated as (2R,5S)-2-isopropyl-3,6-dimethoxy-5-(4,4,4-trifluoro-3,3-dimethylbutyl)-2,5-dihydropyrazine, the R,S diastereomer, as a yellow oil. The second-eluting isomer, designated as the R,R diastereomer, (2R,5R)-2-isopropyl-3,6-dimethoxy-5-(4,4,4-trifluoro-3,3-dimethylbutyl)-2,5-dihydropyrazine, was isolated in 28% yield.

Step C: Methyl (S)-2-amino-6,6,6-trifluoro-5,5-dimethylhexanoate. To a stirred solution of (2R,5S)-2-isopropyl-3,6-dimethoxy-5-(4,4,4-trifluoro-3,3-dimethylbutyl)-2,5-dihydropyrazine (1.15 g, 3.57 mmol, Step B, first-eluting isomer) in ACN (14.3 mL) at rt was added aqueous HCl (14.3 mL, 1 M). After stirring at rt for 2 h, the reaction mixture was poured onto saturated aqueous NaHCO₃ at 0° C. and the mixture was then extracted with EtOAc (3×150 mL). The combined organic layers were washed with brine, dried over anhydrous MgSO₄, filtered, and concentrated to dryness to give an oil that was used without further purification.

Step D: Methyl (S)-2-((tert-butoxycarbonyl)amino)-6,6,6-trifluoro-5,5-dimethylhexanoate. To a solution of methyl (S)-2-amino-6,6,6-trifluoro-5,5-dimethylhexanoate (811 mg, 3.57 mmol, Step C) in DCM (15.1 mL) was added Boc₂O (1.56 g, 7.14 mmol) and the resulting mixture was stirred at rt for 24 h. The reaction mixture was quenched with aqueous HCl (10 mL, 1 M), and the layers were separated. The organic layer was washed with aqueous HCl (10 mL, 1 M), water and brine, dried over anhydrous MgSO₄, filtered, and concentrated to dryness to give an oil that was used without further purification.

Step E: (S)-2-((tert-Butoxycarbonyl)amino)-6,6,6-trifluoro-5,5-dimethylhexanoic acid. To a solution of methyl (S)-2-((tert-butoxycarbonyl)amino)-6,6,6-trifluoro-5,5-dimethylhexanoate (925 mg, 2.83 mmol, Step D) in THF (22.4 mL) at 0° C. was added aqueous LiOH (8.50 mL, 1 M) and the resulting mixture was allowed to warm to rt, and was stirred for 2 h. The pH of the reaction mixture was then adjusted to pH 2 by the addition of aqueous HCl (1 M). This mixture was extracted with EtOAc (3×60 mL). The combined organic layers were washed with brine, dried over anhydrous MgSO₄, filtered, and concentrated to dryness to give a clear oil that was used without further purification.

Step F: tert-Butyl (S)—(1-(dimethyl(oxo)-λ⁶-sulfaneylidene)-7,7,7-trifluoro-6,6-dimethyl-2-oxoheptan-3-yl)carbamate. To a suspension of trimethylsulfoxonium chloride (0.581 g, 4.52 mmol) in THF (7 mL) was added a solution of t-BuOK (4.24 mL, 4.24 mmol, 1 M in THF) and the resulting suspension was allowed to stir at rt for 2 h to make mixture A. Separately, a solution of (S)-2-((tert-butoxycarbonyl)amino)-6,6,6-trifluoro-5,5-dimethylhexanoic acid (885 mg, 2.83 mmol, Step E) in THF (7 mL) was cooled to 0° C. and CDI (550 mg, 3.39 mmol) was added and this resulting mixture was stirred for 2 h at 0° C. to make mixture B. Mixture B was then added via cannula to mixture A to make mixture C. Mixture C was stirred at rt. After 2 h, mixture C was filtered through diatomaceous earth (e.g., Celite®), the filter cake rinsed with THF, and the filtrate was concentrated and purified via silica gel chromatography (0-100% EtOAc/hexanes) to afford the title compound (56% yield) as a white foam.

Intermediate 54 tert-Butyl (S)—(5,5,5-trifluoro-1-(7-formylimidazo[1,2-b]pyridazin-2-yl)-4,4-dimethylpentyl)carbamate

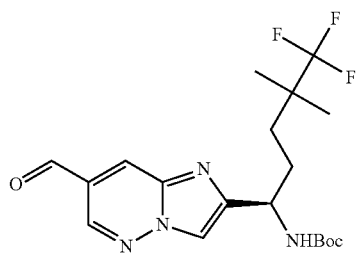 [SMILES: CC(C)(C)OC(=O)N[C@H](CCC(C)(C)C(F)(F)F)c1cn2ncc(C=O)cc2n1]

Step A: tert-Butyl (S)—(1-(7-chloroimidazo[1,2-b]pyridazin-2-yl)-5,5,5-trifluoro-4,4-dimethylpentyl)carbamate. 5-Chloropyridazin-3-amine (1.00 g, 7.72 mmol) and tert-Butyl (S)—(1-(dimethyl(oxo)-λ⁶-sulfaneylidene)-7,7,7-trifluoro-6,6-dimethyl-2-oxoheptan-3-yl)carbamate (3.29 g, 8.49 mmol, Intermediate 53) were dissolved in toluene (21 mL). 4 Å Molecular sieves (2.00 g), NaOTf (66.4 mg, 0.386 mmol), and chloro(cyclopentadienyl)bis(triphenylphosphine)ruthenium(II) (141 mg, 0.193 mmol) were then added sequentially, and the resulting mixture was heated at 85° C. for 16 h. The reaction mixture was then concentrated onto diatomaceous earth (e.g., Celite®) and purified by silica gel chromatography (0-100% EtOAc/hexanes) to afford the title compound in 30% yield.

Step B: tert-Butyl (S)—(5,5,5-trifluoro-4,4-dimethyl-1-(7-vinylimidazo[1,2-b]pyridazin-2-yl)pentyl)carbamate. tert-Butyl (S)—(1-(7-chloroimidazo[1,2-b]pyridazin-2-yl)-5,5,5-trifluoro-4,4-dimethylpentyl)carbamate (0.960 mg, 2.28 mmol, Step A), potassium trifluoro(vinyl)borate (0.460 g, 3.43 mmol), and K₃PO₄ (1.46 g, 6.90 mmol) were added under a positive pressure of nitrogen gas to a reactor containing a mixture of 1,4-dioxane and water (24 mL, 5:1 v/v, sparged with N₂ before use). The mixture was heated at 85° C., and then RuPhos Pd G3 (49.7 mg, 60.0 µmol) was added, and the mixture was heated at 85° C. for 6 h. After this time, the mixture was allowed to cool to rt and then concentrated to remove most of the 1,4-dioxane. The residue was diluted with EtOAc and water, the layers were separated, and the aqueous layer was extracted twice with EtOAc. The organic layers were combined, washed with brine, dried over anhydrous MgSO₄, filtered, and concentrated to dryness to afford the title compound as a brown foam, which was used without further purification.

Step C: tert-Butyl (S)—(5,5,5-trifluoro-1-(7-formylimidazo[1,2-b]pyridazin-2-yl)-4,4-dimethylpentyl)carbamate. A solution of NaIO₄ (2.43 g, 11.4 mmol) in water (55 mL) was added to a solution of tert-Butyl (S)—(5,5,5-trifluoro-4,4-dimethyl-1-(7-vinylimidazo[1,2-b]pyridazin-2-yl)pentyl)carbamate (8.81 g, 22.5 mmol, Step B) in 1,4-dioxane (55 mL). The resulting solution was then cooled with an ice bath to about 12° C. and K₂OsO₄·2H₂O (42.0 mg, 0.114 mmol) was added. The reaction mixture was removed from the ice bath and stirred for 1 h. The resulting thick suspension was diluted with water and the solution was extracted with EtOAc (4×). The combined organic layers were washed with brine, dried over anhydrous Na₂SO₄, filtered, concentrated onto diatomaceous earth, and purified by silica gel chromatography (0-50% acetone/hexanes) to afford the title compound in 64% yield.

161

Intermediate 55

(S)-5,5,5-Trifluoro-4,4-dimethyl-1-(7-(((S)-4-methyl-2-oxo-4-(trifluoromethyl)imidazolidin-1-yl)methyl)imidazo[1,2-b]pyridazin-2-yl)pentan-1-aminium 2,2,2-trifluoroacetate

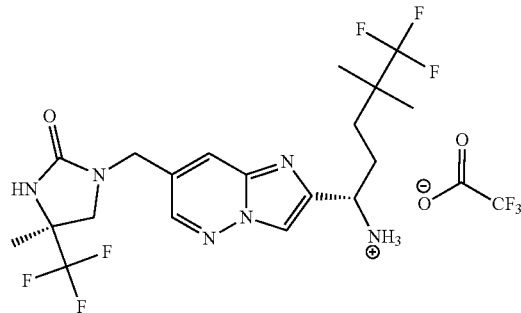 [SMILES: CC(C)(CC[C@H]([NH3+])c1cn2ncc(CN3C[C@@](C)(C(F)(F)F)NC3=O)cc2n1)C(F)(F)F ; O=C([O-])C(F)(F)F]

Step A: tert-Butyl ((S)-1-(7-(((((S)-2-amino-3,3,3-trifluoro-2-methylpropyl)amino)methyl)imidazo[1,2-b]pyridazin-2-yl)-5,5,5-trifluoro-4,4-dimethylpentyl)carbamate. tert-Butyl (S)—(5,5,5-trifluoro-1-(7-formylimidazo[1,2-b]pyridazin-2-yl)-4,4-dimethylpentyl)carbamate (125 mg, 0.302 mmol, Intermediate 54) was dissolved in DCE (3 mL) and then (2S)-3,3,3-trifluoro-2-methyl-1,2-propanediamine hydrochloride (77.8 mg, 0.362 mmol), TEA (0.126 mL, 0.905 mmol), and Ti(i-PrO)₄ (0.177 mL, 0.603 mmol) were sequentially added. The resulting mixture was heated at 50° C. for 3 h. The reaction mixture was cooled to rt and then AcOH (86.3 µL, 1.5 mmol), MeOH (0.339 mL), and NaCNBH₃ (56.9 mg, 0.905 mmol) were sequentially added. The resulting mixture was stirred at rt for 1.5 h. The reaction was diluted with saturated aqueous NaHCO₃ and EtOAc and filtered through diatomaceous earth. The filtrate was then extracted with EtOAc (3×). The combined organic layers were washed with brine, dried over anhydrous Na₂SO₄, filtered, and concentrated to dryness to afford the title compound which was used without further purification.

Step B: tert-Butyl ((S)-5,5,5-trifluoro-4,4-dimethyl-1-(7-(((S)-4-methyl-2-oxo-4-(trifluoromethyl)imidazolidin-1-yl)methyl)imidazo[1,2-b]pyridazin-2-yl)pentyl)carbamate. The title compound was synthesized in a manner analogous to Intermediate 12 Step C using tert-butyl ((S)-1-(7-((((S)-2-amino-3,3,3-trifluoro-2-methylpropyl)amino)methyl)imidazo[1,2-b]pyridazin-2-yl)-5,5,5-trifluoro-4,4-dimethylpentyl)carbamate (Step A) in place of tert-Butyl ((R)-1-(7-((S)-1-(((S*)-2-amino-3,3,3-trifluoropropyl-1,1-d₂)amino)-2-methoxyethyl)imidazo[1,2-b]pyridazin-2-yl)-2-((1,1,1-trifluoro-2-methylpropan-2-yl)oxy)ethyl)carbamate. The residue was purified by silica gel chromatography (0-100% acetone/hexanes) to provide the title compound in 33% yield.

Step C: (S)-5,5,5-Trifluoro-4,4-dimethyl-1-(7-(((S)-4-methyl-2-oxo-4-(trifluoromethyl)imidazolidin-1-yl)methyl)imidazo[1,2-b]pyridazin-2-yl)pentan-1-aminium 2,2,2-trifluoroacetate. tert-Butyl ((S)-5,5,5-trifluoro-4,4-dimethyl-1-(7-(((S)-4-methyl-2-oxo-4-(trifluoromethyl)imidazolidin-1-yl)methyl)imidazo[1,2-b]pyridazin-2-yl)pentyl)carbamate

162

(68 mg, 0.12 mmol, Step B) was dissolved in DCM (0.6 mL) and the mixture was cooled to 0° C. TFA (0.6 mL) was added dropwise and the reaction was stirred at 0° C. for 1 h. After this time, the reaction was warmed to rt and concentrated to dryness to afford the title compound that was used without further purification.

Intermediate 56

(S)-5,5,5-Trifluoro-4,4-dimethyl-1-(7-(((R)-4-methyl-2-oxo-4-(trifluoromethyl)imidazolidin-1-yl)methyl)imidazo[1,2-b]pyridazin-2-yl)pentan-1-aminium 2,2,2-trifluoroacetate

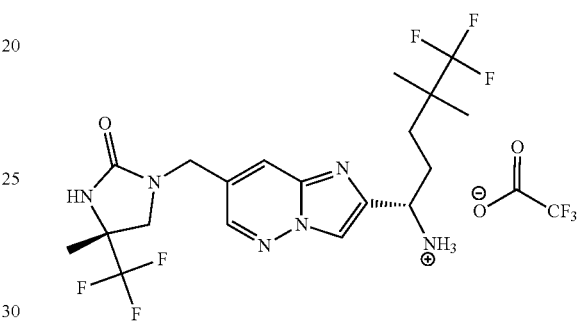

Step A: tert-Butyl ((S)-1-(7-((((R)-2-amino-3,3,3-trifluoro-2-methylpropyl)amino)methyl)imidazo[1,2-b]pyridazin-2-yl)-5,5,5-trifluoro-4,4-dimethylpentyl)carbamate. The title compound was synthesized in a manner analogous to Intermediate 55 Step A using (2R)-3,3,3-trifluoro-2-methyl-1,2-propanediamine hydrochloride in place of (2S)-3,3,3-trifluoro-2-methyl-1,2-propanediamine hydrochloride and was used without further purification.

Step B: tert-Butyl ((S)-5,5,5-trifluoro-4,4-dimethyl-1-(7-(((R)-4-methyl-2-oxo-4-(trifluoromethyl)imidazolidin-1-yl)methyl)imidazo[1,2-b]pyridazin-2-yl)pentyl)carbamate. The title compound was synthesized in a manner analogous to Intermediate 12 Step C using tert-butyl ((S)-1-(7-((((R)-2-amino-3,3,3-trifluoro-2-methylpropyl)amino)methyl)imidazo[1,2-b]pyridazin-2-yl)-5,5,5-trifluoro-4,4-dimethylpentyl)carbamate (Step A) in place of tert-Butyl ((R)-1-(7-((S)-1-(((S*)-2-amino-3,3,3-trifluoropropyl-1,1-d₂)amino)-2-methoxyethyl)imidazo[1,2-b]pyridazin-2-yl)-2-((1,1,1-trifluoro-2-methylpropan-2-yl)oxy)ethyl)carbamate. The residue was purified by silica gel chromatography (0-100% acetone/hexanes) to provide the title compound in 20% yield.

Step C: (S)-5,5,5-Trifluoro-4,4-dimethyl-1-(7-(((R)-4-methyl-2-oxo-4-(trifluoromethyl)imidazolidin-1-yl)methyl)imidazo[1,2-b]pyridazin-2-yl)pentan-1-aminium 2,2,2-trifluoroacetate. The title compound was synthesized in a manner analogous to Intermediate 55 Step C using tert-Butyl ((S)-5,5,5-trifluoro-4,4-dimethyl-1-(7-(((R)-4-methyl-2-oxo-4-(trifluoromethyl)imidazolidin-1-yl)methyl)imidazo[1,2-b]pyridazin-2-yl)pentyl)carbamate (Step B) in place of tert-Butyl((S)-5,5,5-trifluoro-4,4-dimethyl-1-(7-((S)-4-methyl-2-oxo-4-(trifluoromethyl)imidazolidin-1-yl)methyl)imidazo[1,2-b]pyridazin-2-yl)pentyl)carbamate and was used without further purification.

Example 1

(S)—N-((4,4-Difluorocyclohexyl)(7-((2-oxoimidazolidin-1-yl)methyl)imidazo[1,2-b]pyridazin-2-yl)methyl)-4-methyl-1,2,5-oxadiazole-3-carboxamide

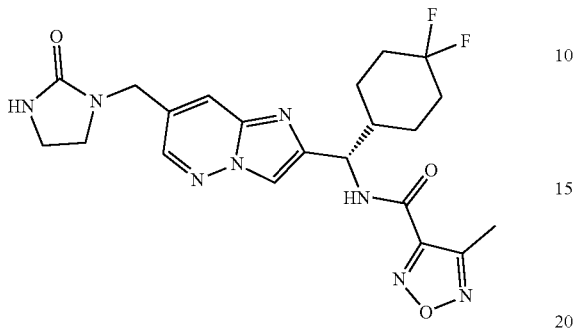

To a stirred solution of 4-methyl-1,2,5-oxadiazole-3-carboxylic acid (52.7 mg, 0.412 mmol) and 1-propanephosphonic anhydride (0.221 mL, 0.370 mmol, 50% in EtOAc) in EtOAc (1.0 mL) was added N,N-diisopropylethylamine (0.141 mL, 0.823 mmol). After 5 min, (S)-1-((2-(amino(4,4-difluorocyclohexyl)methyl)imidazo[1,2-b]pyridazin-7-yl)methyl)imidazolidin-2-one (75 mg, 0.206 mmol, Intermediate 1) in DCM (2 mL) was added. After 16 h at rt, the reaction was diluted with aqueous HCl (15 mL, 0.05 M) and the aqueous layer was extracted with EtOAc (3×5 mL). The combined organics were washed with saturated aqueous NaHCO₃ (10 mL), dried over anhydrous Na₂SO₄, filtered, and concentrated. The reaction mixture was dissolved in DMSO and purified by preparative HPLC (C18, 5 μm, 50×250 mm, 10-100% MeCN/water (20 mM NH₄OH)) to give the title compound as a white solid (23.3% yield). $^1$H NMR (600 MHz, DMSO-$d_6$) δ 9.41 (d, J=9.0 Hz, 1H), 8.39 (d, J=1.9 Hz, 1H), 8.24 (s, 1H), 7.89 (dd, J=0.8, 1.9 Hz, 1H), 6.55 (s, 1H), 5.17 (t, J=8.6 Hz, 1H), 4.32 (s, 2H), 3.30-3.28 (m, 2H), 3.28-3.22 (m, 2H), 2.46 (s, 3H), 2.22-2.13 (m, 1H), 2.08-1.93 (m, 2H), 1.90 (d, J=12.6 Hz, 1H), 1.84-1.70 (m, 2H), 1.61 (d, J=13.0 Hz, 1H), 1.43-1.34 (m, 1H), 1.32-1.20 (m, 1H). MS (ESI) m/z: [M+H]⁺ Found 475.1.

Example 2

(S)-4-Cyclopropyl-N-((4,4-difluorocyclohexyl)(7-((2-oxoimidazolidin-1-yl)methyl)imidazo[1,2-b]pyridazin-2-yl)methyl)-1,2,5-oxadiazole-3-carboxamide

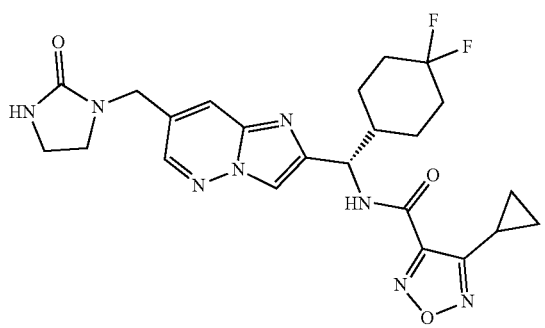 [SMILES: O=C(N[C@H](c1cn2ncc(CN3CCNC3=O)cc2n1)C1CCC(F)(F)CC1)c1nonc1C1CC1]

The title compound was synthesized in a manner analogous to Example 1 using 4-cyclopropyl-1,2,5-oxadiazole-3-carboxylic acid in place of 4-methyl-1,2,5-oxadiazole-3-carboxylic acid to provide the title compound as a white solid (15.4% yield). $^1$H NMR (600 MHz, DMSO-$d_6$) δ 9.48 (d, J=9.0 Hz, 1H), 8.39 (d, J=2.1 Hz, 1H), 8.23 (s, 1H), 7.89 (dd, J=0.8, 1.9 Hz, 1H), 6.55 (s, 1H), 5.19 (t, J=8.5 Hz, 1H), 4.32 (s, 2H), 3.30-3.28 (m, 2H), 3.28-3.23 (m, 2H), 2.35-2.25 (m, 1H), 2.22-2.14 (m, 1H), 2.09-1.94 (m, 2H), 1.89 (d, J=12.6 Hz, 1H), 1.85-1.71 (m, 2H), 1.62 (d, J=12.4 Hz, 1H), 1.44-1.34 (m, 1H), 1.33-1.24 (m, 1H), 1.15-1.08 (m, 2H), 0.99-0.92 (m, 2H). MS (ESI) m/z: [M+H]⁺ Found 501.1.

Example 3

(S)—N-((4,4-Difluorocyclohexyl)(7-((2-oxoimidazolidin-1-yl)methyl)imidazo[1,2-b]pyridazin-2-yl)methyl)-1-isopropyl-1H-pyrazole-5-carboxamide

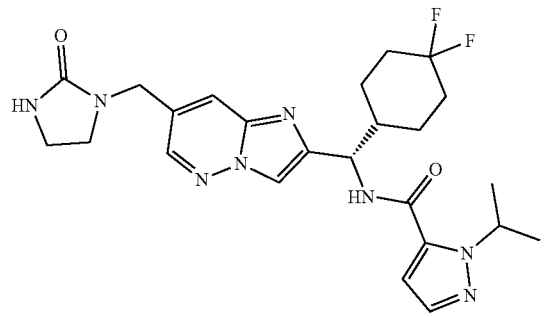 [SMILES: CC(C)n1nccc1C(=O)N[C@H](c1cn2ncc(CN3CCNC3=O)cc2n1)C1CCC(F)(F)CC1]

The title compound was synthesized in a manner analogous to Example 1 using 1-isopropyl-1H-pyrazole-5-carboxylic acid in place of 4-methyl-1,2,5-oxadiazole-3-carboxylic acid to provide the title compound as a white solid (31.3% yield). $^1$H NMR (600 MHz, DMSO-$d_6$) δ 8.71 (d, J=9.2 Hz, 1H), 8.38 (d, J=2.1 Hz, 1H), 8.21 (s, 1H), 7.88 (dd, J=0.8, 1.9 Hz, 1H), 7.48 (d, J=1.9 Hz, 1H), 6.91 (d, J=1.9 Hz, 1H), 6.55 (s, 1H), 5.37 (spt, J=6.6 Hz, 1H), 5.15 (t, J=8.7 Hz, 1H), 4.32 (s, 2H), 3.29 (dd, J=3.6, 6.3 Hz, 2H), 3.27-3.23 (m, 2H), 2.21-2.14 (m, 1H), 2.09-1.93 (m, 2H), 1.87 (d, J=12.2 Hz, 1H), 1.83-1.69 (m, 2H), 1.62 (d, J=13.0 Hz, 1H), 1.42-1.37 (m, 1H), 1.36 (d, J=6.5 Hz, 3H), 1.33 (d, J=6.7 Hz, 3H), 1.30-1.20 (m, 1H). MS (ESI) m/z: [M+H]⁺ Found 501.2.

Example 4

4-Cyclopropyl-N—((S)—(4,4-difluorocyclohexyl)(7-(((S)-4-methyl-2-oxoimidazolidin-1-yl)methyl)imidazo[1,2-b]pyridazin-2-yl)methyl)-1,2,5-oxadiazole-3-carboxamide

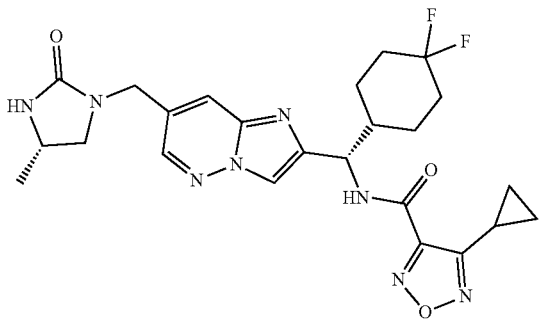 [SMILES: C[C@H]1CN(Cc2cnn3cc([C@@H](NC(=O)c4nonc4C4CC4)C4CCC(F)(F)CC4)nc3c2)C(=O)N1]

The title compound was synthesized in a manner analogous to Example 1 using (S)-1-((2-((S)-amino(4,4-difluorocyclohexyl)methyl)imidazo[1,2-b]pyridazin-7-yl)methyl)-4-methylimidazolidin-2-one (Intermediate 2) in place of (S)-1-((2-(amino(4,4-difluorocyclohexyl)methyl)imidazo[1,2-b]pyridazin-7-yl)methyl)imidazolidin-2-one and 4-cyclopropyl-1,2,5-oxadiazole-3-carboxylic acid in place of 4-methyl-1,2,5-oxadiazole-3-carboxylic acid to provide the title compound as a white solid (19.7% yield). $^1$H NMR (500 MHz, DMSO-d$_6$) δ 9.48 (d, J=9.0 Hz, 1H), 8.38 (d, J=2.0 Hz, 1H), 8.24 (s, 1H), 7.87 (d, J=1.1 Hz, 1H), 6.71 (s, 1H), 5.19 (t, J=8.6 Hz, 1H), 4.37-4.31 (m, 1H), 4.31-4.25 (m, 1H), 3.71-3.60 (m, 1H), 3.43 (t, J=8.4 Hz, 1H), 2.83 (dd, J=6.5, 8.6 Hz, 1H), 2.30-2.25 (m, 1H), 2.22-2.12 (m, 1H), 2.10-1.93 (m, 2H), 1.93-1.69 (m, 3H), 1.62 (d, J=12.6 Hz, 1H), 1.44-1.34 (m, 1H), 1.33-1.24 (m, 1H), 1.14-1.10 (m, 2H), 1.09 (d, J=6.1 Hz, 3H), 0.99-0.92 (m, 2H). MS (ESI) m/z: [M+H]$^+$ Found 514.8.

Example 5

N—((S)—(4,4-Difluorocyclohexyl)(7-(((S)-4-methyl-2-oxoimidazolidin-1-yl)methyl)imidazo[1,2-b]pyridazin-2-yl)methyl)-1-isopropyl-1H-pyrazole-5-carboxamide

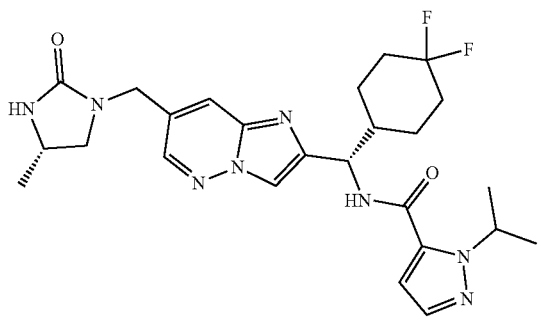 [SMILES: CC(C)n1nccc1C(=O)N[C@H](c1cn2ncc(CN3C[C@H](C)NC3=O)cc2n1)C1CCC(F)(F)CC1]

The title compound was synthesized in a manner analogous to Example 1 using (S)-1-((2-((S)-amino(4,4-difluorocyclohexyl)methyl)imidazo[1,2-b]pyridazin-7-yl)methyl)-4-methylimidazolidin-2-one (Intermediate 2) in place of (S)-1-((2-(amino(4,4-difluorocyclohexyl)methyl)imidazo[1,2-b]pyridazin-7-yl)methyl)imidazolidin-2-one and 1-isopropyl-1H-pyrazole-5-carboxylic acid in place of 4-methyl-1,2,5-oxadiazole-3-carboxylic acid to provide the title compound as a white solid (14.8% yield). $^1$H NMR (500 MHz, DMSO-d$_6$) δ 8.72 (d, J=9.0 Hz, 1H), 8.37 (d, J=2.0 Hz, 1H), 8.21 (s, 1H), 7.87-7.84 (m, 1H), 7.48 (d, J=1.9 Hz, 1H), 6.91 (d, J=1.9 Hz, 1H), 6.70 (s, 1H), 5.37 (spt, J=6.6 Hz, 1H), 5.15 (t, J=8.7 Hz, 1H), 4.37-4.25 (m, 2H), 3.70-3.61 (m, 1H), 3.42 (t, J=8.4 Hz, 1H), 2.82 (dd, J=6.5, 8.6 Hz, 1H), 2.23-2.11 (m, 1H), 2.10-1.92 (m, 2H), 1.91-1.68 (m, 3H), 1.61 (d, J=11.5 Hz, 1H), 1.43-1.37 (m, 1H), 1.36 (d, J=6.6 Hz, 3H), 1.33 (d, J=6.6 Hz, 3H), 1.30-1.20 (m, 1H), 1.09 (d, J=6.1 Hz, 3H). MS (ESI) m/z: [M+H]$^+$ Found 514.9.

Example 6

4-Cyclopropyl-N—((S)—(4,4-difluorocyclohexyl)(7-(((R)-4-methyl-2-oxoimidazolidin-1-yl)methyl)imidazo[1,2-b]pyridazin-2-yl)methyl)-1,2,5-oxadiazole-3-carboxamide

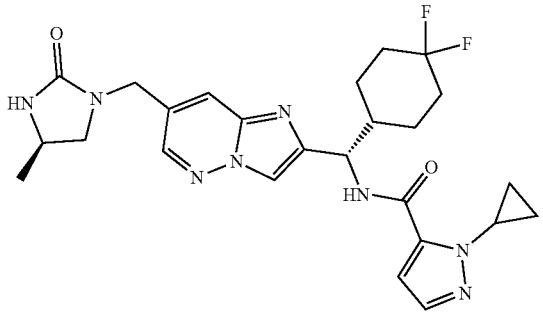 [SMILES: C[C@@H]1CN(Cc2cnn3cc([C@@H](NC(=O)c4ccnn4C4CC4)C4CCC(F)(F)CC4)nc3c2)C(=O)N1]

The title compound was synthesized in a manner analogous to Example 1 using (R)-1-((2-((S)-amino(4,4-difluorocyclohexyl)methyl)imidazo[1,2-b]pyridazin-7-yl)methyl)-4-methylimidazolidin-2-one (Intermediate 3) in place of (S)-1-((2-(amino(4,4-difluorocyclohexyl)methyl)imidazo[1,2-b]pyridazin-7-yl)methyl)imidazolidin-2-one and 4-cyclopropyl-1,2,5-oxadiazole-3-carboxylic acid in place of 4-methyl-1,2,5-oxadiazole-3-carboxylic acid to provide the title compound as a white solid (25.7% yield). $^1$H NMR (500 MHz, DMSO-d$_6$) δ 9.48 (d, J=9.0 Hz, 1H), 8.38 (d, J=2.0 Hz, 1H), 8.24 (s, 1H), 7.87 (dd, J=0.8, 1.9 Hz, 1H), 6.71 (s, 1H), 5.19 (t, J=8.5 Hz, 1H), 4.37-4.31 (m, 1H), 4.30-4.24 (m, 1H), 3.70-3.61 (m, 1H), 3.43 (t, J=8.4 Hz, 1H), 2.83 (dd, J=6.5, 8.6 Hz, 1H), 2.33-2.22 (m, 1H), 2.23-2.12 (m, 1H), 2.09-1.94 (m, 2H), 1.89 (d, J=13.0 Hz, 1H), 1.85-1.69 (m, 2H), 1.62 (d, J=12.3 Hz, 1H), 1.44-1.34 (m, 1H), 1.33-1.23 (m, 1H), 1.14-1.11 (m, 2H), 1.10 (d, J=6.1 Hz, 3H), 0.98-0.92 (m, 2H). MS (ESI) m/z: [M+H]$^+$ Found 514.8.

Example 7

4-Cyclopropyl-N—((S)-(7-(((3aR*,6aS*)-5,5-difluoro-2-oxohexahydrocyclopenta[d]imidazol-1(2H)-yl)methyl)imidazo[1,2-b]pyridazin-2-yl)(4,4-difluorocyclohexyl)methyl)-1,2,5-oxadiazole-3-carboxamide

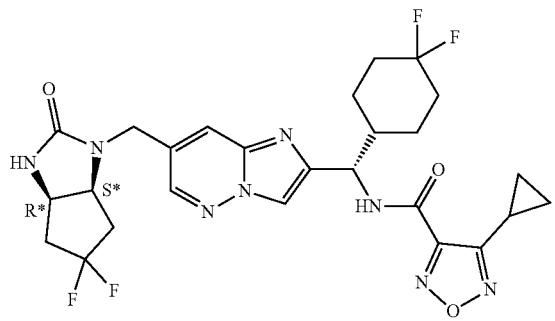 [SMILES: O=C(N[C@H](c1cn2ncc(CN3C(=O)N[C@@H]4CC(F)(F)C[C@@H]43)cc2n1)C1CCC(F)(F)CC1)c1nonc1C1CC1]

Example 8

4-Cyclopropyl-N—((S)-(7-(((3aS*,6aR*)-5,5-difluoro-2-oxohexahydrocyclopenta[d]imidazol-1(2H)-yl)methyl)imidazo[1,2-b]pyridazin-2-yl)(4,4-difluorocyclohexyl)methyl)-1,2,5-oxadiazole-3-carboxamide

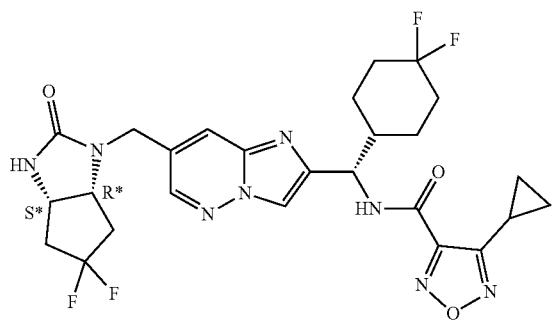 [SMILES: O=C(N[C@H](c1cn2ncc(CN3C(=O)N[C@H]4CC(F)(F)C[C@H]43)cc2n1)C1CCC(F)(F)CC1)c1nonc1C1CC1]

Step A: tert-Butyl ((1S)-(7-((2-((tert-butoxycarbonyl)amino)-4,4-difluorocyclopentyl)amino)methyl)imidazo[1,2-b]pyridazin-2-yl)(4,4-difluorocyclohexyl)methyl)carbamate. tert-Butyl (S)—((4,4-difluorocyclohexyl)(7-formylimidazo[1,2-b]pyridazin-2-yl)methyl)carbamate (106 mg, 0.269 mmol), rac-tert-butyl N-[(1R,2S)-2-amino-4,4-difluorocyclopentyl]carbamate (63.9 mg, 0.271 mmol), TEA (0.11 mL, 0.81 mmol) and anhydrous DCM (2.15 mL) were added to a reaction vial. The resulting mixture was stirred for 2 h at 25° C., and was then treated with NaBH$_3$CN (59 mg, 0.94 mmol), methanol (0.25 mL) and AcOH (0.077 mL). The resulting mixture was stirred for another 2 h at 25° C. The reaction mixture was then poured into saturated aqueous NaHCO$_3$, the pH of the reaction mixture was adjusted to pH 11 by the addition of 3 M aqueous NaOH and then the resulting solution was extracted with DCM (40 mL×3). The combined organic extracts were washed with brine (2×30 mL), dried over anhydrous Na$_2$SO$_4$, filtered, and concentrated to dryness under reduced pressure to provide the title compound as a yellow foam, which was used without further purification.

Step B: tert-Butyl ((1S)-(7-((5,5-difluoro-2-oxohexahydrocyclopenta[d]imidazol-1(2H)-yl)methyl)imidazo[1,2-b]pyridazin-2-yl)(4,4-difluorocyclohexyl)methyl)carbamate. tert-Butyl (1S)-(7-((2-((tert-butoxycarbonyl)amino)-4,4-difluorocyclopentyl)amino)methyl)imidazo[1,2-b]pyridazin-2-yl)(4,4-difluorocyclohexyl)methyl)carbamate (138.3 mg, 0.225 mmol, Step A) and THF (1.5 mL) were added to a reaction vial. To the vial was then added potassium tert-pentoxide (0.51 mL, 1.01 mmol, 2 M in THF) and the reaction mixture was stirred at 50° C. for 1 h. The reaction mixture was then poured into saturated aqueous NaHCO$_3$ and extracted with EtOAc (3×20 mL). The combined organic layers were washed with 0.1 M aqueous HCl and brine, dried over anhydrous Na$_2$SO$_4$, filtered, and concentrated to dryness to afford a yellow oil. This oil was purified by silica gel chromatography (0-100% EtOAc (with 10% MeOH) in hexanes) to afford the title compound (37% yield over two steps) as a yellow foam.

Step C: 1-((2-((S)-Amino(4,4-difluorocyclohexyl)methyl)imidazo[1,2-b]pyridazinyl)methyl)-5,5-difluorohexahydrocyclopenta[d]imidazol-2(1H)-one. To a vial containing tert-butyl ((1S)-(7-((5,5-difluoro-2-oxohexahydrocyclopenta[d]imidazol-1(2H)-yl)methyl)imidazo[1,2-b]pyridazin-2-yl)(4,4-difluorocyclohexyl)methyl)carbamate (44.9 mg, 0.083 mmol, Step B) was added TFA (0.5 mL) and the reaction mixture was allowed to stir at rt for 1 h. The reaction mixture was then concentrated under reduced pressure to remove any residual TFA and then diluted with saturated aqueous NaHCO$_3$ and allowed to stir for 5 min. The aqueous layer was then extracted with EtOAc (3×20 mL). The combined organic layers were washed with brine, dried over anhydrous Na$_2$SO$_4$, filtered, and concentrated to afford the title compound (87% yield) as a yellow foam, which was used without further purification.

Step D: 4-Cyclopropyl-N-((1S)-(7-((5,5-difluoro-2-oxohexahydrocyclopenta[d]imidazol-1(2H)-yl)methyl)imidazo[1,2-b]pyridazin-2-yl)(4,4-difluorocyclohexyl)methyl)-1,2,5-oxadiazole-3-carboxamide. A reaction vial was charged with 4-cyclopropyl-1,2,5-oxadiazole-3-carboxylic acid (22.3 mg, 0.145 mmol), EtOAc (0.36 mL), T$_3$P (0.078 mL, 0.13 mmol, 50% w/v solution in EtOAc), and DIPEA (0.05 mL, 0.29 mmol) and the reaction mixture was allowed to stir at rt for 5 min. A solution of 1-((2-((S)-amino(4,4-difluorocyclohexyl)methyl)imidazo[1,2-b]pyridazin-7-yl)methyl)-5,5-difluorohexahydrocyclopenta[d]imidazol-2(1H)-one (31.9 mg, 0.073 mmol, Step C) in DCM (2 mL) was then added to the reaction mixture and the resulting reaction mixture was allowed to stir at rt for 17 h. The reaction mixture was then concentrated to remove solvent, dissolved in minimal MeOH, and applied directly to acidic reverse phase HPLC purification (Waters XSelect CSH C18, 5 μm, 19×100 mm; 25-60% H$_2$O (with 0.16% TFA) in MeCN (with 0.16% TFA)) to afford the title compound (25% yield) as a white powder after lyophilization.

Step E: 4-Cyclopropyl-N—((S)-(7-(((3aR*,6aS*)-5,5-difluoro-2-oxohexahydrocyclopenta[d]imidazol-1(2H)-yl)methyl)imidazo[1,2-b]pyridazin-2-yl)(4,4-difluorocyclohexyl)methyl)-1,2,5-oxadiazole-3-carboxamide. 4-Cyclopropyl-N-((1S)-(7-((5,5-difluoro-2-oxohexahydrocyclopenta[d]imidazol-1(2H)-yl)methyl)imidazo[1,2-b]pyridazin-2-yl)(4,4-difluorocyclohexyl)methyl)-1,2,5-oxadiazole-3-carboxamide (10.6 mg, Step D) was purified by chiral SFC (Chiralpak IC3 5 μm, 250×21 Mm, Mobile phase: 25% methanol, 75% CO$_2$) to afford two diastereomers. The first eluting diastereomer was 4-cyclopropyl-N—((S)-(7-(((3aR*,6aS*)-5,5-difluoro-2-oxohexahydrocyclopenta[d]imidazol-1(2H)-yl)methyl)imidazo[1,2-b]

pyridazin-2-yl)(4,4-difluorocyclohexyl)methyl)-1,2,5-oxadiazole-3-carboxamide (Example 7, 17% yield) that was isolated as a white solid after lyophilization. The second eluting diastereomer was 4-cyclopropyl-N—((S)-(7-(((3aS*,6aR*)-5,5-difluoro-2-oxohexahydrocyclopenta[d]imidazol-1(2H)-yl)methyl)imidazo[1,2-b]pyridazin-2-yl)(4,4-difluorocyclohexyl)methyl)-1,2,5-oxadiazole-3-carboxamide (Example 8, 18% yield) that was isolated as a white solid after lyophilization. Data for Example 7: $^1$H NMR (500 MHz, DMSO-$d_6$) δ 9.48 (d, J=9.0 Hz, 1H), 8.37 (d, J=2.0 Hz, 1H), 8.24 (s, 1H), 7.90 (d, J=1.9 Hz, 1H), 6.92 (s, 1H), 5.19 (m, 1H), 4.53 (m, 1H), 4.22-4.16 (m, 3H), 2.32-2.23 (m, 3H), 2.23-1.94 (m, 4H), 1.90 (m, 1H), 1.86-1.70 (m, 2H), 1.62 (m, 1H), 1.44-1.34 (m, 1H), 1.34-1.22 (m, 2H), 1.11 (m, 2H), 0.96 (m, 2H). MS (ESI) m/z: [M+H]$^+$ Found 577.3.

Data for Example 8: 1 $^1$H NMR (400 MHz, DMSO-$d_6$) δ 9.48 (d, J=9.0 Hz, 1H), 8.37 (d, J=2.0 Hz, 1H), 8.23 (s, 1H), 7.90 (d, J=2.0 Hz, 1H), 6.92 (s, 1H), 5.22-5.16 (m, 1H), 4.53 (d, J=16.1 Hz, 1H), 4.23-4.16 (m, 3H), 2.31-2.24 (m, 3H), 2.23-1.94 (m, 4H), 1.94-1.86 (m, 1H), 1.86-1.69 (m, 2H), 1.66-1.58 (m, 1H), 1.43-1.34 (m, 1H), 1.34-1.22 (m, 2H), 1.14-1.08 (m, 2H), 0.98-0.93 (m, 2H). MS (ESI) m/z: [M+H]$^+$ Found 577.3.

Example 9

N—((R)-1-(7-((S)-2-Methoxy-1-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)-4-methyl-1,2,5-oxadiazole-3-carboxamide

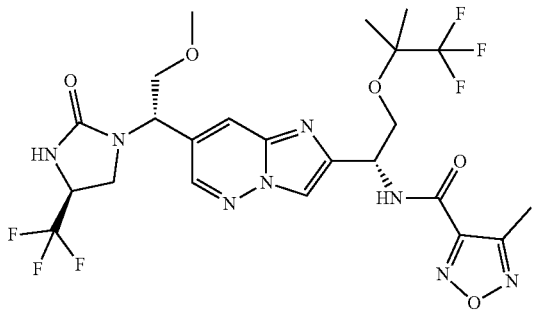 [SMILES: COC[C@H](c1cnn2cc([C@H](COC(C)(C)C(F)(F)F)NC(=O)c3nonc3C)nc2c1)N1C[C@@H](C(F)(F)F)NC1=O]

(S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one (34 mg, 0.068 mmol, Intermediate 4) was dissolved in DCM (1.5 mL) along with 4-methyl-1,2,5-oxadiazole carboxylic acid (22 mg, 0.174 mmol) and N,N-diisopropylethylamine (0.05 mL, 4.2 mmol). The reaction mixture was stirred for 10 min at rt before 1-propanephosphonic anhydride (50% in ethyl acetate, 0.05 mL, 0.168 mmol) was added in one portion. The reaction was stirred at rt for 5 h then concentrated and the resulting oil was purified by reverse phase basic preparative HPLC (0-100% acetonitrile/(20 mM NH$_4$OH)) to provide the title compound as a white foam (35% yield). $^1$H NMR (600 MHz, Methanol-$d_4$) δ 8.38 (d, J=2.1 Hz, 1H), 8.12 (t, J=0.7 Hz, 1H), 7.88-7.85 (m, 1H), 5.56-5.52 (m, 1H), 5.24-5.18 (m, 1H), 4.83 (s, 4H), 4.39-4.32 (m, 1H), 4.12-4.08 (m, 1H), 4.07-3.98 (m, 2H), 3.99-3.89 (m, 2H), 3.52-3.48 (m, 1H), 3.44 (s, 3H), 2.55 (s, 3H), 1.41-1.34 (m, 6H). MS (ESI) m/z: [M+H]$^+$ Found 609.2.

Example 10

4-Cyclopropyl-N—((R)-1-(7-((S)-2-methoxy-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)-1,2,5-oxadiazole-3-carboxamide

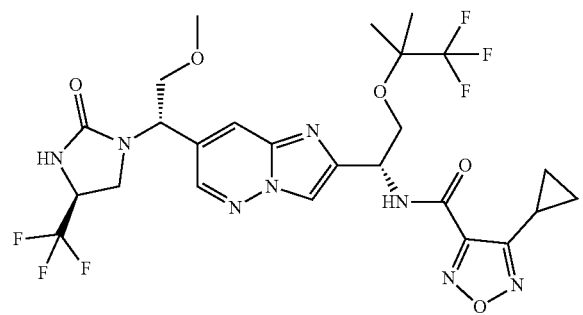 [SMILES: COC[C@H](c1cnn2cc([C@H](COC(C)(C)C(F)(F)F)NC(=O)c3nonc3C3CC3)nc2c1)N1C[C@@H](C(F)(F)F)NC1=O]

(S)—((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one (28 mg, 0.056 mmol, Intermediate 4) was dissolved in acetonitrile (0.5 mL) along with N,N-diisopropylethylamine (0.014 mL, 0.084 mmol) and 2,5-dioxopyrrolidin-1-yl 4-cyclopropyl-1,2,5-oxadiazole-3-carboxylate (15.5 mg, 0.062 mmol, Intermediate 5). The reaction was stirred for 4 h at rt, then diluted with DMF and purified by reverse phase basic preparative HPLC (0-100% acetonitrile/(20 mM NH$_4$OH)) to provide the title compound as a white foam (4.2% yield). $^1$H NMR (600 MHz, Methanol-$d_4$) δ 8.38 (d, J=2.1 Hz, 1H), 8.13 (d, J=0.7 Hz, 1H), 7.88-7.87 (m, 1H), 5.58-5.54 (m, 1H), 5.23-5.19 (m, 1H), 4.39-4.32 (m, 1H), 4.13-4.09 (m, 1H), 4.07-3.98 (m, 2H), 3.97-3.91 (m, 2H), 3.52-3.48 (m, 1H), 3.44 (s, 3H), 2.48-2.42 (m, 1H), 1.39 (d, J=4.8 Hz, 6H), 1.18-1.14 (m, 2H), 1.07-1.04 (m, 2H). MS (ESI) m/z: [M+H]$^+$ Found 635.3.

Example 11

1-Isopropyl-N—((R)-1-(7-((S)-2-methoxy-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)-1H-pyrazole-5-carboxamide

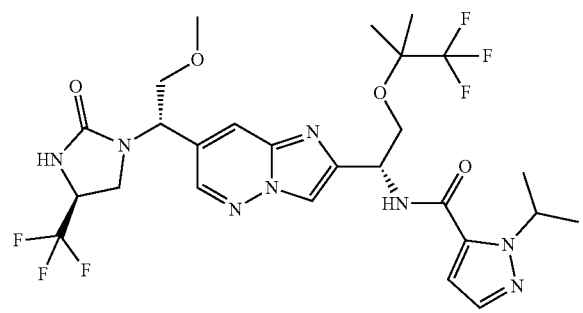 [SMILES: COC[C@H](c1cnn2cc([C@H](COC(C)(C)C(F)(F)F)NC(=O)c3ccnn3C(C)C)nc2c1)N1C[C@@H](C(F)(F)F)NC1=O]

(S)—((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one (28 mg, 0.056 mmol, Intermediate 4) was dissolved in DMF (0.5 mL) along with 1-(propan-2-yl)-1H-pyrazole-5-carboxylic acid (9.5 mg, 0.062 mmol) and N,N-diisopropylethylamine (0.050 mL, 0.287 mmol). This mixture was stirred at rt for 10 min before HATU (24 mg, 0.062 mmol) was added and the resulting mixture was stirred at rt for 40 min. At this time, the reaction mixture was diluted with DMF and purified by reverse phase basic preparative HPLC (0-100% acetonitrile/(20 mM NH$_4$OH)) to provide the title compound as a white foam (49% yield). $^1$H NMR (600 MHz, Methanol-d$_4$) δ 8.40 (d, J=2.1 Hz, 1H), 8.12 (d, J=0.7 Hz, 1H), 7.90-7.88 (m, 1H), 7.53 (d, J=2.0 Hz, 1H), 6.79 (d, J=2.1 Hz, 1H), 5.57-5.49 (m, 1H), 5.47-5.39 (m, 1H), 5.25-5.21 (m, 1H), 4.42-4.33 (m, 1H), 4.14-4.09 (m, 1H), 4.05-3.99 (m, 2H), 3.99-3.92 (m, 2H), 3.54-3.50 (m, 1H), 3.46 (s, 3H), 1.48 (t, J=6.6 Hz, 6H), 1.42-1.39 (s, 6H). MS (ESI) m/z: [M+H]$^+$ Found 635.3.

Example 12

1-(Ethyl-d$_5$)-N—((R)-1-(7-((S)-2-methoxy-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)-1H-pyrazole-5-carboxamide

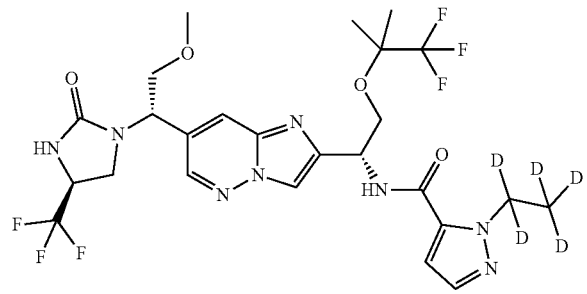 [SMILES: [2H]C([2H])([2H])C([2H])([2H])n1nccc1C(=O)N[C@@H](COC(C)(C)C(F)(F)F)c1cn2ncc([C@@H](COC)N3C[C@@H](C(F)(F)F)NC3=O)cc2n1]

(S)—((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one (28 mg, 0.056 mmol, Intermediate 4) was dissolved in DMF (0.5 mL) along with 1-(ethyl-d$_5$)-1H-pyrazole-5-carboxylic acid (9.1 mg, 0.63 mmol), and N,N-diisopropylethylamine (0.050 mL, 0.287 mmol).

This mixture was stirred at rt for 10 min before HATU (24 mg, 0.062 mmol) was added and the reaction mixture was stirred at rt for 40 min. After this time, the reaction was diluted with DMF and purified by reverse phase basic preparative HPLC (0-100% acetonitrile/(20 mM aqueous NH$_4$OH)) to provide the title compound as a white foam (34% yield). $^1$H NMR (400 MHz, Methanol-d$_4$) δ 8.38 (d, J=2.1 Hz, 1H), 8.12-8.09 (m, 1H), 7.88-7.85 (m, 1H), 7.50 (d, J=2.1 Hz, 1H), 6.84 (d, J=2.1 Hz, 1H), 5.54-5.49 (m, 1H), 5.24-5.18 (m, 1H), 4.41-429 (m, 1H), 4.16-4.06 (m, 1H), 4.05-3.89 (m, 4H), 3.53-3.47 (m, 1H), 3.44 (s, 3H), 1.40-1.36 (s, 6H). MS (ESI) m/z: [M+H]$^+$ Found 626.3.

Example 13

4-Cyclopropyl-N—((S)-4,4,4-trifluoro-1-(7-((S)-2-methoxy-1-((S)-2-oxo-4-(trifluoromethyl)imidazolidin-1-yl)ethyl)imidazo[1,2-b]pyridazin-2-yl)-3,3-dimethylbutyl)-1,2,5-oxadiazole-3-carboxamide

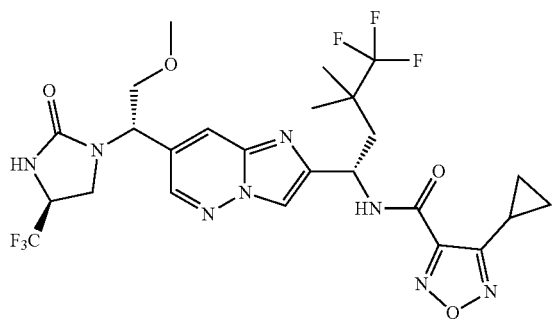 [SMILES: COC[C@H](c1cnn2cc([C@H](CC(C)(C)C(F)(F)F)NC(=O)c3nonc3C3CC3)nc2c1)N1C[C@@H](C(F)(F)F)NC1=O]

The title compound was prepared as described for the synthesis of Example 10 using (S)-1-((S)-1-(2-((S)-1-amino-4,4,4-trifluoro-3,3-dimethylbutyl)imidazo[1,2-b]pyridazin-7-yl) methoxyethyl)-4-(trifluoromethyl)imidazolidin-2-one (Intermediate 6) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and purification by silica gel chromatography (0-100% EtOAc (with 10% MeOH)/hexanes) followed by an additional purification by silica gel chromatography (0-100% acetone/hexanes) afforded the title compound as a white foam (56% yield). $^1$H NMR (400 MHz, DMSO-d$_6$) δ 9.74 (d, J=8.7 Hz, 1H), 8.39 (d, J=2.1 Hz, 1H), 8.23 (s, 1H), 7.96-7.88 (m, 1H), 7.72 (d, J=2.2 Hz, 1H), 5.52-5.42 (m, 1H), 5.17-5.07 (m, 1H), 4.47 (s, 1H), 3.96-3.73 (m, 3H), 3.48-3.39 (m, 1H), 3.34 (s, 3H), 2.43-2.32 (m, 2H), 2.32-2.22 (m, 1H), 1.20 (d, J=7.5 Hz, 6H), 1.17-1.10 (m, 2H), 1.05-0.90 (m, 2H). MS (ESI) m/z: [M+H]$^+$ Found 619.2.

Example 14

4-Methyl-N—((S)-4,4,4-trifluoro-1-(7-((S)-2-methoxy-1-((S)-2-oxo-4-(trifluoromethyl)imidazolidin-1-yl)ethyl)imidazo[1,2-b]pyridazin-2-yl)-3,3-dimethylbutyl)-1,2,5-oxadiazole-3-carboxamide

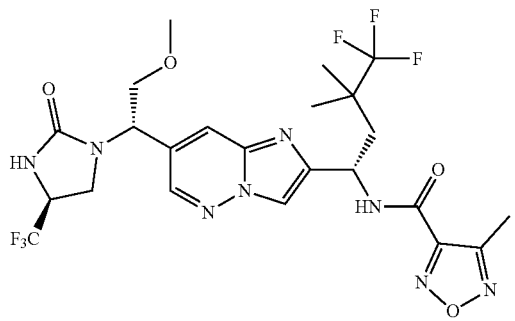 [SMILES: COC[C@H](c1cnn2cc([C@H](CC(C)(C)C(F)(F)F)NC(=O)c3nonc3C)nc2c1)N1C[C@@H](C(F)(F)F)NC1=O]

The title compound was prepared as described for the synthesis of Example 10 using (S)-1-((S)-1-(2-((S)-1- amino-4,4,4-trifluoro-3,3-dimethylbutyl)imidazo[1,2-b]pyridazin-7-yl)-2-methoxyethyl)-4-(trifluoromethyl)imidazolidin-2-one (Intermediate 6) in place of (S)—((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate and an additional purification by silica gel chromatography (0-100% EtOAc (with 10% MeOH)/hexanes) to afford the title compound as a white foam (68% yield). $^1$H NMR (400 MHz, DMSO-d$_6$) δ 9.70 (d, J=8.7 Hz, 1H), 8.38 (d, J=2.1 Hz, 1H), 8.22 (d, J=0.9 Hz, 1H), 7.97-7.89 (m, 1H), 7.71 (d, J=2.2 Hz, 1H), 5.51-5.38 (m, 1H), 5.18-5.07 (m, 1H), 4.54-4.41 (m, 1H), 3.99-3.72 (m, 3H), 3.49-3.40 (m, 1H), 3.34 (s, 3H), 2.50 (s, 3H), 2.44-2.23 (m, 2H), 1.20 (s, 3H), 1.19 (s, 3H). MS (ESI) m/z: [M+H]$^+$ Found 593.3.

Example 15

1-Isopropyl-N—((S)-4,4,4-trifluoro-1-(7-((S)-2-methoxy-((S)-2-oxo-4-(trifluoromethyl)imidazolidin-1-yl)ethyl)imidazo[1,2-b]pyridazin-2-yl)-3,3-dimethylbutyl)-1H-pyrazole-5-carboxamide

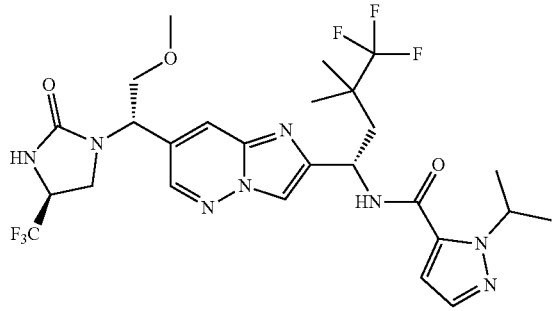 [SMILES: COC[C@H](c1cnn2cc([C@H](CC(C)(C)C(F)(F)F)NC(=O)c3ccnn3C(C)C)nc2c1)N1C[C@@H](C(F)(F)F)NC1=O]

The title compound was prepared as described for the synthesis of Example 10 using (S)-1-((S)-1-(2-((S)-1-amino-4,4,4-trifluoro-3,3-dimethylbutyl)imidazo[1,2-b]pyridazin-7-yl)-2-methoxyethyl)-4-(trifluoromethyl)imidazolidin-2-one (Intermediate 6) in place of (S)—((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 1-isopropyl-1H-pyrazole-5-carboxylate (Intermediate 7) in place of 2,5-dioxopyrrolidin-1-yl 4-cyclopropyl-1,2,5-oxadiazole-3-carboxylate to afford the title compound as a white foam (78% yield). $^1$H NMR (400 MHz, DMSO-d$_6$) δ 8.94 (d, J=8.8 Hz, 1H), 8.38 (d, J=2.1 Hz, 1H), 8.13 (d, J=0.7 Hz, 1H), 7.94-7.88 (m, 1H), 7.71 (d, J=2.1 Hz, 1H), 7.51 (d, J=2.0 Hz, 1H), 6.95-6.85 (m, 1H), 5.52-5.38 (m, 2H), 5.16-5.08 (m, 1H), 4.53-4.41 (m, 1H), 3.99-3.82 (m, 2H), 3.82-3.74 (m, 1H), 3.47-3.40 (m, 1H), 3.34 (s, 3H), 2.40-2.17 (m, 2H), 1.38-1.35 (m, 6H), 1.19 (s, 3H), 1.19 (s, 3H). MS (ESI) m/z: [M+H]$^+$ Found 619.3.

Example 16

4-Cyclopropyl-N—((R)-1-(7-((S)-2-methoxy-1-((S*)-2-oxo-4-(trifluoromethyl)imidazolidin-1-yl-5,5-d$_2$)ethyl)imidazo[1,2-b]pyridazin-2-yl)-2-(1,1,1-trifluoro-2-methylpropan-2-yl)oxy)ethyl)-1,2,5-oxadiazole-3-carboxamide

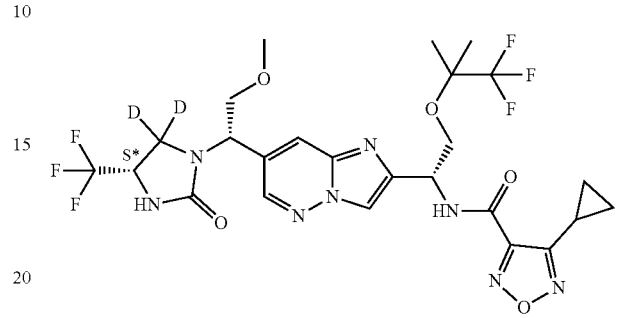

The title compound was prepared as described for the synthesis of Example 10 using (S*)—((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one-5,5-d$_2$ (Intermediate 12) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and purification by silica gel chromatography (0-100% EtOAc (with 10% MeOH)/hexanes) followed by an additional purification by silica gel chromatography (0-10% (2 M NH$_3$ in MeOH)/DCM) to afford the title compound as a colorless gel (75% yield). $^1$H NMR (500 MHz, Methanol-d$_4$) δ 8.40 (d, J=2.1 Hz, 1H), 8.25-8.07 (m, 1H), 8.03-7.80 (m, 1H), 5.61-5.53 (m, 1H), 5.25-5.18 (m, 1H), 4.41-4.29 (m, 1H), 4.14-4.08 (m, 1H), 4.08-3.97 (m, 2H), 3.97-3.89 (m, 1H), 3.44 (s, 3H), 2.52-2.40 (m, 1H), 1.44-1.34 (m, 6H), 1.19-1.11 (m, 2H), 1.09-1.02 (m, 2H). MS (ESI) m/z: [M+H]$^+$ Found 637.2.

Example 17

N—[(S)—[7-[(R)-Cyclopropyl-[(4R)-4-cyclopropyl-2-oxo-imidazolidin-1-yl]methyl]imidazo[1,2-b]pyridazin-2-yl]-(4,4-difluorocyclohexyl)methyl]-4-methyl-1,2,5-oxadiazole-3-carboxamide

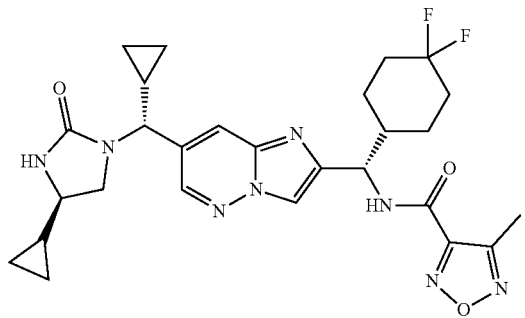 [SMILES: Cc1nonc1C(=O)N[C@H](c1cn2ncc([C@@H](C3CC3)N3C[C@@H](C4CC4)NC3=O)cc2n1)C1CCC(F)(F)CC1]

Step A: Benzyl ((R)-2-(((R)-2-((S)—((tert-butoxycarbonyl)amino)(4,4-difluorocyclohexyl)methyl)imidazo[1,2-b]

pyridazin-7-yl)(cyclopropyl)methyl)amino)-1-cyclopropyl-ethyl)carbamate. A mixture of tert-Butyl ((S)-(7-((R)-amino (cy cl op r opyl)methyl)imidazo[1,2-b]pyridazin-2-yl)(4,4-difluorocyclohexyl)methyl)carbamate (500 mg, 1.15 mmol), benzyl (R)-4-cyclopropyl-1,2,3-oxathiazolidine-3-carboxylate 2,2-dioxide (683 mg, 2.3 mmol, Intermediate 13) and $Cs_2CO_3$ (1.12 g, 3.44 mmol) in ACN (5 mL) and THF (5 mL) was heated at 60° C. for 16 h. The reaction mixture was diluted with water (10 mL) and extracted with EtOAc (2×20 mL). The organic layers were combined, dried over anhydrous $Na_2SO_4$, filtered and concentrated to dryness. The residue was purified by preparative HPLC (Welch Xtimate C18 5 µm, 150×30 mm, 42-72% ACN/water (with 0.225% formic acid)) to provide the title compound as a white solid after lyophilization (27% yield).

Step B: tert-Butyl ((S)-(7-((R)—(((R)-2-amino-2-cyclopropylethyl)amino)(cyclopropyl)methyl)imidazo[1,2-b]pyridazin-2-yl)(4,4-difluorocyclohexyl)methyl)carbamate. The title compound (94% yield) was prepared as described for the synthesis of Intermediate 12 Step B using benzyl ((R)-2-(((R)-(2-((S)—((tert-butoxycarbonyl)amino)(4,4-difluorocyclohexyl)methyl)imidazo[1,2-b]pyridazin-7-yl)(cyclopropyl)methyl)amino)-1-cyclopropylethyl)carbamate (Step A) in place of tert-Butyl ((R)-1-(6-chloro-7-((5S*,8S)-3-oxo-1-phenyl-5-(trifluoromethyl)-2,10-dioxa-4,7-diazaundecan-8-yl-6,6-d₂)imidazo[1,2-b]pyridazin-2-yl)-2-((1,1,1-trifluoro-2-methylpropan-2-yl)oxy)ethyl)carbamate.

Step C: tert-Butyl ((S)-(7-((R)-cyclopropyl((R)-4-cyclopropyl-2-oxoimidazolidin-1-yl)methyl)imidazo[1,2-b]pyridazin-2-yl)(4,4-difluorocyclohexyl)methyl)carbamate. The title compound (76% yield) was prepared as described for the synthesis of Intermediate 12 Step C using tert-Butyl ((S)-(7-((R)—(((R)-2-amino-2-cyclopropylethyl)amino)(cyclopropyl)methyl)imidazo[1,2-b]pyridazin-2-yl)(4,4-difluorocyclohexyl)methyl)carbamate (Step B) in place of tert-Butyl ((R)-1-(7-((S)-1-(((S*)-2-amino-3,3,3-trifluoropropyl-1,1-d₂)amino)-2-methoxyethyl)imidazo[1,2-b]pyridazin-2-yl)-2-((I, 1,1-trifluoro-2-methylpropan-2-yl)oxy)ethyl)carbamate.

Step D: (R)-1-((R)-(2-((S)-Amino(4,4-difluorocyclohexyl)methyl)imidazo[1,2-b]pyridazin-7-yl)(cyclopropyl)methyl)-4-cyclopropylimidazolidin-2-one dihydrochloride. A solution of tert-Butyl ((S)-(7-((R)-cyclopropyl((R)-4-cyclopropyl-2-oxoimidazolidinyl-yl)methyl)imidazo[1,2-b]pyridazin-2-yl)(4,4-difluorocyclohexyl)methyl)carbamate (120 mg, 0.22 mmol, Step C) in HCl (10 mL, 40 mmol, 4 M in MeOH) was stirred at rt for 1 h in a sealed tube. The reaction mixture was concentrated to dryness to provide the title compound as a white solid, which was used without further purification.

Step E: N—[(S)—[7-[(R)-Cyclopropyl-[(4R)-4-cyclopropyl-2-oxo-imidazolidin yl]methyl]imidazo[1,2-b]pyridazin-2-yl]-(4,4-difluorocyclohexyl)methyl]-4-methyl-1,2,5-oxadiazole-3-carboxamide. A mixture of 4-methyl-1,2,5-oxadiazole-3-carboxylic acid (50 mg, 0.39 mmol), DIPEA (0.34 mL, 1.9 mmol) and $T_3P$ (369 mg, 0.58 mmol, 50% w/v solution in EtOAc) in DCM (10 mL) was heated at 30° C. for 30 min. Then, (R)-1-((R)-(2-((S)-amino(4,4-difluorocyclohexyl)methyl)imidazo[1,2-b]pyridazin-7-yl)(cyclopropyl)methyl)-4-cyclopropylimidazolidin-2-one dihydrochloride (100 mg, 0.19 mmol, Step D) was added and the resulting mixture was heated at 30° C. for 16 h. The mixture was diluted with DCM (30 mL), washed with water (10 mL), dried, filtered and concentrated to dryness. The residue was purified initially by silica gel chromatography (0-100% EtOAc/petroleum ether) and then further purified by SFC (DAICEL CHIRALPAK AD column, 10 µm, 250×30 mm, 25% EtOH (with 0.1% of 25% aqueous $NH_3$)/$CO_2$) to provide the title compound as a white solid (57% yield) after lyophilization. $^1H$ NMR (400 MHz, DMSO-$d_6$) δ 9.43 (d, J=8.8 Hz, 1H), 8.40 (d, J=2.0 Hz, 1H), 8.25 (s, 1H), 8.02 (s, 1H), 6.77 (s, 1H), 5.26-5.08 (m, 1H), 4.09 (d, J=10.4 Hz, 1H), 3.70 (t, J=8.4 Hz, 1H), 3.17-3.08 (m, 1H), 3.03-2.96 (m, 1H), 2.47 (s, 3H), 2.26-2.13 (m, 1H), 2.11-1.89 (m, 3H), 1.86-1.68 (m, 2H), 1.66-1.57 (m, 1H), 1.56-1.18 (m, 4H), 0.90-0.79 (m, 1H), 0.77-0.67 (m, 1H), 0.67-0.56 (m, 1H), 0.51-0.41 (m, 1H), 0.40-0.30 (m, 2H), 0.23-0.11 (m, 2H). MS (ESI) m/z: [M+H]⁺ Found 555.4.

Example 18

N—[(S)—[7-[(R)-Cyclopropyl-[(4R)-4-isopropyl-2-oxo-imidazolidin-1-yl]methyl]imidazo[1,2-b]pyridazin-2-yl]-(4,4-difluorocyclohexyl)methyl]-4-methyl-1,2,5-oxadiazole-3-carboxamide

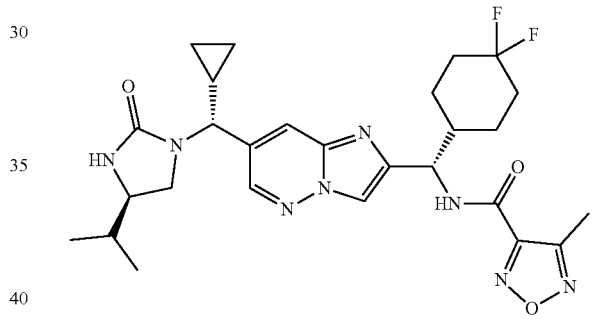

Step A: Benzyl ((R)-1-(((R)-(2-((S)—((tert-butoxycarbonyl)amino)(4,4-difluorocyclohexyl)methyl)imidazo[1,2-b]pyridazin-7-yl)(cyclopropyl)methyl)amino) methylbutan-2-yl)carbamate. The title compound (31% yield) was prepared as described for the synthesis of Example 17 Step A using benzyl (R)-4-isopropyl-1,2,3-oxathiazolidine carboxylate 2,2-dioxide (Intermediate 14) in place of benzyl (R)-4-cyclopropyl-1,2,3-oxathiazolidine-3-carboxylate 2,2-dioxide and heating at 30° C. for 16 h. The residue was initially purified by silica gel chromatography (0-10% MeOH/DCM) and then subsequently further purified by preparative HPLC ((Welch Xtimate C18 5 µm, 150×30 mm, 40-70% ACN/water (with 0.225% formic acid)).

Step B: tert-Butyl ((S)-(7-((R)—(((R)-2-amino-3-methylbutyl)amino)(cyclopropyl)methyl)imidazo[1,2-b]pyridazin-2-yl)(4,4-difluorocyclohexyl)methyl)carbamate. The title compound (88% yield) was prepared as described for the synthesis of Intermediate 12 Step B using benzyl ((R)-1-(((R)-(2-((S)—((tert-butoxycarbonyl)amino)(4,4-difluorocyclohexyl)methyl)imidazo[1,2-b]pyridazin-7-yl)(cyclopropyl)methyl)amino)-3-methylbutan-2-yl)carbamate (Step A) in place of tert-Butyl ((R)-1-(6-chloro-7-((5S*,8S)-3-oxo-1-phenyl-5-(trifluoromethyl)-2,10-dioxa-4,7-diazaundecan-8-yl-6,6-d₂)imidazo[1,2-b]pyridazin-2-yl)-2-((1,1,1-trifluoro-2-methylpropan-2-yl)oxy)ethyl)carbamate and 10% wet Pd/C in place of 10% Pd/C.

Step C: tert-Butyl ((S)-(7-((R)-cyclopropyl((R)-4-isopropyl-2-oxoimidazolidin-1-yl)methyl)imidazo[1,2-b]pyridazin-2-yl)(4,4-difluorocyclohexyl)methyl)carbamate. The title compound was prepared as described for the synthesis of Intermediate 12 Step C using tert-Butyl ((S)-(7-((R)—(((R)-2-amino-3-methylbutyl)amino)(cyclopropyl)methyl)imidazo[1,2-b]pyridazin-2-yl)(4,4-difluorocyclohexyl)methyl)carbamate (Step B) in place of tert-Butyl ((R)-1-(7-((S)-1-(((S*)-2-amino-3,3,3-trifluoropropyl-1,1-d₂)amino)-2-methoxyethyl)imidazo[1,2-b]pyridazin-2-yl)-2-((1,1,1-trifluoro-2-methylpropan-2-yl)oxy)ethyl)carbamate. The residue was purified by silica gel chromatography (0-10% MeOH/DCM) to provide the title compound in 64% yield.

Step D: (R)-1-((R)-(2-((S)-Amino(4,4-difluorocyclohexyl)methyl)imidazo[1,2-b]pyridazin-7-yl)(cyclopropyl)methyl)-4-isopropylimidazolidin-2-one hydrochloride. The title compound (100% yield) was prepared as described for the synthesis of Example 17 Step D using tert-Butyl ((S)-(7-((R)-cyclopropyl((R)-4-isopropyl-2-oxoimidazolidin-1-yl)methyl)imidazo[1,2-b]pyridazin-2-yl)(4,4-difluorocyclohexyl)methyl)carbamate (Step C) in place of tert-Butyl ((S)-(7-((R)-cyclopropyl((R)-4-cyclopropyl-2-oxoimidazolidin-1-yl)methyl)imidazo[1,2-b]pyridazin-2-yl)(4,4-difluorocyclohexyl)methyl)carbamate and 4 M HCl in 1,4-dioxane in place of 4 M HCl in MeOH.

Step E: N—[(S)—[7-[(R)-Cyclopropyl-[(4R)-4-isopropyl-2-oxo-imidazolidin-1-yl]methyl]imidazo[1,2-b]pyridazin-2-yl]-(4,4-difluorocyclohexyl)methyl]-4-methyl-1,2,5-oxadiazole-3-carboxamide. A mixture of (R)-1-((R)-(2-((S)-amino(4,4-difluorocyclohexyl)methyl)imidazo[1,2-b]pyridazin-7-yl)(cyclopropyl)methyl)-4-isopropylimidazolidin-2-one hydrochloride (80 mg, 0.16 mmol, Step D), 4-methyl-1,2,5-oxadiazole-3-carboxylic acid (42 mg, 0.33 mmol), DIPEA (0.11 mL, 0.66 mmol), HOBt (45 mg, 0.33 mmol) and EDCI (63 mg, 0.33 mmol) in ACN (3 mL) was heated at 30° C. for 16 h. Then the mixture was heated at 50° C. for 2.5 h. After that time, the mixture was partitioned between EtOAc (25 mL) and saturated aqueous NH₄Cl (15 mL). The layers were separated and the organic layer was washed with saturated aqueous NaHCO₃ (15 mL) then brine (10 mL), dried over anhydrous Na₂SO₄, filtered and concentrated to dryness. The residue was purified by preparative HPLC (Boston Prime C18, 5 μm, 150×30 mm, 50-80% ACN/(water with NH₄OH and NH₄HCO₃)) to provide the title compound as a white solid after lyophilization (12% yield). ¹H NMR (400 MHz, DMSO-d₆) δ 9.53-9.36 (m, 1H), 8.38-8.33 (m, 1H), 8.25 (s, 1H), 8.03-7.99 (m, 1H), 6.90-6.72 (m, 1H), 5.25-5.07 (m, 1H), 4.17-3.96 (m, 1H), 3.66-3.62 (m, 1H), 3.38-3.34 (m, 2H), 2.96-2.88 (m, 1H), 2.47 (s, 3H), 2.24-2.13 (m, 1H), 2.10-1.96 (m, 2H), 1.95-1.88 (m, 1H), 1.86-1.69 (m, 2H), 1.65-1.58 (m, 1H), 1.55-1.46 (m, 2H), 1.42-1.32 (m, 1H), 0.79-0.71 (m, 7H), 0.67-0.59 (m, 1H), 0.49-0.32 (m, 2H). MS (ESI) m/z: [M+H]⁺ Found 557.3.

Example 19

N—((S)-(7-((R)-Cyclopropyl((R*)-2-oxo-4-(2,2,2-trifluoroethyl)imidazolidin-1-yl)methyl)imidazo[1,2-b]pyridazin-2-yl)(4,4-difluorocyclohexyl)methyl)-4-methyl-1,2,5-oxadiazole-3-carboxamide

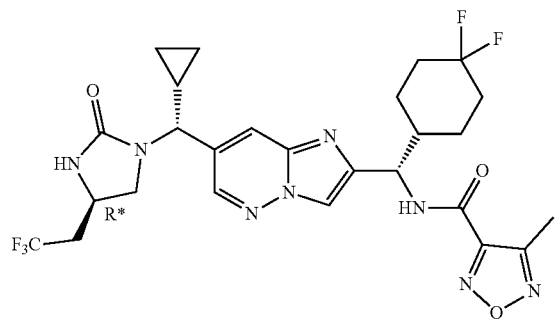 [SMILES: Cc1nonc1C(=O)N[C@H](c1cn2ncc([C@@H](C3CC3)N3C[C@@H](CC(F)(F)F)NC3=O)cc2n1)C1CCC(F)(F)CC1]

Step A: tert-Butyl ((S)-(7-((R)-cyclopropyl((R*)-2-oxo-4-(2,2,2-trifluoroethyl)imidazolidin-1-yl)methyl)imidazo[1,2-b]pyridazin-2-yl)(4,4-difluorocyclohexyl)methyl)carbamate. The title compound was prepared as described for the synthesis of Intermediate 12 Step C using tert-Butyl ((S)-(7-((R)—(((R*)-2-amino-4,4,4-trifluorobutyl)amino)(cyclopropyl)methyl)imidazo[1,2-b]pyridazin-2-yl)(4,4-difluorocyclohexyl)methyl)carbamate (Intermediate 16) in place of tert-Butyl ((R)-1-(7-((S)-1-(((S*)-2-amino-3,3,3-trifluoropropyl-1,1-d₂)amino)-2-methoxyethyl)imidazo[1,2-b]pyridazin-2-yl)-2-((1,1,1-trifluoro-2-methylpropan-2-yl)oxy)ethyl)carbamate. The residue was purified by silica gel chromatography (0-15% MeOH/DCM) to provide the title compound as a yellow oil (92% yield).

Step B: (R*)-1-((R)-(2-((S)-Amino(4,4-difluorocyclohexyl)methyl)imidazo[1,2-b]pyridazin-7-yl)(cyclopropyl)methyl)-4-(2,2,2-trifluoroethyl)imidazolidin-2-one. The title compound (80% yield) was prepared as described for the synthesis of Example 17 Step D using tert-Butyl ((S)-(7-((R)-cyclopropyl ((R*)-2-oxo-4-(2,2,2-trifluoroethyl)imidazolidin-1-yl)methyl)imidazo[1,2-b]pyridazin-2-yl)(4,4-difluorocyclohexyl)methyl)carbamate (Step A) in place of tert-Butyl ((S)-(7-((R)-cyclopropyl((R)-4-cyclopropyl-2-oxoimidazolidin-1-yl)methyl)imidazo[1,2-b]pyridazin-2-yl)(4,4-difluorocyclohexyl)methyl)carbamate.

Step C: N—((S)-(7-(((R)-Cyclopropyl((R*)-2-oxo-4-(2,2,2-trifluoroethyl)imidazolidin-1-yl)methyl)imidazo[1,2-b]pyridazin-2-yl)(4,4-difluorocyclohexyl)methyl)-4-methyl-1,2,5-oxadiazole-3-carboxamide. A mixture of (R*)-1-((R)-(2-((S)-amino(4,4-difluorocyclohexyl)methyl)imidazo[1,2-b]pyridazin-7-yl)(cyclopropyl)methyl)-4-(2,2,2-trifluoroethyl)imidazolidin-2-one (76 mg, 0.16 mmol, Step B), 4-methyl-1,2,5-oxadiazole-3-carboxylic acid (30 mg, 0.23 mmol), DIPEA (0.082 mL, 0.47 mmol) and T₃P (129 mg, 0.2 mmol, 50% w/v solution in EtOAc) in DCM (1.5 mL) was stirred at rt for 3 h. The reaction mixture was then concentrated to dryness and the residue was purified by silica gel chromatography (0-100% EtOAc/petroleum ether) to provide the title compound as a white solid (47% yield). ¹H NMR (400 MHz, DMSO-d₆) δ 9.43 (d, J=8.8 Hz, 1H), 8.47 (d, J=2.0 Hz, 1H), 8.24 (s, 1H), 8.06 (s, 1H), 6.78 (s, 1H), 5.19-5.15 (m, 1H), 4.11-4.08 (m, 1H), 3.96-3.89 (m, 1H), 3.57-3.53 (m, 1H), 3.32-3.27 (m, 1H), 2.64-2.54 (m, 1H), 2.47 (s, 3H), 2.20-2.17 (m, 1H), 2.09-1.88 (m, 3H), 1.87-1.69 (m, 2H), 1.63-1.61 (m, 1H), 1.51-1.43 (m, 1H), 1.41-1.35 (m, 1H), 1.35-1.21 (m, 2H), 0.75-0.68 (m, 1H), 0.67-0.60 (m, 1H), 0.53-0.47 (m, 1H), 0.42-0.37 (m, 1H). MS (ESI) m/z: [M+H]$^+$ Found 597.3.

Example 20

N—((S)-(7-((R)-Cyclopropyl((S*)-2-oxo-4-(2,2,2-trifluoroethyl)imidazolidin-1-yl)methyl)imidazo[1,2-b]pyridazin-2-yl)(4,4-difluorocyclohexyl)methyl)-4-methyl-1,2,5-oxadiazole-3-carboxamide

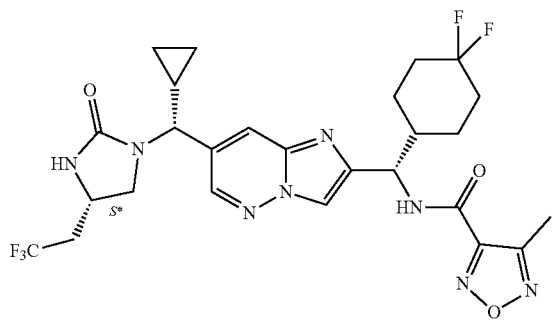 [SMILES: Cc1nonc1C(=O)N[C@H](c1cn2ncc([C@@H](C3CC3)N3C[C@H](CC(F)(F)F)NC3=O)cc2n1)C1CCC(F)(F)CC1]

Step A: tert-Butyl ((S)-(7-((R)-cyclopropyl((S*)-2-oxo-4-(2,2,2-trifluoroethyl)imidazolidin-1-yl)methyl)imidazo[1,2-b]pyridazin-2-yl)(4,4-difluorocyclohexyl)methyl)carbamate. The title compound (92% yield) was prepared as described for the synthesis of Example 19 Step A using tert-Butyl ((S)-(7-((R)—(((S*)-2-amino-4,4,4-trifluorobutyl)amino)(cyclopropyl)methyl)imidazo[1,2-b]pyridazin-2-yl)(4,4-difluorocyclohexyl)methyl)carbamate (Intermediate 17) in place of tert-Butyl ((S)-(7-((R)—(((R*)-2-amino-4,4,4-trifluorobutyl)amino)(cyclopropyl)methyl)imidazo[1,2-b]pyridazin-2-yl)(4,4-difluorocyclohexyl)methyl)carbamate.

Step B: (S*)-1-((R)-(2-((S)-Amino(4,4-difluorocyclohexyl)methyl)imidazo[1,2-b]pyridazin-7-yl)(cyclopropyl)methyl)-4-(2,2,2-trifluoroethyl)imidazolidin-2-one. The title compound (82% yield) was prepared as described for the synthesis of Example 17 Step D using tert-Butyl ((S)-(7-((R)-cyclopropyl((S*)-2-oxo-4-(2,2,2-trifluoroethyl)imidazolidin-1-yl)methyl)imidazo[1,2-b]pyridazin-2-yl)(4,4-difluorocyclohexyl)methyl)carbamate (Step A) in place of tert-Butyl ((S)-(7-((R)-cyclopropyl((R)-4-cyclopropyl-2-oxoimidazolidin-1-yl)methyl)imidazo[1,2-b]pyridazin-2-yl)(4,4-difluorocyclohexyl)methyl)carbamate.

Step C: N—((S)-(7-((R)-Cyclopropyl((S*)-2-oxo-4-(2,2,2-trifluoroethyl)imidazolidin-1-yl)methyl)imidazo[1,2-b]pyridazin-2-yl)(4,4-difluorocyclohexyl)methyl)-4-methyl-1,2,5-oxadiazole-3-carboxamide. The title compound (71% yield) was prepared as described for the synthesis of Example 19 Step C using (S*)-1-((R)-(2-((S)-amino(4,4-difluorocyclohexyl)methyl)imidazo[1,2-b]pyridazin-7-yl)(cyclopropyl)methyl)-4-(2,2,2-trifluoroethyl)imidazolidin-2-one (Step B) in place of (R*)-1-((R)-(2-((S)-amino(4,4-difluorocyclohexyl)methyl)imidazo[1,2-b]pyridazin-7-yl)(cyclopropyl)methyl)-4-(2,2,2-trifluoroethyl)imidazolidin-2-one. $^1$H NMR (400 MHz, DMSO-d$_6$) δ 9.38 (d, J=8.8 Hz, 1H), 8.44 (d, J=1.6 Hz, 1H), 8.24 (s, 1H), 8.05 (s, 1H), 6.79 (s, 1H), 5.20-5.15 (m, 1H), 4.10-4.08 (m, 1H), 3.95-3.87 (m, 1H), 3.79-3.74 (m, 1H), 3.08-3.04 (m, 1H), 2.60-2.54 (m, 1H), 2.47 (s, 3H), 2.20-2.18 (m, 1H), 2.09-1.89 (m, 3H), 1.85-1.69 (m, 2H), 1.65-1.61 (m, 1H), 1.56-1.49 (m, 1H), 1.44-1.34 (m, 1H), 1.31-1.21 (m, 2H), 0.72-0.69 (m, 1H), 0.66-0.63 (m, 1H), 0.48-0.36 (m, 2H). MS (ESI) m/z: [M+H]$^+$ Found 597.3.

Example 21

N—[(S)—[7-[(R)-Cyclopropyl-(6-oxo-5,7-diazaspiro[2.4]heptan-5-yl)methyl]imidazo[1,2-b]pyridazin-2-yl]-(4,4-difluorocyclohexyl)methyl]-4-methyl-1,2,5-oxadiazole-3-carboxamide

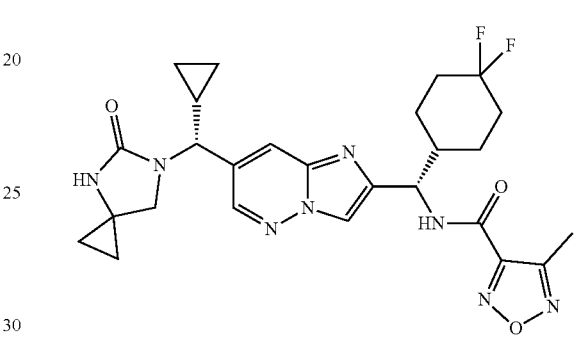

Step A: tert-Butyl ((S)-(7-((R)-(((1-(((benzyloxy)carbonyl)amino)cyclopropyl)methyl)amino)(cyclopropyl)methyl)imidazo[1,2-b]pyridazin-2-yl)(4,4-difluorocyclohexyl)methyl)carbamate. A mixture of tert-Butyl ((S)-(7-((R)-amino(cyclopropyl)methyl)imidazo[1,2-b]pyridazin-2-yl)(4,4-difluorocyclohexyl)methyl)carbamate (0.71 g, 1.63 mmol), benzyl (1-formylcyclopropyl)carbamate (0.43 g, 1.96 mmol, Intermediate 18) and tetraethoxytitanium (0.69 mL, 3.27 mmol) in MeOH (10 mL) was stirred at rt for 1 h. Then, sodium cyanoborohydride (154 mg, 2.45 mmol) was added and the resulting mixture stirred at rt for 16 h. The reaction mixture was filtered and concentrated to dryness to give a yellow solid. The solid was purified by preparative HPLC (Welch Xtimate C18 column, 5 μm, 150×30 mm, 38-68% ACN/water (with 0.225% formic acid)) to provide the title compound in 41% yield.

Step B: tert-Butyl ((S)-(7-((R)-(((1-aminocyclopropyl)methyl)amino)(cyclopropyl)methyl)imidazo[1,2-b]pyridazin-2-yl)(4,4-difluorocyclohexyl)methyl)carbamate. The title compound was prepared as described for the synthesis of Intermediate 12 Step B using tert-Butyl ((S)-(7-((R)-(((1-(((benzyloxy)carbonyl)amino)cyclopropyl)methyl)amino)(cyclopropyl)methyl)imidazo[1,2-b]pyridazin-2-yl)(4,4-difluorocyclohexyl)methyl)carbamate (Step A) in place of tert-Butyl ((R)-1-(6-chloro-7-((5S*,8S)-3-oxo-1-phenyl-5-(trifluoromethyl)-2,10-dioxa-4,7-diazaundecan-8-yl-6,6-d$_2$)imidazo[1,2-b]pyridazin-2-yl)-2-((1,1,1-trifluoro-2-methylpropan-2-yl)oxy)ethyl)carbamate. The residue was purified by preparative HPLC (Welch Xtimate C18 column, 5 μm, 150×30 mm, 38-68% ACN/water (with 0.225% formic acid)) to provide the title compound in 26% yield.

Step C: tert-Butyl ((S)-(7-((R)-cyclopropyl(5-oxo-4,6-diazaspiro[2.4]heptan-6-yl)methyl)imidazo[1,2-b]pyridazin-2-yl)(4,4-difluorocyclohexyl)methyl)carbamate. A mixture of tert-Butyl ((S)-(7-((R)-((((1-aminocyclopropyl)methyl)amino)(cyclopropyl)methyl)imidazo[1,2-b]pyridazin-2-yl)(4,4-difluorocyclohexyl)methyl)carbamate (80 mg, 0.16 mmol, Step B) and CDI (77 mg, 0.48 mmol) in anhydrous THF (2 mL) was heated at 65° C. for 2 h. The mixture was then cooled to rt, diluted with water (100 mL) and extracted with EtOAc (2×100 mL). The organic layers were combined, washed with water (2×100 mL) and brine (100 mL), dried over anhydrous $Na_2SO_4$, filtered, and concentrated to dryness. The residue was purified by preparative HPLC (Welch Xtimate C18 column, 5 μm, 150×30 mm, 50-80% ACN/water (with $NH_4OH$ and $NH_4HCO_3$)) to provide the title compound as a white solid (38% yield).

Step D: 6-((R)-(2-((S)-Amino(4,4-difluorocyclohexyl)methyl)imidazo[1,2-b]pyridazin-7-yl)(cyclopropyl)methyl)-4,6-diazaspiro[2.4]heptan-5-one hydrochloride. The title compound was prepared as described for the synthesis of Example 17 Step D using tert-Butyl ((S)-(7-((R)-cyclopropyl(5-oxo-4,6-diazaspiro[2.4]heptan-6-yl)methyl)imidazo[1,2-b]pyridazin-2-yl)(4,4-difluorocyclohexyl)methyl)carbamate (Step C) in place of tert-Butyl ((S)-(7-((R)-cyclopropyl(R)-4-cyclopropyl-2-oxoimidazolidin-1-yl)methyl)imidazo[1,2-b]pyridazin-2-yl)(4,4-difluorocyclohexyl)methyl)carbamate and 4 M HCl in 1,4-dioxane in place of 4 M HCl in MeOH. The mixture was stirred at rt for 90 min instead of 60 min to provide the title compound in 74% yield.

Step E: N—[(S)—[7-[(R)-Cyclopropyl-(6-oxo-5,7-diazaspiro[2.4]heptan-5-yl)methyl]imidazo[1,2-b]pyridazin-2-yl]-(4,4-difluorocyclohexyl)methyl]-4-methyl-1,2,5-oxadiazole-3-carboxamide. A mixture of 6-((R)-(2-((S)-amino(4,4-difluorocyclohexyl)methyl)imidazo[1,2-b]pyridazin-7-yl)(cyclopropyl)methyl)-4,6-diazaspiro[2.4]heptan-5-one hydrochloride (34 mg, 0.079 mmol, Step D), 2,5-dioxopyrrolidin-1-yl 4-methyl-1,2,5-oxadiazole-3-carboxylate (39 mg, 0.17 mmol) and TEA (0.055 mL, 0.39 mmol) in anhydrous DCM (2 mL) was stirred at rt for 6 h. The mixture was then diluted with water (30 mL) and extracted with EtOAc (2×30 mL). The organic layers were combined, washed with water (2×50 mL) and brine (50 mL), dried over anhydrous $Na_2SO_4$, filtered and concentrated to dryness. The residue was purified by silica gel chromatography (0-90% EtOAc/petroleum ether) to provide the title compound as a white solid after lyophilization (17% yield). $^1$H NMR (400 MHz, DMSO-$d_6$) δ 9.49-9.35 (m, 1H), 8.45-8.35 (m, 1H), 8.25 (s, 1H), 8.01 (s, 1H), 6.69 (s, 1H), 5.22-5.08 (m, 1H), 4.21-4.10 (m, 1H), 3.66-3.55 (m, 1H), 3.29-3.22 (m, 1H), 2.46 (s, 3H), 2.23-2.12 (m, 1H), 2.10-1.97 (m, 2H), 1.94-1.87 (m, 1H), 1.85-1.69 (m, 2H), 1.65-1.56 (m, 1H), 1.54-1.44 (m, 1H), 1.41-1.34 (m, 1H), 1.31-1.24 (m, 1H), 0.78-0.56 (m, 6H), 0.53-0.35 (m, 2H). MS (ESI) m/z: [M+H]$^+$ Found 541.3.

Example 22

N—((S)-(7-((S)—(1-Cyanocyclobutyl)((S)-2-oxo-4-(trifluoromethyl)imidazolidin-1-yl)methyl)imidazo[1,2-b]pyridazin-2-yl)(4,4-difluorocyclohexyl)methyl)-4-methyl-1,2,5-oxadiazole-3-carboxamide

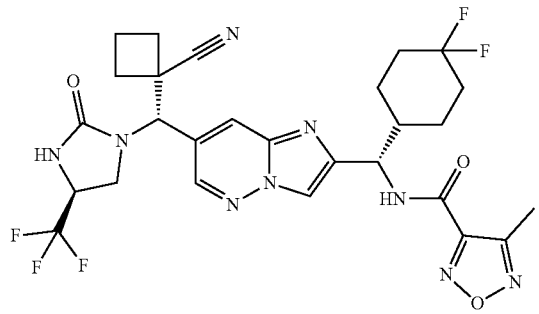 [SMILES: Cc1nonc1C(=O)N[C@H](c1cn2ncc([C@H](N3C[C@@H](C(F)(F)F)NC3=O)C3(C#N)CCC3)cc2n1)C1CCC(F)(F)CC1]

The title compound (38% yield) was prepared as described for the synthesis of Example 1 using 1-((S)—(2-((S)-amino(4,4-difluorocyclohexyl)methyl)imidazo[1,2-b]pyridazin-7-yl)((S)-2-oxo-4-(trifluoromethyl)imidazolidin-1-yl)methyl)cyclobutane-1-carbonitrile (Intermediate 19) in place of (S)-1-((2-(amino(4,4-difluorocyclohexyl)methyl)imidazo[1,2-b]pyridazin-7-yl)methyl)imidazolidin-2-one. $^1$H NMR (500 MHz, DMSO-$d_6$) δ 9.44 (d, J=9.0 Hz, 1H), 8.32 (s, 1H), 8.24 (d, J=2.3 Hz, 1H), 8.03-8.00 (m, 1H), 7.91-7.89 (m, 1H), 5.46-5.44 (m, 1H), 5.22-5.16 (m, 1H), 4.58-4.47 (m, 1H), 3.88 (t, J=10.0 Hz, 1H), 3.40-3.36 (m, 1H), 2.60-2.52 (m, 3H), 2.46 (s, 3H), 2.44-2.35 (m, 1H), 2.25-2.13 (m, 2H), 2.10-1.89 (m, 4H), 1.87-1.69 (m, 2H), 1.67-1.58 (m, 1H), 1.45-1.34 (m, 1H), 1.34-1.22 (m, 1H). MS (ESI) m/z: [M+H]$^+$ Found 622.3.

Example 23

N-((1R)-1-(7-(2-Methoxy-1-((S)-4-methyl-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)-4-methyl-1,2,5-oxadiazole-3-carboxamide

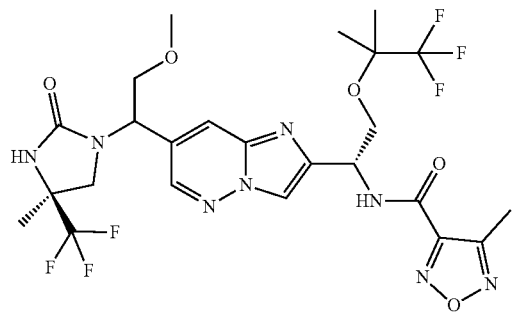

The title compound (6% yield) was prepared as described for the synthesis of Example 10 using (4S)-1-(1-(2-((R)-1-amino-2-((1,1,1-trifluoro-2-methylpropan-2-yl)oxy)ethyl)imidazo[1,2-b]pyridazin-7-yl)-2-methoxyethyl)-4-methyl-4-(trifluoromethyl)imidazolidin-2-one (Intermediate 20) in place of (S)-1-((S)-1-(2-((R)-1-amino-2-((1,1,1-trifluoro-2- methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. $^1$H NMR (500 MHz, DMSO-d$_6$) δ 9.42 (d, J=8.5 Hz, 1H), 8.39 (d, J=2.1 Hz, 1H), 8.23 (s, 1H), 7.92-7.88 (m, 1H), 7.74 (s, 1H), 5.45-5.33 (m, 1H), 5.16-5.08 (m, 1H), 4.05-3.99 (m, 1H), 3.98-3.82 (m, 3H), 3.55 (d, J=10.1 Hz, 1H), 3.43 (d, J=10.3 Hz, 1H), 3.33 (s, 3H), 2.49 (s, 3H), 1.41 (s, 3H), 1.36-1.33 (m, 6H). MS (ESI) m/z: [M+H]$^+$ Found 623.3.

Example 24

4-Cyclopropyl-N—((R)-1-(7-(((S)-2-oxo-4-(trifluoromethyl)imidazolidin-1-yl)methyl)imidazo[1,2-b]pyridazin-2-yl)-2-(1,1,1-trifluoro-2-methylpropan-2-yl)oxy)ethyl)-1,2,5-oxadiazole-3-carboxamide

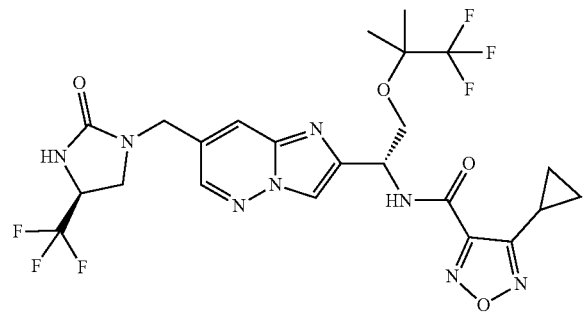 [SMILES: CC(C)(OC[C@H](NC(=O)c1nonc1C1CC1)c1cn2ncc(CN3C[C@@H](C(F)(F)F)NC3=O)cc2n1)C(F)(F)F]

The title compound (45% yield) was synthesized in a manner analogous to Example 10 using (S)-1-((2-((R)-1-amino-2-((1,1,1-trifluoro-2-methylpropan-2-yl)oxy)ethyl)imidazo[1,2-b]pyridazin-7-yl)methyl)-4-(trifluoromethyl)imidazolidin-2-one (Intermediate 21) in place of (S)—((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one. $^1$H NMR (400 MHz, Methanol-d$_4$) δ 8.37 (d, J=2.0 Hz, 1H), 8.13 (s, 1H), 7.87-7.77 (m, 1H), 5.55 (t, J=5.9 Hz, 1H), 4.62-4.50 (m, 2H), 4.49-4.27 (m, 2H), 4.18-3.98 (m, 2H), 3.74 (t, J=10.0 Hz, 1H), 3.59-3.46 (m, 1H), 2.54-2.36 (m, 1H), 1.45-1.34 (m, 6H), 1.23-1.12 (m, 1H), 1.09-0.93 (m, 2H). MS (ESI) m/z: [M+H]$^+$ Found 591.2.

Example 25

N—((S)-(7-((S)-1-((R)-4-(1-Cyanocyclopropyl)-2-oxoimidazolidin-1-yl)-2-methoxyethyl)imidazo[1,2-b]pyridazin-2-yl)(4,4-difluorocyclohexyl)methyl)-4-methyl-1,2,5-oxadiazole-3-carboxamide

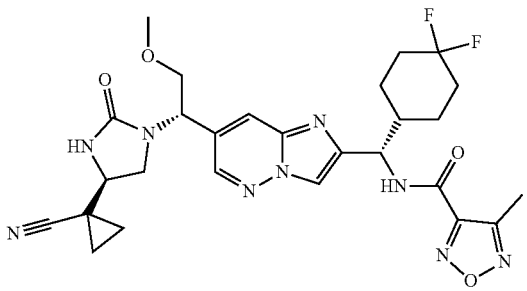 [SMILES: COC[C@H](c1cnn2cc([C@@H](NC(=O)c3nonc3C)C3CCC(F)(F)CC3)nc2c1)N1C[C@@H](C2(C#N)CC2)NC1=O]

The title compound was synthesized in a manner analogous to Example 10 using (S)-(7-((S)-1-((R)-4-(1-cyanocyclopropyl)-2-oxoimidazolidin-1-yl)-2-methoxyethyl)imidazo[1,2-b]pyridazin-2-yl)(4,4-difluorocyclohexyl)methanaminium 2,2,2-trifluoroacetate (Intermediate 24) in place of (S)—((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. The residue was purified by preparative HPLC (C18, 5 μm, 50×250 mm, 10-100% MeCN/water (20 mM NH$_4$OH)) to provide the title compound in 44% yield. $^1$H NMR (600 MHz, DMSO-d$_6$) δ 9.33 (d, J=9.0 Hz, 1H), 8.36 (d, J=2.1 Hz, 1H), 8.17 (s, 1H), 7.93-7.86 (m, 1H), 7.23-7.12 (m, 1H), 5.10 (t, J=8.6 Hz, 1H), 5.07-5.01 (m, 1H), 3.85-3.74 (m, 2H), 3.69-3.62 (m, 1H), 3.26 (s, 3H), 3.21-3.17 (m, 2H), 2.39 (s, 3H), 2.19-2.06 (m, 1H), 2.03-1.86 (m, 2H), 1.86-1.78 (m, 1H), 1.77-1.63 (m, 2H), 1.57-1.48 (m, 1H), 1.36-1.26 (m, 1H), 1.26-1.17 (m, 1H), 1.17-1.11 (m, 1H), 1.11-1.05 (m, 1H), 0.98-0.89 (m, 1H), 0.89-0.83 (m, 1H). MS (ESI) m/z: [M+H]$^+$ Found 584.3.

Example 26

N—((S)—(4,4-Difluorocyclohexyl)(7-((S)-1-((S)-4-(difluoromethyl)-2-oxoimidazolidin-1-yl)-2-methoxyethyl)imidazo[1,2-b]pyridazin-2-yl)methyl)-4-methyl-1,2,5-oxadiazole-3-carboxamide

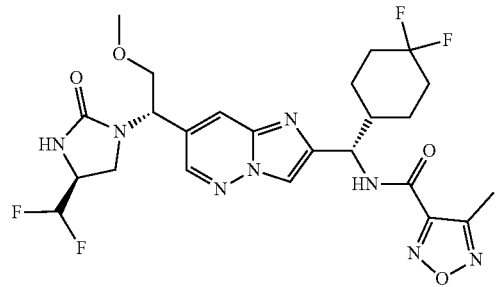 [SMILES: COC[C@H](c1cnn2cc([C@@H](NC(=O)c3nonc3C)C3CCC(F)(F)CC3)nc2c1)N1C[C@@H](C(F)F)NC1=O]

The title compound was synthesized in a manner analogous to Example 10 using (S)—(4,4-difluorocyclohexyl)(7-((S)-1-((S)-4-(difluoromethyl)-2-oxoimidazolidin-1-yl)-2-methoxyethyl)imidazo[1,2-b]pyridazin-2-yl)methanaminium chloride (Intermediate 26) in place of (S)—((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. The residue was purified by preparative HPLC (C18, 5 μm, 50×250 mm, 10-100% MeCN/water (20 mM NH$_4$OH)) to provide the title compound in 48% yield. $^1$H NMR (600 MHz, DMSO-d$_6$) δ 8.85 (d, J=2.1 Hz, 1H), 8.78-8.72 (m, 1H), 8.62 (s, 1H), 8.40-8.33 (m, 1H), 6.73 (s, 1H), 6.41 (td, J=55.9, 4.1 Hz, 1H), 5.81-5.75 (m, 1H), 5.69-5.64 (m, 1H), 4.56-4.43 (m, 3H), 4.29 (t, J=9.6 Hz, 1H), 3.92 (dd, J=9.7, 4.7 Hz, 1H), 3.88 (s, 3H), 3.00 (s, 3H), 2.78-2.67 (m, 1H), 2.54-2.52 (m, 1H), 2.33-2.15 (m, 3H), 2.05-1.91 (m, 1H), 1.90-1.79 (m, 1H), 1.79-1.68 (m, 1H), 0.61-0.54 (m, 1H). MS (ESI) m/z: [M+H]$^+$ Found 569.2.

Example 27

N-((1R,2R)-1-(7-((S)-2-Methoxy-1-((S)-2-oxo-4-(trifluoromethyl)imidazolidin-1-yl)ethyl)imidazo[1,2-b]pyridazin-2-yl)-2-(((R)-1,1,1-trifluoropropan-2-yl)oxy)propyl)-4-methyl-1,2,5-oxadiazole-3-carboxamide

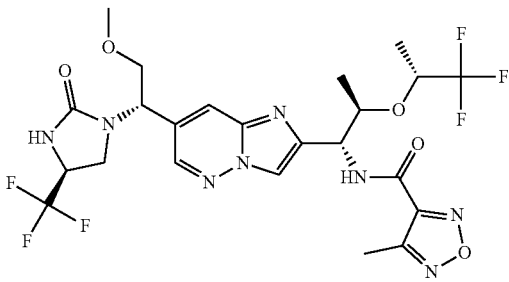 [SMILES: COC[C@H](c1cnn2cc([C@@H](NC(=O)c3nonc3C)[C@@H](C)O[C@H](C)C(F)(F)F)nc2c1)N1C[C@@H](C(F)(F)F)NC1=O]

The title compound was synthesized in a manner analogous to Example 10 using (1R,2R)-1-(7-((S)-2-methoxy-1-((S)-2-oxo-4-(trifluoromethyl)imidazolidin-1-yl)ethyl)imidazo[1,2-b]pyridazin-2-yl)-2-(((R)-1,1,1-trifluoropropan-2-yl)oxy)propan-1-aminium 2,2,2-trifluoroacetate (Intermediate 29) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. The residue was purified by preparative HPLC (C18, 5 μm, 50×250 mm, 10-100% MeCN/water (20 mM NH$_4$OH)) to provide the title compound in 47% yield. $^1$H NMR (500 MHz, DMSO-d$_6$) δ 9.34 (d, J=9.2 Hz, 1H), 8.41 (d, J=2.1 Hz, 1H), 8.27 (s, 1H), 7.91-7.85 (m, 1H), 7.75-7.66 (m, 1H), 5.27 (dd, J=9.2, 6.8 Hz, 1H), 5.19-5.07 (m, 1H), 4.52-4.40 (m, 1H), 4.38-4.18 (m, 2H), 3.98-3.73 (m, 3H), 3.50-3.44 (m, 1H), 3.33 (s, 3H), 2.48 (s, 3H), 1.11 (d, J=6.3 Hz, 3H), 1.06 (d, J=6.4 Hz, 3H). MS (ESI) m/z: [M+H]$^+$ Found 609.3.

Example 28

N—((S)—(4,4-Difluorocyclohexyl)(7-(((S)-4-methyl-2-oxo-4-(trifluoromethyl)imidazolidin-1-yl)methyl)imidazo[1,2-b]pyridazin-2-yl)methyl)-4-methyl-1,2,5-oxadiazole-3-carboxamide

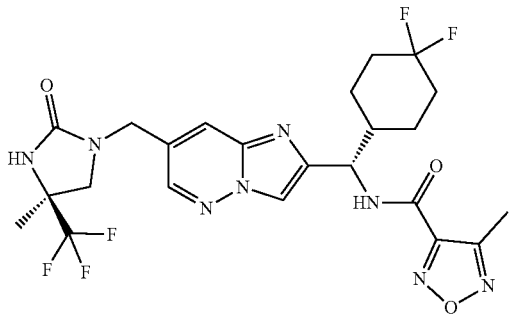

The title compound (60% yield) was synthesized in a manner analogous to Example 10 using (S)-1-((2-((S)-amino(4,4-difluorocyclohexyl)methyl)imidazo[1,2-b]pyridazin-7-yl)methyl)-4-methyl-4-(trifluoromethyl)imidazolidin-2-one (Intermediate 32) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. $^1$H NMR (500 MHz, DMSO-d$_6$) δ 9.43 (d, J=9.0 Hz, 1H), 8.35 (d, J=2.1 Hz, 1H), 8.25 (s, 1H), 7.84 (d, J=1.3 Hz, 1H), 7.73 (s, 1H), 5.23-5.12 (m, 1H), 4.51-4.27 (m, 2H), 3.60-3.50 (m, 1H), 3.33 (br s, 1H), 2.46 (s, 3H), 2.24-2.11 (m, 1H), 2.09-1.94 (m, 2H), 1.93-1.86 (m, 1H), 1.85-1.69 (m, 2H), 1.61 (br dd, J=1.3, 12.8 Hz, 1H), 1.44-1.21 (m, 5H). MS (ESI) m/z: [M+H]$^+$ Found 557.2.

Example 29

4-Cyclopropyl-N—((S)—(4,4-difluorocyclohexyl)(7-(0)-4-methyl-2-oxo-4-(trifluoromethyl)imidazolidin-1-yl)methyl)imidazo[1,2-b]pyridazin-2-yl)methyl)-1,2,5-oxadiazole-3-carboxamide

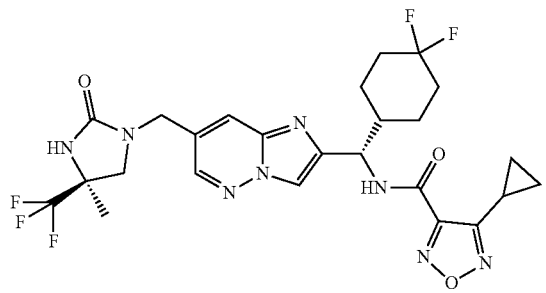 [SMILES: C[C@@]1(C(F)(F)F)CN(Cc2cnn3cc([C@@H](NC(=O)c4nonc4C4CC4)C4CCC(F)(F)CC4)nc3c2)C(=O)N1]

The title compound (84% yield) was synthesized in a manner analogous to Example 10 using (S)-1-((2-((S)-amino(4,4-difluorocyclohexyl)methyl)imidazo[1,2-b]pyridazin-7-yl)methyl)-4-methyl-4-(trifluoromethyl)imidazolidin-2-one (Intermediate 32) in place of (S)—((S)-1-(2-((R)-1-amino-2-((1,1,1-trifluoro-2-methylpropan-2-yl)oxy) ethyl)imidazo[1,2-b]pyridazin-7-yl)-2-methoxyethyl)-4-(trifluoromethyl)imidazolidin-2-one. $^1$H NMR (500 MHz, DMSO-$d_6$) δ 9.56-9.42 (m, 1H), 8.38-8.33 (m, 1H), 8.27-8.22 (m, 1H), 7.87-7.82 (m, 1H), 7.76-7.70 (m, 1H), 5.23-5.16 (m, 1H), 4.47-4.27 (m, 2H), 3.59-3.51 (m, 1H), 2.31-2.23 (m, 1H), 2.23-2.13 (m, 1H), 2.11-1.94 (m, 2H), 1.94-1.86 (m, 1H), 1.86-1.70 (m, 2H), 1.66-1.57 (m, 1H), 1.44-1.21 (m, 6H), 1.16-1.06 (m, 2H), 1.01-0.91 (m, 2H). MS (ESI) m/z: [M+H]$^+$ Found 583.3.

Example 30

N—((R)-1-(7-((S)-2-Methoxy-((S)-4-methyl-2-oxo-4-(trifluoromethyl)imidazolidin-1-yl)ethyl)imidazo [1,2-b]pyridazin-2-yl)-2-(1,1,1-trifluoro-2-methyl-propan-2-yl)oxy)ethyl)-4-methyl-1,2,5-oxadiazole-3-carboxamide

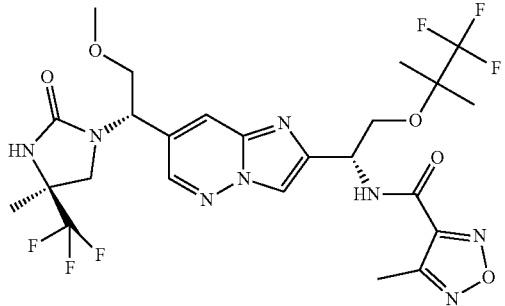 [SMILES: COC[C@H](c1cnn2cc([C@H](COC(C)(C)C(F)(F)F)NC(=O)c3nonc3C)nc2c1)N1C[C@@](C)(C(F)(F)F)NC1=O]

The title compound was synthesized in a manner analogous to Example 10 using (S)-1-((S)-1-(2-((R)-1-amino-2-((1,1,1-trifluoro-2-methylpropan-2-yl)oxy)ethyl)imidazo[1, 2-b]pyridazin-7-yl)-2-methoxyethyl)-4-methyl-4-(trifluoromethyl)imidazolidin-2-one (Intermediate KS3) in place of (S)—((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. N—((R)-1-(7-((S)-2-Methoxy-1-((R,S)-4-methyl-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)-4-methyl-1,2,5-oxadiazole-3-carboxamide was obtained initially. The (R) and (S) diastereomers of N—((R)-1-(7-((S)-2-methoxy-1-((R,S)-4-methyl-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)-4-methyl-1,2,5-oxadiazole-3-carboxamide were separated and purified via chiral SFC (Stationary phase: Chiralpak IE 5 μm, 250×21 Mm, Mobile phase: 30% MeOH, 70% CO$_2$). The second eluting diastereomer was designated as N—((R)-1-(7-((S)-2-methoxy-((S)-4-methyl-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)-4-methyl-1,2,5-oxadiazole-3-carboxamide and was obtained in 29% yield. $^1$H NMR (500 MHz, DMSO-$d_6$) δ 9.42 (d, J=8.5 Hz, 1H), 8.39 (d, J=2.1 Hz, 1H), 8.23 (s, 1H), 7.92-7.88 (m, 1H), 7.74 (s, 1H), 5.39 (dt, J=5.1, 8.3 Hz, 1H), 5.16-5.09 (m, 1H), 4.05-3.99 (m, 1H), 3.98-3.83 (m, 3H), 3.55 (d, J=10.3 Hz, 1H), 3.45-3.41 (m, 1H), 3.33 (s, 3H), 2.49-2.49 (m, 3H), 1.41 (s, 3H), 1.34 (d, J=4.3 Hz, 6H). MS (ESI) m/z: [M+H]$^+$ Found 623.3.

Example 31

4-Methyl-N—((S)-5,5,5-trifluoro-1-(7-((S)-2-methoxy-1-((S)-4-methyl-2-oxo-4-(trifluoromethyl) imidazolidin-1-yl)ethyl)imidazo[1,2-b]pyridazin-2-yl)-4,4-dimethylpentyl)-1,2,5-oxadiazole-3-carboxamide

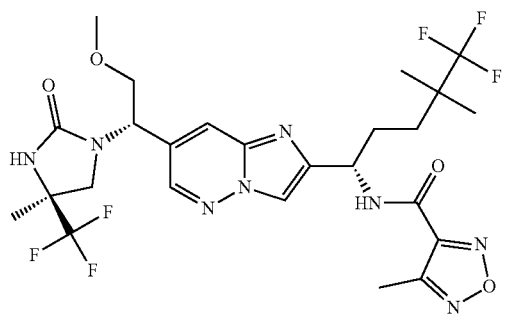 [SMILES: COC[C@H](c1cnn2cc([C@H](CCC(C)(C)C(F)(F)F)NC(=O)c3nonc3C)nc2c1)N1C[C@@](C)(C(F)(F)F)NC1=O]

The title compound was synthesized in a manner analogous to Example 10 using (S)-1-((S)-1-(2-((S)-1-amino-5, 5,5-trifluoro-4,4-dimethylpentyl)imidazo[1,2-b]pyridazin-7-yl)-2-methoxyethyl)-4-methyl-4-(trifluoromethyl) imidazolidin-2-one (Intermediate 35) in place of (S)-1-((S)-1-(2-((R)-1-amino-2-((1,1,1-trifluoro-2-methylpropan-2-yl) oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. 4-Methyl-N—((S)-5,5,5-trifluoro-1-(7-((S)-2-methoxy-1-((R,S)-4-methyl-2-oxo-4-(trifluoromethyl)imidazolidin-1-yl)ethyl) imidazo[1,2-b]pyridazin-2-yl)-4,4-dimethylpentyl)-1,2,5-oxadiazole-3-carboxamide was obtained initially. The (R) and (S) diastereomers of 4-methyl-N—((S)-5,5,5-trifluoro-1-(7-((S)-2-methoxy-1-((R,S)-4-methyl-2-oxo-4-(trifluoromethyl)imidazolidin-1-yl)ethyl)imidazo[1,2-b]pyridazin-2-yl)-4,4-dimethylpentyl)-1,2,5-oxadiazole-3-carboxamide were separated and purified via chiral SFC (Stationary phase: Whelk O1 SS 5 μm, 250×21 Mm, Mobile phase: 30% MeOH:IPA (1:1), 70% CO$_2$). The first eluting diastereomer was designated as 4-methyl-N—((S)-5,5,5-trifluoro-1-(7-((S)-2-methoxy-1—((S)-4-methyl-2-oxo-4-(trifluoromethyl)imidazolidin-1-yl)ethyl)imidazo[1,2-b]pyridazin-2-yl)-4,4-dimethylpentyl)-1,2,5-oxadiazole-3-carboxamide and was obtained in 37% yield. $^1$H NMR (500 MHz, DMSO-$d_6$) δ 9.54-9.48 (m, 1H), 8.39-8.36 (m, 1H), 8.20 (s, 1H), 7.91-7.88 (m, 1H), 7.76-7.71 (m, 1H), 5.25-5.17 (m, 1H), 5.15-5.08 (m, 1H), 3.94-3.81 (m, 2H), 3.56 (d, J=10.1 Hz, 1H), 3.43 (d, J=10.3 Hz, 1H), 3.33 (s, 3H), 2.49-2.49 (m, 3H), 2.03-1.93 (m, 2H), 1.69-1.60 (m, 1H), 1.56-1.49 (m, 1H), 1.41 (s, 3H), 1.09 (s, 6H). MS (ESI) m/z: [M+H]$^+$ Found 621.2.

Example 32

(1R*,2R*)—N—((R)-1-(7-((S)-2-Methoxy-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)-2-(trifluoromethyl)cyclopropane-1-carboxamide

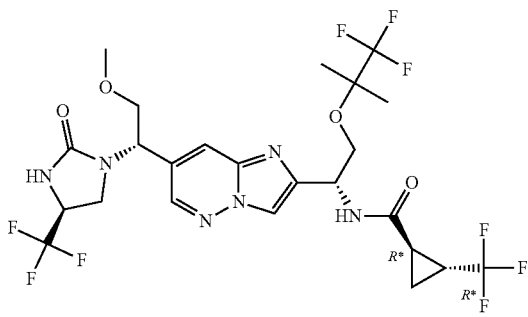 [SMILES: COC[C@H](c1cnn2cc([C@H](COC(C)(C)C(F)(F)F)NC(=O)[C@@H]3C[C@H]3C(F)(F)F)nc2c1)N1C[C@@H](C(F)(F)F)NC1=O]

Example 33

(1S*,2S*)—N—((R)-1-(7-((S)-2-Methoxy-1-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)-2-(trifluoromethyl)cyclopropane-1-carboxamide

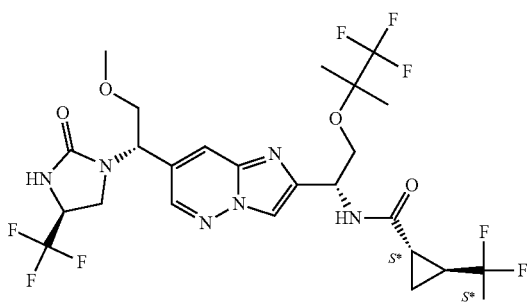

The title compounds were prepared as described for the synthesis of Example 11 using 2-(trifluoromethyl)cyclopropane-1-carboxylic acid in place of 1-(propan-2-yl)-1H-pyrazole carboxylic acid to afford two diastereomers that were separated via SFC ((Stationary phase: Whelk-01 SS 5 µm, 250×21 Mm, Mobile phase: 15% Methanol, 85% CO$_2$). The first eluting isomer was designated as the (1R*,2R*) isomer, Example 32, (15.2% yield) and the second eluting isomer was designated as the (1S*,2S*) isomer, Example 33, (16% yield). Data for Example 32: $^1$H NMR (600 MHz, CD$_3$OD) δ 8.41 (d, J=2.1 Hz, 1H), 8.09 (d, J=0.8 Hz, 1H), 7.91-7.87 (m, 1H), 5.39-5.34 (m, 1H), 5.27-5.22 (m, 1H), 4.44-4.35 (m, 1H), 4.07-4.01 (m, 2H), 4.01-3.94 (m, 3H), 3.53 (dd, J=10.4, 3.8 Hz, 1H), 3.48 (s, 3H), 2.28-2.22 (m, 1H), 2.19-2.09 (m, 1H), 1.39 (d, J=1.7 Hz, 6H), 1.37-1.31 (m, 1H), 1.28-1.21 (m, 1H). MS (ESI) m/z: [M+H]$^+$ Found 635.4. Data for Example 33: $^1$H NMR (600 MHz, CD$_3$OD) δ 8.41 (d, J=2.1 Hz, 1H), 8.08 (d, J=0.8 Hz, 1H), 7.91-7.88 (m, 1H), 5.38-5.32 (m, 1H), 5.27-5.22 (m, 1H), 4.43-4.35 (m, 1H), 4.07-3.94 (m, 5H), 3.53 (dd, J=10.4, 3.8 Hz, 1H), 3.48 (s, 3H), 2.28-2.20 (m, 1H), 2.20-2.12 (m, 1H), 1.38 (d, J=1.0 Hz, 6H), 1.36-1.30 (m, 1H), 1.29-1.23 (m, 1H). MS (ESI) m/z: [M+H]$^+$ Found 635.4.

Example 34

4-Cyclopropyl-N—((R)-1-(7-((S)-2-methoxy-1-((R)-2-oxo-4-(trifluoromethyl)imidazolidin-1-yl-4,5,5-d$_3$)ethyl)imidazo[1,2-b]pyridazin-2-yl)-2-((1,1,1-trifluoro-2-methylpropan-2-yl)oxy)ethyl)-1,2,5-oxadiazole-3-carboxamide

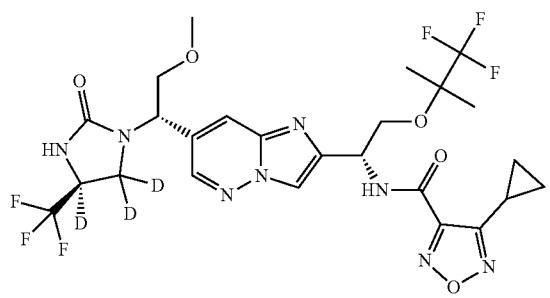 [SMILES: [2H]C1([2H])N([C@H](COC)c2cnn3cc([C@H](COC(C)(C)C(F)(F)F)NC(=O)c4nonc4C4CC4)nc3c2)C(=O)N[C@]1([2H])C(F)(F)F]

The title compound (43% yield) was prepared as described for the synthesis of Example 10 using (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one-4,5,5-d$_3$ (Intermediate 36) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one. 1H NMR (500 MHz, CD$_3$OD) δ 8.41 (d, J=2.2 Hz, 1H), 8.15 (s, 1H), 7.92-7.88 (m, 1H), 5.62-5.56 (m, 1H), 5.27-5.21 (m, 1H), 4.59 (s, 0.5H), 4.18-4.11 (m, 1H), 4.11-4.00 (m, 2H), 3.99-3.93 (m, 1H), 3.47 (s, 3H), 3.34 (p, J=1.6 Hz, 1H), 2.52-2.43 (m, 1H), 1.42 (d, J=3.8 Hz, 6H), 1.23-1.14 (m, 2H), 1.11-1.02 (m, 2H). MS (ESI) m/z: [M+H]$^+$ Found 638.3.

Example 35

N—((R)-1-(7-((S)-2-Methoxy-1-((R)-2-oxo-4-(trifluoromethyl)imidazolidin-1-yl-4,5,5-d$_3$)ethyl)imidazo[1,2-b]pyridazin-2-yl)-2-((1,1,1-trifluoro-2-methylpropan-2-yl)oxy)ethyl)-4-methyl-1,2,5-oxadiazole-3-carboxamide

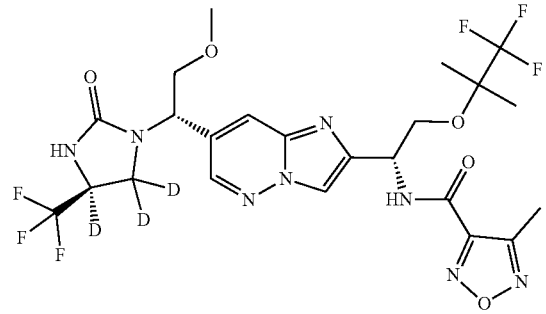 [SMILES: [2H]C1([2H])N([C@H](COC)c2cnn3cc([C@H](COC(C)(C)C(F)(F)F)NC(=O)c4nonc4C)nc3c2)C(=O)N[C@]1([2H])C(F)(F)F]

The title compound (53% yield) was prepared as described for the synthesis of Example 10 using (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one-4,5,5-d₃ (Intermediate 36) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. ¹H NMR (600 MHz, CD₃OD) δ 8.44 (d, J=2.2 Hz, 1H), 8.18 (d, J=0.8 Hz, 1H), 7.94-7.90 (m, 1H), 5.62-5.57 (m, 1H), 5.30-5.22 (m, 1H), 4.19-4.13 (m, 1H), 4.13-4.03 (m, 2H), 4.01-3.97 (m, 1H), 3.50 (s, 3H), 2.61 (s, 3H), 1.44 (d, J=5.4 Hz, 6H). MS (ESI) m/z: [M+H]⁺ Found 612.2.

Example 36

1-Isopropyl-N—((R)-1-(7-((S)-2-methoxy-1-((S)-2-oxo-4-(trifluoromethyl)imidazolidin-1-yl)ethyl)imidazo[1,2-b]pyridazin-2-yl)-2-((1,1,1-trifluoro-2-methylpropan-2-yl)oxy)ethyl)-1H-1,2,4-triazole-5-carboxamide

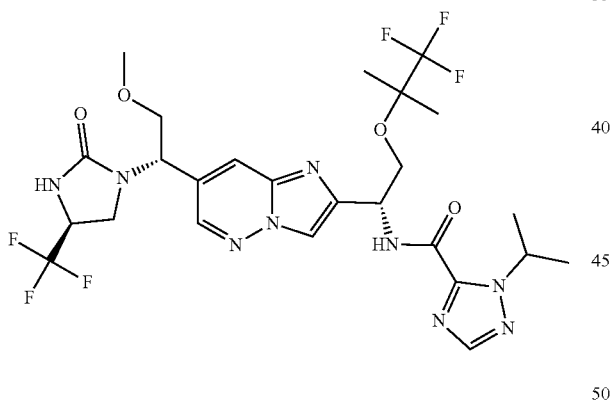

The title compound (37.3% yield) was prepared as described for the synthesis of Example 11 using lithium-1-isopropyl-1H-1,2,4-triazole-5-carboxylate in place of 1-(propan-2-yl)-1H-pyrazole-5-carboxylic acid. ¹H NMR (600 MHz, CD₃OD) δ 8.41 (d, J=2.2 Hz, 1H), 8.16 (d, J=0.8 Hz, 1H), 8.00 (d, J=0.6 Hz, 1H), 7.92-7.88 (m, 1H), 5.75-5.68 (m, 1H), 5.56-5.51 (m, 1H), 5.27-5.22 (m, 1H), 4.42-4.35 (m, 1H), 4.16-4.07 (m, 2H), 4.07-4.01 (m, 1H), 4.00-3.94 (m, 2H), 3.53 (dd, J=10.4, 3.8 Hz, 1H), 3.47 (s, 3H), 1.52 (dd, J=6.7, 5.4 Hz, 6H), 1.40 (d, J=8.3 Hz, 6H), 1.32 (s, 1H). MS (ESI) m/z: [M+H]⁺ Found 636.4.

Example 37

N—((S)-1-(7-((S)-2-Cyclopropoxy-((S)-2-oxo-4-(trifluoromethyl)imidazolidin-1-yl)ethyl)imidazo[1,2-b]pyridazin-2-yl)-5,5,5-trifluoro-4,4-dimethylpentyl)-4-methyl-1,2,5-oxadiazole-3-carboxamide The title compound (64% yield) was prepared as described for the synthesis of Example 10 using (S)-1-((S)-1-(2-((S)-1-amino-4,4,4-trifluoro-3,3-dimethylbutyl)imidazo[1,2-b]pyridazin-7-yl)-2-cyclopropoxyethyl)-4-(trifluoromethyl)imidazolidin-2-one (Intermediate 40) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. ¹H NMR (400 MHz, DMSO-d₆) δ 9.71 (d, J=8.7 Hz, 1H), 8.38 (d, J=2.1 Hz, 1H), 8.23 (s, 1H), 7.97-7.90 (m, 1H), 7.70 (d, J=2.2 Hz, 1H), 5.51-5.39 (m, 1H), 5.15-5.04 (m, 1H), 4.47 (s, 1H), 4.06-3.91 (m, 2H), 3.83-3.72 (m, 1H), 3.48-3.36 (m, 2H) 2.48 (s, 3H), 2.44-2.36 (m, 1H), 2.36-2.20 (m, 1H), 1.20 (d, J=5.4 Hz, 6H), 0.62-0.37 (m, 4H). MS (ESI) m/z: [M+H]⁺ Found 619.2.

Example 38

N—((S)-1-(7-((S)-2-Cyclopropoxy-((S)-2-oxo-4-(trifluoromethyl)imidazolidin-1-yl)ethyl)imidazo[1,2-b]pyridazin-2-yl)-5,5,5-trifluoro-4,4-dimethylpentyl)-4-methyl-1,2,5-oxadiazole-3-carboxamide

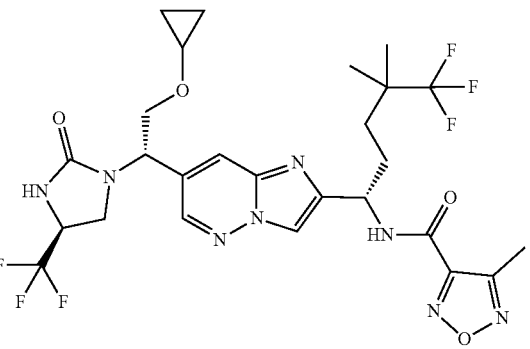

The title compound was prepared as described for the synthesis of Example 10 using (S)-1-((S)-1-(2-((S)-1-amino-5,5,5-trifluoro-4,4-dimethylpentyl)imidazo[1,2-b]pyridazin-7-yl)-2-cyclopropoxyethyl)-4-(trifluoromethyl)imidazolidin-2-one (Intermediate 41) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. The material also underwent an additional purification by silica gel chromatography (0-10% (2 M $NH_3$ in MeOH)/DCM) to afford the title compound as a white foam (58% yield). $^1$H NMR (400 MHz, DMSO-$d_6$) δ 9.52 (d, J=8.5 Hz, 1H), 8.39 (d, J=2.1 Hz, 1H), 8.21 (d, J=0.7 Hz, 1H), 7.96-7.88 (m, 1H), 7.70 (d, J=2.3 Hz, 1H), 5.27-5.17 (m, 1H), 5.14-5.06 (m, 1H), 4.53-4.40 (m, 1H), 4.06-3.92 (m, 2H), 3.83-3.72 (m, 1H), 3.48-3.37 (m, 2H), 2.48 (s, 3H), 2.17-2.06 (m, 1H), 2.05-1.93 (m, 1H), 1.71-1.60 (m, 1H), 1.58-1.46 (m, 1H), 1.09 (d, J=1.6 Hz, 6H), 0.58-0.42 (m, 4H). MS (ESI) m/z: [M+H]$^+$ Found 633.3.

Example 39

N—((S)-1-(7-((S)-2-Cyclopropoxy-((S)-2-oxo-4-(trifluoromethyl)imidazolidin-1-yl)ethyl)imidazo[1,2-b]pyridazin-2-yl)-5,5,5-trifluoro-4,4-dimethylpentyl)-4-cyclopropyl-1,2,5-oxadiazole-3-carboxamide

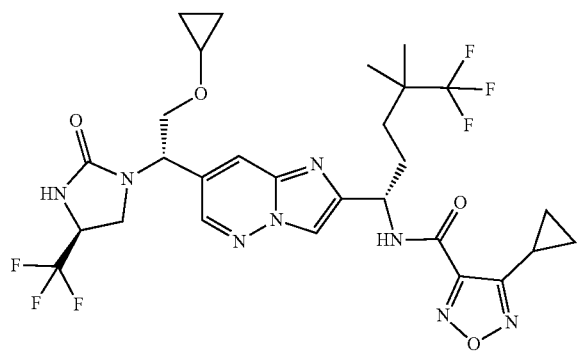 [SMILES: CC(C)(CC[C@H](NC(=O)c1nonc1C1CC1)c1cn2ncc([C@@H](COC3CC3)N3C[C@@H](C(F)(F)F)NC3=O)cc2n1)C(F)(F)F]

The title compound (66% yield) was prepared as described for the synthesis of Example 10 using (S)—((S)-1-(2-((S)-1-amino-5,5,5-trifluoro-4,4-dimethylpentyl)imidazo[1,2-b]pyridazin-7-yl)-2-cyclopropoxyethyl)-4-(trifluoromethyl)imidazolidin-2-one (Intermediate 41) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one. $^1$H NMR (400 MHz, DMSO-$d_6$) δ 9.56 (d, J=8.5 Hz, 1H), 8.40 (d, J=2.1 Hz, 1H), 8.21 (s, 1H), 7.95-7.86 (m, 1H), 7.71 (d, J=2.3 Hz, 1H), 5.30-5.19 (m, 1H), 5.14-5.06 (m, 1H), 4.54-4.42 (m, 1H), 4.05-3.93 (m, 2H), 3.83-3.72 (m, 1H), 3.47-3.38 (m, 2H), 2.40-2.30 (m, 2H), 2.17-2.06 (m, 1H), 2.06-1.90 (m, 1H), 1.72-1.61 (m, 1H), 1.61-1.48 (m, 1H), 1.19-1.05 (m, 7H), 1.03-0.94 (m, 2H), 0.60-0.38 (m, 4H). MS (ESI) m/z: [M+H]$^+$ Found 659.2.

Example 40

N—((S)—(4,4-Difluorocyclohexyl)(7-((R*)-3-methoxy-1-((S)-2-oxo-4-(trifluoromethyl)imidazolidin-1-yl)propyl)imidazo[1,2-b]pyridazin-2-yl)methyl)-4-methyl-1,2,5-oxadiazole-3-carboxamide

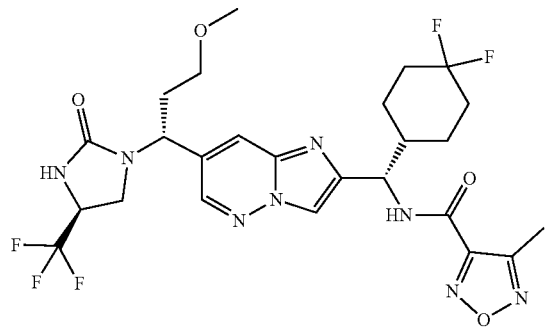 [SMILES: COCC[C@H](c1cnn2cc([C@@H](NC(=O)c3nonc3C)C3CCC(F)(F)CC3)nc2c1)N1C[C@@H](C(F)(F)F)NC1=O]

The title compound was prepared as described for the synthesis of Example 10 using (S)-1-((R*)-1-(2-((S)-amino (4,4-difluorocyclohexyl)methyl)imidazo[1,2-b]pyridazin-7-yl)-3-methoxypropyl)-4-(trifluoromethyl)imidazolidin-2-one (Intermediate 43) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. The material also underwent an additional purification by silica gel chromatography (0-10% (2 M $NH_3$ in MeOH)/DCM) to afford the title compound as a white foam (75% yield). $^1$H NMR (400 MHz, DMSO-$d_6$) δ 9.41 (d, J=9.0 Hz, 1H), 8.38 (d, J=2.1 Hz, 1H), 8.26 (s, 1H), 7.98 (d, J=2.1 Hz, 1H), 7.62 (d, J=2.3 Hz, 1H), 5.22-5.13 (m, 1H), 5.06-4.96 (m, 1H), 4.49-4.36 (m, 1H), 3.79-3.68 (m, 1H), 3.42-3.34 (m, 2H), 3.24 (s, 3H), 3.23-3.15 (m, 1H), 2.47 (s, 3H), 2.36-2.13 (m, 3H), 2.13-1.67 (m, 5H), 1.67-1.56 (m, 1H), 1.46-1.22 (m, 2H). MS (ESI) m/z: [M+H]$^+$ Found 601.2.

Example 41

4-Cyclopropyl-N—((S)—(4,4-difluorocyclohexyl)(7-((R)-3-methoxy-1-((S)-2-oxo-4-(trifluoromethyl)imidazolidin-1-yl)propyl)imidazo[1,2-b]pyridazin-2-yl)methyl)-1,2,5-oxadiazole-3-carboxamide

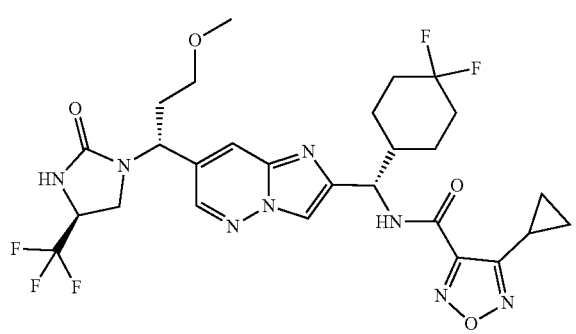 [SMILES: COCC[C@H](c1cnn2cc([C@@H](NC(=O)c3nonc3C3CC3)C3CCC(F)(F)CC3)nc2c1)N1C[C@@H](C(F)(F)F)NC1=O]

195

The title compound (67% yield) was prepared as described for the synthesis of Example 10 using (S)-1-((R*)-1-(2-((S)-amino(4,4-difluorocyclohexyl)methyl)imidazo[1,2-b]pyridazin-7-yl)-3-methoxypropyl)-4-(trifluoromethyl)imidazolidin-2-one (Intermediate 43) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one. $^1$H NMR (400 MHz, DMSO-d$_6$) δ 9.48 (d, J=9.0 Hz, 1H), 8.38 (d, J=2.1 Hz, 1H), 8.26 (s, 1H), 7.98 (d, J=2.1 Hz, 1H), 7.62 (d, J=2.3 Hz, 1H), 5.25-5.16 (m, 1H), 5.06-4.97 (m, 1H), 4.43 (s, 1H), 3.79-3.70 (m, 1H), 3.44-3.33 (m, 2H), 3.24 (s, 3H), 3.23-3.16 (m, 1H), 2.33-2.14 (m, 4H), 2.14-1.69 (m, 5H), 1.68-1.57 (m, 1H), 1.47-1.22 (m, 2H), 1.17-1.07 (m, 2H), 0.99-0.92 (m, 2H). MS (ESI) m/z: [M+H]$^+$ Found 627.2.

Example 42

N—((S)—(4,4-Difluorocyclohexyl)(7-((R*)-3-methoxy-1-((S)-2-oxo-4-(trifluoromethyl)imidazolidin-1-yl)propyl)imidazo[1,2-b]pyridazin-2-yl)methyl)-4-methoxy-1,2,5-oxadiazole-3-carboxamide

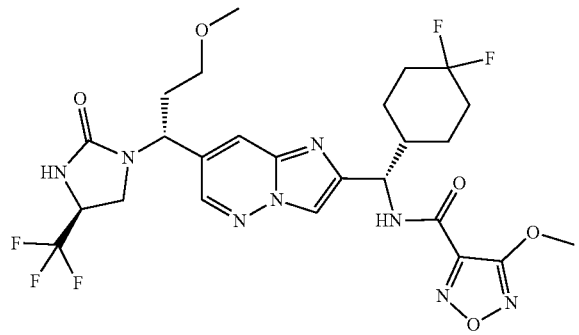 [SMILES: COCC[C@H](c1cnn2cc([C@@H](NC(=O)c3nonc3OC)C3CCC(F)(F)CC3)nc2c1)N1C[C@@H](C(F)(F)F)NC1=O]

The title compound was prepared as described for the synthesis of Example 1 using (S)-1-((R*)-1-(2-((S)-amino(4,4-difluorocyclohexyl)methyl)imidazo[1,2-b]pyridazin-7-yl)-3-methoxypropyl)-4-(trifluoromethyl)imidazolidin-2-one (Intermediate 43) in place of (S)-1-((2-(amino(4,4-difluorocyclohexyl)methyl)imidazo[1,2-b]pyridazin-7-yl)methyl)imidazolidin-2-one and 4-methoxy-1,2,5-oxadiazole-3-carboxylic acid in place of 4-methyl-1,2,5-oxadiazole-3-carboxylic acid. The material underwent an additional purification by silica gel chromatography (0-10% ((2 M NH$_3$ in MeOH)/DCM) to afford the title compound as a white foam (75% yield). $^1$H NMR (400 MHz, DMSO-d$_6$) δ 8.39 (d, J=2.1 Hz, 1H), 8.23 (s, 1H), 7.98 (d, J=2.1 Hz, 1H), 7.62 (d, J=2.3 Hz, 1H), 5.21-5.13 (m, 1H), 5.05-4.97 (m, 1H), 4.49-4.36 (m, 1H), 4.09 (s, 3H), 3.79-3.71 (m, 1H), 3.40-3.34 (m, 2H), 3.24 (s, 3H), 3.22-3.17 (m, 1H), 2.32-2.10 (m, 3H), 2.10-1.93 (m, 2H), 1.93-1.67 (m, 3H), 1.68-1.56 (m, 1H), 1.45-1.14 (m, 3H). MS (ESI) m/z: [M+H]$^+$ Found 617.2.

196

Example 43

N—((S)-(7-((S)-2-Cyclopropoxy-1-((S)-2-oxo-4-(trifluoromethyl)imidazolidin-1-yl)ethyl)imidazo[1,2-b]pyridazin-2-yl)(4,4-difluorocyclohexyl)methyl)-1-isopropyl-1H-pyrazole-5-carboxamide

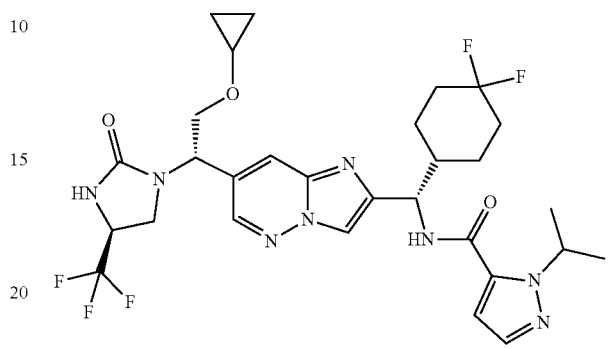

Example 44

N—((S)-(7-((R)-2-Cyclopropoxy-1-((S)-2-oxo-4-(trifluoromethyl)imidazolidin-1-yl)ethyl)imidazo[1,2-b]pyridazin-2-yl)(4,4-difluorocyclohexyl)methyl)-1-isopropyl-1H-pyrazole-5-carboxamide

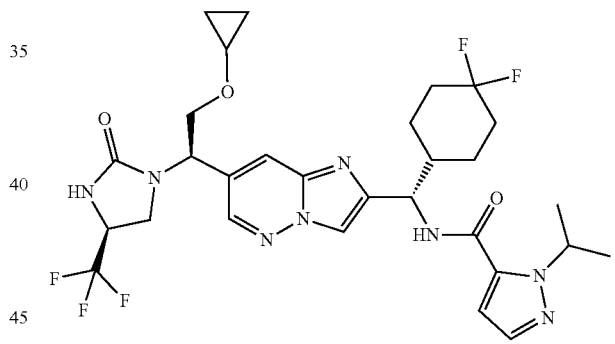

The title compounds were synthesized in a manner analogous to Example 10 using (S)-1-((S)-1-(2-((S)-amino(4,4-difluorocyclohexyl)methyl)imidazo[1,2-b]pyridazin-7-yl)-2-cyclopropoxyethyl)-4-(trifluoromethyl)imidazolidin-2-one (Intermediate 52) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 1-isopropyl-1H-pyrazole-5-carboxylate (Intermediate 7) in place of 2,5-dioxopyrrolidin-1-yl 4-cyclopropyl-1,2,5-oxadiazole-3-carboxylate. The diastereomers were separated via SFC (Stationary phase: Whelk O1 SS 5 μm, 250×21 Mm, Mobile phase: 20% methanol, 80% CO$_2$) to afford the first eluting isomer (Example 43) in 33% yield and the second eluting isomer (Example 44) in 5% yield. Data for Example 43: $^1$H NMR (500 MHz, DMSO-d$_6$) δ 8.75-8.72 (m, 1H), 8.40 (d, J=2.1 Hz, 1H), 8.23 (s, 1H), 7.88-7.86 (m, 1H), 7.72-7.69 (m, 1H), 7.51-7.47 (m, 1H), 6.93-6.90 (m, 1H), 5.41-5.34 (m, 1H), 5.19-5.14 (m, 1H), 5.12-5.08 (m, 1H), 4.52-4.45 (m, 1H), 4.04-3.92 (m, 2H), 3.78 (t, J=10.1 Hz, 1H), 3.50-3.39 (m, 3H), 2.23-2.15 (m, 1H), 2.10-1.96 (m, 2H), 1.93-1.85 (m, 1H), 1.85-1.71 (m, 2H), 1.68-1.59 (m, 1H), 1.43-1.39 (m, 1H), 1.38-1.32 (m, 6H), 0.56-0.43 (m, 4H). MS (ESI) m/z: [M+H]$^+$ Found 639.0. Data for Example 44: $^1$H NMR (500 MHz, DMSO-$d_6$) δ 8.72-8.70 (m, 1H), 8.44-8.42 (m, 1H), 8.23-8.22 (m, 1H), 8.00-7.98 (m, 1H), 7.62-7.59 (m, 1H), 7.49-7.48 (m, 1H), 6.91-6.89 (m, 1H), 5.41-5.33 (m, 1H), 5.19-5.13 (m, 1H), 5.13-5.08 (m, 1H), 4.42-4.35 (m, 1H), 3.99-3.95 (m, 2H), 3.61-3.56 (m, 1H), 3.49-3.45 (m, 2H), 2.22-2.11 (m, 1H), 2.10-1.95 (m, 2H), 1.92-1.85 (m, 1H), 1.85-1.70 (m, 2H), 1.66-1.59 (m, 1H), 1.43-1.38 (m, 1H), 1.37-1.35 (m, 3H), 1.34-1.32 (m, 3H), 1.27-1.23 (m, 1H), 0.49-0.44 (m, 4H). MS (ESI) m/z: [M+H]$^+$ Found 639.0.

Example 45

N—((R)-1-(7-((S)-2-Cyclopropoxy-1-((S)-2-oxo-4-(trifluoromethyl)imidazolidin-1-yl)ethyl)imidazo[1,2-b]pyridazin-2-yl)-2-(1,1,1-trifluoro-2-methylpropan-2-yl)oxy)ethyl)-4-methyl-1,2,5-oxadiazole-3-carboxamide

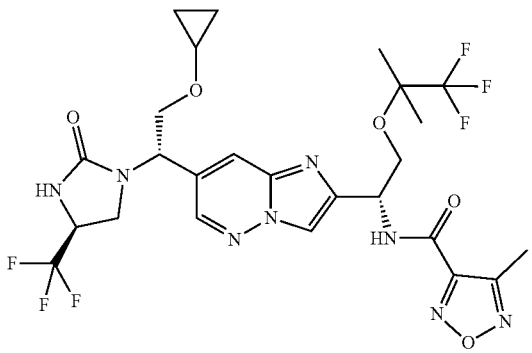 [SMILES: Cc1nonc1C(=O)N[C@@H](COC(C)(C)C(F)(F)F)c1cn2ncc([C@@H](COC3CC3)N3C[C@@H](C(F)(F)F)NC3=O)cc2n1]

The title compound was synthesized in a manner analogous to Example 10 using (S)-1-((S)-1-(2-((R)-1-amino-2-((1,1,1-trifluoro-2-methylpropan-2-yl)oxy)ethyl)imidazo[1,2-b]pyridazin-7-yl)-2-cyclopropoxyethyl)-4-(trifluoromethyl)imidazolidin-2-one (Intermediate 47) in place of OH—((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. Purification by preparative HPLC (X-Bridge Prep C18 5 μm column, 50×250 mm, 5-100% acetonitrile/water (with 20 mM NH$_4$OH)) afforded the title compound in 31% yield. $^1$H NMR (500 MHz, DMSO-$d_6$) δ 9.43 (d, J=8.6 Hz, 1H), 8.40 (d, J=2.1 Hz, 1H), 8.23 (s, 1H), 7.93-7.89 (m, 1H), 7.70 (d, J=2.3 Hz, 1H), 5.43-5.35 (m, 1H), 5.13-5.07 (m, 1H), 4.47 (s, 1H), 4.05-3.91 (m, 4H), 3.77 (t, J=10.1 Hz, 1H), 3.44-3.37 (m, 2H), 2.50 (s, 3H), 1.34 (d, J=4.2 Hz, 6H), 0.56-0.47 (m, 2H), 0.47-0.43 (m, 2H). MS (ESI) m/z: [M+H]$^+$ Found 635.5.

Example 46

(S)—N-((7-((2,2-Difluoro-6-oxo-5,7-diazaspiro[3.4]octan-7-yl)methyl)imidazo[1,2-b]pyridazin-2-yl)(4,4-difluorocyclohexyl)methyl)-1-isopropyl-1H-pyrazole-5-carboxamide

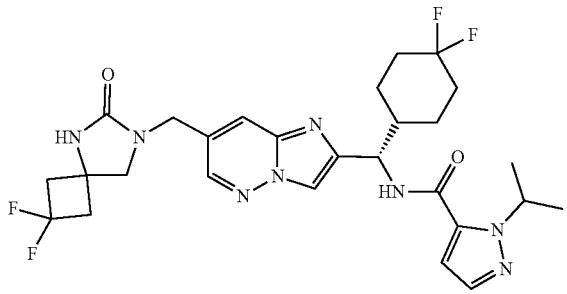 [SMILES: CC(C)n1nccc1C(=O)N[C@H](c1cn2ncc(CN3CC4(CC(F)(F)C4)NC3=O)cc2n1)C1CCC(F)(F)CC1]

Step A: tert-Butyl (S)—((4,4-difluorocyclohexyl)(7-(hydroxymethyl)imidazo[1,2-b]pyridazin-2-yl)methyl)carbamate. A solution of tert-Butyl (S)—((4,4-difluorocyclohexyl)(7-formylimidazo[1,2-b]pyridazin-2-yl)methyl)carbamate (800 mg, 2.03 mmol) in MeOH (7 mL) was cooled to 0° C. and then sodium borohydride (194 mg, 5.07 mmol) was added. The resulting mixture was stirred for 30 min while it warmed to rt. The reaction mixture was quenched with water (8 mL) and the aqueous layer was extracted with EtOAc (3×20 mL). The combined organic layers were washed with brine, dried over anhydrous Na$_2$SO$_4$, filtered, and concentrated to dryness to give a yellow-white powder. The solid was purified by silica gel chromatography (10-100% EtOAc (10% MeOH)/hexanes) to afford the title compound (81% yield) as a white powder.

Step B: (S)—(2-(Amino(4,4-difluorocyclohexyl)methyl)imidazo[1,2-b]pyridazin-7-yl)methanol. A solution of tert-Butyl (S)—((4,4-difluorocyclohexyl)(7-(hydroxymethyl)imidazo[1,2-b]pyridazin-2-yl)methyl)carbamate (450 mg, 1.14 mmol, Step A) in DCM (11 mL) was cooled to 0° C. and TFA was added dropwise. The resulting mixture was stirred for 3.5 h while the ice bath warmed to rt. The reaction mixture was concentrated to dryness and then dissolved in saturated aqueous NaHCO$_3$. The pH of the mixture was adjusted to pH 11 by the addition of sodium carbonate and then it was extracted with DCM:IPA (4:1, 5×25 mL). The combined organic layers were washed with brine, dried over anhydrous Na$_2$SO$_4$, filtered and concentrated to dryness. Purification by preparative HPLC (X-Bridge Prep C18 5 μm, 50×250 mm, 5-100% acetonitrile/water (with 20 mM NH$_4$OH)) afforded the title compound (86% yield).

Step C: (S)—(2-((4,4-Difluorocyclohexyl)(1-isopropyl-1H-pyrazole-5-carboxamido)methyl)imidazo[1,2-b]pyridazin-7-yl)methyl 1-isopropyl-1H-pyrazole-5-carboxylate. To a solution of (S)—(2-(amino(4,4-difluorocyclohexyl)methyl)imidazo[1,2-b]pyridazin-7-yl)methanol (232 mg, 0.78 mmol, Step B) in MeCN (4 mL) was added DIPEA (0.337 mL, 1.96 mmol). The resulting mixture was stirred at rt for 5 min and then 2,5-dioxopyrrolidin-1-yl 1-isopropyl-1H-pyrazole-5-carboxylate (236 mg, 0.94 mmol, Intermediate 7) was added. The reaction mixture was stirred at rt for 40 min, concentrated to dryness and the title compound was used without further purification.

Step D: (S)—N-((4,4-Difluorocyclohexyl)(7-(hydroxymethyl)imidazo[1,2-b]pyridazin-2-yl)methyl)-1-isopropyl- 1H-pyrazole-5-carboxamide. To (S)-(2-((4,4-difluorocyclohexyl)(1-isopropyl-1H-pyrazole-5-carboxamido)methyl)imidazo[1,2-b]pyridazin-7-yl)methyl 1-isopropyl-1H-pyrazole-5-carboxylate (454 mg, 0.80 mmol, Step C) were added NaOH (128 mg, 3.19 mmol), THF (2 mL) and water (1 mL) sequentially. The resulting mixture was heated at 45° C. for 18 h. Then, additional NaOH (64 mg, 1.60 mmol) was added and the mixture was heated for 1 h at 45° C. After that time, additional water (3 mL) and THF (1.5 mL) were added and the mixture was heated at 45° C. for 3.5 h. The reaction was quenched by the addition of 2 M aqueous HCl (1.5 mL) and then the organic solvent was removed in vacuo. The remaining aqueous layer was extracted with DCM:IPA (4:1, 5×5 mL). The combined organic layers were dried over anhydrous Na$_2$SO$_4$, filtered, and concentrated to dryness. The residue was purified by silica gel chromatography (10-100% (10% MeOH in EtOAc)/hexanes) to afford the title compound (54% yield).

Step E: (S)—N-((7-(Bromomethyl)imidazo[1,2-b]pyridazin-2-yl)(4,4-difluorocyclohexyl)methyl)-1-isopropyl-1H-pyrazole-5-carboxamide. To a solution of (S)—N-((4,4-difluorocyclohexyl)(7-(hydroxymethyl)imidazo[1,2-b]pyridazin-2-yl)methyl)-1-isopropyl-1H-pyrazole-5-carboxamide (202 mg, 0.47 mmol, Step D) in DCM (9 mL) was added polymer-bound triphenylphosphine (311 mg, 0.93 mmol) and 1H-imidazole (38.6 mg, 0.56 mmol). The resulting mixture was cooled to 0° C. and carbon tetrabromide (186 mg, 0.56 mmol) was added. The reaction mixture was stirred for 30 min while the ice bath was allowed to warm to rt. The reaction was cooled to 0° C. and additional polymer-bound triphenylphosphine (156 mg, 0.47 mmol), 1H-imidazole (32.1 mg, 0.47 mmol), and carbon tetrabromide (155 mg, 0.47 mmol) were added. The resulting mixture was stirred for 40 min while the ice bath was allowed to warm to rt. The reaction mixture was filtered, the solids rinsed with DCM, and the filtrate concentrated to dryness. The residue was purified by silica gel chromatography (0-100% EtOAc/hexanes) to afford the title compound (21% yield).

Step F: tert-Butyl (S)—(1-((((2-((4,4-difluorocyclohexyl)(1-isopropyl-1H-pyrazole-5-carboxamido)methyl)imidazo[1,2-b]pyridazin-7-yl)methyl)amino)methyl)-3,3-difluorocyclobutyl)carbamate. To a solution of (S)—N-((7-(bromomethyl)imidazo[1,2-b]pyridazin-2-yl)(4,4-difluorocyclohexyl)methyl)-1-isopropyl-1H-pyrazole-5-carboxamide (48 mg, 0.10 mmol, Step E) in DCM (2 mL) were added carbonic acid dicesium (63.1 mg, 0.194 mmol) and tert-Butyl (1-(aminomethyl)-3,3-difluorocyclobutyl)carbamate (27.5 mg, 0.116 mmol) and the resulting mixture was stirred at rt for 3 h. To the mixture was added DIPEA (0.05 mL, 0.291 mmol) and then the mixture was concentrated to dryness. The residue was dissolved in MeCN (2 mL) and a few drops of DMF were added. The resulting mixture was stirred at rt for 18 h. The reaction mixture was then partitioned between water and DCM and the organic layer was washed with saturated aqueous NH$_4$Cl. The aqueous layer was extracted with DCM (3×25 mL), and the combined organic layers were dried over anhydrous Na$_2$SO$_4$, filtered, and concentrated to dryness. The residue was purified initially by silica gel chromatography (0-100% EtOAc (10% MeOH)/hexanes) and then further purified by silica gel chromatography (40-100% EtOAc (10% MeOH)/hexanes) to afford the title compound (84% yield).

Step G: (S)—N-((7-((((1-Amino-3,3-difluorocyclobutyl)methyl)amino)methyl)imidazo[1,2-b]pyridazin-2-yl)(4,4-difluorocyclohexyl)methyl)-1-isopropyl-1H-pyrazole-5-carboxamide. To a solution of tert-Butyl (S)—(1-((((2-((4,4-difluorocyclohexyl)(1-isopropyl-1H-pyrazole-5-carboxamido)methyl)imidazo[1,2-b]pyridazin-7-yl)methyl)amino)methyl)-3,3-difluorocyclobutyl)carbamate (53 mg, 0.081 mmol, Step F) in DCM (0.5 mL) were added 4 M HCl in 1,4-dioxane (0.102 mL, 0.41 mmol) and a couple drops of MeOH and the resulting mixture was stirred at rt for 2 h. The reaction was concentrated to dryness, dissolved in DCM:IPA (4:1), and washed with saturated aqueous NaHCO$_3$ (5 mL). The organic layer was dried over anhydrous Na$_2$SO$_4$, filtered, concentrated to dryness and used without further purification (62% yield).

Step H: (S)—N-((7-((2,2-Difluoro-6-oxo-5,7-diazaspiro[3.4]octan-7-yl)methyl)imidazo[1,2-b]pyridazin-2-yl)(4,4-difluorocyclohexyl)methyl)-1-isopropyl-1H-pyrazole-5-carboxamide. To a solution of (S)—N-((7-((((1-amino-3,3-difluorocyclobutyl)methyl)amino)methyl)imidazo[1,2-b]pyridazin-2-yl)(4,4-difluorocyclohexyl)methyl)-1-isopropyl-1H-pyrazole-5-carboxamide (28 mg, 0.051 mmol, Step G) in DCM (0.5 mL) was added DIPEA (0.027 mL, 0.155 mmol) and the mixture was cooled to 0° C. under an atmosphere of N$_2$. To the mixture was added a solution of triphosgene (6.03 mg, 0.02 mmol) in DCM (0.5 mL) dropwise and the resulting mixture was stirred at 0° C. for 35 min. The reaction was quenched by the addition of MeOH (2 mL) and the mixture was concentrated to dryness. Purification by preparative HPLC (X-Bridge Prep C18 5 μm, 50×250 mm, 5-100% acetonitrile/water (with 20 mM NH$_4$OH)) afforded the title compound (44% yield). $^1$H NMR (500 MHz, DMSO-d$_6$) δ 8.73 (d, J=9.1 Hz, 1H), 8.37 (d, J=2.0 Hz, 1H), 8.22 (s, 1H), 7.89-7.87 (m, 1H), 7.50-7.48 (m, 1H), 7.27-7.25 (m, 1H), 6.93-6.91 (m, 1H), 5.37 (quin, J=6.6 Hz, 1H), 5.20-5.13 (m, 1H), 4.34 (s, 2H), 2.85-2.79 (m, 3H), 2.23-2.12 (m, 1H), 2.10-1.94 (m, 3H), 1.92-1.85 (m, 1H), 1.85-1.69 (m, 2H), 1.67-1.59 (m, 1H), 1.38-1.36 (m, 3H), 1.35-1.32 (m, 3H), 1.27-1.22 (m, 4H). MS (ESI) m/z: [M+H]$^+$ Found 577.3.

Example 47

4-Methoxy-N—((S)-5,5,5-trifluoro-1-(7-((S)-2-methoxy-((S)-4-methyl-2-oxo-4-(trifluoromethyl)imidazolidin-1-yl)ethyl)imidazo[1,2-b]pyridazin-2-yl)-4,4-dimethylpentyl)-1,2,5-oxadiazole-3-carboxamide

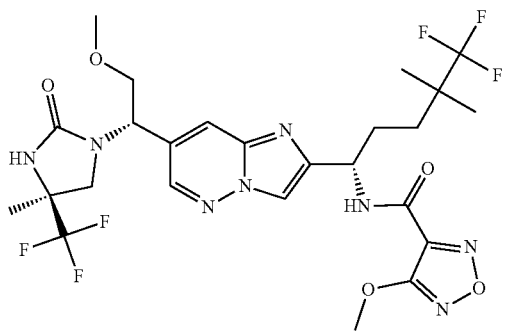 [SMILES: COC[C@H](c1cnn2cc([C@H](CCC(C)(C)C(F)(F)F)NC(=O)c3nonc3OC)nc2c1)N1C[C@@](C)(C(F)(F)F)NC1=O]

The title compound was synthesized in a manner analogous to Example 1 using (S)—((S)-1-(2-((S)-1-amino-5,5,5-trifluoro-4,4-dimethylpentyl)imidazo[1,2-b]pyridazin-7-yl)-2-methoxyethyl)-4-methyl-4-(trifluoromethyl)imidazolidin-2-one (Intermediate 35) in place of (S)-1-((2-(amino(4,4-difluorocyclohexyl)methyl)imidazo[1,2-b]

pyridazin-7-yl)methyl)imidazolidin-2-one and 4-methoxy-1,2,5-oxadiazole-3-carboxylic acid in place of 4-methyl-1,2,5-oxadiazole carboxylic acid to provide the title compound as a white solid (48% yield). $^1$H NMR (500 MHz, DMSO-d$_6$) δ 9.38 (d, J=8.5 Hz, 1H), 8.39 (d, J=2.1 Hz, 1H), 8.18 (s, 1H), 7.92-7.90 (m, 1H), 7.76-7.73 (m, 1H), 5.22-5.16 (m, 1H), 5.15-5.11 (m, 1H), 4.10 (s, 3H), 3.95-3.83 (m, 2H), 3.58 (d, J=10.3 Hz, 1H), 3.44 (d, J=10.3 Hz, 1H), 3.34 (s, 3H), 2.13-2.03 (m, 1H), 2.02-1.90 (m, 1H), 1.63 (dt, J=4.4, 13.2 Hz, 1H), 1.51 (dt, J=4.6, 13.0 Hz, 1H), 1.42 (s, 3H), 1.09 (s, 6H). MS (ESI) m/z: [M+H]$^+$ Found 637.3.

Example 48

4-Methyl-N—((S)-5,5,5-trifluoro-4,4-dimethyl-1-(7-(((S)-4-methyl-2-oxo-4-(trifluoromethyl)imidazolidin-1-yl)methyl)imidazo[1,2-b]pyridazin-2-yl)pentyl)-1,2,5-oxadiazole-3-carboxamide

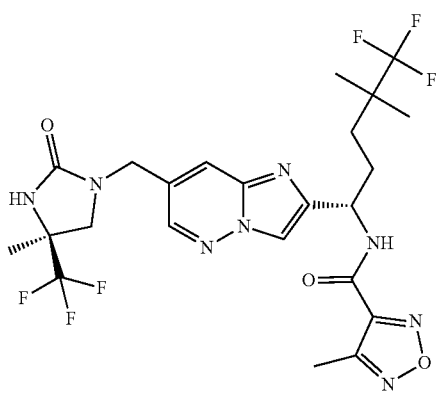 [SMILES: Cc1nonc1C(=O)N[C@@H](CCC(C)(C)C(F)(F)F)c1cn2ncc(CN3C[C@@](C)(C(F)(F)F)NC3=O)cc2n1]

The title compound was prepared as described for the synthesis of Example 10 using (S)-5,5,5-trifluoro-4,4-dimethyl-1-(7-(((S)-4-methyl-2-oxo-4-(trifluoromethyl)imidazolidin-1-yl)methyl)imidazo[1,2-b]pyridazin-2-yl)pentan-1-aminium 2,2,2-trifluoroacetate (Intermediate 55) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. The residue was purified by preparative HPLC (XBridge Prep C18, 5 μm, 50×150 mm; 10-100% MeCN/water (20 mM NH$_4$OH)) to provide the title compound in 13% yield. $^1$H NMR (500 MHz, DMSO-d$_6$) δ 9.52 (d, J=8.6 Hz, 1H), 8.34 (d, J=2.0 Hz, 1H), 8.21-8.16 (m, 1H), 7.88-7.83 (m, 1H), 7.73 (s, 1H), 5.25-5.13 (m, 1H), 4.48-4.41 (m, 1H), 4.37-4.24 (m, 1H), 3.53 (d, J=10.1 Hz, 1H), 3.34-3.31 (m, 1H), 2.49 (s, 3H), 2.18-2.03 (m, 1H), 2.03-1.93 (m, 1H), 1.70-1.59 (m, 1H), 1.58-1.47 (m, 1H), 1.39 (s, 3H), 1.12-1.01 (m, 6H). MS (ESI) m/z: [M+H]$^+$ Found 577.3.

Example 49

4-Methyl-N—((S)-5,5,5-trifluoro-4,4-dimethyl-1-(7-(((R)-4-methyl-2-oxo-4-(trifluoromethyl)imidazolidin-1-yl)methyl)imidazo[1,2-b]pyridazin-2-yl)pentyl)-1,2,5-oxadiazole-3-carboxamide

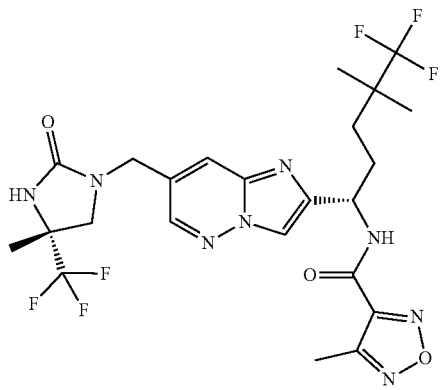 [SMILES: Cc1nonc1C(=O)N[C@@H](CCC(C)(C)C(F)(F)F)c1cn2ncc(CN3C[C@](C)(C(F)(F)F)NC3=O)cc2n1]

The title compound was prepared as described for the synthesis of Example 10 using (S)-5,5,5-trifluoro-4,4-dimethyl-1-(7-(((R)-4-methyl-2-oxo-4-(trifluoromethyl)imidazolidin-1-yl)methyl)imidazo[1,2-b]pyridazin-2-yl)pentan-1-aminium 2,2,2-trifluoroacetate (Intermediate 56) in place of (S)-1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-4-(trifluoromethyl)imidazolidin-2-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate. The residue was purified by preparative HPLC (XBridge Prep C18, 5 μm, 50×150 mm; 10-100% MeCN/water (20 mM NH$_4$OH)) to provide the title compound in 45% yield. $^1$H NMR (500 MHz, DMSO-d$_6$) δ 9.52 (d, J=8.6 Hz, 1H), 8.35 (d, J=2.1 Hz, 1H), 8.20 (d, J=0.7 Hz, 1H), 7.86 (dd, J=2.0, 0.9 Hz, 1H), 7.74 (s, 1H), 5.21 (td, J=8.8, 5.1 Hz, 1H), 4.44 (dd, J=15.8, 1.0 Hz, 1H), 4.32 (dd, J=15.7, 1.0 Hz, 1H), 3.54 (d, J=10.0 Hz, 1H), 3.34-3.32 (m, 1H), 2.50 (s, 3H), 2.16-2.06 (m, 1H), 2.05-1.94 (m, 1H), 1.65 (td, J=13.1, 4.5 Hz, 1H), 1.53 (td, J=13.0, 4.5 Hz, 1H), 1.40 (s, 3H), 1.13-1.06 (m, 6H). MS (ESI) m/z: [M+H]$^+$ Found 577.3.

IN VITRO BIOLOGICAL DATA

IL-17A(FLAG-Tagged): IL-17RA(His-Tagged) Binding Disruption Eu-HTRF Assay

An antibody directed against the FLAG tag of IL-17A (SEQ ID NO:1) is labeled with the HTRF donor chromophore (Europium-cryptate). IL-17A is present as a dimer that is "locked into" this quaternary structure due to the formation of loop-spanning intramolecular disulfide bridges. The construct of IL-17RA used in the assay excludes the outer-membrane portion of the receptor and is fused to a C-terminal 10×His tag (SEQ ID NO:2). An antibody directed against the His tag of the IL-17RA chimera is labeled with the HTRF acceptor chromophore ("D2"). The fluorescence-resonance energy transfer (FRET) depends on the vicinity of the donor chromophore to the acceptor, and interruption of the binding between the IL-17A and IL-17RA causes the reduction/loss of FRET. Therefore, this assay allows to evaluate the compound effect on the binding IL-17A and IL-17RA by monitoring the fluorescence intensity of donor vs acceptor. The assay was run using either Protocol 1 or Protocol 2 described below.

Protocol 1: 40 nL of 2-fold serial diluted compound solution for total 22 dilution points is added into each well of a 1536-well, white, low-volume, non-binding plate (Greiner #782904), then 2 μl of FLAG tagged IL-17A at 2× final concentration (2.5 nM) in solution of PBS+0.01% Triton-X100 is added to each well. The assay plate is briefly centrifuged then incubated for 1 h at rt. A mixed solution is prepared containing 2×5 nM 10HIS×IL-17RA, 2×2.5 nM Eu-anti-FLAG (CISBIO), 2×5 nM D2-anti-HIS (CISBIO) in PBS+0.01% Triton-X100+200 mM Potassium Fluoride (Sigma 60238) and 211.1 of mix is added to each well of the assay plate. The plate is briefly centrifuged then incubated for 2 h at rt. The HTRF intensities at the wavelength of donor (620 nm) and acceptor (665 nm) are measured using BMG Pherastar. The ratio between intensities at two wavelengths is calculated and plotted against the compound concentration and the data is fitted to a one-site competition model to yield $IC_{50}$ of the compound.

Protocol 2. 40 nl of 2-fold serial diluted compound solution for total 22 dilution points is added into each well of a 1536-well, white, low-volume, non-binding plate (Greiner #782904), then 2 μl of FLAG tagged IL-17A at 2× final concentration (1 nM) in solution of PBS+0.01% Triton-X100 is added to each well. The assay plate is briefly centrifuged then incubated for 1 h at rt. A mixed solution is prepared containing 2×5 nM 10HIS×IL-17RA, 2×2.5 nM Eu-anti-FLAG (CISBIO), 2×5 nM D2-anti-HIS (CISBIO) in PBS+0.01% Triton-X100+200 mM Potassium Fluoride (Sigma 60238) and 211.1 of mix is added to each well of the assay plate. The plate is briefly centrifuged then incubated for 2 h at rt. The HTRF intensities at the wavelength of donor (615 nm) and acceptor (665 nm) are measured using BMG Pherastar. The ratio between intensities at two wavelengths is calculated and plotted against the compound concentration and the data is fitted to a one-site competition model to yield $IC_{50}$ of the compound.

IL-17A acts directly on keratinocytes through binding to dimeric receptor IL-17RA/RC and drives the production of a number of inflammatory mediators known to be elevated in psoriasis lesional tissue. IL-17A small molecule inhibitors that block the IL-17A to interact with IL-17R would inhibit the IL-17A signaling in its targeted cells such as keratinocytes. The compound functional activity is evaluated for its impact on IL-17A-induced G-CSF production in human normal keratinocyte (NHK).

NHK Assay

Adult normal human keratinocytes are cultured in keratinocyte growth medium (Lonza) in a flask till reaching ~90% confluence, then cells are transferred to a 384-well plate at density of 3000-4000 cell/well. Recombinant human IL-17A (Gibco PHC9174) is pre-incubated with titrated compound or DMSO for 1 h at rt then added to the cell culture plate. The final concentration of IL-17A is 5 ng/mL and DMSO is 0.2%, in the culture containing 5% FBS. Cells are cultured/treated for 24 h at 37° C. Supernatants are collected and G-CSF production is measured through HTRF technology using Human G-CSF Kit (CisBio). G-CSF concentration was extrapolated from the standard curve and $IC_{50}$ is determined using GraphPad Prism. Cell viability is also evaluated using CellTiter-Glo kit (Promega) and effect of compound on cell viability is compared to DMSO control.

In cases where the compound was tested more than once, the $IC_{50}$ value shown is a simple average of the measured values.

A: $IC_{50}$<4 μm; B: 4 μm <$IC_{50}$<10 μm; C: $IC_{50}$>10 μm
- Not available

TABLE 3

| Example # | IL-17A HTRF $IC_{50}$ (μM) - Protocol 1 | IL-17A HTRF $IC_{50}$ (μM) - Protocol 2 | NHK $IC_{50}$ (μM) |
|---|---|---|---|
| 1 | A | — | B |
| 2 | A | — | A |
| 3 | A | — | A |
| 4 | A | — | A |
| 5 | A | — | C |
| 6 | A | — | A |
| 7 | A | A | A |
| 8 | A | — | A |
| 9 | A | — | A |
| 10 | A | — | A |
| 11 | A | — | A |
| 12 | A | — | A |
| 13 | — | — | A |
| 14 | — | — | A |
| 15 | — | — | A |
| 16 | — | — | A |
| 17 | A | — | A |
| 18 | A | — | A |
| 19 | A | — | A |
| 20 | A | — | A |
| 21 | — | — | A |
| 22 | A | — | A |
| 23 | — | A | A |
| 24 | — | — | A |
| 25 | — | A | A |
| 26 | — | A | A |
| 27 | — | A | A |
| 28 | — | — | A |
| 29 | — | — | A |
| 30 | — | — | A |
| 31 | — | A | A |
| 32 | — | — | A |
| 33 | A | — | A |
| 34 | — | — | A |
| 35 | — | — | A |
| 36 | A | — | A |
| 37 | — | A | A |
| 38 | — | — | A |
| 39 | — | — | A |
| 40 | — | A | A |
| 41 | — | A | A |
| 42 | — | A | A |
| 43 | — | A | A |
| 44 | — | — | A |
| 45 | — | A | A |
| 46 | — | A | B |
| 47 | — | A | A |
| 48 | — | A | A |
| 49 | — | A | A |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

Name: IL-17A-Flag

SEQ ID NO: 1

MATGSRTSLLLAFGLLCLPWLQEGSAGSDYKDDDDKGSGSGSLEVLFQG

PGITIPRNPGCPNSEDKNFPRTVMVNLNIHNRNTNTNPKRSSDYYNRST

```
SPWNLHRNEDPERYPSVIWEAQCRHLGCINADGNVDYHMNSVPIQQEIL

VLRREPPHCPNSFRLEKILVSVGCTCVTPIVHHVQ

Name: IL-17RA
                                              SEQ ID NO: 2
MKFLVNVALVFMVVYISYIYALRLLDHRALVCSQPGLNCTVKNSTCLDD

SWIHPRNLTPSSPKDLQIQLHFAHTQQGDLFPVAHIEWTLQTDASILYL

EGAELSVLQLNTNERLCVRFEFLSKLRHHHRRWRFTFSHFVVDPDQEYE

VTVHHLPKPIPDGDPNHQSKNFLVPDCEHARMKVTTPCMSSGSLWDPNI

TVETLEAHQLRVSFTLWNESTHYQILLTSFPHMENHSCFEHMHHIPAPR

PEEFHQRSNVTLTLRNLKGCCRHQVQIQPFFSSCLNDCLRHSATVSCPE

MPDTPEPIPDYMPLWGSGGHHHHHHHHHH*
```

We claim:
1. A compound or a pharmaceutically acceptable salt thereof, having a formula selected from the group consisting of:
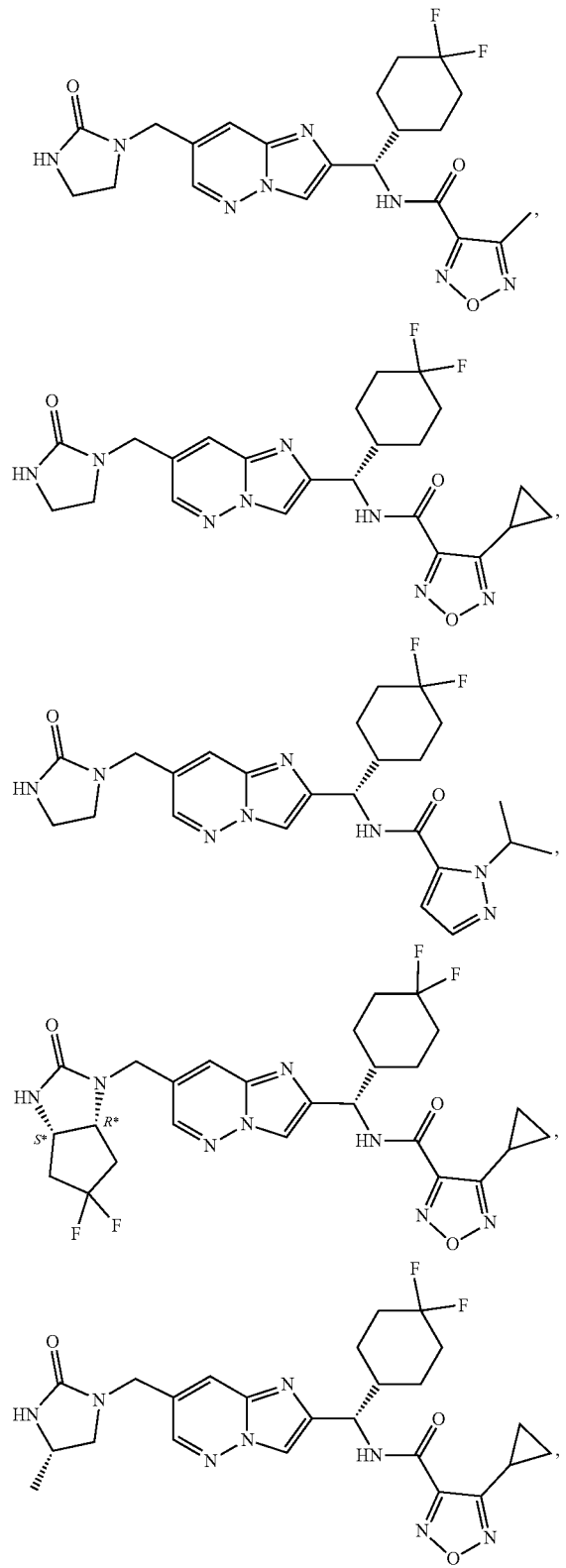
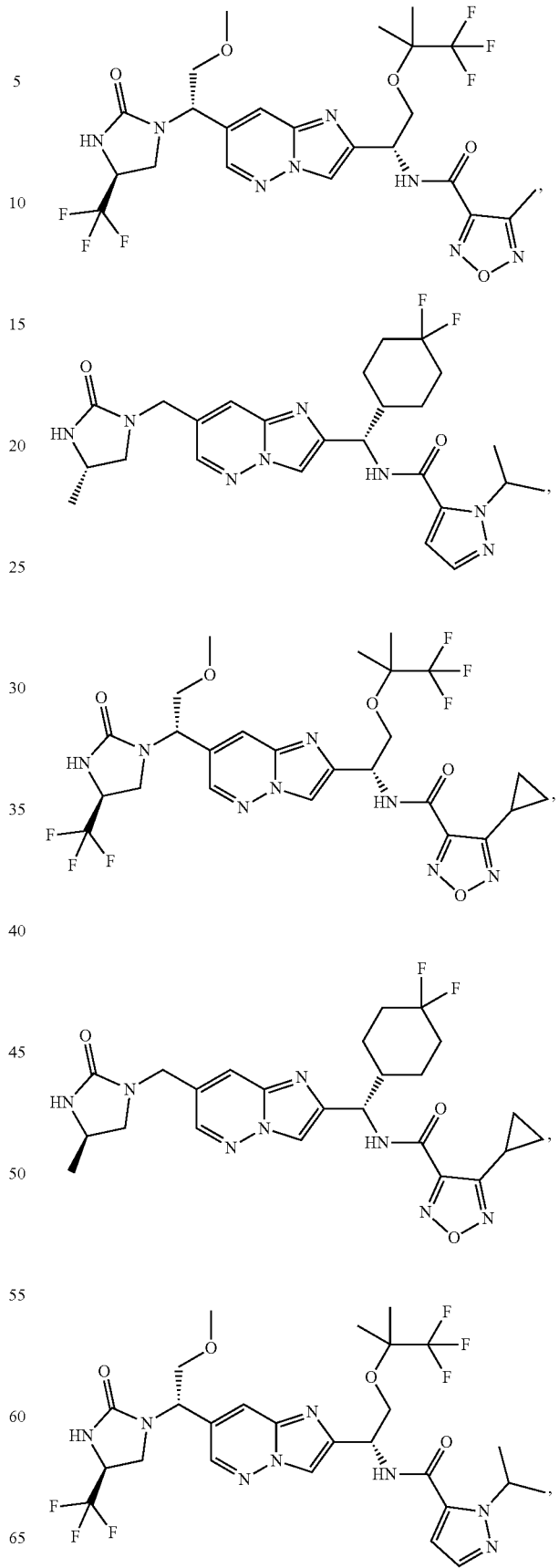

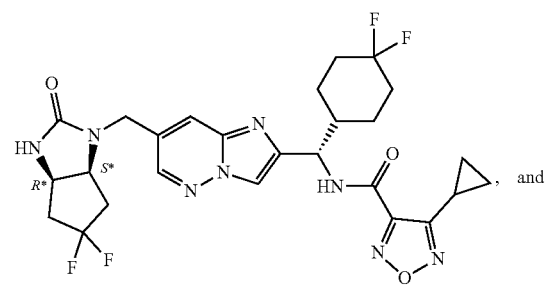
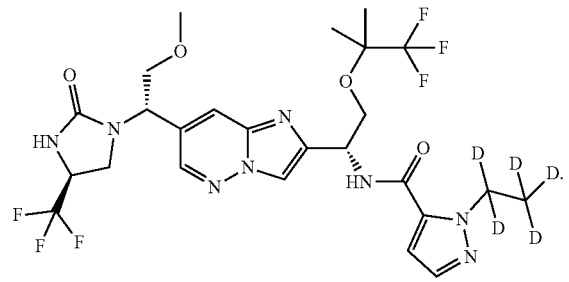
2. A compound or a pharmaceutically acceptable salt thereof, having a formula selected from the group consisting of:
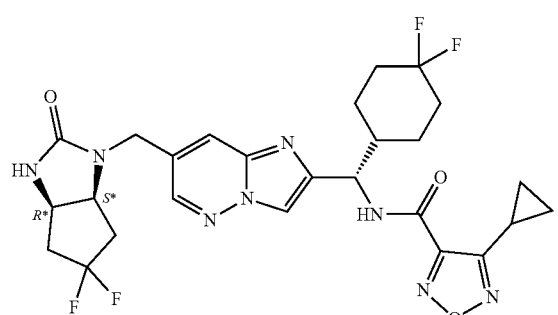
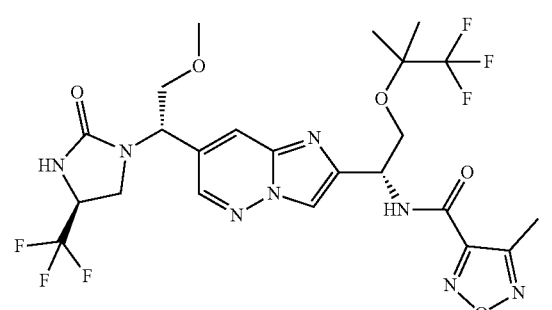
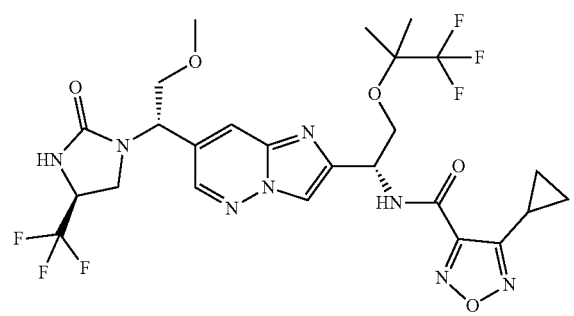
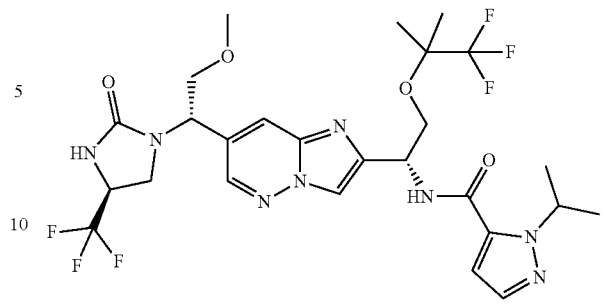
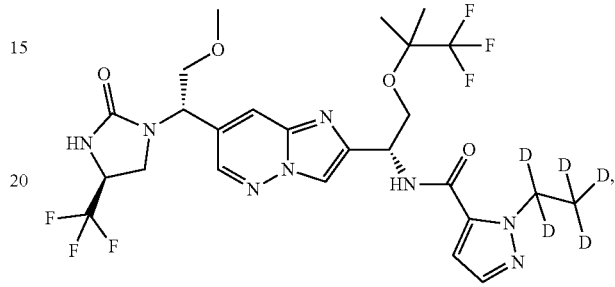
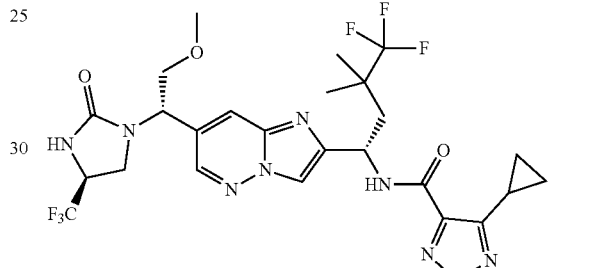
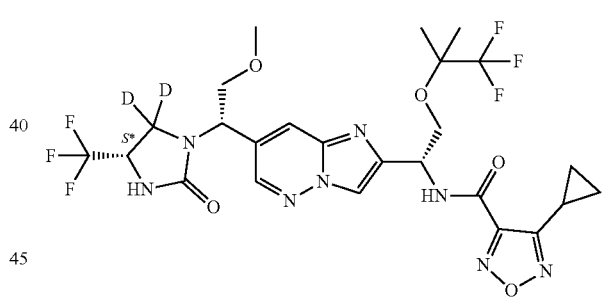
, and
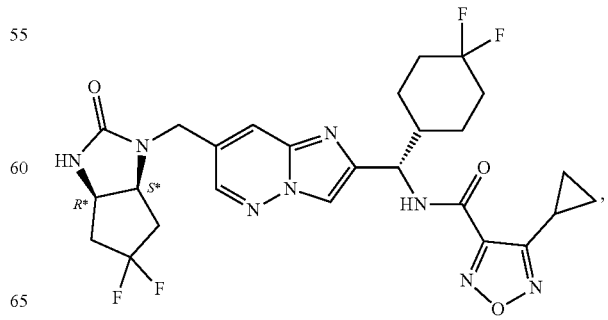
3. A compound or a pharmaceutically acceptable salt thereof, having a formula selected from the group consisting of:

211
-continued
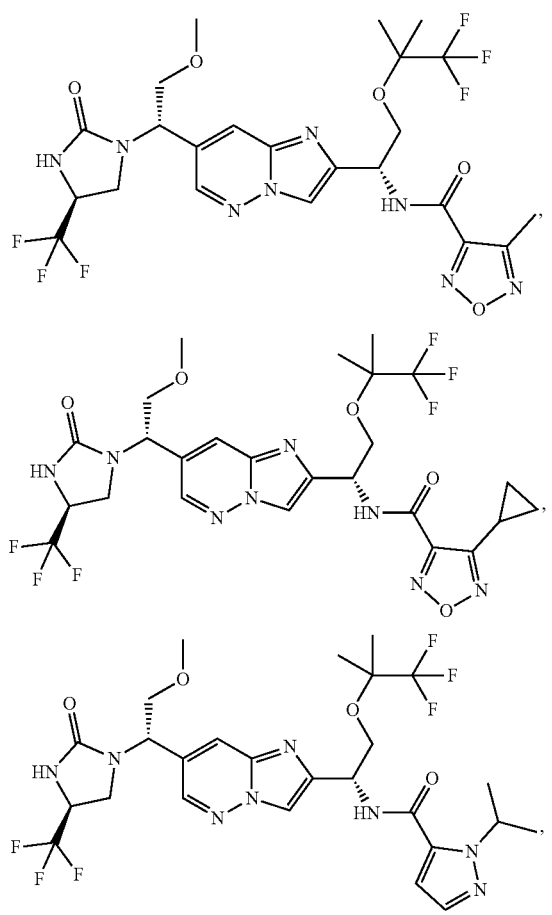
212
-continued
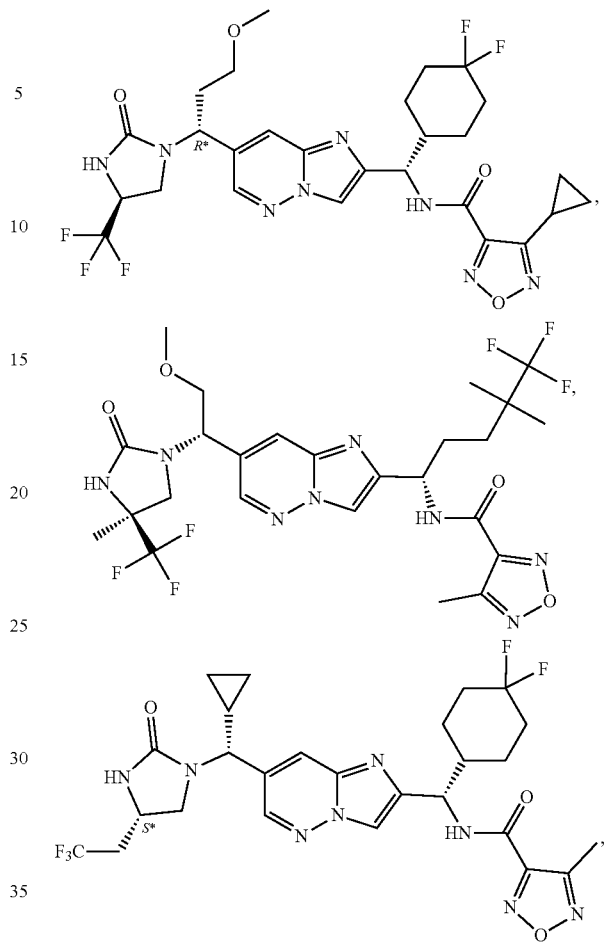
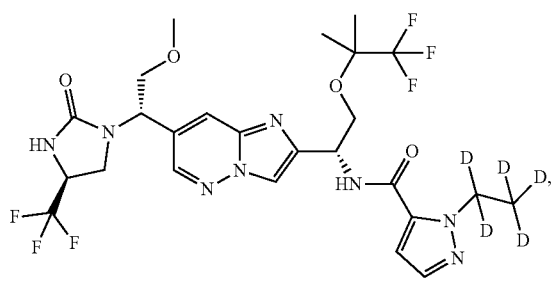
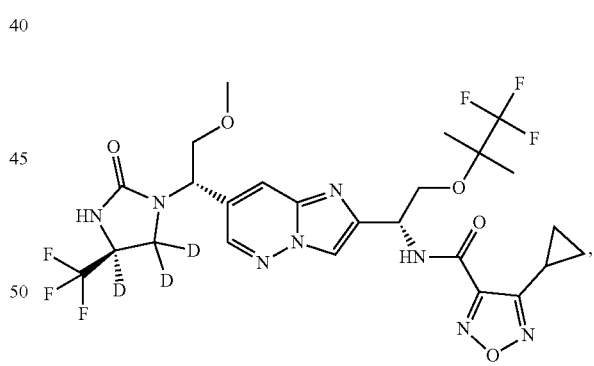
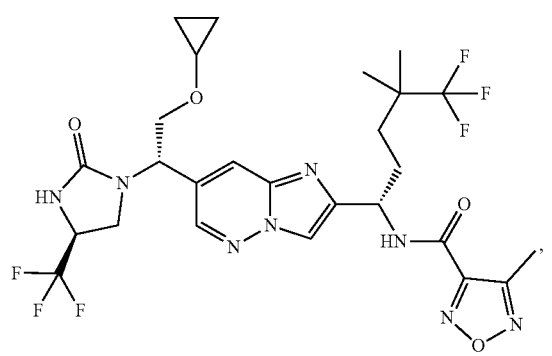
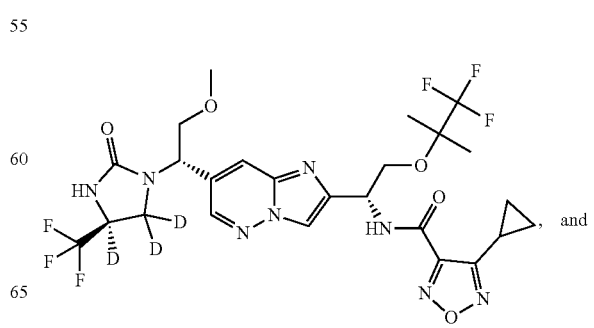

-continued

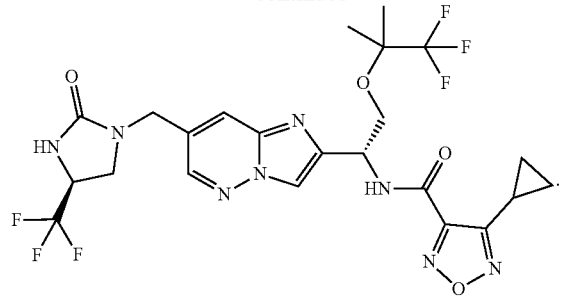

4. The compound of claim 1 or a pharmaceutically acceptable salt thereof, having the following structure:

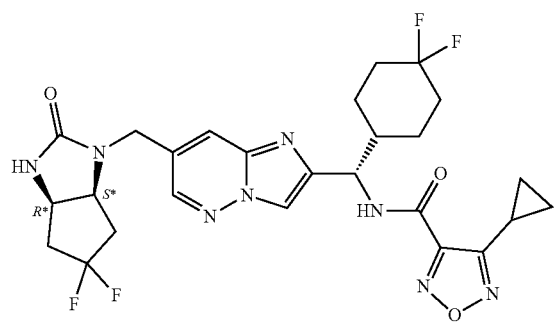

5. The compound of claim 1 or a pharmaceutically acceptable salt thereof, having the following structure:

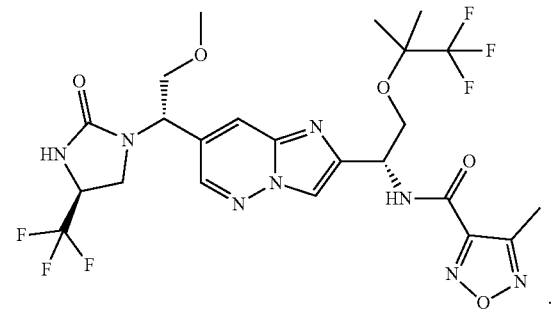 [SMILES: COC[C@H](c1cnn2cc([C@H](COC(C)(C)C(F)(F)F)NC(=O)c3nonc3C)nc2c1)N1C[C@@H](C(F)(F)F)NC1=O]

6. The compound of claim 1 or a pharmaceutically acceptable salt thereof, having the following structure:

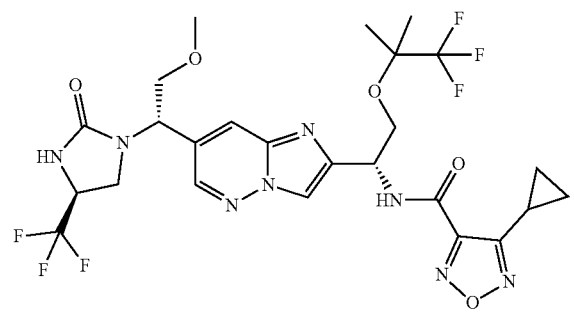

7. The compound of claim 1 or a pharmaceutically acceptable salt thereof, having the following structure:

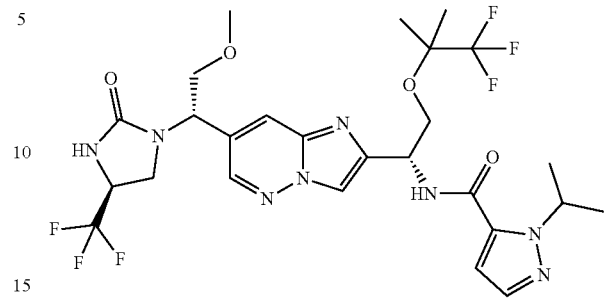

8. The compound of claim 1 or a pharmaceutically acceptable salt thereof, having the following structure:

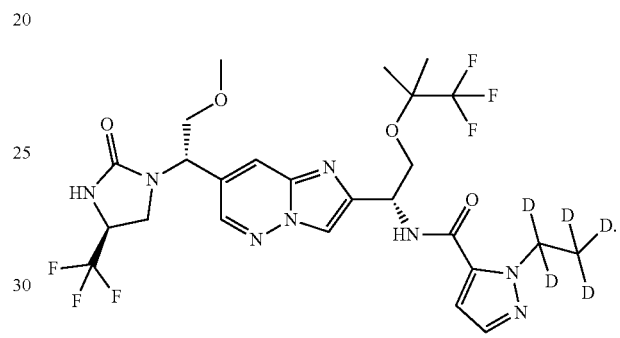

9. The compound of claim 2 or a pharmaceutically acceptable salt thereof, having the following structure:

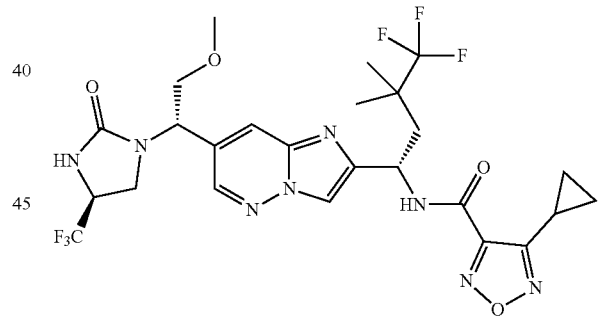

10. The compound of claim 2 or a pharmaceutically acceptable salt thereof, having the following structure:

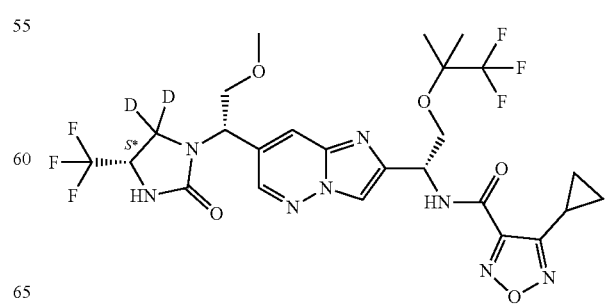

11. The compound of claim 3 or a pharmaceutically acceptable salt thereof, having the following structure:

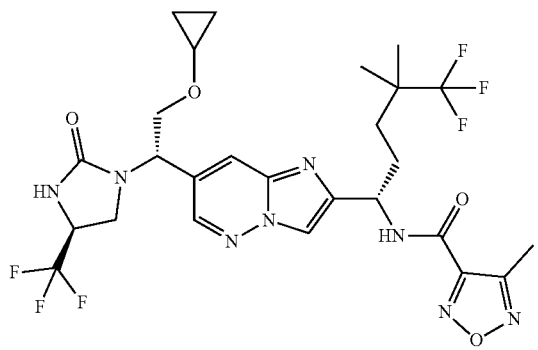

12. The compound of claim 3 or a pharmaceutically acceptable salt thereof, having the following structure:

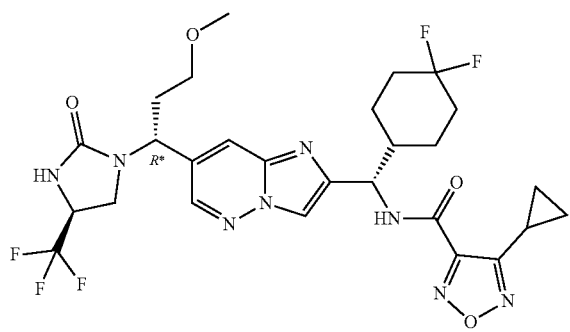

13. The compound of claim 3 or a pharmaceutically acceptable salt thereof, having the following structure:

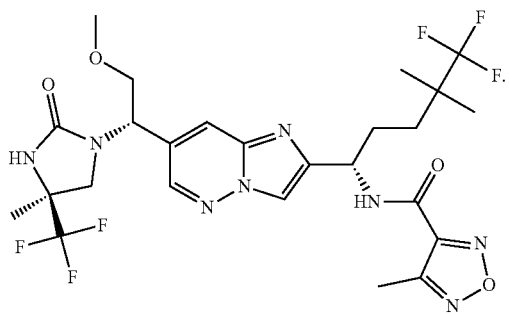 [SMILES: COC[C@H](c1cnn2cc([C@H](CCC(C)(C)C(F)(F)F)NC(=O)c3nonc3C)nc2c1)N1C[C@@](C)(C(F)(F)F)NC1=O]

14. The compound of claim 3 or a pharmaceutically acceptable salt thereof, having the following structure:

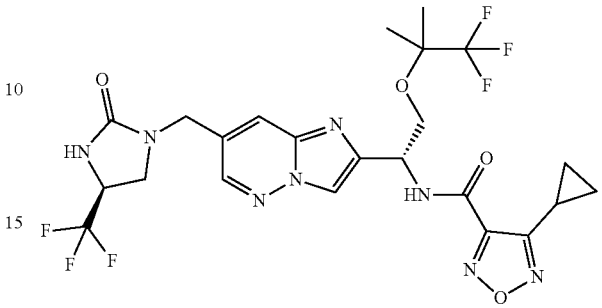

15. The compound of claim 3 or a pharmaceutically acceptable salt thereof, having the following structure:

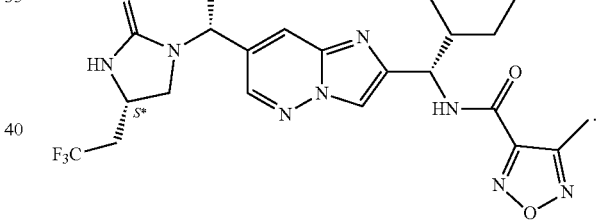

16. The compound of claim 3 or a pharmaceutically acceptable salt thereof, having the following structure:

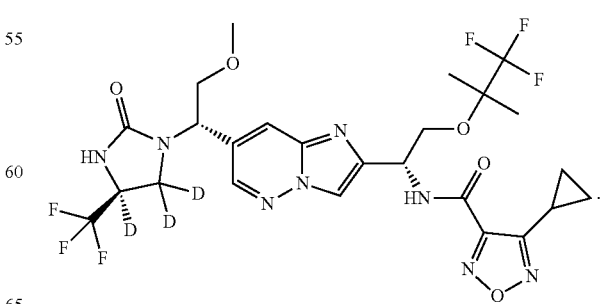

17. The compound of claim 3 or a pharmaceutically acceptable salt thereof, having the following structure:

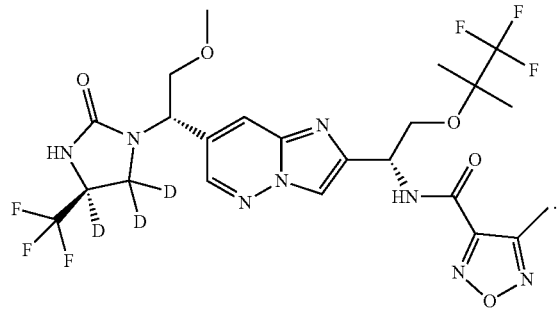 [SMILES: [2H]C1([2H])N([C@H](COC)c2cnn3cc([C@H](COC(C)(C)C(F)(F)F)NC(=O)c4nonc4C)nc3c2)C(=O)N[C@]1([2H])C(F)(F)F ; "."]

18. The compound of claim 1 or a pharmaceutically acceptable salt thereof, having the following formula:

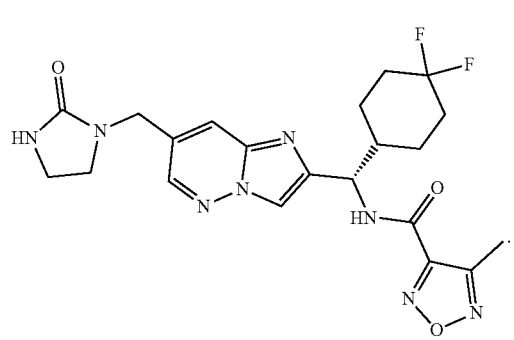 [SMILES: Cc1nonc1C(=O)N[C@H](c1cn2ncc(CN3CCNC3=O)cc2n1)C1CCC(F)(F)CC1]

19. The compound of claim 1 or a pharmaceutically acceptable salt thereof, having the following formula:

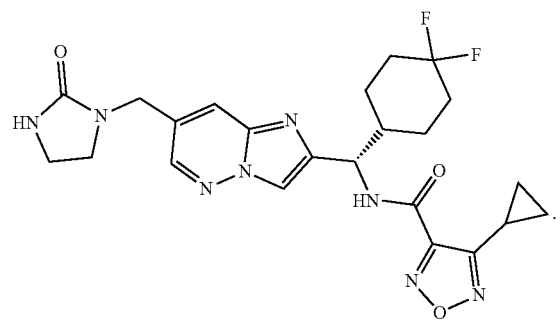 [SMILES: O=C(N[C@H](c1cn2ncc(CN3CCNC3=O)cc2n1)C1CCC(F)(F)CC1)c1nonc1C1CC1]

20. The compound of claim 1 or a pharmaceutically acceptable salt thereof, having the following formula:

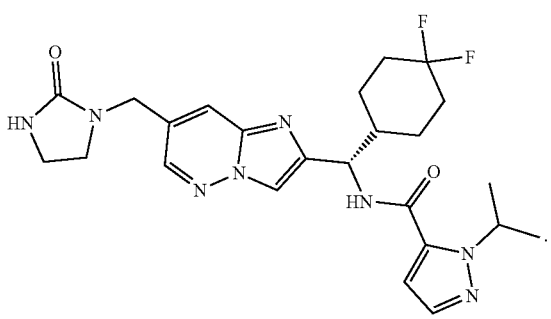 [SMILES: CC(C)n1nccc1C(=O)N[C@H](c1cn2ncc(CN3CCNC3=O)cc2n1)C1CCC(F)(F)CC1]

21. The compound of claim 1 or a pharmaceutically acceptable salt thereof, having the following formula:

22. The compound of claim 1 or a pharmaceutically acceptable salt thereof, having the following formula:

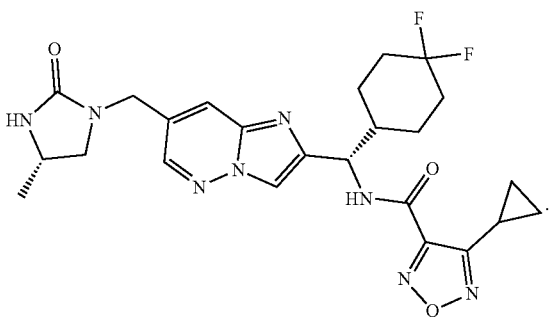 [SMILES: C[C@H]1CN(Cc2cnn3cc([C@@H](NC(=O)c4nonc4C4CC4)C4CCC(F)(F)CC4)nc3c2)C(=O)N1]

23. The compound of claim 1 or a pharmaceutically acceptable salt thereof, having the following formula:
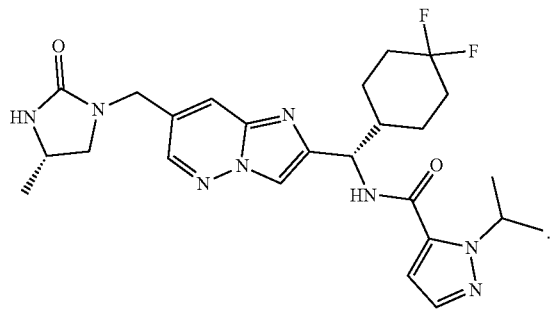 [SMILES: CC(C)n1nccc1C(=O)N[C@H](c1cn2ncc(CN3C[C@H](C)NC3=O)cc2n1)C1CCC(F)(F)CC1]
24. The compound of claim 1 or a pharmaceutically acceptable salt thereof, having the following formula:
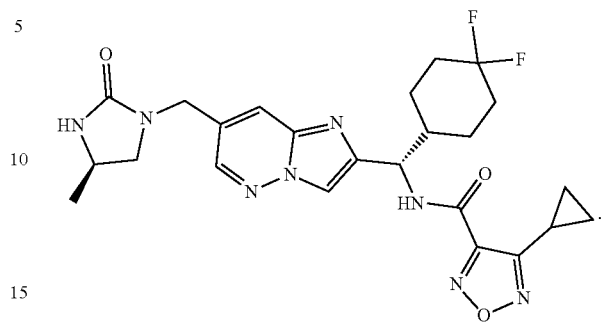
* * * * *